[12] United States Patent
Cheung et al.

(10) Patent No.: US 7,462,614 B2
(45) Date of Patent: Dec. 9, 2008

(54) IMIDAZOTRIAZINE COMPOUNDS

(75) Inventors: Mui Cheung, Durham, NC (US); Nigel Paul King, Harlow (GB); Kevin Wayne Kuntz, Durham, NC (US); Robert Anthony Mook, Jr., Durham, NC (US); Mark Andrew Pobanz, Westfield, IN (US); James Michael Salovich, Durham, NC (US); Brian John Wilson, Durham, NC (US)

(73) Assignee: Smithkline Beecham Corporation, Philadelphia, PA (US)

( * ) Notice: Subject to any disclaimer, the term of this patent is extended or adjusted under 35 U.S.C. 154(b) by 289 days.

(21) Appl. No.: 10/550,434

(22) PCT Filed: Mar. 29, 2004

(86) PCT No.: PCT/US2004/009553

§ 371 (c)(1),
(2), (4) Date: Sep. 21, 2005

(87) PCT Pub. No.: WO2004/087652

PCT Pub. Date: Oct. 14, 2004

(65) Prior Publication Data

US 2006/0217382 A1    Sep. 28, 2006

Related U.S. Application Data

(60) Provisional application No. 60/459,293, filed on Apr. 1, 2003.

(51) Int. Cl.
C07D 487/04    (2006.01)
C07D 401/04    (2006.01)
C07D 401/06    (2006.01)
C07D 401/14    (2006.01)
C07D 403/04    (2006.01)
C07D 403/06    (2006.01)
C07D 403/14    (2006.01)
A61K 31/53    (2006.01)
A61P 35/00    (2006.01)

(52) U.S. Cl. ........................ 514/243; 544/184; 544/182
(58) Field of Classification Search ................. 544/184; 514/243
See application file for complete search history.

(56) References Cited

U.S. PATENT DOCUMENTS

| 3,840,537 | A | 10/1974 | Garside et al. |
| 3,941,785 | A | 3/1976 | Clarke et al. |
| 4,278,673 | A | 7/1981 | Hartley et al. |
| 4,308,384 | A | 12/1981 | Hartley et al. |
| 4,529,692 | A | 7/1985 | Ono et al. |
| 4,838,925 | A | 6/1989 | Tseng |
| 6,362,178 | B1 | 3/2002 | Niewohner et al. |
| 6,566,360 | B1 | 5/2003 | Niewohner et al. |
| 6,890,922 | B2 | 5/2005 | Niewohner et al. |
| 7,122,540 | B2 | 10/2006 | Niewohner et al. |
| 2006/0189615 | A1 | 8/2006 | Niewohner et al. |

FOREIGN PATENT DOCUMENTS

| DE | 10011530 | 9/2001 |
| DE | 10011530 A1 | 9/2001 |
| EP | 1174431 A2 | 10/1996 |
| WO | WO 2004/005291 | 1/2004 |

OTHER PUBLICATIONS

Ahmed FASEB Journal 18, 5-7, 2004.*
Cecil Textbook of Medicine, edited by Bennet, J.C., and Plum F., 20th edition, vol. 1, 1004-1010, 1996.*
Wolft Manfred E. "Burger's Medicinal Chemistry, 5ed, Part 1", John Wiley & Sons, 1995, pp. 975-977.*
Banker, G.S. et al, "Modern Pharmaceutics, 3ed.", Marcel Dekker, New York. 1996, pp. 451 and 596.*
West, Anthony R., Solid State Chemistry and its Applications, Wiley, New York, 1988, pp. 358 & 365.*
Vippagunta et al., Advanced Drug Delivery Reviews 48: 3-26, 2001.*
Cogswell J.P., et al.; Dominant-Negative Polo-Like Kinase T Induces Mitotic Catastrophe Independent of CDC25C Function; Cell Growth & Differentiation: Dec. 2000; 11; 615-628.
Glover, D.M., et al.; Polo-Like Kinases: A Team That Plays Throughout Mitosis; Genes & Development; 1998; 12; 3777-3787.
Wood, K.W., et al.; Past And Future Of The Mitotic Spindle As An Oncology Target; Current Opinion in Pharmacology; 2001; 1; 370-377.
Written Opinion Of The International Searching Authority for International Application No. PCT/US2004/009553 dated Apr. 1, 2003.
Eckerdt, F., et al.; Polo-like kinases and oncogenesis; Oncogene; 2005; 24; 267-276.

(Continued)

*Primary Examiner*—Venkataraman Balasubram
(74) *Attorney, Agent, or Firm*—Bonnie L. Deppenbrack

(57) ABSTRACT

The present invention provides compounds of formula (I):

wherein all variables are as defined herein, pharmaceutical compositions containing the same, processes for preparing the same and their use as pharmaceutical agents.

27 Claims, No Drawings

OTHER PUBLICATIONS

Holtrich, U., et al.; Induction and down-regulation of PLK, a human serine/threonine kinase expressed in proliferating cells and tumors; Proc. Nat. Acad. Sci. USA; 1994; 91; 1736-1740.

Yuan, J., et al.; Polo-like kinase, a novel marker for cellular proliferation; Am. J. Path.; 1997; 150; 1165-1172; abstract only.

Knecht, R., et al.; PLK (polo-like kinse), a new prognostic marker for oropharyngeal carcinomas; Int. J. Cancer; 2000; 89; 535-536.

Knecht, R., et al.; Prognistic Significance of Polo-like Kinase (PLK) Expression in Squamous Cell Carcinomas of the Head and Neck; Cancer Research; 1999; 59; 2794-2797.

MacMillan, J., et al.; Comparative Expression of the Mitotic Regulators SAK and PLK in Colorectal Cancer; Ann. Surg. Oncology; 2001; 8(9); 729-740.

Strebhardt, K., et al.; Prognostic Value of Pololike Kinase Expression in Melanomas; JAMA; 2000; 283; 479-480.

Wolf, G., et al.; Prognostic significance of polo-like kinase (PLK) expression in non-small cell lung cancer; Oncogene; 1997; 14; 543-549.

Takai, N., et al.; Polo-like kinase (PLK) expression in endometrial carcinoma; Cancer Letters; 2001; 169; 41-49.

Takahashi, T., et al.; Polo-like kinase 1 (PLK1) is overexpressed in primary colorectal cancers; Cancer Sci.; 2003; 94(2); 148-152.

Ito, Y., et al.; Polo-like kinase 1 over expression is an early event in the progression of papillary carcinoma; Br. J. Cancer; 2004; 90; 414-418.

Weichert, W., et al.; Polo-like kinase isoform expression is a prognostic factor in ovarian carcinoma; Br. J. Cancer; 2004; 90; 815-821.

Gray, P., et al.; Identification of human polo-like kianse 1 as a potential therapeutic target in pancreatic cancer; Mol. Cancer Ther.; 2004; 3; 641-646.

Whitfield, M., et al.; Common Markers of Proliferation; Nature Reviews Cancer; 2006; 6; 99-106.

Weichert, W., et al.; Polo-like kinase 1 is Overexpressed in Prostate Cancer and Linked to Higher Tumor Grades; Prostate; 2004; 60; 240-245.

* cited by examiner

SEQUENCE LISTING

<160> NUMBER OF SEQ ID NOS: 2

<210> SEQ ID NO 1
<211> LENGTH: 11
<212> TYPE: PRT
<213> ORGANISM: baculovirus infected T.ni cells

<400> SEQUENCE: 1

Met Lys Lys Gly His His His His His His Asp
 1               5                   10

<210> SEQ ID NO 2
<211> LENGTH: 9
<212> TYPE: PRT
<213> ORGANISM: baculovirus infected T.ni cells

<400> SEQUENCE: 2

Ser Phe Asn Asp Thr Leu Asp Phe Asp
 1               5

IMIDAZOTRIAZINE COMPOUNDS

This Application is filed pursuant to 35 U.S.C. §371 as a United States National Phase Application of International Application No. PCT/U.S.2004/009553, filed 29 Mar. 2004, which claims priority to U.S. Provisional Patent Application Ser. No. 60/459,293, filed 1 Apr. 2003.

BACKGROUND OF THE INVENTION

The present invention relates to novel compounds, pharmaceutical formulations comprising these compounds, and the use of these compounds in therapy. More particularly, the present invention relates to novel compounds and methods for treating conditions mediated by Polo-like Kinase, susceptible neoplasms, and other conditions.

Polo-like kinases ("PLK") are evolutionarily conserved serine/threonine kinases that play critical roles in regulating processes in the cell cycle. PLK plays a role in the entry into and the exit from mitosis in diverse organisms from yeast to mammalian cells. PLK includes PLK1, PLK2, and PLK3.

Polo-like kinases are known to be essential for mitosis in yeast, Drosophila, and Xenopus. For example, mutants of the homologous PLK genes in these organisms result in disordered mitotic spindles, and in Drosophila mutations can be embryonic lethal. RNA interference experiments on Drosophila polo have shown that ablation of polo in S2 cells results in G2/M arrest and apoptosis. PLK1 is the human homolog of Drosophila polo. It is believed to be involved in the entry into mitosis through the activation of cdk1 by phosphorylating and activating the phosphatase cdc25C, which in turn removes inhibitory phosphates from cdk1. This sets up an activation loop for cdk1 that leads to mitotic entry. PLK1 also phosphorylates cyclin B1, the cyclin partner of cdk1, resulting in nuclear localization. During mitosis, PLK1 has been shown to play roles in centrosome maturation and microtubule dynamics involved in formation of the mitotic spindle. PLK1 is also involved in the exit of cells from mitosis by phosphorylating and activating subunits of the anaphase-promoting complex (cdc16 and cdc27). PLK1 also phosphorylates cohesin proteins that hold sister chromatids together, exposing separase cleavage sites, and allowing separation of sister chromatids during anaphase. PLK1 may also play a role in cytokinesis through phosphorylation of the kinesin-like motor protein MKLP1. Inhibition of PLK1 thus has the potential to interfere with several stages of mitosis. Expression and activity of PLK protein increases during the cell cycle, reaching its peak during mitosis when it is also maximally phosphorylated. PLK1 mRNA is highly expressed in cells with a high mitotic index. PLK2 (serum-inducible kinase, SNK) and PLK3 (Fibroblast Growth Factor-inducible kinase, FNK) were originally identified as immediate-early genes. PLK2 is not very well characterized, but PLK3 appears to be involved in regulation of cell cycle progression through M phase but functions differently from PLK1. Recent published work suggests that PLK3 plays an important role in the regulation of microtubule dynamics and function of the centrosome during mitosis.

Overexpression of PLK1 appears to be strongly associated with neoplastic cells (including cancers). A published study has shown high levels of PLK1 RNA expression in >80% of lung and breast tumors, with little to no expression in adjacent normal tissue. Several studies have shown correlations between PLK expression, histological grade, and prognosis in several types of cancer. Significant correlations were found between percentages of PLK-positive cells and histological grade of ovarian and endometrial cancer (P<0.001). These studies noted that PLK is strongly expressed in invading endometrial carcinoma cells and that this could reflect the degree of malignancy and proliferation in endometrial carcinoma. Using RT-PCR analysis, PLK overexpression was detected in 97% of esophageal carcinomas and 73% of gastric carcinomas as compared to the corresponding normal tissues. Further, patients with high levels of PLK overexpression in esophageal carcinoma represented a significantly poorer prognosis group than those with low levels of PLK overexpression. In head and neck cancers, elevated mRNA expression of PLK1 was observed in most tumors; a Kaplan-Meier analysis showed that those patients with moderate levels of PLK1 expression survived longer than those with high levels of PLK1 expression. Analysis of patients with non-small cell lung carcinoma showed similar outcomes related to PLK1 expression.

Disruption of mitosis with anti-microtubule drugs has been a successful approach in cancer chemotherapy. The taxanes and vinca alkaloids have been effectively used in the clinic, but they have undesirable side effects. In addition, many tumors appear to have weakened G2/M cell cycle checkpoints; in response to mitotic disruption these tumors attempt to bypass mitosis, leading to mitotic catastrophe and cell death. Several studies suggest that the disruption of mitosis by targeting PLK may be a feasible approach to selective tumor cell destruction. There remains a need in the art for new approaches to the treatment of neoplasms.

BRIEF SUMMARY OF THE INVENTION

According to a first aspect of the invention there is provided a compound of formula (I):

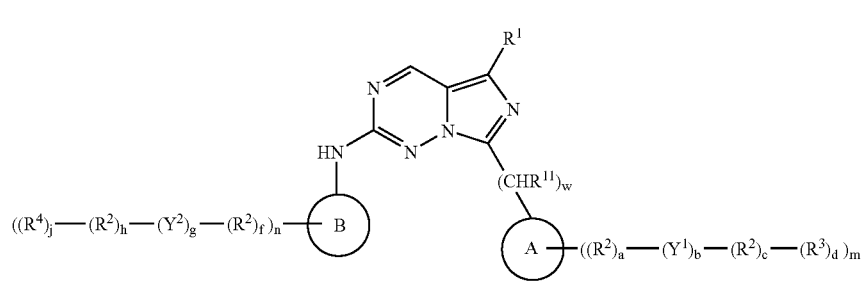

I wherein:
R¹ is alkyl;
w is 0 or 1;
R¹¹ is H or $C_{1-3}$alkyl;
Ring A is selected from the group consisting of cycloalkyl, cycloalkenyl, aryl, 5-13 membered heterocycle and 5-13 membered heteroaryl;
Ring B is selected from the group consisting of cycloalkyl, cycloalkenyl, aryl, 5-13 membered heterocycle and 5-13 membered heteroaryl;
a, b, c, f, g, and h are the same or different and are each independently 0 or 1;
d and j are the same or different and are independently 1 or 2;
each $R^2$ is the same or different and is independently selected from the group consisting of alkylene, alkenylene and alkynylene;
$Y^1$ and $Y^2$ are the same or different and are each independently selected from the group consisting of —O—, —S(O)$_q$— and —N($R^5$)—;
q is 0, 1 or 2;
each $R^3$ and $R^4$ are the same or different and are each independently selected from the group consisting of H, halo, alkyl, alkenyl, alkynyl, cycloalkyl, cycloalkenyl, Ph, Het, —COR⁵, —CSR⁵, —CO₂R⁵, —COPh, —CO₂Ph, —C(O)Het, —C(O)NR⁵R⁶, —C(S)NR⁵R⁶, —C(=NR⁵)R⁶, —C(=NR⁵)NR⁵R⁶, —CR⁵=N—OR⁶, —OR⁵, —OCOR⁵, —S(O)$_p$R⁵, —S(O)₂OH, —S(O)$_p$NR⁵R⁶, —NR⁵R⁶, —NR⁵COR⁶, —NR⁵CO₂R⁶, —NR⁵SO₂R⁶, —NO₂, —CN, —SCN and —N₃;
each p is the same or different and is 0, 1 or 2;
m and n are the same or different and are each independently 0, 1, 2, 3, 4 or 5;
each $R^5$ and each $R^6$ are the same or different and are each independently selected from the group consisting of H, alkyl, alkenyl, alkynyl, cycloalkyl and cycloalkenyl;
Ph is phenyl optionally substituted by one or more substituents selected from the group consisting of halo, alkyl, —CO₂R⁵, —OR⁵, —SO₂R⁵, —SO₂NR⁵R⁶, —NR⁵R⁶, —R²—(NR⁵R⁶)CO₂R⁵, Het, —R²-Het, —CN and —N₃; and
Het is a monocyclic 5-6 membered heterocycle or heteroaryl group containing 1, 2 or 3 heteroatoms selected from the group consisting of N, O and S optionally substituted by one or more substituents selected from the group consisting of halo, alkyl, —CO₂R⁵, —C(O)NR⁵R⁶, —OR⁵, —SO₂R⁵, —SO₂NR⁵R⁶, —NR⁵R⁶, oxo, —CN and —N₃;

or a pharmaceutically acceptable salt, solvate or physiologically functional derivative thereof.

In another aspect of the invention there is provided a pharmaceutical composition comprising a compound of formula (I). In one embodiment, the pharmaceutical composition further comprises a pharmaceutically acceptable carrier, diluent or excipient.

In a third aspect of the invention, there is provided a method for the treatment of a condition mediated by PLK in an animal in need thereof. The method comprises administering to the animal a therapeutically effective amount of a compound of formula (I) or a pharmaceutically acceptable salt, solvate or physiologically functional derivative thereof.

In a fourth aspect of the invention, there is provided a method for the treatment a neoplasm susceptible to PLK in an animal in need thereof. The method comprises administering to the animal a therapeutically effective amount of a compound of formula (I) or a pharmaceutically acceptable salt, solvate or physiologically functional derivative thereof. The neoplasm may be selected from the group consisting of breast cancer, colon cancer, lung cancer, prostate cancer, lymphoma, leukemia, endometrial cancer, melanoma, gastric carcinoma, pancreatic cancer, ovarian cancer, squamous carcinoma, carcinoma of the head and neck, and esophageal carcinoma.

In a fifth aspect of the invention, there is provided a method for the treatment of a PLK-mediated condition characterized by inappropriate cellular proliferation in an animal in need thereof. The method comprises administering to the animal a therapeutically effective amount of a compound of formula (I) or a pharmaceutically acceptable salt, solvate or physiologically functional derivative thereof.

In a sixth aspect, the present invention provides a method for inhibiting proliferation of a cell. The method comprises contacting the cell with an amount of a compound of formula (I) or a pharmaceutically acceptable salt, solvate or physiologically functional derivative thereof sufficient to inhibit proliferation of the cell, wherein the compound inhibits PLK.

In another aspect, the present invention provides a method for inhibiting mitosis in a cell. The method comprises administering to the cell an amount of a compound of formula (I) or a pharmaceutically acceptable salt, solvate or physiologically functional derivative thereof sufficient to inhibit mitosis in the cell, wherein the compound inhibits PLK.

In another aspect, there is provided a process for preparing a compound of formula (I). The process comprises reacting a compound of formula (X):

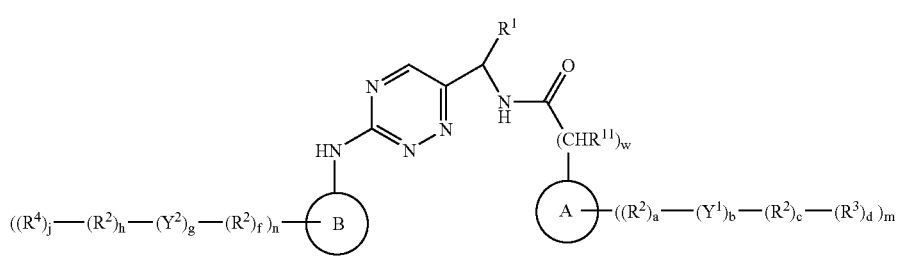

with a cyclization reagent.

In another aspect, the present invention provides another process for preparing a compound of formula (I). The process comprises reacting the compound of formula (XIII):

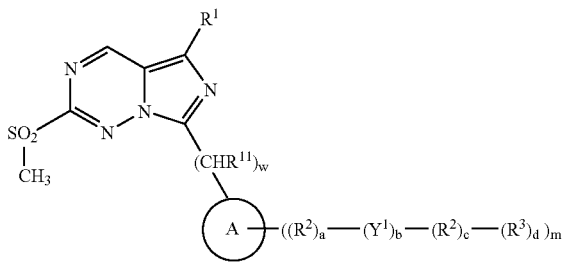

XIII with a compound of formula (VI):

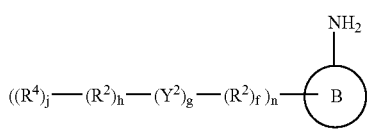

VI

In another aspect, the present invention provides a method for preparing certain compounds of formula (I) wherein:
Ring A is selected from the group consisting of cycloalkyl, aryl, 5-13 membered heterocycle and 5-13 membered heteroaryl;
each $R^2$ is the same or different and is alkylene;
each $R^3$ and $R^4$ are the same or different and are each independently selected from the group consisting of H, halo, alkyl, alkenyl, alkynyl, cycloalkyl, Ph, Het, $-OR^5$, $-S(O)_pR^5$, $-S(O)_2OH$, $-S(O)_pNR^5R^6$, $-NR^5R^6$ and $-NR^5SO_2R^6$;
each $R^5$ and each $R^6$ are the same or different and are each independently selected from the group consisting of H, alkyl and cycloalkyl;
Ph is phenyl optionally substituted by one or more substituents selected from the group consisting of halo, alkyl, $-OR^5$, $-SO_2R^5$, $-SO_2NR^5R^6$, $-NR^5R^6$, Het, and $-R^2$-Het; and
Het is a monocyclic 5-6 membered heterocycle or heteroaryl group containing 1, 2 or 3 heteroatoms selected from the group consisting of N, O and S optionally substituted by one or more substituents selected from the group consisting of halo, alkyl, $-OR^5$, $-SO_2R^5$, $-SO_2NR^5R^6$, $-NR^5R^6$ and oxo.

The process comprises coupling a compound of formula (XVIII):

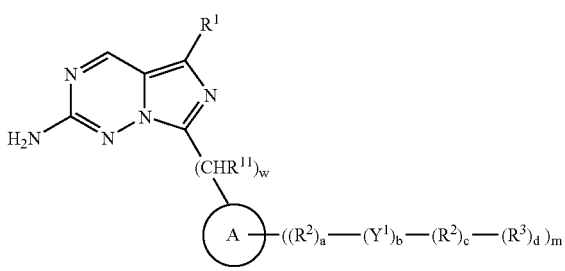

XVIII with a compound of formula (XIX):

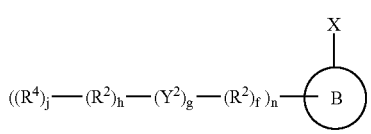

XIX wherein X is Cl, Br, I or triflate.

In another aspect, the present invention provides a radiolabeled compound of formula (I) or a pharmaceutically acceptable salt, solvate or physiologically functional derivative thereof. In one embodiment, the present invention provides a tritiated compound of formula (I) or a pharmaceutically acceptable salt, solvate or physiologically functional derivative thereof. In another aspect, the present invention provides a biotinylated compound of formula (I) or a pharmaceutically acceptable salt, solvate or physiologically functional derivative thereof.

In another aspect, the present invention provides a compound of formula (I) or a pharmaceutically acceptable salt, solvate or physiologically functional derivative thereof for use in therapy.

In yet another aspect, the present invention provides a compound of formula (I) or a pharmaceutically acceptable salt, solvate or physiologically functional derivative thereof for use in the treatment of a condition mediated by PLK in an animal.

In yet another aspect, the present invention provides a compound of formula (I) or a pharmaceutically acceptable salt, solvate or physiologically functional derivative thereof for use in the treatment of a neoplasm susceptible to PLK in an animal.

In another aspect, the present invention provides a compound of formula (I) or a pharmaceutically acceptable salt, solvate or physiologically functional derivative thereof for use in the treatment of a PLK-mediated condition characterized by inappropriate cellular proliferation.

In yet another aspect, the present invention provides a compound of formula (I) or a pharmaceutically acceptable salt, solvate or physiologically functional derivative thereof for use in inhibiting proliferation of a cell, wherein said compound inhibits PLK.

In yet another aspect, the present invention provides a compound of formula (I) or a pharmaceutically acceptable salt, solvate or physiologically functional derivative thereof for use in inhibiting mitosis in a cell, wherein said compound inhibits PLK.

In yet another aspect, the present invention provides the use of a compound of formula (I) or a pharmaceutically acceptable salt, solvate or physiologically functional derivative thereof for the preparation of a medicament for the treatment of condition mediated by PLK in an animal.

In yet another aspect, the present invention provides the use of a compound of formula (I) or a pharmaceutically acceptable salt, solvate or physiologically functional derivative thereof for the preparation of a medicament for the treatment of a neoplasm susceptible to PLK in an animal.

In yet another aspect, the present invention provides the use of a compound of formula (I) or a pharmaceutically acceptable salt, solvate or physiologically functional derivative thereof for the preparation of a medicament for the treatment of a PLK-mediated condition characterized by inappropriate cellular proliferation in an animal.

In yet another aspect, the present invention provides the use of a compound of formula (I) or a pharmaceutically acceptable salt, solvate or physiologically functional derivative thereof for the preparation of a medicament for inhibiting proliferation of a cell, wherein said compound inhibits PLK.

In yet another aspect, the present invention provides the use of a compound of formula (I) or a pharmaceutically acceptable salt, solvate or physiologically functional derivative thereof for the preparation of a medicament for inhibiting mitosis in a cell, wherein said compound inhibits PLK.

In yet another aspect, the present invention provides a pharmaceutical composition comprising a compound of formula (I) for use in the treatment of a neoplasm susceptible to PLK in an animal.

DETAILED DESCRIPTION OF THE INVENTION

As used herein, "a compound of the invention" or "a compound of formula (I)" means a compound of formula (I) or a pharmaceutically acceptable salt, solvate, or physiologically functional derivative thereof. Similarly, with respect to isolatable intermediates such as for example compounds of formula (V), (VII), (VIII), (X) (XI), (XII), (XIII), (XIV), (XV), (XVI), (XVII) and (XVIII) the phrase "a compound of formula (number)," means a compound having that formula or a pharmaceutically acceptable salt, solvate or physiologically functional derivative thereof.

As used herein, the terms "alkyl" (and "alkylene") refer to straight or branched hydrocarbon chains containing from 1 to 8 carbon atoms (unless a different number of atoms is specified). Examples of "alkyl" as used herein include, but are not limited to, methyl, ethyl, n-propyl, n-butyl, n-pentyl, isobutyl, isopropyl, and tert-butyl. Examples of "alkylene" as used herein include, but are not limited to, methylene, ethylene, propylene, butylene, and isobutylene. "Alkyl" and "alkylene" also include substituted alkyl and substituted alkylene. The alkyl or alkylene groups may be optionally substituted one or more times with halogen. Thus, the term "alkyl" includes trifluoromethyl and trifluoroethyl, among other halogenated alkyls.

As used herein, the terms "alkenyl" and "alkenylene" refer to straight or branched hydrocarbon chains containing from 2 to 8 carbon atoms (unless a different number of atoms is specified) and at least one and up to three carbon-carbon double bonds. Examples of "alkenyl" as used herein include, but are not limited to ethenyl and propenyl. "Alkenyl" and "alkenylene" also include substituted alkenyl and substituted alkenylene. The alkenyl or alkenylene groups may be optionally substituted one or more times with halogen.

As used herein, the terms "alkynyl" and "alkynylene" refer to straight or branched hydrocarbon chains containing from 2 to 8 carbon atoms (unless a different number of atoms is specified) and at least one and up to three carbon-carbon triple bonds. Examples of "alkynyl" as used herein include, but are not limited to ethynyl and propynyl. "Alkynyl" and "alkynylene" also include substituted alkynyl and substituted alkynylene. The alkynyl and alkynylene groups may optionally be substituted one or more times with halogen.

As used herein, the term "cycloalkyl" refers to non-aromatic monocyclic carbocyclic rings having from 3 to 8 carbon atoms (unless a different number of atoms is specified) and no carbon-carbon double bonds. "Cycloalkyl" includes by way of example cyclopropyl, cyclobutyl, cyclopentyl, cyclohexyl, cycloheptyl and cyclooctyl. "Cycloalkyl" also includes substituted cycloalkyl. The cycloalkyl may optionally be substituted on any available carbon with one or more substituents selected from the group consisting of halo, $C_{1-3}$alkyl (including perhaloalkyl, e.g., perfluoroalkyl), —OH, —O—$C_{1-3}$alkyl, —NH$_2$, —NH($C_{1-3}$alkyl) —N($C_{1-3}$alkyl)$_2$, oxo, —CN and —N$_3$. Particular cycloalkyl groups include $C_{3-6}$cycloalkyl and substituted $C_{3-6}$cycloalkyl.

As used herein, the term "cycloalkenyl" refers to a non-aromatic monocyclic carbocyclic ring having from 3 to 8 carbon atoms (unless a different number of atoms is specified) and up to 3 carbon-carbon double bonds. "Cycloalkenyl" includes by way of example cyclobutenyl, cyclopentenyl and cyclohexenyl. "Cycloalkenyl" also includes substituted cycloalkenyl. The cycloalkenyl may optionally be substituted on any available carbon with one or more substituents selected from the group consisting of halo, $C_{1-3}$alkyl (including perhaloalkyl, e.g., perfluoroalkyl), —OH, —O—$C_{1-3}$alkyl, —NH$_2$, —NH($C_{1-3}$alkyl) —N($C_{1-3}$alkyl)$_2$, oxo, —CN and —N$_3$.

The terms "halo" and "halogen" refer to fluorine, chlorine, bromine and iodine.

The term "oxo" as used herein refers to the group =O attached directly to a carbon atom of a hydrocarbon ring (i.e., cycloalkenyl, aryl, heterocycle or heteroaryl ring) as well as —N-oxides, sulfones and sulfoxides wherein the N or S are atoms of a heterocyclic or heteroaryl ring.

The term "aryl" refers to monocyclic carbocyclic groups and fused bicyclic carbocyclic groups having from 6 to 13 carbon atoms (unless a different number of atoms is specified) and having at least one aromatic ring. Examples of particular aryl groups include but are not limited to phenyl and naphthyl.

The terms "heterocycle" and "heterocyclic" refer to monocyclic saturated or unsaturated non-aromatic groups and fused bicyclic saturated or unsaturated non-aromatic groups, having the specified number of members and containing 1, 2, 3 or 4 heteroatoms selected from N, O and S (unless a different number of heteroatoms is specified). Examples of particular heterocyclic groups include but are not limited to tetrahydrofuran, dihydropyran, tetrahydropyran, pyran, oxetane, thietane, 1,4-dioxane, 1,3-dioxane, 1,3-dioxalane, piperidine, piperazine, tetrahydropyrimidine, pyrrolidine, morpholine, thiomorpholine, thiazolidine, oxazolidine, tetrahydrothiopyran, tetrahydrothiophene, and the like.

The term "heteroaryl" refers to aromatic monocyclic groups and fused bicyclic groups wherein at least one ring is aromatic, having the specified number of members and containing 1, 2, 3, or 4 heteroatoms selected from N, O and S (unless a different number of heteroatoms is specified). Examples of particular heteroaryl groups include but are not limited to furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, and indazole.

The term "members" (and variants thereof e.g., "membered") in the context of heterocyclic and heteroaryl groups refers to the total atoms, carbon and heteroatoms N, O and/or S, which form the ring. Thus, an example of a 6-membered heterocyclic ring is piperidine and an example of a 6-membered heteroaryl ring is pyridine.

As used herein, the term "optionally" means that the subsequently described event(s) may or may not occur, and includes both event(s) that occur and events that do not occur.

The present invention provides compounds of formula (I):

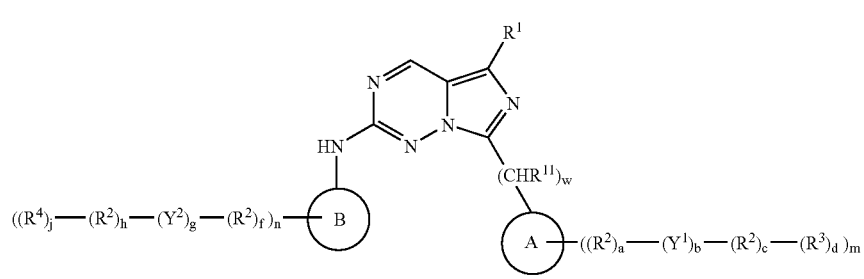

I wherein:
- $R^1$ is alkyl;
- w is 0 or 1;
- $R^{11}$ is H or $C_{1-3}$alkyl;
- Ring A is selected from the group consisting of cycloalkyl, cycloalkenyl, aryl, 5-13 membered heterocycle and 5-13 membered heteroaryl;
- Ring B is selected from the group consisting of cycloalkyl, cycloalkenyl, aryl, 5-13 membered heterocycle and 5-13 membered heteroaryl;
- a, b, c, f, g, and h are the same or different and are each independently 0 or 1;
- d and j are the same or different and are independently 1 or 2;
- each $R^2$ is the same or different and is independently selected from the group consisting of alkylene, alkenylene and alkynylene;
- $Y^1$ and $Y^2$ are the same or different and are each independently selected from the group consisting of —O—, —S(O)$_q$— and —N(R$^5$)—;
- q is 0, 1 or 2;
- each $R^3$ and $R^4$ are the same or different and are each independently selected from the group consisting of H, halo, alkyl, alkenyl, alkynyl, cycloalkyl, cycloalkenyl, Ph, Het, —COR$^5$, —CSR$^5$, —CO$_2$R$^5$, —COPh, —CO$_2$Ph, —C(O)Het, —C(O)NR$^5$R$^6$, —C(S)NR$^5$R$^6$, —C(=NR$^5$)R$^6$, —C(=NR$^5$)NR$^5$R$^6$, —CR$^5$=N—OR$^6$, —OR$^5$, —OCOR$^5$, —S(O)$_p$R$^5$, —S(O)$_2$OH, —S(O)$_p$NR$^5$R$^6$, —NR$^5$R$^6$, —NR$^5$COR$^6$, —NR$^5$CO$_2$R$^6$, —NR$^5$SO$_2$R$^6$, —NO$_2$, —CN, —SCN and —N$_3$;
- each p is the same or different and is 0, 1 or 2;
- m and n are the same or different and are each independently 0, 1, 2, 3, 4 or 5;
- each $R^5$ and each $R^6$ are the same or different and are each independently selected from the group consisting of H, alkyl, alkenyl, alkynyl, cycloalkyl and cycloalkenyl;
- Ph is phenyl optionally substituted by one or more substituents selected from the group consisting of halo, alkyl, —CO$_2$R$^5$, —OR$^5$, —SO$_2$R$^5$, —SO$_2$NR$^5$R$^6$, —NR$^5$R$^6$, —R$^2$—(NR$^5$R$^6$)CO$_2$R$^5$, Het, —R$^2$-Het, —CN and —N$_3$; and
- Het is a monocyclic 5-6 membered heterocycle or heteroaryl group containing 1, 2 or 3 heteroatoms selected from the group consisting of N, O and S optionally substituted by one or more substituents selected from the group consisting of halo, alkyl, —CO$_2$R$^5$, —C(O)NR$^5$R$^6$, —OR$^5$, —SO$_2$R$^5$, —SO$_2$NR$^5$R$^6$, —NR$^5$R$^5$, oxo, —CN and —N$_3$;

or a pharmaceutically acceptable salt, solvate or physiologically functional derivative thereof.

In one embodiment, the compounds of formula (I) are defined wherein $R^1$ is $C_{1-3}$ alkyl. In one particular embodiment, $R^1$ is selected from the group consisting of methyl, ethyl and isopropyl, or any subset thereof. In one embodiment, $R^1$ is methyl.

In one embodiment, the compounds of formula (I) are defined wherein w is 0, i.e., the Ring A is bound directly to the imiazotriazine ring. In another embodiment, the compound of formula (I) is defined wherein w is 1. In the embodiment wherein w is 1, $R^{11}$ is H or $C_{1-3}$ alkyl. In one embodiment wherein w is 1, $R^{11}$ is $C_{1-3}$alkyl. In one particular embodiment, $R^{11}$ is methyl.

In one embodiment, Ring A is selected from the group consisting of $C_{5-6}$cycloalkyl, $C_{5-6}$cycloalkenyl, phenyl, 5-9 membered heterocycle and 5-9 membered heteroaryl, or any subset thereof. In one embodiment, Ring A is selected from the group consisting of $C_{5-6}$cycloalkyl, $C_{5-6}$cycloalkenyl, phenyl, 5-9 membered heterocycle containing 1 or 2 heteroatoms selected from N, O and S, and 5-9 membered heteroaryl containing 1 or 2 heteroatoms selected from N, O, and S, or any subset thereof. Specific examples of moieties defining Ring A within the compounds of formula (I) include but are not limited to cyclopentyl, cyclohexyl, cyclohexenyl, phenyl, indene, naphthyl, pyrrolidine, pyrroline, imidazolidine, imidazoline, pyrazoline, pyrazolidine, piperidine, dioxolane, dioxane, morpholine, dithiane, thiomorpholine, piperazine, furan, thiophene, pyrrole, oxazole, thiazole, imidazole, pyrazole, isoxazole, isothiazole, pyran, pyridine, pyridazine, pyrimidine, pyrazine, triazine, indolizine, indole, isoindole, indoline, benzofuran, benzodioxolane, benzothiophene, indazole, benzimidazole, benzthiazole, purine, quinolizine, quinoline, and isoquinoline.

In one embodiment, the compounds of formula (I) are defined wherein Ring A is selected from the group consisting of aryl and 5-13 membered heteoraryl. In one embodiment, Ring A is selected from the group consisting of cyclohexyl, cyclohexenyl, phenyl, furan, thiophene, pyrrole, pyridine, isoindole, quinoline, benzodioxolane, indole and pyrimidine, or any subset thereof. In one embodiment, Ring A is selected from the group consisting of phenyl, thiophene, pyridine and pyrimidine, or any subset thereof. In one embodiment, Ring A is aryl. In one particular embodiment, Ring A is phenyl.

In one embodiment, Ring B is selected from the group consisting of $C_{5-6}$cycloalkyl, $C_{5-6}$cycloalkenyl, phenyl, 5-9 membered heterocycle and 5-9 membered heteroaryl, or any subset thereof. In one embodiment, Ring B is selected from the group consisting of $C_{5-6}$cycloalkyl, $C_{5-6}$cycloalkenyl, phenyl, 5-9 membered heterocycle containing 1 or 2 heteroatoms selected from N, O and S, and 5-9 membered heteroaryl containing 1 or 2 heteroatoms selected from N, O, and S, or any subset thereof. Specific examples of moieties defining Ring B within the compounds of formula (I) include but are not limited to cyclopentyl, cyclohexyl, cyclohexenyl, phenyl, indene, naphthyl, pyrrolidine, pyrroline, imidazolidine, imidazoline, pyrazoline, pyrazolidine, piperidine, dioxolane, dioxane, morpholine, dithiane, thiomorpholine, piperazine, furan, thiophene, pyrrole, oxazole, thiazole, imidazole, pyrazole, isoxazole, isothiazole, pyran, pyridine, pyridazine, pyrimidine, pyrazine, triazine, indolizine, indole, isoindole, indoline, benzofuran, benzodioxolane, benzothiophene, indazole, benzimidazole, benzthiazole, purine, quinolizine, quinoline, and isoquinoline. In one embodiment, Ring B is selected from the group consisting of phenyl and 5-9 membered heteroaryl, or any subset thereof. In one embodiment, Ring B is selected from the group consisting of phenyl and 5-9 membered heteroaryl containing 1 or 2 heteroatoms selected from N, O, and S, or any subset thereof. In one embodiment, Ring B is selected from the group consisting of phenyl and and 5-6 membered heteroaryl containing 1 or 2 heteroatoms selected from N, O and S, or any subset thereof.

In one embodiment, the compounds of formula (I) are defined wherein Ring B is selected from the group consisting of aryl and 5-6 membered heteoraryl. In one embodiment, Ring B is selected from the group consisting of phenyl, furan, thiophene, pyrrole, pyridine, pyrimidine and benzodioxolane, or any subset thereof. In one embodiment, Ring B is selected from the group consisting of phenyl, pyridine, and pyrimidine, or any subset thereof. In one embodiment, Ring B is aryl. In one particular embodiment, Ring B is phenyl.

m is defined in a manner consistent with the definition of Ring A. In one embodiment, the compounds of formula (I) are defined wherein m is 0, 1, 2 or 3. In one embodiment m is 0, 1 or 2. In one embodiment m is 1, 2 or 3. In one particular embodiment m is 1 or 2. In one particular embodiment m is 1.

n is defined in a manner consistent with the definition of Ring B. In one embodiment, the compounds of formula (I) are defined wherein n is 0, 1, 2 or 3. In one embodiment n is 1, 2 or 3. In one particular embodiment n is 2 or 3. In one particular embodiment n is 3.

In one embodiment of the present invention, a is 0. In one embodiment of the present invention f is 0. In one embodiment c is 0. In one embodiment, h is 0.

In particular embodiments, wherein any one or more of a, c, f, and h is 1, each $R^2$ is the same or different and is independently selected from the group consisting of alkylene and alkenylene. In one particular embodiment, each $R^2$ is the same or different and is independently selected from the group consisting of $C_{1-3}$alkylene and $C_{1-3}$alkenylene. In one embodiment wherein any one or more of a, c, f, and h is 1, each $R^2$ is $C_{1-3}$alkylene.

In one embodiment of the invention b is 0.

In the embodiment of the invention wherein b is 1, $Y^1$ is selected from the group consisting of —O—, —S(O)$_q$— and —N($R^5$)—. Specific examples of groups defining $Y^1$ include but are not limited to —O—, —S—, —SO$_2$—, —N(H)— and —N(CH$_3$)—. In one embodiment wherein b is 1, $Y^1$ is selected from the group consisting of —O— and —N($R^5$)—. In one particular embodiment wherein b is 1, $Y^1$ is selected from the group consisting of —O— and —N(H)—.

In one embodiment of the invention, g is 0.

In the embodiment of the invention wherein g is 1, $Y^2$ is selected from the group consisting of —O—, —S(O)$_q$— and —N($R^5$)—. Specific examples of groups defining $Y^2$ include but are not limited to —O—, —S—, —SO$_2$—, —N(H)— and —N(CH$_3$)—. In one embodiment wherein g is 1, $Y^2$ is selected from the group consisting of —O— and —N($R^5$)—. In one particular embodiment wherein g is 1, $Y^2$ is —O—.

In the compounds of formula (I), when d is 2, then c is 1 and —($R^2$)$_c$— represents a di-substituted alkylene, alkenylene, or alkynylene. In one embodiment, the compounds of formula (I) are defined wherein d is 1.

As will be apparent to those skilled in the art, the particular definition of $R^3$ in the compounds of formula (I) will be selected in a manner that is consistent with the definitions selected for —($Y^1$)$_b$— and —($R^2$)$_c$—, so as to avoid interpreting the definitions of those terms in a manner that would yield chemically impossible or improbable compounds of formula (I) based upon the general knowledge of those skilled in the art of organic chemistry. In one embodiment of the invention, each $R^3$ is the same or different and is independently selected from the group consisting of H, halo, alkyl, alkenyl, cycloalkyl, Ph, Het, —COR$^5$, —CO$_2$R$^5$, —COPh, —C(O)NR$^5$R$^6$, —OR$^5$, —S(O)$_p$R$^5$, —S(O)$_p$NR$^5$R$^6$, —NR$^5$R$^6$, —NO$_2$, —CN and —N$_3$, or any subset thereof. In one particular embodiment, each $R^3$ is the same or different and is independently selected from the group consisting of H, halo, alkyl, Ph, —COR$^5$, —CO$_2$R$^5$, —COPh, —C(O)NR$^5$R$^6$, —OR$^5$, —NR$^5$R$^6$, —NO$_2$ and —CN, or any subset thereof. In one embodiment the compounds of formula (I) are defined wherein d is 1 and $R^3$ is selected from the group consisting of H, halo, alkyl, Ph, —COR$^5$, —CO$_2$R$^5$, —COPh, —C(O)NR$^5$R$^6$, —OR$^5$, —NR$^5$R$^6$, —NO$_2$ and —CN, or any subset thereof. In one particular embodiment, $R^3$ is selected from the group consisting of H, —CO$_2$R$^5$ and —NR$^5$R$^6$, or any subset thereof.

Specific examples of some groups defining $R^3$ include but are not limited to H, fluoro, chloro, bromo, methyl, trifluoromethyl, ethyl, trifluoroethyl, propyl, isopropyl, butyl, isobutyl, t-butyl, ethenyl, propenyl, cyclopentyl, cyclohexyl, phenyl, substituted phenyl, —C(O)H, —C(O)methyl, —C(O)ethyl, —C(O)propyl, —C(O)isopropyl, —C(O)cyclopropyl, —C(O)phenyl, —CO$_2$H, —CO$_2$-methyl, —CO$_2$-ethyl, —CO$_2$-propyl, —CO$_2$-isopropyl, —C(O)NH$_2$, —C(O)N(H)alkyl, —C(O)N(alkyl)$_2$, —C(O)N(H)cycloalkyl, —C(O)N(alkyl)cycloalkyl, —O-methyl, —O-trifluoromethyl, —O-ethyl, —O-propyl, —O-isopropyl, —O-butyl, —O-isobutyl, —O-t-butyl, —O-cyclopropyl, —O-cyclobutyl, —O-cyclopentyl, —O-cyclohexyl, —S-methyl, —S-ethyl, —S-propyl, —S-isopropyl, —S-butyl, —S-isobutyl, —S-t-butyl, —S-cyclopropyl, —S-cyclobutyl, —S-cyclopentyl, —S-cyclohexyl, —SO$_2$-methyl, —SO$_2$-ethyl, —SO$_2$-propyl, —SO$_2$-isopropyl, —SO$_2$—OH, —SO$_2$—NH$_2$, —SO$_2$—N(H)alkyl, —SO$_2$—N(alkyl)$_2$, —SO$_2$—N(H)cycloalkyl, —SO$_2$—N(alkyl)cycloalkyl, —NH$_2$, —N(H)alkyl, —N(alkyl)$_2$, —N(H)cycloalkyl, —N(alkyl)cycloalkyl, —N(H)COH, —N(H)CO-methyl, —N(H)CO-ethyl, —NO$_2$, and —CN, or any subset thereof.

In one embodiment, the compounds of formula (I) are defined wherein:
  when b is 1, $Y^1$ is —O— and c is 0, then $R^3$ is not, —OR$^5$, —OCOR$^5$, —NR$^5$COR$^6$, —NR$^5$CO$_2$R$^6$, —NR$^5$SO$_2$R$^6$, —SCN or —N$_3$;
  when b is 1, $Y^1$ is —S(O)$_q$—, q is 2 and c is 0, then $R^3$ is not, —S(O)$_p$R$^5$ where p is 2 (i.e., —SO$_2$R$^5$), —S(O)$_2$OH, —S(O)$_p$NR$^5$R$^6$ where p is 2 (i.e., —SO$_2$NR$^5$R$^6$), —NO$_2$, —CN, —SCN or —N$_3$; and
  when b is 1, $Y^1$ is —N($R^5$)—, and c is 0, then $R^3$ is not, —NO$_2$, —SCN or —N$_3$.

In one embodiment, the compounds of formula (I) are defined wherein:
  when b is 1, $Y^1$ is —O— and c is 0, then $R^3$ is not —OR$^5$, —OCOR$^5$, —NR$^5$R$^6$, —NR$^5$COR$^6$, —NR$^5$CO$_2$R$^6$, —NR$^5$SO$_2$R$^6$, —CN, —SCN or —N$_3$;
  when b is 1, $Y^1$ is —S(O)$_q$— and c is 0, then $R^3$ is not —OCOR$^5$, —S(O)$_p$R$^5$, —S(O)$_2$OH, —S(O)$_p$NR$^5$R$^6$, —NO$_2$, —CN, —SCN or —N$_3$; and
  when b is 1, $Y^1$ is —N($R^5$)— and c is 0, then $R^3$ is not —OR$^5$, —OCOR$^5$, —NR$^5$CO$_2$R$^6$, —NO$_2$, —SCN or —N$_3$.

In a particular embodiment of the invention, the compounds of formula (I) are defined wherein when b is 1 and c is 0, then $R^3$ is not —OR$^5$, —OCOR$^5$, —S(O)$_p$R$^5$, —S(O)$_2$OH, —S(O)$_p$NR$^5$R$^6$, —NR$^5$R$^6$, —NR$^5$COR$^6$, —NR$^5$CO$_2$R$^6$, —NR$^5$SO$_2$R$^6$, —NO$_2$, —SCN or —N$_3$.

In the compounds of formula (I), when j is 2, then h is 1 and —($R^2$)$_h$— represents a di-substituted alkylene, alkenylene, or alkynylene. In one embodiment, the compounds of formula (I) are defined wherein j is 1.

As will be apparent to those skilled in the art, the particular definition of $R^4$ in the compounds of formula (I) will be selected in a manner that is consistent with the definitions selected for —($Y^2$)— and —($R^2$)$_h$—, so as to avoid interpreting the definitions of those terms in a manner that would yield chemically impossible or improbable compounds of formula (I) based upon the general knowledge of those skilled in the art of organic chemistry. In one embodiment of the invention, each $R^4$ is the same or different and is independently selected from the group consisting of H, halo, alkyl, alkenyl, cycloalkyl, Ph, Het, —COR$^5$, —CO$_2$R$^5$, —C(O)NR$^5$R$^6$, —OR$^5$, —S(O)$_p$R$^5$, —S(O)$_2$OH, —S(O)$_p$NR$^5$R$^6$, —NR$^5$R$^6$, —NR$^5$COR$^6$, —NO$_2$ and —CN, or any subset thereof, or any subset thereof. In one embodiment, each $R^4$ is the same or different and is independently selected from the group consisting of H, halo, alkyl, —COR$^5$, —CO$_2$R$^5$, —C(O)NR$^5$R$^6$, —OR$^5$, —S(O)$_p$R$^5$, —S(O)$_2$OH, —S(O)$_p$NR$^5$R$^6$ and —NO$_2$, or any subset thereof, or any subset thereof. In one particular embodiment, the compounds of formula (I) are defined wherein j is 1 and $R^4$ is selected from the group consisting of H, halo, alkyl, —$COR^5$, —$CO_2R^5$, —$C(O)NR^5R^6$, —$OR^5$, —$S(O)_pR^5$, —$S(O)_2OH$, —$S(O)_pNR^5R^6$ and —$NO_2$, or any subset thereof, or any subset thereof. In one particular embodiment, $R^4$ is selected from the group consisting of H, alkyl and —$OR^5$ or any subset thereof.

Specific examples of some groups defining $R^4$ include but are not limited to H, fluoro, chloro, bromo, methyl, trifluoromethyl, ethyl, trifluoroethyl, propyl, isopropyl, butyl, isobutyl, t-butyl, ethenyl, propenyl, cyclopentyl, cyclohexyl, phenyl, substituted phenyl, —C(O)H, —C(O)methyl, —C(O)ethyl, —C(O)propyl, —C(O)isopropl, —C(O)cyclopropyl, —$CO_2H$, —$CO_2$-methyl, —$CO_2$-ethyl, —$CO_2$-propyl, —$CO_2$-isopropyl, —$C(O)NH_2$, —C(O)N(H)alkyl, —$C(O)N(alkyl)_2$, —C(O)N(H)cycloalkyl, —C(O)N(alkyl)cycloalkyl, —O-methyl, —O-trifluoromethyl, —O-ethyl, —O-propyl, —O-isopropyl, —O-butyl, —O-isobutyl, —O-t-butyl, —O-cyclopropyl, —O-cyclobutyl, —O-cyclopentyl, —O-cyclohexyl, —S-methyl, —S-ethyl, —S-propyl, —S-isopropyl, —S-butyl, —S-isobutyl, —S-t-butyl, —S-cyclopropyl, —S-cyclobutyl, —S-cyclopentyl, —S-cyclohexyl, —$SO_2$-methyl, —$SO_2$-ethyl, —$SO_2$-propyl, —$SO_2$-isopropyl, —$SO_2$—OH, —$SO_2$—$NH_2$, —$SO_2$—N(H)alkyl, —$SO_2$—N(alkyl)$_2$, —$SO_2$—N(H)cycloalkyl, —$SO_2$—N(alkyl)cycloalkyl, —$NH_2$, —N(H)alkyl, —N(alkyl)$_2$, —N(H)cycloalkyl, —N(alkyl)cycloalkyl, —N(H)COH, —N(H)CO-methyl, —N(H)CO-ethyl, —$NO_2$, and —CN.

In one embodiment, the compounds of formula (I) are defined wherein:

when g is 1, $Y^2$ is —O— and h is 0, then $R^4$ is not, —$OR^5$, —$OCOR^5$, —$NR^5COR^6$, —$NR^5CO_2R^6$, —$NR^5SO_2R^6$, —SCN or —$N_3$;

when g is 1, $Y^2$ is —$S(O)_q$—, q is 2 and h is 0, then $R^4$ is not, —$S(O)_pR^5$ where p is 2 (i.e., —$SO_2R^5$), —$S(O)_2OH$, —$S(O)_pNR^5R^6$ where p is 2 (i.e., —$SO_2NR^5R^6$), —$NO_2$, —CN, —SCN or —$N_3$; and when g is 1, $Y^2$ is $N(R^5)$, and h is 0, then $R^4$ is not, —$NO_2$, —SCN or —$N_3$.

In one embodiment, the compounds of formula (I) are defined wherein:

when g is 1, $Y^2$ is —O— and h is 0, then $R^4$ is not —$OR^5$, —$OCOR^5$, —$NR^5R^6$, —$NR^5COR^6$, —$NR^5CO_2R^6$, —$NR^5SO_2R^6$, —CN, —SCN or —$N_3$;

when g is 1, $Y^2$ is —$S(O)_q$— and h is 0, then $R^4$ is not —$OCOR^5$, —$S(O)_pR^5$, —$S(O)_pNR^5R^6$, —$NO_2$, —CN, —SCN or —$N_3$; and when g is 1, $Y^2$ is —$N(R^5)$— and h is 0, then $R^4$ is not —$OR^5$, —$OCOR^5$, —$NR^5CO_2R^6$, —$NO_2$, —SCN or —$N_3$.

In one particular embodiment, the compounds of formula (I) are defined wherein when g is 1 and h is 0, then $R^4$ is not —$OR^5$, —$OCOR^5$, —$S(O)_pR^5$, —$S(O)_pNR^5R^6$, —$NR^5R^6$, —$NR^5COR^6$, —$NR^5CO_2R^6$, —$NR^5SO_2R^6$, —$NO_2$, —SCN or —$N_3$.

In the definitions of $Y^1$, $Y^2$, $R^3$ and $R^4$, each $R^5$ and each $R^6$ are the same or different and are each independently selected from the group consisting of H, alkyl, alkenyl, alkynyl, cycloalkyl and cycloalkenyl. In one embodiment each $R^5$ and each $R^6$ are the same or different and are each independently selected from the group consisting of H, $C_{1-3}$alkyl, $C_{2-4}$alkenyl, $C_{2-4}$alkynyl, $C_{3-6}$cycloalkyl and $C_{3-6}$cycloalkenyl. Specific examples of groups defining $R^5$ and $R^6$ include but are not limited to H, methyl, trifluoromethyl, ethyl, trifluoroethyl, propyl, isopropyl, butyl, isobutyl, t-butyl, ethenyl, propenyl, ethynyl, cyclopropyl, cyclobutyl, cyclopentyl, cyclohexyl and cyclohexenyl. In one embodiment, each $R^5$ and each $R^6$ are the same or different and are each independently selected from the group consisting of H, alkyl, alkenyl and cycloalkyl, more particularly, H, $C_{1-3}$alkyl, $C_{2-4}$alkenyl and $C_{3-6}$cycloalkyl. In one particular embodiment, each $R^5$ and each $R^6$ are the same or different and are each independently selected from the group consisting of H and alkyl, more particular H and $C_{1-3}$alkyl.

In the compounds of formula (I), Ph is phenyl optionally substituted by one or more substituents selected from the group consisting of halo, alkyl, —$CO_2R^5$, —$OR^5$, —$SO_2R^5$, —$SO_2NR^5R^6$, —$NR^5R^6$, —$R^2$—$(NR^5R^6)CO_2R^5$, Het, —CN and —$N_3$.

—$R^2$—$(NR^5R^6)CO_2R^5$ refers to the disubstituted moiety:

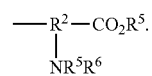

In this moiety, there is no requirement that both the carboxylic acid group and the amine group be bound to the same carbon atom. Specific examples of such moieties include but are not limited to:

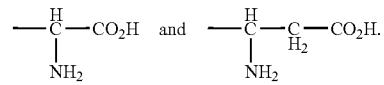

In one embodiment, Ph is phenyl optionally substituted by one or two substituents selected from the group consisting of halo, alkyl, —$CO_2R^5$, —$OR^5$, —$SO_2R^5$, —$SO_2NR^5R^6$, —$NR^5R^6$, —$R^2$—$(NR^5R^6)CO_2R^5$, Het, —$R^2$-Het, —CN and —$N_3$.

In one embodiment of the definition of Ph, each $R^5$ and each $R^6$ are the same or different and are each independently selected from the group consisting of H and alkyl, more particular H and $C_{1-3}$alkyl; and each $R^2$ is $C_{1-3}$alkylene or $C_{1-3}$alkenylene, more particularly methylene, ethylene or ethenylene.

In the compounds of formula (I), Het is a monocyclic 5-6 membered heterocycle or 5-6 membered heteroaryl group containing 1, 2 or 3 heteroatoms selected from the group consisting of N, O, and S, and optionally substituted by one or more substituents selected from the group consisting of halo, alkyl, —$CO_2R^5$, —$C(O)NR^5R^6$, —$OR^5$, —$SO_2R^5$, —$SO_2NR^5R^6$, —$NR^5R^6$, oxo, —CN and —$N_3$. In one embodiment, Het is an optionally substituted monocyclic 5-6 membered heterocycle or 5-6 membered heteroaryl group containing 1 or 2 heteroatoms selected from the group consisting of N, O, and S, wherein the optional substituents are described above. In one embodiment of the definition of Het, each $R^5$ and each $R^6$ are the same or different and are each independently selected from the group consisting of H and alkyl, more particular H and $C_{1-3}$alkyl.

It is to be understood that the present invention includes all combinations and subsets of the particular groups and/or embodiments defined hereinabove.

Specific compounds of formula (I) include but are not limited to:

5-Methyl-7-phenyl-N-(3,4,5-trimethoxyphenyl)imidazo[5,1-f][1,2,4]triazin-2-amine;

5-Methyl-7-(2-nitrophenyl)-N-(3,4,5-trimethoxyphenyl)imidazo[5,1-f][1,2,4]triazin-2-amine;

7-(2-Bromophenyl)-5-methyl-N-(3,4,5-trimethoxyphenyl)imidazo[5,1-f][1,2,4]triazin-2-amine;

7-(4-Fluorophenyl)-5-methyl-N-(3,4,5-trimethoxyphenyl)imidazo[5,1-f][1,2,4]triazin-2-amine;

5-Methyl-7-[3-(trifluoromethyl)phenyl]-N-(3,4,5-trimethoxyphenyl)imidazo[5,1-f][1,2,4]triazin-2-amine;

2,2-Dimethyl-N-(2-{5-methyl-2-[(3,4,5-trimethoxyphenyl)amino]imidazo[5,1-f][1,2,4]triazin-7-yl}phenyl)propanamide;

2,2,2-Trifluoro-N-(2-{5-methyl-2-[(3,4,5-trimethoxyphenyl)amino]imidazo[5,1-f][1,2,4]triazin-7-yl}phenyl)acetamide;

3-{5-Methyl-2-[(3,4,5-trimethoxyphenyl)amino]imidazo[5,1-f][1,2,4]triazin-7-yl}benzonitrile;

7-(3-Bromophenyl)-5-methyl-N-(3,4,5-trimethoxyphenyl)imidazo[5,1-f][1,2,4]triazin-2-amine;

7-(3-Bromothien-2-yl)-5-methyl-N-(3,4,5-trimethoxyphenyl)imidazo[5,1-f][1,2,4]triazin-2-amine;

7-(5-Bromopyridin-3-yl)-5-methyl-N-(3,4,5-trimethoxyphenyl)imidazo-[5,1-f][1,2,4]triazin-2-amine;

Methyl 3-{5-methyl-2-[(3,4,5-trimethoxyphenyl)amino]imidazo[5,1-f][1,2,4]triazin-7-yl}benzoate;

7-(5-Bromothien-2-yl)-5-methyl-N-(3,4,5-trimethoxyphenyl)imidazo[5,1-f][1,2,4]triazin-2-amine;

7-(3-Bromophenyl)-N-[5-(ethylsulfonyl)-2-methoxyphenyl]-5-methylimidazo[5,1-f][1,2,4]triazin-2-amine;

7-(3-Bromophenyl)-N-(3-chloro-4-morpholin-4-ylphenyl)-5-methylimidazo[5,1-f][1,2,4]triazin-2-amine;

3-{5-Methyl-2-[(3,4,5-trimethoxyphenyl)amino]imidazo[5,1-f][1,2,4]triazin-7-yl}benzamide;

(2E)-3-(3-{5-Methyl-2-[(3,4,5-trimethoxyphenyl)amino]imidazo[5,1-f][1,2,4]triazin-7-yl}phenyl)prop-2-enamide;

5-Methyl-N-(4-nitrophenyl)-7-phenylimidazo[5,1-f][1,2,4]triazin-2-amine;

2-{3-[(5-Methyl-7-phenylimidazo[5,1-f][1,2,4]triazin-2-yl)amino]phenyl}ethanol;

4-[(5-Methyl-7-phenylimidazo[5,1-f][1,2,4]triazin-2-yl)amino]benzenesulfonamide;

7-(2-Methoxyphenyl)-5-methyl-N-(3,4,5-trimethoxyphenyl)imidazo[5,1-f][1,2,4]triazin-2-amine;

2-{5-Methyl-2-[(3,4,5-trimethoxyphenyl)amino]imidazo[5,1-f][1,2,4]triazin-7-yl}phenol;

2-{5-Methyl-2-[(3,4,5-trimethoxyphenyl)amino]imidazo[5,1-f][1,2,4]triazin-7-yl}phenyl acetate;

5-Methyl-7-[4-(trifluoromethyl)phenyl]-N-(3,4,5-trimethoxyphenyl)-imidazo[5,1-f][1,2,4]triazin-2-amine;

N-Methyl-N-{4-[(5-methyl-7-phenylimidazo[5,1-f][1,2,4]triazin-2-yl)amino]phenyl}urea;

5-Methyl-7-phenyl-N-[3-(trifluoromethyl)phenyl]imidazo[5,1-f][1,2,4]triazin-2-amine;

(3-{5-Methyl-2-[(3,4,5-trimethoxyphenyl)amino]imidazo[5,1-f][1,2,4]triazin-7-yl}phenyl)(phenyl)methanone;

7-(1,3-Benzodioxol-5-yl)-5-methyl-N-(3,4,5-trimethoxyphenyl)imidazo-[5,1-f][1,2,4]triazin-2-amine;

Methyl 4-{5-methyl-2-[(3,4,5-trimethoxyphenyl)amino]imidazo[5,1-t][1,2,4]triazin-7-yl}benzoate;

5-Methyl-7-(3-phenoxyphenyl)-N-(3,4,5-trimethoxyphenyl)imidazo[5,1-t][1,2,4]triazin-2-amine;

7-(3-Aminophenyl)-5-methyl-N-(3,4,5-trimethoxyphenyl)imidazo[5,1-f][1,2,4]triazin-2-amine;

7-(1H-Indol-2-yl)-5-methyl-N-(3,4,5-trimethoxyphenyl)imidazo[5,1-f][1,2,4]triazin-2-amine;

5-Methyl-7-(5-nitro-1H-pyrrol-2-yl)-N-(3,4,5-trimethoxyphenyl)imidazo[5,1-f][1,2,4]triazin-2-amine;

5-Methyl-7-(1-methyl-1H-pyrrol-2-yl)-N-(3,4,5-trimethoxyphenyl)-imidazo[5,1-f][1,2,4]triazin-2-amine;

5-Methyl-7-(1-methyl-1H-indol-3-yl)-N-(3,4,5-trimethoxyphenyl)imidazo[5,1-f][1,2,4]triazin-2-amine;

7-(3-Furyl)-5-methyl-N-(3,4,5-trimethoxyphenyl)imidazo[5,1-f][1,2,4]triazin-2-amine;

7-(1H-Indol-5-yl)-5-methyl-N-(3,4,5-trimethoxyphenyl)imidazo[5,1-f][1,2,4]triazin-2-amine;

2-[(2-{5-Methyl-2-[(3,4,5-trimethoxyphenyl)amino]imidazo[5,1-f][1,2,4]triazin-7-yl}phenyl)thio]benzonitrile;

5-Methyl-7-(2-{[3-(trifluoromethyl)phenyl]amino}phenyl)-N-(3,4,5-trimethoxyphenyl)imidazo[5,1-f][1,2,4]triazin-2-amine;

5-Methyl-7-quinolin-8-yl-N-(3,4,5-trimethoxyphenyl)imidazo[5,1-f][1,2,4]triazin-2-amine;

3-({5-Methyl-7-[3-(trifluoromethyl)phenyl]imidazo[5,1-f][1,2,4]triazin-2-yl}amino)benzenesulfonamide;

N-Methyl-N-[4-({5-methyl-7-[3-(trifluoromethyl)phenyl]imidazo[5,1-f][1,2,4]triazin-2-yl}amino)phenyl]urea;

N-[4-Methoxy-3-({5-methyl-7-[3-(trifluoromethyl)phenyl]imidazo[5,1-f][1,2,4]triazin-2-yl}amino)phenyl]acetamide;

2-[3-({5-Methyl-7-[3-(trifluoromethyl)phenyl]imidazo[5,1-f][1,2,4]triazin-2-yl}amino)phenyl]ethanol;

4-({5-Methyl-7-[3-(trifluoromethyl)phenyl]imidazo[5,1-f][1,2,4]triazin-2-yl}amino)benzenesulfonamide;

N-[4-({5-Methyl-7-[3-(trifluoromethyl)phenyl]imidazo[5,1-f][1,2,4]triazin-2-yl}amino)phenyl]acetamide;

N-[3-({5-Methyl-7-[3-(trifluoromethyl)phenyl]imidazo[5,1-f][1,2,4]triazin-2-yl}amino)phenyl]acetamide;

tert-Butyl 3-({5-methyl-7-[3-(trifluoromethyl)phenyl]imidazo[5,1-f][1,2,4]triazin-2-yl}amino)benzylcarbamate;

4-({5-Methyl-7-[3-(trifluoromethyl)phenyl]imidazo[5,1-f][1,2,4]triazin-2-yl}amino)phenol;

5-Methyl-N-[4-(2-pyrrolidin-1-ylethoxy)phenyl]-7-[3-(trifluoromethyl)phenyl]-imidazo[5,1-f][1,2,4]triazin-2-amine;

N-(5-Fluoro-2-methoxyphenyl)-5-methyl-7-[3-(trifluoromethyl)phenyl]imidazo[5,1-f][1,2,4]triazin-2-amine;

N-{2-[4-Methoxy-3-({5-methyl-7-[3-(trifluoromethyl)phenyl]imidazo[5,1-f][1,2,4]triazin-2-yl}amino)phenyl]ethyl}acetamide;

N-[5-(2-Aminoethyl)-2-methoxyphenyl]-5-methyl-7-[3-(trifluoromethyl)phenyl]imidazo[5,1-f][1,2,4]triazin-2-amine;

N-(2,4-Dimethoxyphenyl)-5-methyl-7-[3-(trifluoromethyl)phenyl]imidazo[5,1-f][1,2,4]triazin-2-amine;

N-(2,5-Dimethoxyphenyl)-5-methyl-7-[3-(trifluoromethyl)phenyl]imidazo[5,1-f][1,2,4]triazin-2-amine;

Ethyl 5-({5-methyl-7-[3-(trifluoromethyl)phenyl]imidazo[5,1-f][1,2,4]triazin-2-yl}amino)nicotinate;

2-{3-[(5-Methyl-7-phenylimidazo[5,1-f][1,2,4]triazin-2-yl)amino]phenyl}ethanesulfonic acid;

5-Methyl-7-[3-(1H-pyrazol-4-ylethynyl)phenyl]-N-(3,4,5-trimethoxyphenyl)imidazo[5,1-f][1,2,4]triazin-2-amine;

3'-{5-Methyl-2-[(3,4,5-trimethoxyphenyl)amino]imidazo[5,1-f][1,2,4]triazin-7-yl}-1,1'-biphenyl-3-carboxylic acid;

2-Amino-3-(3'-{5-methyl-2-[(3,4,5-trimethoxyphenyl)amino]imidazo-[5,1-f][1,2,4]triazin-7-yl}-1,1'-biphenyl-4-yl)propanoic acid;

5-Methyl-7-[2'-(trifluoromethyl)-1,1'-biphenyl-3-yl]-N-(3,4,5-trimethoxyphenyl)-imidazo[5,1-f][1,2,4]triazin-2-amine;

(2Z)-3-(3-{5-Methyl-2-[(3,4,5-trimethoxyphenyl)amino]imidazo[5,1-f][1,2,4]triazin-7-yl}phenyl)-3-phenyl-prop-2-enamide;
7-(3-{[5-(Ethylsulfonyl)-2-methoxyphenyl]amino}phenyl)-5-methyl-N-(3,4,5-trimethoxyphenyl)imidazo[5,1-f][1,2,4]triazin-2-amine;
5-Methyl-7-(3-{[4-(1H1,2,4-triazol-1-ylmethyl)phenyl]amino}phenyl)-N-(3,4,5-trimethoxyphenyl)imidazo[5,1-f][1,2,4]triazin-2-amine;
7-(3-{[4-(1H-imidazol-1-yl)phenyl]amino}phenyl)-5-methyl-N-(3,4,5-trimethoxyphenyl)imidazo[5,1-f][1,2,4]triazin-2-amine;
7-{3-[(3-Chloro-4-morpholin-4-ylphenyl)amino]phenyl}-5-methyl-N-(3,4,5-trimethoxyphenyl)imidazo[5,1-f][1,2,4]triazin-2-amine;
N,N-Dimethyl-1-{3-[(3-{5-methyl-2-[(3,4,5-trimethoxyphenyl)amino]imidazo[5,1-f][1,2,4]triazin-7-yl}phenyl)amino]phenyl}methanesulfonamide;
5-Methyl-7-[3-({4-[(4-methylpiperazin-1-yl)methyl]phenyl}-amino)phenyl]-N-(3,4,5-trimethoxyphenyl)imidazo[5,1-f][1,2,4]triazin-2-amine;
N-Cyclopropyl-3-[(3-{5-methyl-2-[(3,4,5-trimethoxyphenyl)amino]imidazo[5,1-f][1,2,4]triazin-7-yl}phenyl)amino]benzenesulfonamide;
7-(5-Bromo-2-thienyl)-5-methyl-N-[4-(methyloxy)phenyl]imidazo[5,1-f][1,2,4]triazin-2-amine;
7-(3-Bromo-2-thienyl)-5-methyl-N-[4-(methyloxy)phenyl]imidazo[5,1-f][1,2,4]triazin-2-amine;
5-Methyl-N-[4-(methyloxy)phenyl]-7-(tetrahydro-2H-pyran-4-yl)imidazo[5,1-f][1,2,4]triazin-2-amine;
5-Methyl-7-[2-(methyloxy)phenyl]-N-[4-(methyloxy)phenyl]imidazo[5,1-f][1,2,4]triazin-2-amine;
5-Methyl-7-[3-(methyloxy)phenyl]-N-[4-(methyloxy)phenyl]imidazo[5,1-f][1,2,4]triazin-2-amine;
7-(2-Chlorophenyl)-5-methyl-N-[4-(methyloxy)phenyl]imidazo[5,1-f][1,2,4]triazin-2-amine;
5-Methyl-7-(1-methyl-1H-indol-3-yl)-N-[4-(methyloxy)phenyl]imidazo[5,1-f][1,2,4]triazin-2-amine;
5-Methyl-N-[4-(methyloxy)phenyl]-7-(1-phenylethyl)imidazo[5,1-f][1,2,4]triazin-2-amine;
5-Methyl-7-(1-methyl-1H-indol-2-yl)-N-[4-(methyloxy)phenyl]imidazo[5,1-f][1,2,4]triazin-2-amine;
5-Methyl-N-[4-(methyloxy)phenyl]-7-(3-thienyl)imidazo[5,1-f][1,2,4]triazin-2-amine;
7-(3-Furanyl)-5-methyl-N-[4-(methyloxy)phenyl]imidazo-[5,1-f][1,2,4]triazin-2-amine;
7-(2-Furanyl)-5-methyl-N-[4-(methyloxy)phenyl]imidazo-[5,1-f][1,2,4]triazin-2-amine;
7-(4-Fluorophenyl)-5-methyl-N-[4-(methyloxy)phenyl]imidazo[5,1-f][1,2,4]triazin-2-amine;
5-Methyl-N-[4-(methyloxy)phenyl]-7-(2-thienyl)imidazo[5,1-f][1,2,4]triazin-2-amine;
7-Cyclopropyl-5-methyl-N-[4-(methyloxy)phenyl]-imidazo[5,1-f][1,2,4]triazin-2-amine;
7-Cyclohexyl-5-methyl-N-[4-(methyloxy)phenyl]imidazo[5,1-f][1,2,4]triazin-2-amine;
7-(2-FluorophenylFluorophenyl)-5-methyl-N-[4-(methyloxy)phenyl]imidazo[5,1-f][1,2,4]triazin-2-amine;
5-Methyl-N,7-bis[4-(methyloxy)phenyl]imidazo[5,1-f][1,2,4]triazin-2-amine;
5-Methyl-N-[4-(methyloxy)phenyl]-7-(phenylmethyl)imidazo[5,1-f][1,2,4]triazin-2-amine;
7-(3-Fluorophenyl)-5-methyl-N-[4-(methyloxy)phenyl]imidazo[5,1-f][1,2,4]triazin-2-amine;
7-Cyclohexyl-5-methyl-N-[3,4,5-tris(methyloxy)phenyl]imidazo[5,1-f][1,2,4]triazin-2-amine;
7-(Cyclohexylmethyl)-5-methyl-N-[4-(methyloxy)phenyl]-imidazo[5,1-f][1,2,4]triazin-2-amine;
N-[3,4-Bis(methyloxy)phenyl]-5-methyl-7-phenylimidazo[5,1-f][1,2,4]triazin-2-amine;
N-[3,5-Bis(methyloxy)phenyl]-5-methyl-7-phenylimidazo[5,1-f][1,2,4]triazin-2-amine;
N-{4-[(5-Methyl-7-phenylimidazo[5,1-f][1,2,4]triazin-2-yl)amino]phenyl}acetamide;
5-Methyl-N-[4-(methylthio)phenyl]-7-phenylimidazo[5,1-f][1,2,4]triazin-2-amine;
N-(4-{[2-(Dimethylamino)ethyl]oxy}phenyl)-5-methyl-7-phenylimidazo[5,1-f][1,2,4]triazin-2-amine;
5-Methyl-7-phenyl-N-(4-{[2-(1-piperidinyl)ethyl]oxy}phenyl)-imidazo[5,1-f][1,2,4]triazin-2-amine;
N-(3-{[2-(Dimethylamino)ethyl]oxy}phenyl)-5-methyl-7-phenylimidazo[5,1-f][1,2,4]triazin-2-amine;
N-(1-Acetyl-2,3-dihydro-1H-indol-5-yl)-5-methyl-7-phenylimidazo[5,1-f][1,2,4]triazin-2-amine;
N-Cyclohexyl-5-methyl-7-phenylimidazo[5,1-f][1,2,4]triazin-2-amine;
5-Methyl-7-phenyl-N-(tetrahydro-2H-pyran-4-yl)imidazo[5,1-f][1,2,4]triazin-2-amine;
5-Methyl-N-(4-{[2-(4-morpholinyl)ethyl]oxy}phenyl)-7-phenylimidazo[5,1-f][1,2,4]triazin-2-amine;
5-Methyl-N-(3-{[2-(4-morpholinyl)ethyl]oxy}phenyl)-7-phenylimidazo[5,1-f][1,2,4]triazin-2-amine;
5-Methyl-N-[4-(methyloxy)phenyl]-7-phenylimidazo[5,1-f][1,2,4]triazin-2-amine;
5-Methyl-N,7-diphenylimidazo[5,1-f][1,2,4]triazin-2-amine; and
5-Methyl-N-[3-(methyloxy)phenyl]-7-phenylimidazo[5,1-f][1,2,4]triazin-2-amine;

and pharmaceutically acceptable salts, solvates and physiologically functional derivatives thereof.

It will be appreciated by those skilled in the art that the compounds of the present invention may also be utilized in the form of a pharmaceutically acceptable salt or solvate or physiologically functional derivative thereof. The pharmaceutically acceptable salts of the compounds of formula (I) include conventional salts formed from pharmaceutically acceptable inorganic or organic acids or bases as well as quaternary ammonium salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic (mesylate), naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts which are useful as intermediates in obtaining the compounds of the invention or pharmaceutically acceptable salts thereof. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts.

The term "solvate" as used herein refers to a complex of variable stoichiometry formed by a solute (a compound of formula (I)) and a solvent. Solvents, by way of example, include water, methanol, ethanol, or acetic acid.

The term "physiologically functional derivative" as used herein refers to any pharmaceutically acceptable derivative of a compound of the present invention, for example, an ester or an amide of a compound of formula (I), which upon administration to an animal, particularly a mammal, such as a human, is capable of providing (directly or indirectly) a compound of the present invention or an active metabolite thereof. See, for example, Burger's Medicinal Chemistry And Drug Discovery, 5th Edition, Vol 1: Principles And Practice.

Processes for preparing pharmaceutically acceptable salts, solvates and physiologically functional derivatives of the compounds of formula (I) are conventional in the art. See, e.g., Burger's Medicinal Chemistry And Drug Discovery 5th Edition, Vol 1: Principles And Practice.

As will be apparent to those skilled in the art, in the processes described below for the preparation of compounds of formula (I), certain intermediates, may be in the form of pharmaceutically acceptable salts, solvates or physiologically functional derivatives of the compound. Those terms as applied to any intermediate employed in the process of preparing compounds of formula (I) have the same meanings as noted above with respect to compounds of formula (I). Processes for preparing pharmaceutically acceptable salts, solvates and physiologically functional derivatives of such intermediates are known in the art and are analogous to the process for preparing pharmaceutically acceptable salts, solvates and physiologically functional derivatives of the compounds of formula (I).

Certain compounds of formula (I) may exist in stereoisomeric forms (e.g. they may contain one or more asymmetric carbon atoms or may exhibit cis-trans isomerism). The individual stereoisomers (enantiomers and diastereomers) and mixtures of these are included within the scope of the present invention. The present invention also covers the individual isomers of the compounds represented by formula (I) as mixtures with isomers thereof in which one or more chiral centres are inverted. Certain compounds of formula (I) may be prepared as a mixture of regioisomers. The present invention covers both the mixture of regioisomers as well as the individual compounds. Likewise, it is understood that compounds of formula (I) may exist in tautomeric forms other than that shown in the formula and these are also included within the scope of the present invention.

The compounds of the present invention are typically inhibitors of PLK, particularly PLK1. By "PLK inhibitor" is meant a compound which exhibits $pIC_{50}$ greater than 4 in the PLK Inhibition assay described below in the examples or an $IC_{50}$ less than 100 µM in the Methylene Blue Growth Inhibition assay described below in the examples; more particularly a PLK inhibitor is a compound which exhibits a $pIC_{50}$ greater than 5 or an $IC_{50}$ less than 10 µM using the methods described in the examples below.

The present invention further provides compounds of formula (I) for use in medical therapy in an animal, e.g. a mammal such as a human. In particular, the present invention provides compounds of formula (I) for use in the treatment of a condition mediated by PLK, particularly PLK1. The present invention also provides compounds of formula (I) for use in the treatment of a neoplasm susceptible to PLK. The present invention provides compounds of formula (I) for use in treating a PLK-mediated condition characterized by inappropriate cellular proliferation. The present invention also provides compounds of formula (I) for use in inhibiting proliferation of a cell via PLK. The present invention also provides compounds of formula (I) for use in inhibiting mitosis in a cell, via PLK.

The present invention provides methods for the treatment of several conditions or diseases, all of which comprise the step of administering a therapeutically effective amount of a compound of formula (I). As used herein, the term "treatment" refers to alleviating the specified condition, eliminating or reducing the symptoms of the condition, slowing or eliminating the progression of the condition and preventing or delaying the reoccurrance of the condition in a previously afflicted subject.

As used herein, the term "therapeutically effective amount" means an amount of a compound of formula (I) which is sufficient, in the subject to which it is administered, to elicit the biological or medical response of a cell culture, tissue, system, animal (including human) that is being sought, for instance, by a researcher or clinician. For example, a therapeutically effective amount of a compound of formula (I) for the treatment of a condition mediated by PLK is an amount sufficient to treat the PLK mediated condition in the subject. Similarly, a therapeutically effective amount of a compound of formula (I) for the treatment of a susceptible neoplasm is an amount sufficient to treat the susceptible neoplasm in the subject. In one embodiment of the present invention, the therapeutically effective amount of a compound of formula (I) is an amount sufficient to inhibit cell mitosis. In one embodiment of the present invention, a therapeutically effective amount of a compound of formula (I) is an amount sufficient to regulate, modulate, bind or inhibit PLK, or specifically PLK1.

The precise therapeutically effective amount of the compounds of formula (I) will depend on a number of factors including, but not limited to, the age and weight of the subject being treated, the precise disorder requiring treatment and its severity, the nature of the formulation, and the route of administration, and will ultimately be at the discretion of the attendant physcian or veternarian. Typically, the compound of formula (I) will be given for treatment in the range of 0.1 to 200 mg/kg body weight of recipient (animal) per day and more usually in the range of 1 to 100 mg/kg body weight per day. Acceptable daily dosages, may be from about 0.1 to about 2000 mg/day, and preferably from about 0.1 to about 100 mg/day.

As one aspect, the present invention provides methods of regulating, modulating, binding, or inhibiting PLK for the treatment of conditions mediated by PLK. "Regulating, modulating, binding or inhibiting PLK" refers to regulating, modulating, binding or inhibiting PLK activity, as well as regulating, modulating, binding or inhibiting overexpression of PLK. Such conditions include certain neoplasms (including cancers and tumors) which have been associated with PLK and conditions characterized by inappropriate cellular proliferation.

The present invention provides a method for treating a condition mediated by PLK in an animal such as a mammal (e.g., a human), which method comprises administering to the animal a therapeutically effective amount of the compound of formula (I). Conditions which are mediated by PLK are known in the art and include but are not limited to neoplasms and conditions characterized by inappropriate cellular proliferation.

The present invention also provides a method for treating a susceptible neoplasm (cancer or tumor) in an animal such as a mammal (e.g., a human), which method comprises administering to the animal a therapeutically effective amount of the compound of formula (I). "Susceptible neoplasm" as used herein refers to neoplasms which are susceptible to treatment with a PLK inhibitor. Neoplasms which have been associated with PLK and are therefore susceptible to treatment with a PLK inhibitor are known in the art, and include both primary and metastatic tumors and cancers. For example, susceptible neoplasms within the scope of the present invention include but are not limited to breast cancer, colon cancer, lung cancer (including small cell lung cancer and non-small cell lung cancer), prostate cancer, lymphoma, leukemia, endometrial cancer, melanoma, gastric carcinoma, ovarian cancer, pancreatic cancer, squamous carcinoma, carcinoma of the head and neck, and esophageal carcinoma. The compounds of formula (I) can be used alone in the treatment of such susceptible neoplasms or can be used to provide additive or synergistic effects with certain existing chemotherapies, and/or be used to restore effectiveness of certain existing chemotherapies and radiation.

The present invention also provides a method for treating a PLK-mediated condition characterized by inappropriate cellular proliferation. By "inappropriate cellular proliferation" is meant cellular proliferation resulting from inappropriate cell growth, cellular proliferation resulting from excessive cell division, cellular proliferation resulting from cell division at an accelerated rate, cellular proliferation resulting from inappropriate cell survival, and/or cellular proliferation in a normal cell occurring at a normal rate, which is nevertheless undesired. PLK-mediated conditions characterized by inappropriate cellular proliferation include but are not limited to neoplasms, blood vessel proliferative disorders, fibrotic disorders, mesangial cell proliferative disorders and metabolic diseases. Blood vessel proliferative disorders include arthritis and restenosis. Fibrotic disorders include hepatic cirrhosis and atherosclerosis. Mesangial cell proliferative disorders include glomerulonephritis, malignant nephrosclerosis, thrombotic microangiopathy syndromes, organ transplant rejection and glomerulopathies. Metabolic disorders include psoriasis, chronic wound healing, inflammation and neurodegenerative diseases. Osteoarthritis and other osteoclast proliferation dependent diseases of excess bone resorption are examples of conditions characterized by inappropriate cellular proliferation in which the cellular proliferation occurs in normal cells at a normal rate, but is nevertheless undesired.

The present invention also provides a method for inhibiting proliferation of a cell, which method comprises contacting the cell with an amount of a compound of formula (I) sufficient to inhibit proliferation of the cell, wherein the compound inhibits PLK. In one particular embodiment, the cell is a neoplastic cell. In one particular embodiment, the cell is an inappropriately proliferative cell. The term "inappropriately proliferative cell" as used herein refers to cells that grow inappropriately (abnormally), cells that divide excessively or at an accelerated rate, cells that inappropriately (abnormally) survive and/or normal cells that proliferate at a normal rate but for which proliferation is undesired. Neoplastic cells (including cancer cells) are an example of inappropriately proliferative cells but are not the only inappropriately proliferative cells.

PLK is essential for cellular mitosis and accordingly, the compounds of formula (I) are effective for inhibiting mitosis. "Inhibiting mitosis" refers to inhibiting the entry into the M phase of the cell cycle, inhibiting the normal progression of the M phase of the cell cycle once M phase has been entered and inhibiting the normal exit from the M phase of the cell cycle. Thus, the compounds of the present invention may inhibit mitosis by inhibiting the cell's entry into mitosis, by inhibiting the cell's progression through mitosis or by inhibiting the cell's exit from mitosis. As one aspect, the present invention provides a method for inhibiting mitosis in a cell, which method comprises administering to the cell an amount of a compound of formula (I) sufficient to inhibit mitosis, wherein the compound inhibits PLK. In one particular embodiment, the cell is a neoplastic cell. In one particular embodiment, the cell is an inappropriately proliferative cell.

The present invention also provides the use of a compound of formula (I) for the preparation of a medicament for the treatment of condition mediated by PLK in an animal, such as a mammal (e.g., a human). The present invention further provides the use of a compound of formula (I) for the preparation of a medicament for the treatment of a susceptible neoplasm in an animal. The present invention further provides the use of a compound of formula (I) for the preparation of a medicament for the treatment of a PLK-mediated condition characterized by inappropriate cellular proliferation. The present invention further provides the use of a compound of formula (I) for the preparation of a medicament for inhibiting proliferation of a cell, wherein the compound inhibits PLK. The present invention further provides the use of a compound of formula (I) for the preparation of a medicament for inhibiting mitosis in a cell, wherein the compound inhibits PLK.

While it is possible that, for use in therapy, a therapeutically effective amount of a compound of formula (I) may be administered as the raw chemical, it is typically presented as the active ingredient of a pharmaceutical composition or formulation. Accordingly, the invention further provides a pharmaceutical composition comprising a compound of the formula (I). The pharmaceutical composition may further comprise one or more pharmaceutically acceptable carriers, diluents, and/or excipients. The carrier(s), diluent(s) and/or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I) with one or more pharmaceutically acceptable carriers, diluents and/or excipients.

Pharmaceutical formulations may be presented in unit dose form containing a predetermined amount of active ingredient per unit dose. Such a unit may contain a therapeutically effective dose of the compound of formula (I) or a fraction of a therapeutically effective dose such that multiple unit dosage forms might be administered at a given time to achieve the desired therapeutically effective dose. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of active ingredient. Syrups can be prepared by dissolving the compound in a suitably flavored aqueous solution, while elixirs are prepared through the use of a non-toxic alcoholic vehicle.

Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I) can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula (I) may also be delivered by the use of monoclonal antibodies as individual carriers to which the compound molecules are coupled. The compounds may also be coupled with soluble polymers as targetable drug carriers. Such polymers can include peptides, polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research,* 3(6):318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers or insufflators. Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavouring agents.

In the above-described methods of treatment and uses, a compound of formula (I) may be employed alone, in combination with one or more other compounds of formula (I) or in combination with other therapeutic agents. In particular, in methods of treating conditions mediated by PLK and methods of treating susceptible neoplasms, combination with other chemotherapeutic, hormonal and/or antibody agents is envisaged as well as combination with surgical therapy and radiotherapy. The term "chemotherapeutic" as used herein refers to any chemical agent having a therapeutic effect on the subject to which it is administered. "Chemotherapeutic" agents include but are not limited to anti-neoplastic agents, analgesics and anti-emetics. As used herein, "anti-neoplastic agents" include both cytostatic and cytotoxic agents. Combination therapies according to the present invention thus comprise the administration of at least one compound of formula (I) and the use of at least one other cancer treatment method. In one embodiment, combination therapies according to the present invention comprise the administration of at least one compound of formula (I) and at least one other chemotherapeutic agent. In one particular embodiment, the present invention comprises the administration of at least one compound of formula (I) and at least one anti-neoplastic agent. As an additional aspect, the present invention provides the methods of treatment and uses as described above, which comprise administering a compound of formula (I) together with at least one chemotherapeutic agent. In one particular embodiment, the chemotherapeutic agent is an anti-neoplastic agent. In another embodiment, the present invention provides a pharmaceutical composition as described above further comprising at least one other chemotherapeutic agent, more particularly, the chemotherapeutic agent is an anti-neoplastic agent. Typically, any chemotherapeutic agent that has activity versus a susceptible neoplasm being treated may be utilized in combination with the compounds of formula (I), provided that the particular agent is clinically compatible with therapy employing a compound of formula (I). Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and antifolate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids. Examples of diterpenoids include, but are not limited to, paclitaxel and its analog docetaxel. Examples of vinca alkaloids include, but are not limited to, vinblastine, vincristine, and vinorelbine.

Platinum coordination complexes are non-phase specific anti-neoplastic agents, which are interactive with DNA. The platinum complexes enter tumor cells, undergo aquation and form intra- and interstrand crosslinks with DNA causing adverse biological effects to the tumor. Examples of platinum coordination complexes include, but are not limited to, cisplatin and carboplatin.

Alkylating agents are non-phase anti-neoplastic specific agents and strong electrophiles. Typically, alkylating agents form covalent linkages, by alkylation, to DNA through nucleophilic moieties of the DNA molecule such as phosphate, amino, and hydroxyl groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Antibiotic chemotherapeutic agents are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand-breaks. The strand-breaks accumulate and cell death follows. Examples of epipodophyllotoxins include, but are not limited to, etoposide and teniposide.

Antimetabolite neoplastic agents are phase specific antineoplastic agents that act at S phase (DNA synthesis) of the cell cycle by inhibiting DNA synthesis or by inhibiting purine or pyrimidine ba,se synthesis and thereby limiting DNA synthesis. Consequently, S phase does not proceed and cell death follows. Examples of antimetabolite anti-neoplastic agents include, but are not limited to, fluorouracil, methotrexate, cytarabine, mecaptopurine and thioguanine.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin.

Hormones and hormonal analogues are useful compounds for treating cancers in which there is a relationship between the hormone(s) and growth and/or lack of growth of the cancer. Examples of hormones and hormonal analogues believed to be useful in the treatment of neoplasms include, but are not limited to, adrenocorti-costeroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene and iodoxyfene useful in the treatment of hormone dependent breast carcinoma; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagonists such as goserelin acetate and luprolide.

Signal transduction pathway inhibitors are those inhibitors which block or inhibit a chemical process which evokes an intracellular change. As used herein this change is cell proliferation or differentiation. Signal tranduction inhibitors useful in the present invention include inhibitors of receptor tyrosine kinases, non-receptor tyrosine kinases, SH2/SH3 domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in toe regulation of cell growth and are sometimes termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr, ErbB2 and ErbB4), platelet derived growth factor receptor (PDGFr), vascular endothelial growth factor receptor (VEGFR), tyrosine kinase with immunoglobulin-like and epidermal growth factor homology domains (TIE-2), insulin growth factor-I receptor (IGF-I), macrophage colony stimulating factor (cfms), BTK, cKit, cMet, fibroblast growth factor (FGF) receptors, Trk receptors (TrkA, TrkB, and TrkC), ephrin (eph) receptors, and the RET protooncogene. Several inhibitors of growth factor receptors are under development and include ligand antagonists, antibodies, tyrosine kinase inhibitors, anti-sense oligonucleotides and aptamers. Growth factor receptors and agents that inhibit growth factor receptor function are described, for instance, in Kath, John C., Exp. Opin. Ther. Patents (2000) 10(6):803-818; Shawver et al DDT Vol 2, No. 2 February 1997; and Lofts, F. J. et al, "Growth Factor Receptors as Targets", New Molecular Targets for Cancer Chemotherapy, Ed. Workman, Paul and Kerr, David, CRC Press 1994, London.

Tyrosine kinases, which are not growth factor receptor kinases are termed non-receptor tyrosine kinases. Non-receptor tyrosine kinases useful in the present invention, which are targets or potential targets of anti-neoplastic drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotherapy and Stem Cell Research 8 (5): 465-80; and Bolen, J. B., Brugge, J. S., (1997) Annual Review of Immunology. 15: 371-404.

SH2/SH3 domain blockers are agents that disrupt SH2 or SH3 domain binding in a variety of enzymes or adaptor proteins including, Pl3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (Rao, Mitogen-Activated Extracellular Signal-Regulated Kinase (MEKs), and Extracellular Signal-Regulated Kinases (ERKs); and Protein kinase C family member blockers including blockers of subtypes of PKCs (alpha, beta, gamma, epsilon, mu, lambda, iota, zeta), IkB kinase family (IKKa, IKKb), PKB family kinases, Akt kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78:3-27, Lackey, K. et al Bioorganic and Medicinal Chemistry Letters, (10), 2000, 223-226; and Martinez-lacaci, L., et al, Int. J. Cancer (2000), 88(1), 44-52.

Inhibitors of Phosphotidyl Inositol-3 Kinase family members including blockers of Pl3-kinase, ATM, DNA-PK, and Ku are also useful in combination with the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer Res, (2000) 60(6), 1541-1545.

Also useful in combination with the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC Press 1994, London.

Another group of signal transduction pathway inhibitors useful in combination with the present invention are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block Ras activation in cells containing wild type mutant Ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9(2)99-102; and BioChim. Biophys. Acta, (1989) 1423(3):19-30.

As mentioned above, antibodies to receptor kinase ligand binding may also serve as signal transduction inhibitors. This group of signal transduction pathway inhibitors includes the use of humanized antibodies to the extracellular ligand binding domain of receptor tyrosine kinases. For example, Imclone C225 EGFR specific antibody (see Green, M. C. et al, Monoclonal Antibody Therapy for Solid Tumors, Cancer Treat. Rev., (2000), 26(4), 269-286); Herceptin® ErbB2 antibody (see Tyrosine Kinase Signaling in Breast Cancer:ErbB Family Receptor Tyrosine Kinases, Breast Cancer Res., 2000, 2(3), 176-183); and 2CB VEGFR2 specific antibody (see Brekken, R. A. et al, Selective Inhibition of VEGFR2 Activity by a Monoclonal Anti-VEGF Antibody Blocks Tumor Growth in Mice, Cancer Res. (2000) 60, 5117-5124).

Receptor kinase angiogenesis inhibitors may also find use in the present invention. Inhibitors of angiogenesis related VEGFR and TIE2 are discussed above in regard to signal transduction inhibitors (both receptors are receptor tyrosine kinases). Other inhibitors may be used in combination with the compounds of the present invention. For example, anti-VEGF antibodies, which do not recognize VEGFR (the receptor tyrosine kinase), but bind to the ligand; small molecule inhibitors of integrin (alpha$_v$, beta$_3$) that will inhibit angiogenesis; endostatin and angiostatin (non-RTK) may also prove useful in combination with PLK inhibitors.

Agents used in immunotherapeutic regimens may also be useful in combination with the compounds of formula (I).

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al., *J. Clin. Oncol.* 18:1812-1823 (2000); and Kitada S et al., *Antisense Res. Dev.* 4:71-79 (1994).

Cell cycle signaling inhibitors inhibit molecules involved in the control of the cell cycle. Cyclin dependent kinases (CDKs) and their interaction cyclins control progression through the eukaryotic cell cycle. The coordinated activation and inactivation of different cyclin/CDK complexes is necessary for normal progression through the cell cycle. Several inhibitors of cell cycle signaling are under development. For instance, examples of cyclin dependent kinases, including CDK2, CDK4, and CDK6 and inhibitors for the same are described in, for instance, Rosania, et al., *Exp. Opin. Ther. Patents* 10(2):215-230 (2000).

In one embodiment, the methods of the present invention comprise administering to the animal a compound of formula (I) in combination with a signal transduction pathway inhibitor, particularly gefitinib (IRESSA®).

The methods and uses employing these combinations may comprise the administration of the compound of formula (I) and the other chemotherapeutic/anti-neoplastic agent either sequentially in any order or simultaneously in separate or combined pharmaceutical compositions. When combined in the same formulation it will be appreciated that the two compounds must be stable and compatible with each other and the other components of the formulation and may be formulated for administration.

When formulated separately they may be provided in any convenient formulation, in such a manner as are known for such compounds in the art. When a compound of formula (I) is used in combination with a chemotherapeutic agent, the dose of each compound may differ from that when the compound is used alone. Appropriate doses will be readily appreciated by those skilled in the art. The appropriate dose of the compound(s) of formula (I) and the other therapeutically active agent(s) and the relative timings of administration will be selected in order to achieve the desired combined therapeutic effect, and are within the expertise and discretion of the attendant clinician.

Compounds of formula (I) may be conveniently prepared by the process outlined in Scheme 1 below.

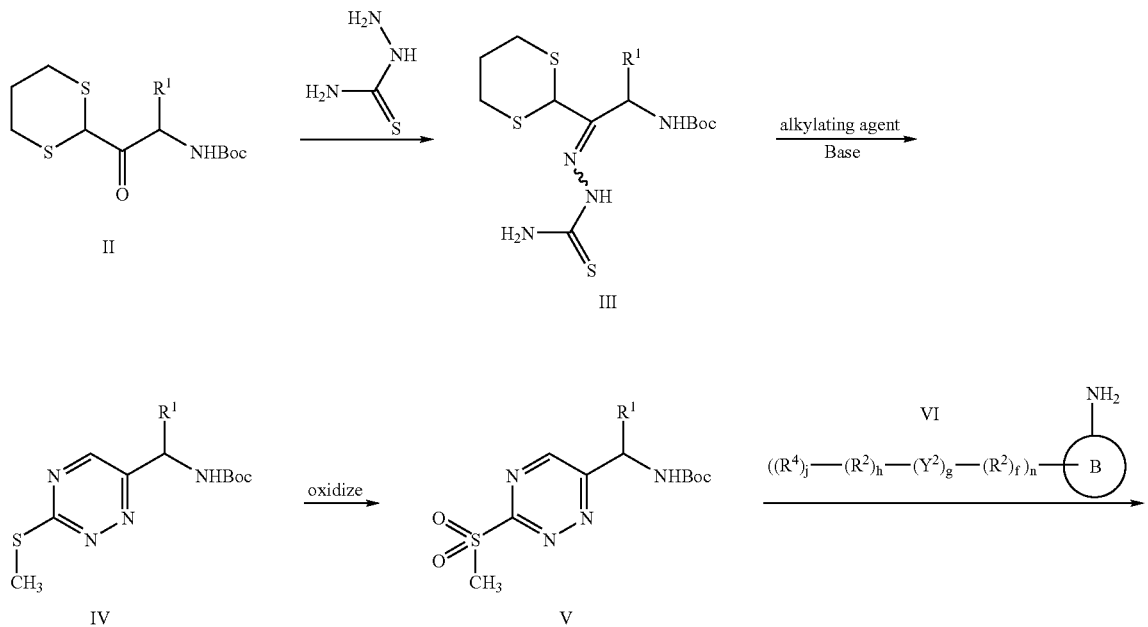

-continued
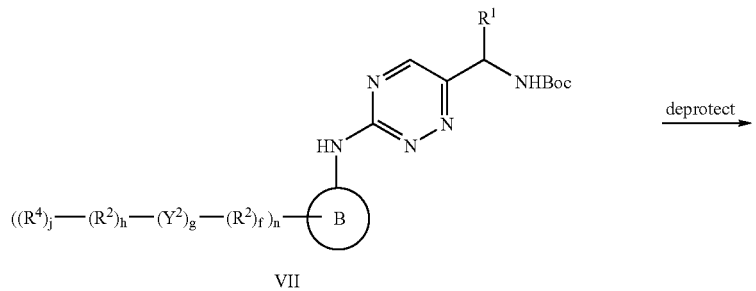
VII
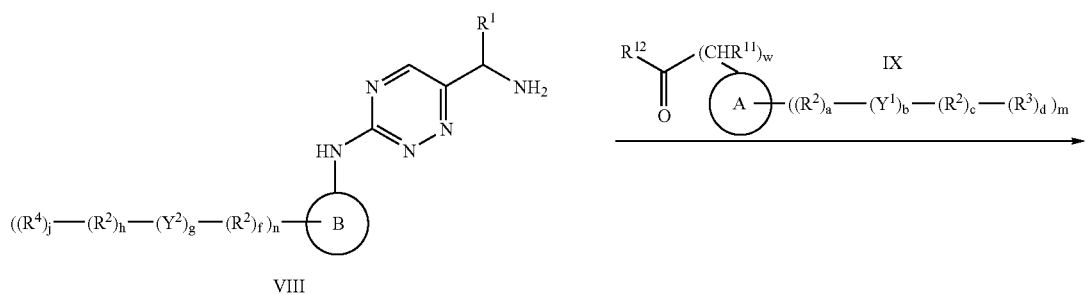
VIII
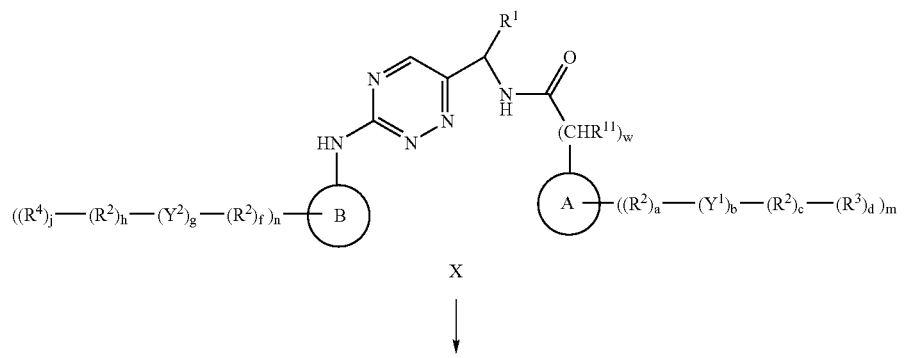
X
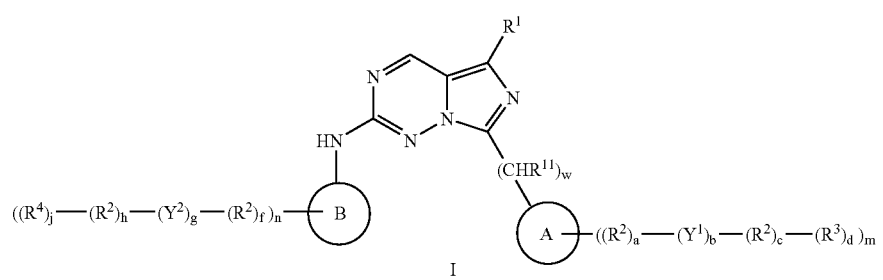
I wherein:
w is 0 or 1;
$R^{11}$ is H or $C_{1-3}$alkyl;
$R^1$ is alkyl;
Ring A is selected from the group consisting of cycloalkyl, cycloalkenyl, aryl, 5-13 membered heterocycle and 5-13 membered heteroaryl;
Ring B is selected from the group consisting of cycloalkyl, cycloalkenyl, aryl, 5-13 membered heterocycle and 5-13 membered heteroaryl;
a, b, c, f, g, and h are the same or different and are each independently 0 or 1;
d and j are the same or different and are independently 1 or 2;
each $R^2$ is the same or different and is independently selected from the group consisting of alkylene, alkenylene and alkynylene;
$Y^1$ and $Y^2$ are the same or different and are each independently selected from the group consisting of —O—, —S(O)$_q$— and —N($R^5$)—;
q is 0, 1 or 2;
each $R^3$ and $R^4$ are the same or different and are each independently selected from the group consisting of H, halo, alkyl, alkenyl, alkynyl, cycloalkyl, cycloalkenyl, Ph, Het, —COR$^5$, —CSR$^5$, —CO$_2$R$^5$, —COPh, —CO$_2$Ph, —C(O)Het, —C(O)NR$^5$R$^6$, —C(S)NR$^5$R$^6$, —C(=NR$^5$)R$^6$, —C(=NR$^5$)NR$^5$R$^6$, —CR$^5$=N—OR$^6$, —OR$^5$, —OCOR$^5$, —S(O)$_p$R$^5$, —S(O)$_2$OH, —S(O)$_p$NR$^5$R$^6$, —NR$^5$R$^6$, —NR$^5$COR$^6$, —NR$^5$CO$_2$R$^6$, —NR$^5$SO$_2$R$^6$, —NO$_2$, —CN, —SCN and —N$_3$;

each p is the same or different and is 0, 1 or 2;
m and n are the same or different and are each independently 0, 1, 2, 3, 4 or 5;
each $R^5$ and each $R^6$ are the same or different and are each independently selected from the group consisting of H, alkyl, alkenyl, alkynyl, cycloalkyl and cycloalkenyl;
$R^{12}$ is OH or halo, particularly chloro;
Ph is phenyl optionally substituted by one or more substituents selected from the group consisting of halo, alkyl, —CO$_2$R$^5$, —OR$^5$, —SO$_2$R$^5$, —SO$_2$NR$^5$R$^6$, —NR$^5$R$^6$, —R$^2$—(NR$^5$R$^6$)CO$_2$R$^5$, Het, —R$^2$-Het, —CN and —N$_3$;
Het is a monocyclic 5-6 membered heterocycle or heteroaryl group containing 1, 2 or 3 heteroatoms selected from the group consisting of N, O, and S optionally substituted by one or more substituents selected from the group consisting of halo, alkyl, —CO$_2$R$^5$, —C(O)NR$^5$R$^6$, —OR$^5$, —SO$_2$R$^5$, —SO$_2$NR$^5$R$^6$, —NR$^5$R$^6$, oxo, —CN and —N$_3$; and
Boc is a N-tert-butoxycarbonyl protecting group.

Generally, the process for preparing the compounds of formula (I) (all formulas and all variables having been defined above in connection with Scheme 1) comprises the steps of:
(a) reacting a compound of formula (II) with thiosemicarbazide to prepare a compound of formula (III);
(b) reacting the compound of formula (III) with an alkylating agent and aqueous base to prepare a compound of formula (IV);
(c) oxidizing the compound of formula (IV) to prepare a compound of formula (V);
(d) reacting the compound of formula (V) with a compound of formula (VI) to prepare a compound of formula (VII);
(e) deprotecting the compound of formula (VII) to prepare a compound of formula (VIII);
(f) reacting the compound of formula (VIII) with a compound of formula (IX) to prepare a compound of formula (X); and
(g) reacting the compound of formula (X) with a cyclization reagent to prepare a compound of formula (I).

The order of the foregoing steps is not critical to the practice of the invention and the process may be practiced by performing the steps in any suitable order based on the knowledge of those skilled in the art.

More specifically, a compound of formula (I) may be prepared by reacting a compound of formula (X):

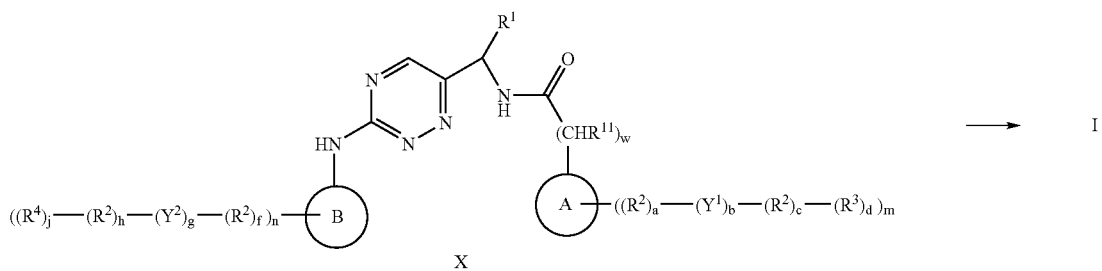

wherein all variables are as defined above, with a cyclization reagent.

In one particular embodiment, the cyclization reagent is a dehydrative cyclization reagent. The reaction is typically carried out neat or in a suitable solvent. The reaction may be optionally heated to a temperature of from about 20 to 150° C. Examples of suitable cyclization reagents include but are not limited to, phosphorous oxychloride, thionylchloride, oxalylchloride, and polyphosphoric acid. Suitable solvents include but are not limited to, 1,2-dichloroethane, dichloromethane, chloroform and pyridine. The reaction may be carried out in the presence or absence of further additives. Examples of suitable additives include but are not limited to, 1,2,4-triazole, N,N-dimethylformamide, and tetrabutylammonium chloride.

A compound of formula (X) may be prepared by reacting a compound of formula (IX) with a compound of formula (VIII).

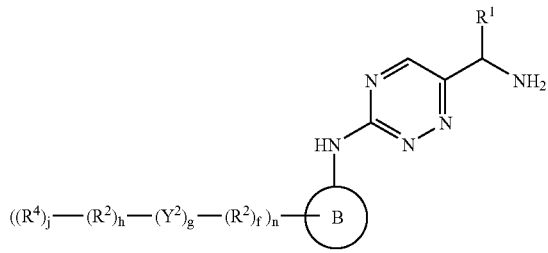
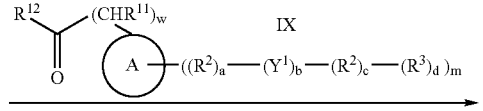

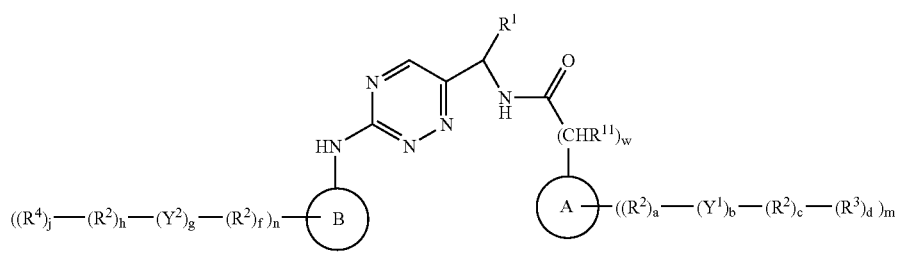

wherein all variables are as defined above.

In one embodiment, the compound of formula (VIII) is reacted with the compound of formula (IX) and a suitable activating agent. Suitable activating agents are commercially available and include but are not limited to, O-(7-azabenzotriazol-1-yl)-N,N,N'N'-tetramethyluronium hexafluorophosphate (HATU), 1-(3-dimethylamino-propyl)-3-ethylcarbodiimide hydrochloride, 1,1'-carbonyldiimidazole and oxalylchloride, and the like. The reaction is typically carried out in the presence of a base. Suitable bases include but are not limited to, triethylamine, N,N-diisopropylethylamine, 2,4,6-collidine and 2,6-lutidine. Reaction of the compound of formula (IX) with the activating agent produces the activated ester of the compound of formula (IX). It will be apparent to those skilled in the art that the activated ester of the compound of formula (IX) may be generated and reacted with the compound of formula (VIII) in situ or may be isolated prior to reaction with a compound of formula (VIII). The reaction is typically carried out in an inert solvent. Suitable solvents include but are not limited to, N,N-dimethylformamide, dichloromethane, acetonitrile, tetrahydrofuran, dioxane, and 1,2-dimethyl-ethylene glycol. The compounds of formula (IX) are commercially available or can be prepared using conventional techniques known to those skilled in the art.

Compounds of formula (VIII) may be prepared by deprotecting a compound of formula (VII).

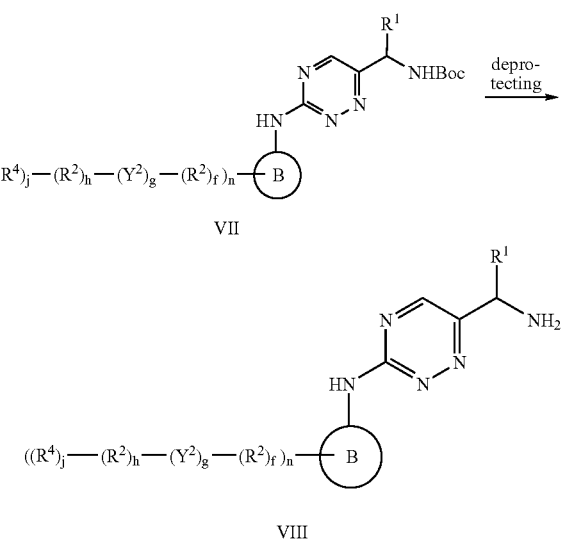

wherein all variables are as defined above.

A compound of formula (VII) may be deprotected by reacting the compound of formula (VII) with a suitable acid. Suitable acids include but are not limited to, trifluoroacetic acid and hydrochloric acid. The reaction may be carried out neat or in a suitable solvent. Suitable solvents include but are not limited to methanol, dichloromethane and dioxane.

A compound of formula (VII) may be prepared by reacting a compound of formula (V) with a compound of formula (VI).

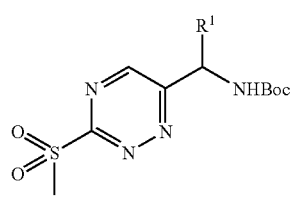

V

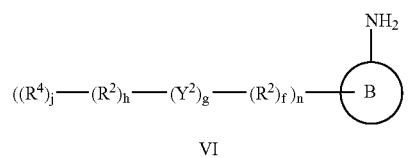

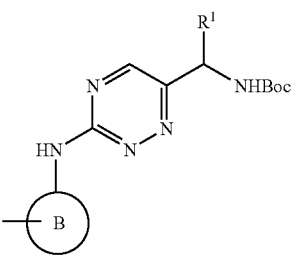

VII wherein all variables are as defined above in connection with Scheme 1.

In one embodiment, the reaction is carried out in the presence of an acid catalyst. Suitable acids include but are not limited to 4-toulenesulfonic acid, 3-chlorobenzoic acid and hydrochloric acid. Suitable solvents include but are not limited to, tetrahydofuran, dioxane and N,N-dimethylformamide. Typically, the reaction is carried out in an inert solvent. The reaction may optionally be heated to from about 40 to about 80° C. Preferably the reaction is performed by reacting equimolar amounts of a compound of formula (V) with a compound of formula (VI), but the reaction may also be performed in the presence of an excess of compound of the formula (VI).

The compounds of formula (VI) are commercially available or can be prepared using conventional techniques known to those skilled in the art.

Compounds of formula (V) may be prepared by oxidizing a compound of formula (IV).

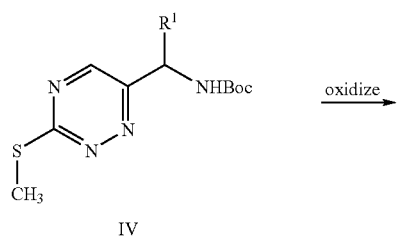

IV

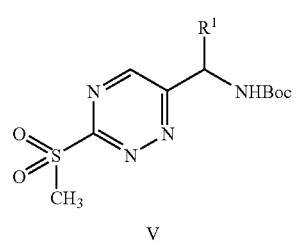

V wherein all variables are as defined above in connection with Scheme 1.

The reaction is typically carried out in an inert solvent. Suitable solvents include but are not limited to, dichloromethane, 1,2-dichloroethane and chloroform. Suitable oxidizing reagents include but are not limited to, m-chloroperbenzoic acid (mCPBA) and the like.

Compounds of formula (IV) may be prepared by reacting a compound of formula (III) with an alkylating agent and aqueous base.

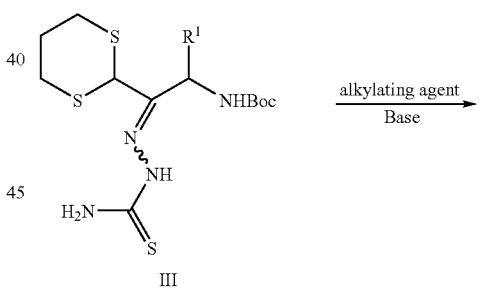

wherein all variables are as defined above.

Suitable alkylating agents include but are not limited to, iodomethane. Suitable bases include but are not limited to, calcium carbonate, cesium carbonate, potassium carbonate and sodium hydroxide. The reaction is typically carried out in a mixture of an organic solvent and water. The reaction may optionally be heated to from about 40 to about 60° C. Suitable organic solvents include but are not limited to, acetonitrile.

Compounds of formula (III) may be prepared by reacting a compound of formula (II) with thiosemicarbazide.

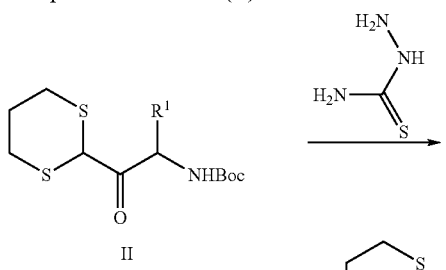

wherein all variables are as defined above.

In one embodiment, the reaction is carried out in the presence of an acid catalyst. Suitable acids include but are not limited to, 4-toluenesulfonic acid. The reaction is typically carried out in an inert solvent. Suitable solvents include but are not limited to, ethanol and toluene. The reaction may optionally be heated to from about 40 to about 110° C.

The compounds of formula (II) may be prepared according to procedures described in the literature from the corresponding Weinreb amides. See, Brown, P., et al., *J. Med. Chem.* 39:446-457 (1996). The Weinreb amides are commercially available or may be prepared from the corresponding acids by procedures know to those skilled in the art. See, Brown, P., et al., *J. Med. Chem.* 39: 446-457 (1996).

As noted above, the steps of the foregoing synthesis may be carried out in any suitable order as will be appreciated by those skilled in the art. For example, a suitable alternative synthesis route is outlined in Scheme 1-A below.

Scheme 1-A

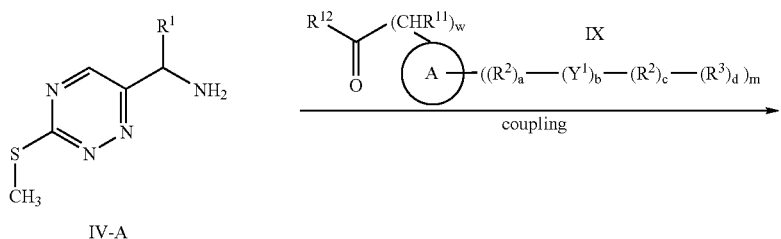

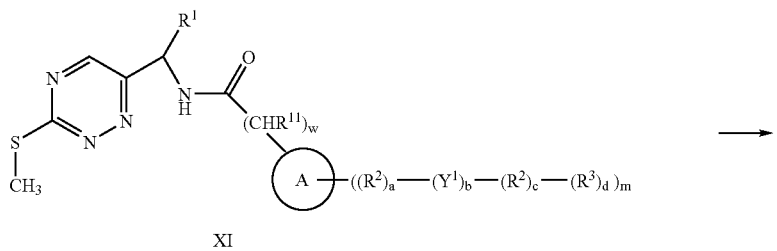

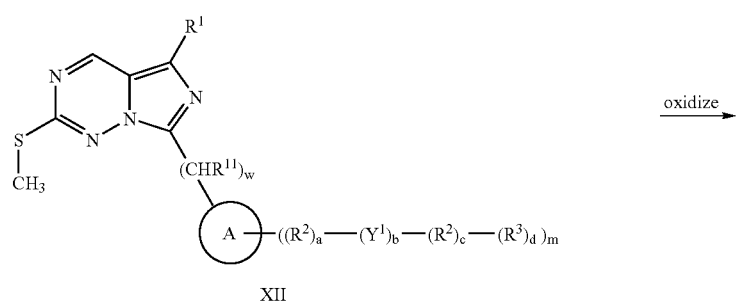

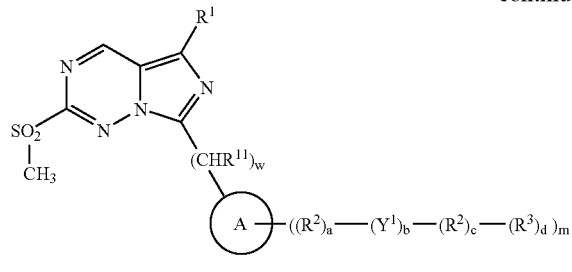
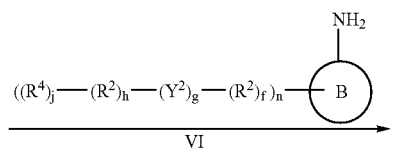

XIII

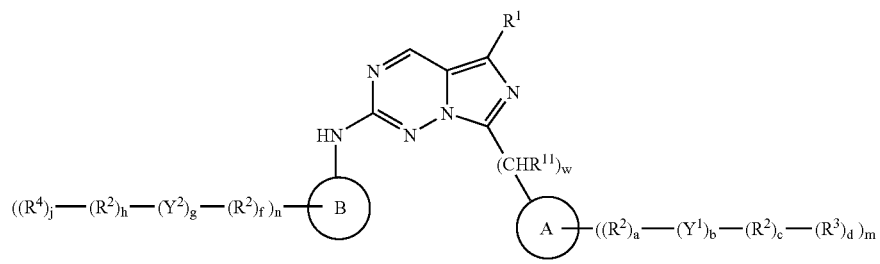

I wherein all variables are as defined above.

Generally, the process for preparing the compounds of formula (I) according to Scheme 1-A comprises the steps of:

(a) reacting a deprotected compound of formula (IV-A) with a compound of formula (IX) to prepare a compound of formula (XI);

(b) reacting the compound of formula (XI) with a cyclization reagent to prepare a compound of formula (XII);

(c) oxidizing the compound of formula (XII) to prepare a compound of formula (XIII); and (d) reacting the compound of formula (XIII) with a compound of formula (VI) to prepare a compound of formula (I).

The reaction of the compound of formula (XIII) with a compound of formula (VI) may be carried out in a manner analogous to the reaction of the compound of formula (V) and (VI) in Scheme 1. In one embodiment, the compound of formula (XIII) with a compound of formula (VI) is carried out at elevated temperatures, for example at about 180° C. In another embodiment, the compound of formula (XIII) is reacted with the compound of formula (VI) by adding the compound of formula (XIII) in solution to a solution containing the compound of formula (VI) and a base (e.g., n-butyl lithium) in a polar aprotic solvent such as tetrahydrofuran at about −78° C. and then slowing warming the solution to room temperature.

The oxidation of the compound of formula (XII) may be carried out in a manner analogous to the oxidation of the compound of formula (IV) in Scheme 1.

The cyclization of the compound of formula (XI) may be carried out in a manner analogous to the cyclization of the compound of formula (III) in Scheme 1.

The coupling reaction of the compound of formula (IV-A) with the compound of formula (IX) may be carried out in a manner analogous to the coupling reaction of the compound of formula (VIII) with the compound of formula (IX).

The compound of formula (IV-A) may be prepared by deprotecting the compound of formula (IV) from Scheme 1. Suitable methods for deprotection of the compound of formula (IV) are analogous to those described above for the deprotection of the compound of formula (VII) according to Scheme 1.

As will be appreciated by those skilled in the art, the foregoing synthesis may also be carried out by starting with the sulfide analogue of formula (XI), and subsequently displacing the corresponding sulfone with the aniline of formula (VI) prior to carrying out the cyclization step, according to Scheme 1-B below.

Scheme 1-B

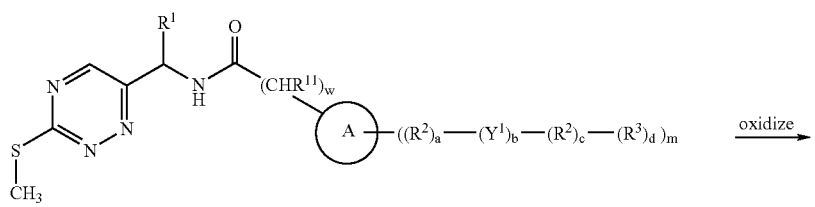

XI

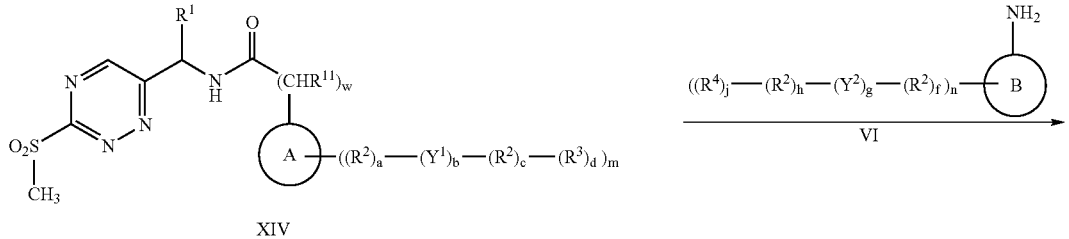

XIV

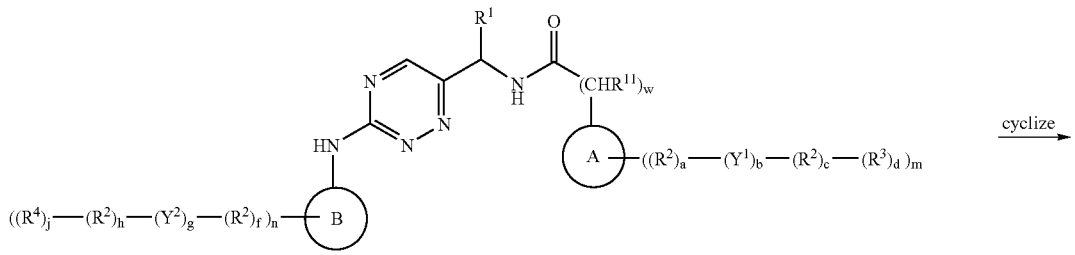

X

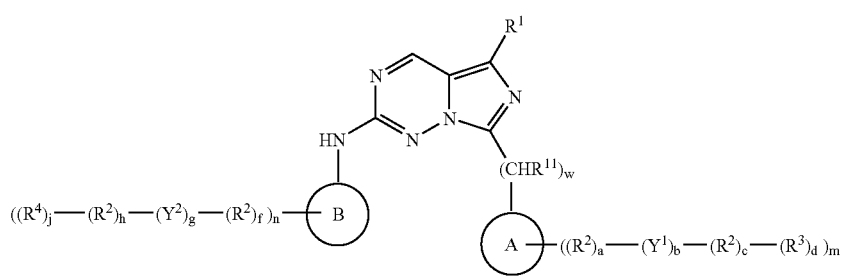

I wherein all variables are as defined above.

Generally, the process for preparing the compounds of formula (I) according to Scheme 1-B comprises the steps of:
(a) oxidizing the compound of formula (XI) to prepare a compound of formula (XIV);
(b) reacting the compound of formula (XIV) with the compound of formula (VI) to prepare a compound of formula (X); and
(c) reacting the compound fo formula (X) with a cyclization reagent to prepare a compound of formula (I).

The oxidation of the compound of formula (XI) may be carried out using in a manner analogous to the oxidation of the compound of formula (IV) according to Scheme 1, or the oxidation of the compound of formula (XII) in Scheme 1-A.

The displacement of the sulfone in the compound of formula (XIV) using the aniline of formula (VI) may be carried out in a manner analogous to the displacement of the sulfone on the compound of formula (V) according to Scheme 1.

The cyclization of the compound of formula (X) is described above in connection with Scheme 1.

In another embodiment of the present invention, a compound of formula (I) may be prepared according to the process outlined in Scheme 2 below.

Scheme 2

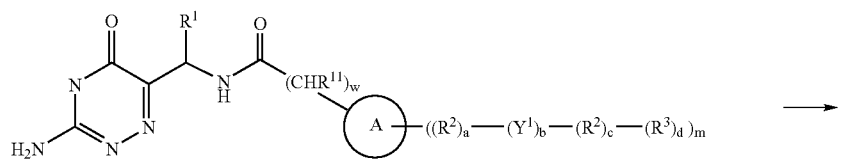

XV

-continued

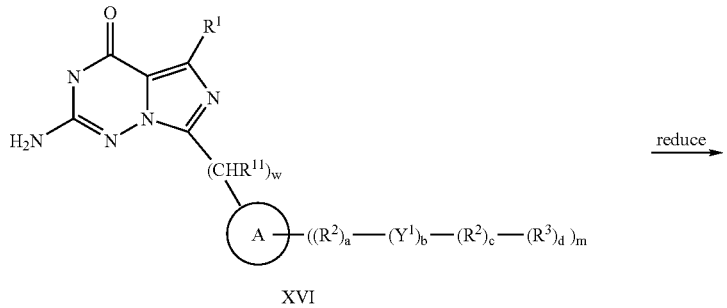

XVI

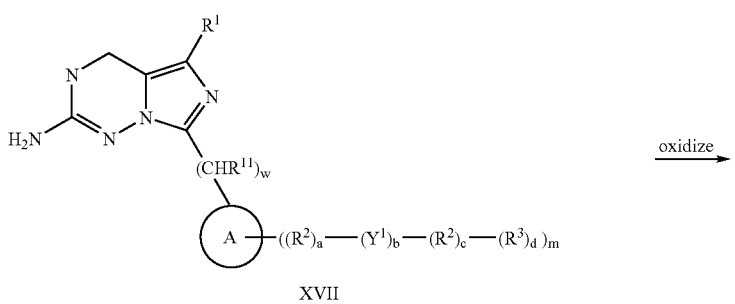

XVII

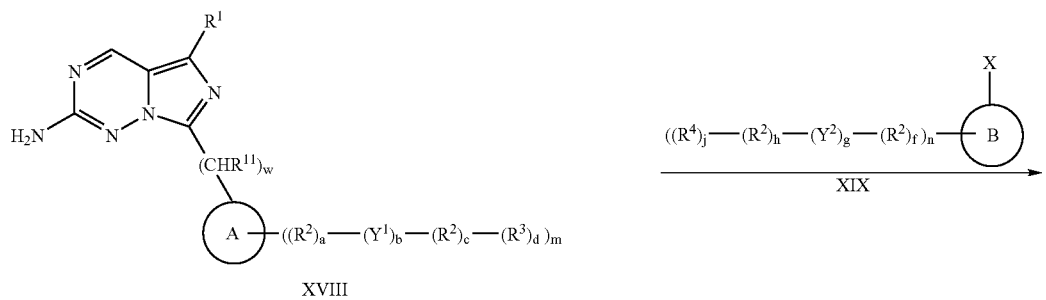

XVIII

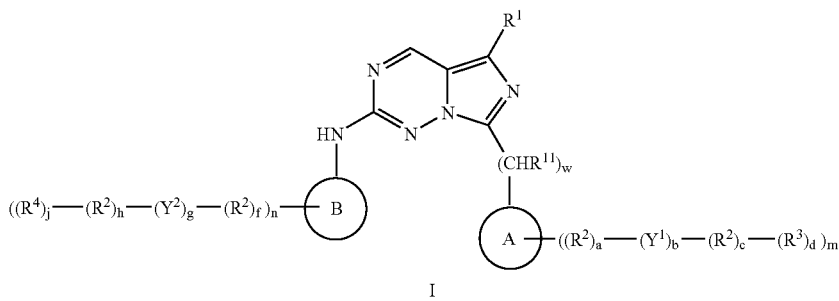

I wherein:
w is 0 or 1;
$R^{11}$ is H or $C_{1-3}$alkyl;
$R^1$ is alkyl;
Ring A is selected from the group consisting of cycloalkyl, aryl, 5-13 membered heterocycle and 5-13 membered heteroaryl;
Ring B is selected from the group consisting of cycloalkyl, aryl, 5-13 membered heterocycle and 5-13 membered heteroaryl;
a, b, c, f, g, and h are the same or different and are each independently 0 or 1;
d and j are the same or different and are independently 1 or 2;
each $R^2$ is the same or different and is alkylene;

$Y^1$ and $Y^2$ are the same or different and are each independently selected from the group consisting of —O—, —S(O)$_q$— and —N($R^5$)—;
q is 0, 1 or 2;
each $R^3$ and $R^4$ are the same or different and are each independently selected from the group consisting of H, halo, alkyl, alkenyl, alkynyl, cycloalkyl, Ph, Het, —O$R^5$, —S(O)$_p R^5$, —S(O)$_2$OH, —S(O)$_p$N$R^5 R^6$, —N$R^5 R^6$ and —N$R^5 SO_2 R^6$;
each p is the same or different and is 0, 1 or 2;
m and n are the same or different and are each independently 0, 1, 2, 3, 4 or 5;
each $R^5$ and each $R^6$ are the same or different and are each independently selected from the group consisting of H, alkyl and cycloalkyl;

Ph is phenyl optionally substituted by one or more substituents selected from the group consisting of halo, alkyl, —OR⁵, —SO₂R⁵, —SO₂NR⁵R⁶, —NR⁵R⁶, Het, and —R²-Het;

Het is a monocyclic 5-6 membered heterocycle or heteroaryl group containing 1, 2 or 3 heteroatoms selected from the group consisting of N, O, and S optionally substituted by one or more substituents selected from the group consisting of halo, alkyl, —OR⁵, —SO₂R⁵, —SO₂NR⁵R⁶, —NR⁵R⁶ and oxo; and X is Cl, Br, I or triflate.

Generally, the process for preparing the compounds of formula (I) (all formulas and all other variables having been defined above in connection with Scheme 2) comprises the steps of:
(a) reacting a compound of formula (XV) with a cyclization reagent to prepare a compound of formula (XVI);
(b) reducing the compound of formula (XVI) with a reducing agent to prepare a compound of formula (XVII);
(c) oxidizing a compound of formula (XVII) with an oxidizing reagent to prepare a compound of formula (XVIII); and
(d) reacting (i.e., coupling) a compound of formula (XVIII) with a compound of formula (XIX) to prepare a compound of formula (I).

The order of the foregoing steps is not critical to the practice of the invention and the process may be practiced by performing the steps in any suitable order based on the knowledge of those skilled in the art.

More specifically, a compound of formula (I) can be prepared by coupling a compound of formula (XVIII) with a compound of formula (XIX).

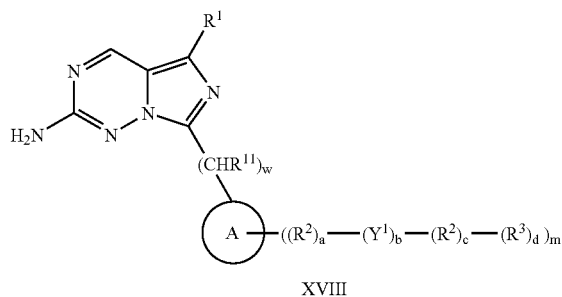

XVIII

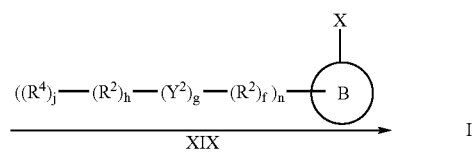

wherein all variables are as defined above in connection with Scheme 2.

The coupling reaction may be accomplished using techniques known in the art for Buchwald-Hartwig amination. Typically, the reaction is carried out in the presence of a palladium salt, a suitable ligand and a base. Typically, the reaction is carried out in an inert solvent. The reaction may be optionally heated to a temperature of from about 20 to about 150° C. Examples of suitable palladium salts include but are not limited to, palladium (II) acetate and tris(dibenzylideneacetone)dipalladium (0). Suitable ligands include but are not limited to 2,2'-bis(diphenylphosphino)-1,1'-binapthyl, tri-t-butylphosphine, 2-(di-t-butylphosphino)biphenyl and 1,1'-bis(diphenylphosphino)ferrocene. Suitable bases include but are not limited to, sodium t-butoxide and cesium carbonate. Suitable solvents include but are not limited to, dioxane, toluene and ethylene glycol dimethyl ether. Compounds of formula (XIX) are commercially available or may be prepared using conventional techniques.

A compound of formula (XVIII) can be prepared by oxidizing a compound of formula (XVII) with an oxidizing agent.

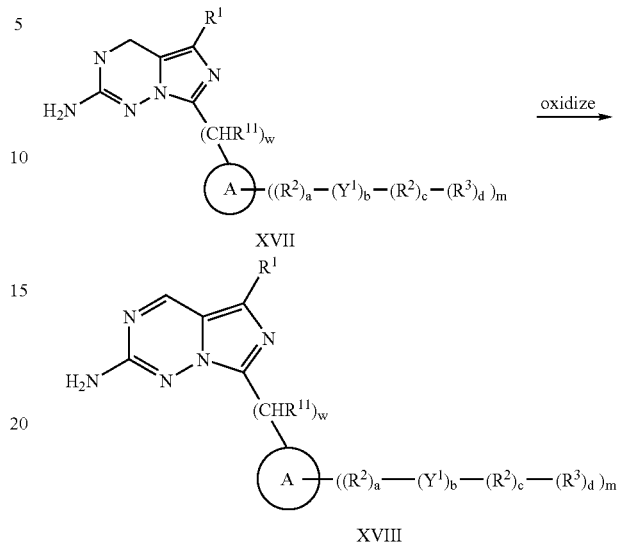

wherein all variables are as defined above in connection with Scheme 2.

The reaction is typically carried out in an inert solvent. The reaction may be optionally heated to a temperature of from about 80 to about 200° C. Examples of suitable oxidizing agents include but are not limited to, palladium (0) on carbon with ambient oxygen. Suitable solvents include but are not limited to, ethanol, toluene, tetrahydrofuran, dioxane, p-cymene, and ethylene glycol dimethyl ether.

A compound of formula (XVII) can be prepared by reducing a compound of formula (XVI) with a reducing agent.

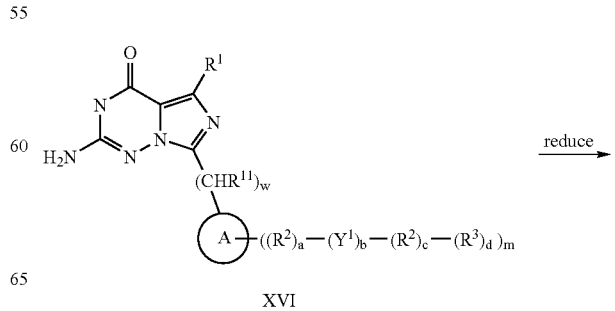

XVI

-continued

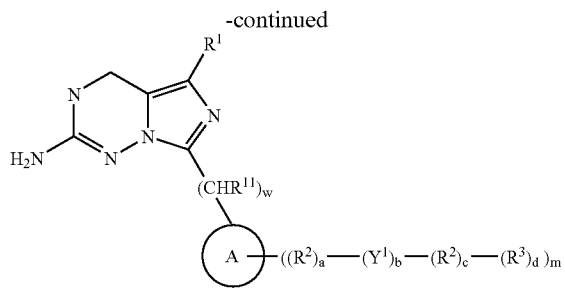

XVII wherein all variables are as defined above in connection with Scheme 2.

The reaction is typically carried out in an inert solvent. The reaction may be optionally heated to a temperature of from about 70 to about 120° C. Examples of suitable reducing agents include but are not limited to, lithium aluminum hydride. Suitable solvents include but are not limited to, tetrahydrofuran and ethylene glycol dimethyl ether.

A compound of formula (XVI) can be prepared by reacting a compound of formula (XV) with a cyclization reagent.

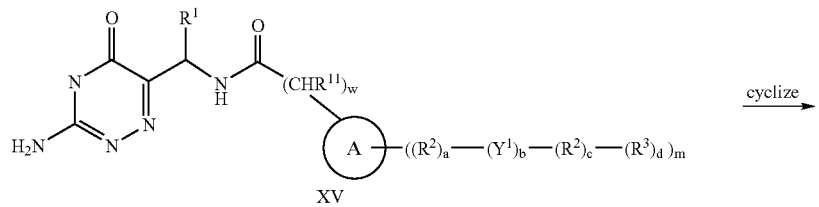

XV

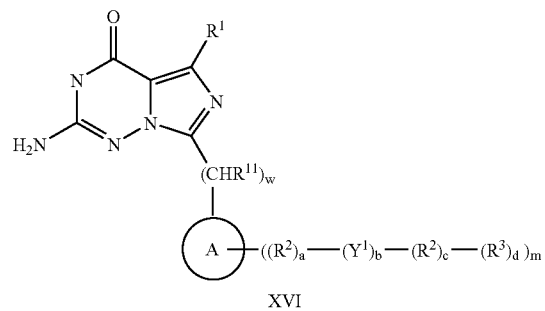

XVI wherein all variables are as defined above in connection with Scheme 2.

The reaction is typically carried out neat or in a suitable solvent. The reaction may be optionally heated to a temperature of from about 20 to about 150° C. Examples of suitable cyclization reagents include but are not limited to, phosphorous oxychloride, thionylchloride, oxalylchloride, and polyphosphoric acid. Examples of suitable additives include but are not limited to, 1,2,4-triazole, N,N-dimethylformamide, and tetrabutylammonium chloride. Suitable solvents include but are not limited to, 1,2-dichloroethane, dichloromethane and chloroform.

Compounds of formula (XV) may be prepared by one skilled in the art according to literature procedures from the corresponding acids and amines. See, Charles, I., et al., *J. Chem. Soc. Perkins Trans. I.* 1139-1146 (1980) and Knutsen, L., et al., *J. Chem. Soc. Perkins Trans. I.* 229-238 (1984).

As will be appreciated by those skilled in the art, a compound of formula (I) prepared according to any of the foregoing synthesis methods may be converted to a different compound of formula (I) using conventional techniques. For example, a compound of formula (I) may be converted to a different compound of formula (I) by palladium catalyzed coupling. There are several conventional reaction mechanisms that may be employed to effect this coupling.

For example a compound of formula (I-A) may be converted to a compound of formula (I-B) using a Heck reaction.

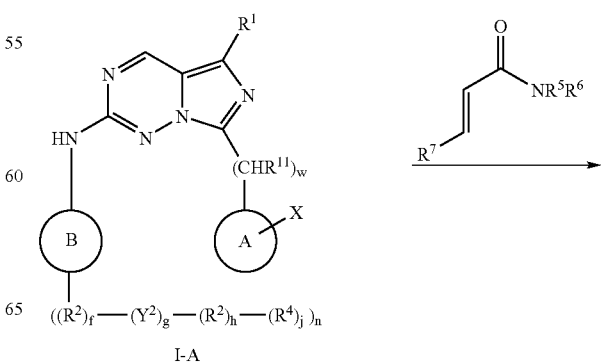

I-A

-continued

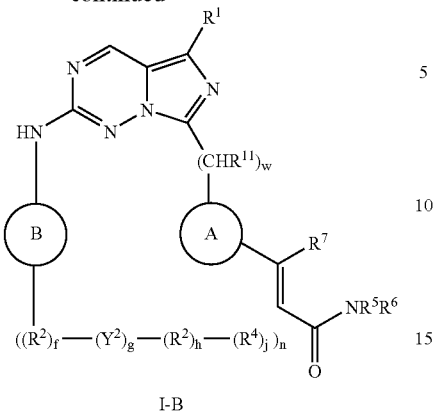

I-B wherein:

Ring A is selected from the group consisting of aryl and 5-13 membered heteroaryl;

the group —$((R^2)_f$—$(Y^2)_g$—$(R^2)_h$—$(R^4)_j)_n$ is not Cl, Br, I or triflate;

X is Cl, Br, I, or triflate;

$R^7$ is H or Ph; and all other variables are as defined above.

Typically, the reaction is carried out in the presence of a catalytic amount of palladium salt, a suitable ligand and a base. The reaction is typically carried out in an inert solvent. The reaction may be optionally heated to a temperature of from about 20 to about 150° C. Examples of suitable palladium salts include but are not limited to, palladium (II) acetate, tris(dibenzylideneacetone)dipalladium (0) and tetrakis(triphenylphosphine) palladium (0). Suitable ligands include but are not limited to triphenylphosphine and tris(o-tolyl)phosphine. Suitable bases include but are not limited to triethylamine and potassium carbonate. Suitable solvents include but are not limited to dioxane, toluene and acetonitrile.

In another embodiment, a compound of formula (I-A) may be converted to a compound of formula (I-C) using Sonagashira reaction conditions.

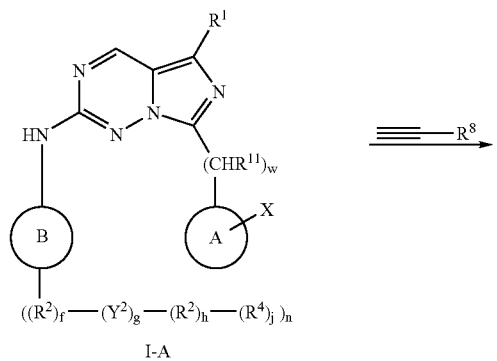

I-A

-continued

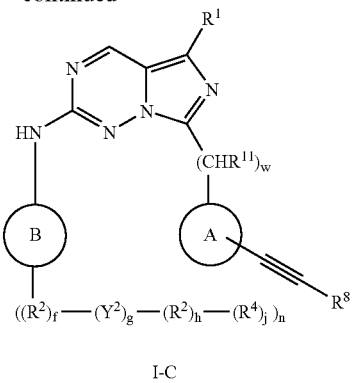

I-C wherein:

Ring A is selected from the group consisting of aryl and 5-13 membered heteroaryl;

the group —$((R^2)_f$—$(Y^2)_g$—$(R^2)_h$—$(R^4)_j)_n$ is not Cl, Br, I or triflate;

X is Cl, Br, I, or triflate;

$R^8$ is —$(R^2)_c$—$R^3$, wherein c, $R^2$ and $R^3$ are as defined above; and all other variables are as defined above.

Typically, the reaction is carried out in the presence of a catalytic amount of palladium salt, a catalytic amount of copper salt, a suitable ligand and a base. The reaction is typically carried out in an inert solvent. The reaction may be optionally heated to a temperature of from about 20 to about 150° C. Examples of suitable palladium salts include but are not limited to, bis(triphenylphosphine)-palladium (II) chloride. Suitable copper salts include but are not limited to copper (I) iodide. Suitable bases include but are not limited to, triethylamine. Suitable solvents include but are not limited to, dimethylformamide.

In another embodiment, a compound of formula (I-A) may be converted to a compound of formula (I-D) using Suzuki reaction conditions.

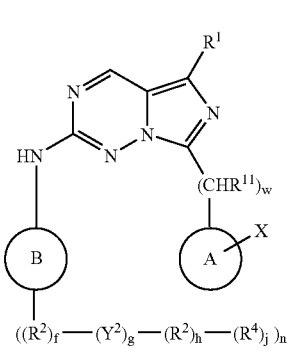 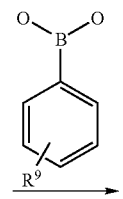

I-A

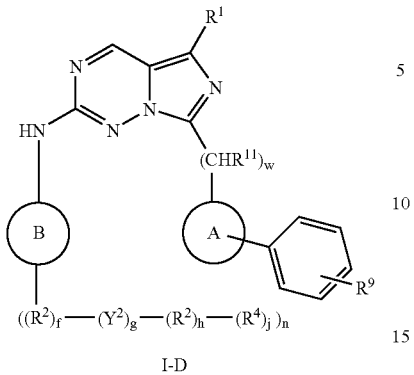

I-D wherein:

Ring A is selected from the group consisting of aryl and 5-13 membered heteroaryl;

the group —$((R^2)_f$—$(Y^2)_g$—$(R^2)_h$—$(R^4)_j)_n$ is not Cl, Br, I or triflate;

X is Cl, Br, I, or triflate;

$R^9$ is selected from the group consisting of halo, alkyl, —$OR^5$, —$SO_2R^5$, —$SO_2NR^5R^6$, —$NR^5R^6$, Het and —$R^2$-Het; and all other variables are as defined above.

Typically, the reaction is carried out in the presence of a catalytic amount of palladium salt, a suitable ligand and a base. The reaction is typically carried out in mixture of an organic solvent and water. The reaction may be optionally heated to a temperature of from about 20 to about 150° C. Examples of suitable palladium salts include but are not limited to, tetrakis(triphenylphosphine) palladium (0). Suitable ligands include but are not limited to, triphenylphosphine and tris(o-tolyl)phosphine. Suitable bases include but are not limited to, potassium carbonate. Suitable organic solvents include but are not limited to, dioxane, acetonitrile and 1,2-dimethyl-ethylene glycol.

In another embodiment, a compound of formula (I-A) is converted to a compound of formula (I-E) using a Buchwald-Hartwig amination.

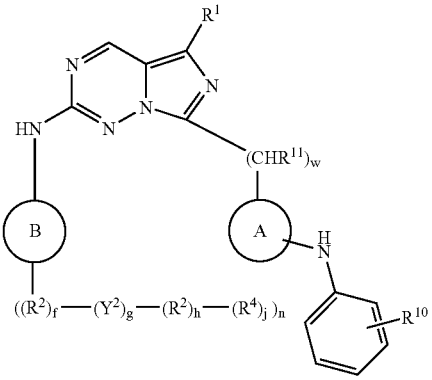

I-E wherein:

Ring A is selected from the group consisting of aryl and 5-13 membered heteroaryl;

the group —$((R^2)_f$—$(Y^2)_g$—$(R^2)_h$—$(R^4)_j)_n$ is not Cl, Br, I or triflate;

X is Cl, Br, I, or triflate;

$R^{10}$ is selected from the group consisting of halo, alkyl, —$OR^5$, —$SO_2R^5$, —$SO_2NR^5R^6$, —$NR^5R^6$, Het and —$R^2$-Het; and all other variables are as defined above.

Typically, the reaction is carried out in the presence of a catalytic amount of palladium salt, a suitable ligand and a base. Typically, the reaction is carried out in an inert solvent. The reaction may be optionally heated to a temperature of from about 20 to about 150° C. Examples of suitable palladium salts include but are not limited to, palladium (II) acetate and tris(dibenzylideneacetone)dipalladium (0). Suitable ligands include but are not limited to 2,2'-bis(diphenylphosphino)-1,1'-binapthyl, tri-t-butylphosphine, 2-(di-t-butylphosphino)biphenyl and 1,1'-bis(diphenylphosphino)ferrocene. Suitable bases include but are not limited to, sodium t-butoxide and cesium carbonate. Suitable solvents include but are not limited to, dioxane, toluene and ethylene glycol dimethyl ether.

In addition, a compound of formula (I) may be converted to a different compound of formula (I) by reacting a compound of formula (I) bearing an ester functionality with a suitable nucleophile. For example, a compound of formula (I-F) may be converted to a compound of formula (I-G) by reacting with an amine.

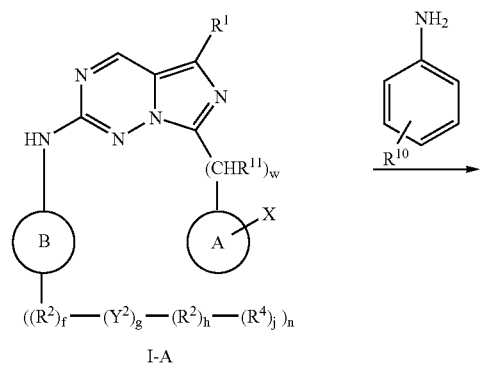

I-A

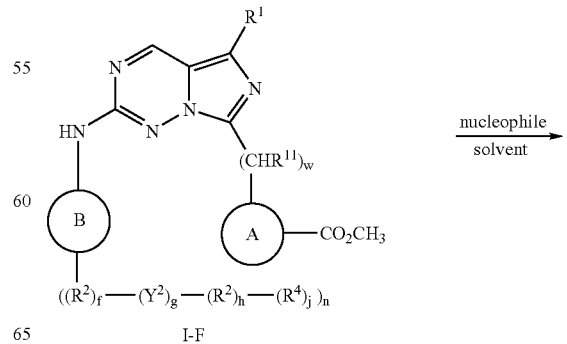

I-F

-continued

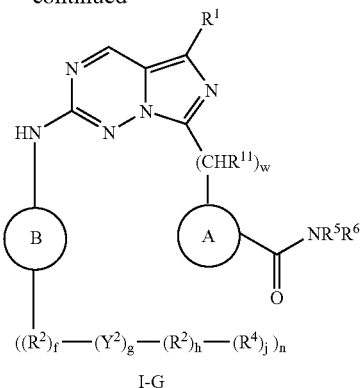

I-G wherein:
Ring A is selected from the group consisting of aryl and 5-13 membered heteroaryl;
the group $-((R^2)_f-(Y^2)_g-(R^2)_h-(R^4)_j)_n$ is not an ester functionality; and
all other variables are as defined above.

Typically, the reaction is carried out by mixing the compound of formula (I-F) with a nucleophile, such as an amine or substituted amine (e.g., $-NR^5R^6$) in an inert solvent. The reaction may be optionally heated to a temperature of from about 20 to about 250° C. Suitable solvents include but are not limited to, methanol, dioxane and tetrahydrofuran.

In another example a compound of formula (I-H) may be hydrolyzed to convert to a compound of formula (I-J).

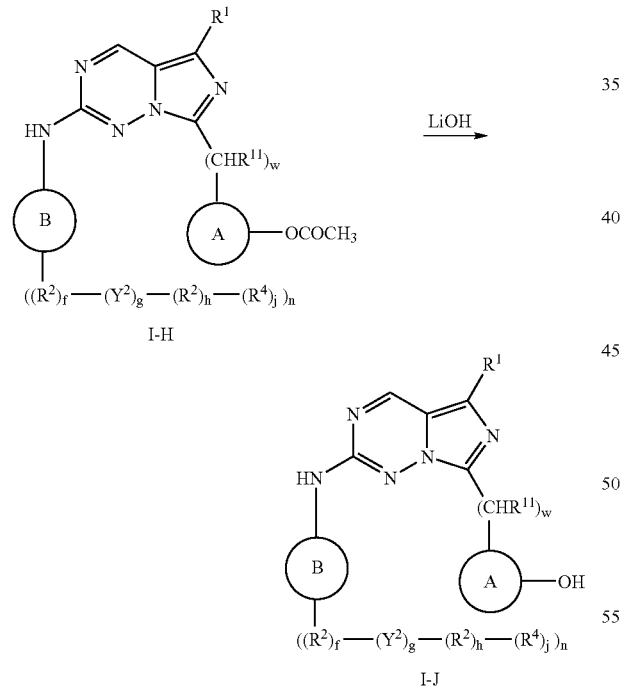

wherein:
Ring A is selected from the group consisting of aryl and 5-13 membered heteroaryl;
the group $-(R^2)_f-(Y^2)_g-(R^2)_h-(R^4)_j)_n$ is not an ester functionality; and
all other variables are as defined above.

Typically, the reaction is carried out by hydroylzing an ester with an aqueous base in a mixture of an organic solvent and water. The reaction may be optionally heated to a temperature of from about 20 to about 100° C. Suitable bases include but are not limited to, lithium hydroxide, sodium hydroxide and potassium hydroxide. Suitable organic solvents include but are not limited to, tetrahydofuran and dioxane.

In each of the foregoing specific examples, the conversion reaction involves changing a functionality on Ring A. As will be apparent to those skilled in the art, such reactions are equally applicable for converting substituents on Ring B. Further, in the foregoing reactions, it is noted that the substituent on Ring B is not the same substituent as that on Ring A. Each of the foregoing reactions may be conducted wherein the substituents on Ring A and Ring B are the same, and will result in the reaction of both substituents on Ring A and Ring B.

Based upon this disclosure and the examples contained herein one skilled in the art can readily convert a compound of formula (I) or a pharmaceutically acceptable salt, solvate or physiologically functional derivative thereof into another compound of formula (I), or a pharmaceutically acceptable salt, solvate or physiologically functional derivative thereof.

The present invention also provides radiolabeled compounds of formula (I) and biotinylated compounds of formula (I) and solid-support-bound versions thereof. Radiolabeled compounds of formula (I) and biotinylated compounds of formula (I) can be prepared using conventional techniques. For example, radiolabeled compounds of formula (I) can be prepared by reacting the compound of formula (I) with tritium gas in the presence of an appropriate catalyst to produce radiolabeled compounds of formula (I). In one embodiment, the compounds of formula (I) are tritiated.

The radiolabeled compounds of formula (I) and biotinylated compounds of formula (I) are useful in assays for the identification of compounds which inhibit PLK, for the identification of compounds for the treatment of a condition mediated by PLK, for the treatment of susceptible neoplasms, for the treatment of conditions characterized by inappropriate proliferation, for the inhibition of proliferation of a cell and for the inhitibion of mitosis in a cell. Accordingly, the present invention provides an assay method for identifying such compounds, which method comprises the step of specifically binding the radiolabeled compound of formula (I) or the biotinylated compound of formula (I) to the target protein or cellular homogenates. More specifically, suitable assay methods will include competition binding assays. The radiolabeled compounds of formula (I) and biotinylated compounds of formula (I) and solid-support-bound verstions thereof, can be employed in assays according to the methods conventional in the art.

The following examples are intended for illustration only and are not intended to limit the scope of the invention in any way, the invention being defined by the claims which follow.

Reagents are commercially available or are prepared according to procedures in the literature.

Intermediate 1: tert-Butyl 2-(1,3-dithian-2-yl)-1-methyl-2-oxoethyl carbamate

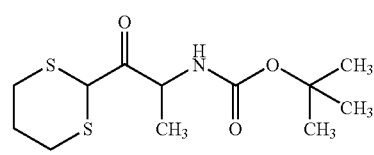

In a similar manner as described in Brown, P., et al., *J. Med. Chem.* 39:446-457 (1996), to a mechanically stirred solution of 1,3-dithiane (310 g 2.6 mol) in tetrahydrofuran (3.0 L)

under a nitrogen atmosphere at −25° C. was added a solution of 2.5 M n-butyl lithium in hexanes (1033 mL, 2.6 mol) at a rate to keep the temperature of the solution between −15 and −25° C. After two hours, N-(tert-butoxycarbonyl)-L-alanine N-methoxy-N-methylamide (240 g, 1.0 mol) was added in portions at such a rate to keep the temperature of the solution below −5° C. After an additional 1.5 hours at −15° C., the reaction was quenched by adding acetic acid (193 mL) to the solution at such a rate to keep the temperature below 15° C. To the solution was added ethyl acetate (1 L) and water (1 L), and the solution was stirred vigorously for thirty seconds. The water layer was removed and washed with ethyl acetate (200 mL). The ethyl acetate layers were combined and washed with water (3 ×1 L), saturated sodium bicarbonate solution (3×1 L) and brine (1 L). The solution was dried with magnesium sulfate, filtered and concentrated under reduced pressure until an oil remained. To the oil was added heptane (1 L) and crystals formed as the solution stood at room temperature overnight. The solution was concentrated under reduced pressure and heptane (1 L) added to form a slurry with the solid. The solid was collected by vacuum filtration, washed with heptane (6×1 L) and hexanes (1 L), and air dried to give tertbutyl butyl 2-(1,3-dithian-2-yl)-1-methyl-2-oxoethyl carbamate (232 g) as a white solid. $^1$H NMR (CDCl$_3$): δ5.08 (br, 1H), 4.63 (br, 1H), 4.42 (s, 1H), 3.31 (dd, J =13.4, 12.4 Hz, 1H), 3.21-3.12 (m, 1H), 2.6-2.51 (m, 2H), 2.16-1.92 (m, 2H) 1.43 (s, 9H), 1.38 (d, J=6.9 Hz, 3H). MS m/z 292, 314 (M+1, M+23)

Intermediate 2: tert-Butyl-2-[(aminocarbonothioyl) hydrazono]-2-(1,3-dithian-2-yl)-1-methylethylcarbamate

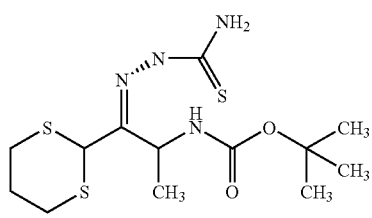

To a mechanically stirred solution of tert-butyl 2-(1,3-dithian-2-yl)-1-methyl-2-oxoethyl carbamate (Intermediate 1) (190 g, 0.65 mol) in ethanol (4.0 L) was added thio semicarbazide (71 g, 0.78 mol) followed by 4-toluenesulfonic acid monohydrate (4.9 g, 26 mmol). The solution was heated to 78° C. causing the solids to dissolve. The solution was stirred at 78° C. for 72 hours adding additional 4-toluenesulfonic acid monohydrate (4.9 g, 26 mmol) after 24 and 48 hours. The solution was allowed to cool to room temperature and concentrated under reduced pressure until about 200 mL remained. Diethylether (1.5 L) was added to the solution and the product crystallized out of the solution over 72 hours. The solid was collected by vacuum filtration, washed with diethylether (4×1 L) and hexanes (2×1 L), and air dried to give tert-butyl-2-[(aminocarbonothioyl)-hydrazono]-2-(1,3-dithian-2-yl)-1-methylethylcarbamate (214 g) as a pale-yellow solid. The filtrate was concentrated under reduced pressure until an oil remained. Diethylether (1 L) and hexanes (3 L) were added to the oil and a second crop of product (44 g) was collected. MS m/z 365 (M+1).

Intermediate 3: tert-Butyl 1-[3-(methylthio)-1,2,4-triazin-6-yl]ethylcarbamate and terbutyl 1-[3-(methylthio)-1,2,4-triazin-5-yl]ethylcarbamate

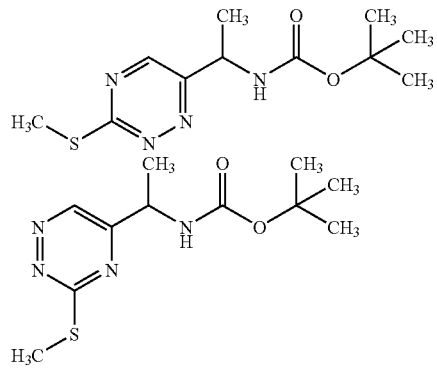

To a mechanically stirred solution of tert-butyl-2-[(aminocarbonothioyl)hydrazono]-2-(1,3-dithian-2-yl)-1-methylethylcarbamate (Intermediate 2) (600 g, 1.6 mol) in acetonitrile (11 L) and water (1.3 L) was added calcium carbonate (490 g, 4.9 mol) followed by slow addition of iodomethane (2.3 kg, 16 mol) using an addition funnel. After the addition was complete, the solution was heated to 40° C. for 24 hours. The solution was allowed to cool to room temperature and concentrated under reduced pressure until about 1.5 L remained. Water (1.0 L) was added to the solution and the product was extracted with ethyl acetate (6×1 L). The combined extracts were washed with water (4×1 L) and brine (1 L). The solution was dried with magnesium sulfate, filtered and concentrated until a red oil remained (190 g). The oil was dissolve in dichloromethane (250 mL) and 25 mL of this solution was loaded into a RediSep silica gel cartridge (330 g; ISCO) and subjected to a gradient elution using dichlormethane to dichloromethane:ethyl acetate (70:30). The separation was repeated in 25 mL portions until all of the solution was consumed. The appropriate (higher Rf) fractions were combined and concentrated under reduced pressure to give tert-butyl 1-[3-(methylthio)-1,2,4-triazin-6-yl]ethylcarbamate (74 g) as a yellow solid. $^1$H NMR (CDCl$_3$): δ8.41 (s, 1H), 5.35 (br, 1H), 4.99 (br, 1H), 2.67 (s, 3H), 1.57 (d, J=6.9 Hz, 3H), 1.42 (s, 9H).). MS m/z 271 (M+1). Additionally, the appropriate (lower Rf) fractions were combined and concentrated under reduced pressure to give the isomer tert-butyl 1-[3-(methylthio)-1,2,4-triazin-5-yl]ethylcarbamate (11 g) as a gold oil. $^1$H NMR (CDCl$_3$): δ8.94 (s, 1H), 5.23 (br, 1H), 4.80 (br, 1H), 2.67 (s, 3H), 1.47 (d, J=7.2 Hz, 3H), 1.43 (s, 9H). MS m/z 271 (M+1).

Intermediate 4: 1-[3-(Methylthio)-1,2,4-triazin-6-yl] ethanamine and 1-[3-(methylthio)-1,2,4-triazin-6-yl] ethanamine hydrochloride

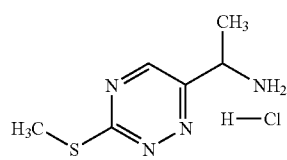

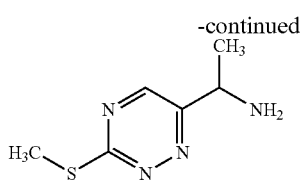

To a stirred solution of tert-butyl 1-[3-(methylthio)-1,2,4-triazin-6-yl]ethylcarbamate (Intermediate 3) (13.3 g, 49 mmol) in methanol (100 mL) was added 4N HCl in dioxane (50 mL). After stirring for 30 minutes the volatiles were removed under reduced pressure to provide a colorless oil. The oil was taken up in ethyl acetate, and the volatiles again removed under reduced pressure to give 1-[3-(methylthio)-1,2,4-triazin-6-yl]ethanamine hydrochloride (10.1 g) as a white solid. MS m/z 171 (M+1). A portion of the white solid (90 mg) was slurried in ethyl acetate and washed with saturated sodium bicarbonate solution causing the solid to dissolve. The volatiles were removed under reduced pressure to give 1-[3-(methylthio)-1,2,4-triazin-6-yl]ethanamine (68 mg) as a foam. MS m/z 171 (M+1).

Intermediate 5: 3-Bromo-N-{1-[3-(methylthio)-1,2,4-triazin-6-yl]ethyl}benzamide

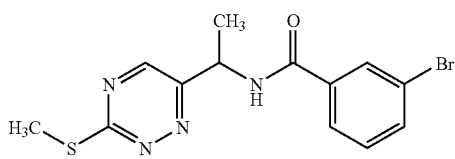

To a stirred solution of 1-[3-(methylthio)-1,2,4-triazin-6-yl]ethanamine hydrochloride (Intermediate 4) (10 g, 49 mmol) in N,N-dimethylformamide (100 mL) was added 3-bromobenzoic acid (11 g, 54 mmol), O-(7-azabenzotriazol-1-yl-N,N,N',N'-tetramethyluronium hexafluorophospahte (20 g, 52 mmol) and triethylamine (24 mL, 170 mmol). After stirring for 18 hours the solution was concentrated under reduced pressure to approximately 50 mL. The solution was diluted with ethyl acetate (200 mL) and washed with 0.1N HCl (2×100 mL) and saturated sodium bicarbonate solution (100 mL). The solution was dried with magnesium sulfate and filtered, and silica gel (25 g) was added to the solution, followed by evaporation of the volatiles under reduced pressure. The pre-adsorbed solids were loaded into a solid loading cartridge and subjected to a gradient elution using ethyl acetate:hexane (0:100) to ethyl acetate:hexanes (40:60) using a RediSep silica gel cartridge (120 g; ISCO). The appropriate fractions were combined and concentrated under reduced pressure to give 3-bromo-N-{1-[3-(methylthio)-1,2,4-triazin-6-yl]ethyl}benzamide (14.5 g) as a white solid. $^1$H NMR (CDCl$_3$): δ8.47(s, 1H), 7.95 (dd, J=1.8, 1.7 Hz, 1H), 7.72 (ddd, J=7.9, 1.6, 1.1 Hz, 1H), 7.64 (ddd, J=7.9, 2.0, 1.1 Hz, 1H), 7.32 (dd, J=8.0, 7.7 Hz, 1H), 7.20 (d, J=7.2 Hz, 1H), 5.47 (dq, J=7.2, 7.0 Hz, 1H), 2.68 (s, 3H), 1.70 (d, J=7.0 Hz, 3H). MS m/z 353, 355 (M+1, M+3).

Intermediate 6: 3-Bromo-N-{1-[3-(methylsulfonyl)-1,2,4-triazin-6-yl]ethyl}benzamide

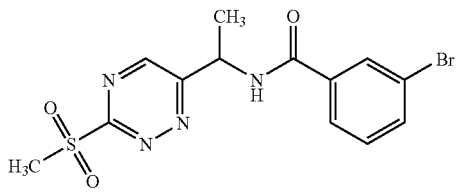

To a stirred solution of 3-bromo-N-{1-[3-(methylthio)-1,2,4-triazin-6-yl]ethyl}benzamide (Intermediate 5) (4.9 g, 14 mmol) in dichloromethane (50 mL) was added 3-chloroperoxybenzoic acid (6.4 g, 28 mmol). After stirring for 3 hours the solution was concentrated under reduced pressure to give a white solid. The solid was slurried in chloroform (100 mL) and washed with saturated sodium bicarbonate solution (2×100 mL) causing all the solid to dissolve. The solution was dried with magnesium sulfate, filtered and the volatiles removed under reduced pressure to give 3-bromo-N-{1-[3-(methylsulfonyl)-1,2,4-triazin-6-yl]ethyl}benzamide (3.8 g) as a white solid. $^1$H NMR (DMSO-d$_6$): δ9.30 (d, J=6.8 Hz, 1H), 9.26 (s, 1H), 8.12 (dd, J=1.8, 1.6 Hz, 1H), 7.89 (ddd, J=7.8, 1.6, 1.1 Hz, 1H), 7.78 (ddd, J=8.0, 2.0, 1.1 Hz, 1H), 7.46 (dd, J=7.9, 7.8 Hz, 1H), 5.67 (dq, J=7.0, 6.8 Hz, 1H), 3.56 (s, 3H), 1.68 (d, J=7.0 Hz, 3H). MS m/z 385, 387 (M+1, M+3).

Intermediate 7: tert-Butyl 1-[3-(methylsulfonyl)-1,2,4-triazin-6-yl]ethylcarbamate

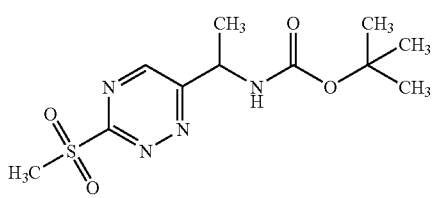

To a stirred solution tert-butyl 1-[3-(methylthio)-1,2,4-triazin-6-yl]ethylcarbamate (Intermediate 3) (1.2 g, 4.5 mmol) in dichloromethane (50 mL) was added 3-chloroperoxybenzoic acid (2.2 g, 9.0 mmol). After stirring for 3 hours the solution was concentrated under reduced pressure to give a white solid. The solid was slurried in chloroform (100 mL) and washed with saturated sodium bicarbonate solution (2×100 mL) causing all the solid to dissolve. The solution was dried with magnesium sulfate, filtered and the volatiles removed under reduced pressure to give tert-butyl 1-[3-(methylsulfonyl)-1,2,4-triazin-6-yl]ethylcarbamate (1.2 g) as a white solid. $^1$H NMR (CDCl$_3$): δ8.87 (s, 1H), 5.30-5.07 (m, 2H), 3.50 (s, 3H), 1.66 (d, J=7.0 Hz, 3H), 1.43 (s, 9H). MS m/z 325 (M+23).

Intermediate 8: tert-Butyl 1-{3-[(3,4,5-trimethoxyphenyl)amino]-1,2,4-triazin-6-yl}ethylcarbamate

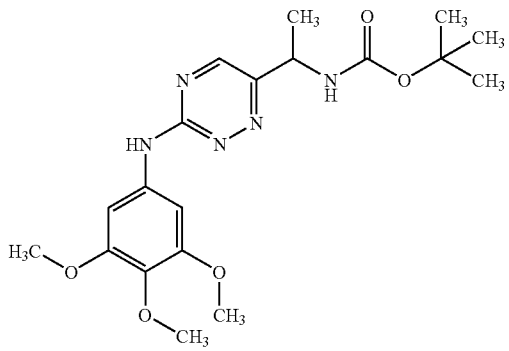

To a stirred solution of tert-butyl 1-[3-(methylsulfonyl)-1,2,4-triazin-6-yl]ethylcarbamate (Intermediate 7) (2.0 g, 6.5 mmol) in tetrahydrofuran (50 mL) was added 3,4,5-trimethoxyaniline (1.8 g, 9.7 mmol) and 4-toluenesulfonic acid monohydrate (60 mg). After stirring for 24 hours, silica gel (10 g) was added to the solution, followed by evaporation of the volatiles under reduced pressure. The pre-adsorbed solids were loaded into a solid loading cartridge and subjected to a gradient elution using ethyl acetate:hexane (20:80) to ethyl acetate:hexanes (50:50) using a RediSep silica gel cartridge (40 g; ISCO). The appropriate fractions were combined and concentrated under reduced pressure to give tert-butyl 1-{3-[(3,4,5-trimethoxyphenyl)amino]-1,2,4-triazin-6-yl}ethylcarbamate (1.3 g) as a white solid. $^1$H NMR (CDCl$_3$): $\delta$8.30 (s, 1H), 7.49 (br, 1H), 6.95 (s, 2H), 5.40-5.30 (m, 1H), 5.00-4.83 (m, 1H), 3.89 (s, 6H), 3.84 (s, 3H), 1.58 (d, J=7.0 Hz, 3H), 1.43 (s, 9H). MS m/z 406 (M+1).

Intermediate 9: 6-(1-Aminoethyl)-N_(3,4,5-trimethoxyphenyl)-1,2,4-triazin-3-amine hydrochloride and 6-(1-aminoethyl)-N-(3,4,5-trimethoxyfhenyl)-1,2,4-triazin-3-amine

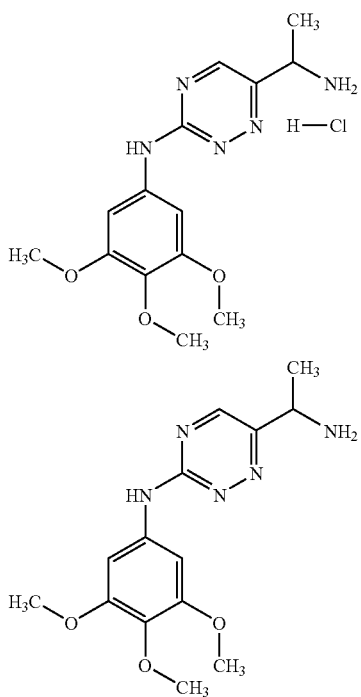

To a stirred solution of tert-butyl 1-[3-(methylthio)-1,2,4-triazin-6-yl]ethylcarbamate (Intermediate 8) (1.2 g, 3.1 mmol) in methanol (10 mL) was added 4N HCl in dioxane (10 mL). After stirring for 30 minutes the volatiles were removed under reduced pressure to provide 6-(1-aminoethyl)-N-(3,4,5-trimethoxyphenyl)-1,2,4-triazin-3-amine hydrochloride as a foam. The foam was dissolved in methanol, ammonium hydroxide was added to neutralize the acid, and silica gel (5 g) was added followed by evaporation of the volatiles under reduced pressure. The pre-adsorbed solids were loaded into a solid loading cartridge and subjected to an isocratic elution using dichloromethane: methanol: ammonium hydroxide (95:4:1) using a RediSep silica gel cartridge (40 g; ISCO). The appropriate fractions were combined and concentrated under reduced pressure to give 6-(1-aminoethyl)-N-(3,4,5-trimethoxyphenyl)-1,2,4-triazin-3-amine (680 mg) as a yellow solid. $^1$H NMR (CDCl$_3$): $\delta$8.42 (s, 1H), 7.38 (s, 1H), 6.97 (s, 2H), 4.38 (d, J=7.0 Hz, 1H), 3.90 (s, 6H), 3.84 (s, 3H), 1.62 (br, 2H), 1.52 (d, J=7.0 Hz, 3H), 1.43 (s, 9H). MS m/z 306 (M+1).

Intermediate 10: 2-Nitro-N-(1-{3-[(3,4,5-trimethoxyphenyl)amino]-1,2,4-triazin-6-yl}ethyl)benzamide

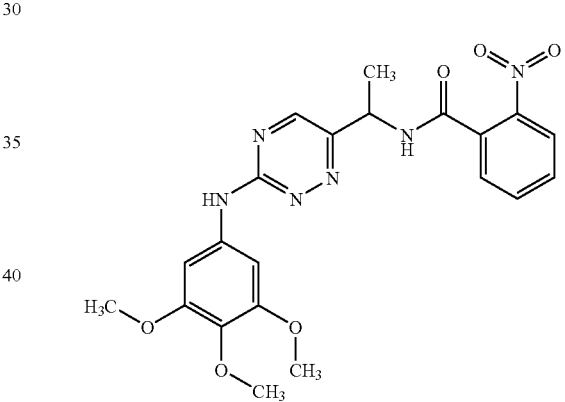

To a stirred solution of 6-(1-aminoethyl)-N-(3,4,5-trimethoxyphenyl)-1,2,4-triazin-3-amine (Intermediate 9) (0.30 g, 1.0 mmol) in dichloromethane (10 mL) cooled to −78° C. was added triethylamine (0.42 mL, 3.0 mmol) and 2-nitrobenzoyl chloride (0.35 mL, 1.5 mmol). After stirring for one hour, the solution was quenched with water and allowed to warm to room temperature. The solution was diluted with dichloromethane (50 mL) and washed with 0.1N HCl (2×50 mL) and brine (50 mL). The solution was dried with magnesium sulfate and filtered, and silica gel (5 g) was added to the solution, followed by evaporation of the volatiles under reduced pressure. The pre-adsorbed solids were loaded into a solid loading cartridge and subjected to a gradient elution using ethyl acetate:hexane (20:80) to ethyl acetate:hexanes (100:0) using a RediSep silica gel cartridge (12 g; ISCO). The appropriate fractions were combined and concentrated under reduced pressure to give 2-nitro-N-(1-{3-[(3,4,5-trimethoxyphenyl)amino]-1,2,4-triazin-6-yl}ethyl)benzamide (0.12 g) as a white solid. MS m/z455 (M+1).

Intermediate 11: N-(1-{3-[(3,4,5-Trimethoxyphenyl)amino]-1,2,4-triazin-6-yl}ethyl)benzamide

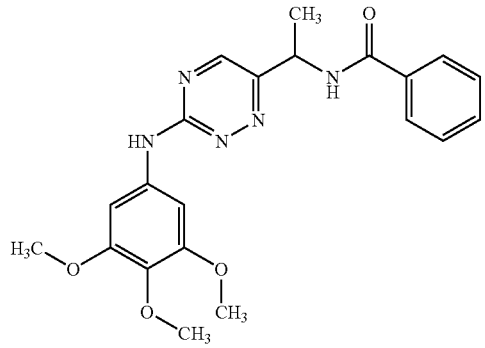

In a similar manner as described for Intermediate 10, 6-(1-aminoethyl)-N-(3,4,5-trimethoxyphenyl)-1,2,4-triazin-3-amine (Intermediate 9) (0.28 g, 0.92 mmol), triethylamine (0.28 mL, 2.0 mmol) and benzoyl chloride (0.14 g, 1.0 mmol) in dichloromethane (10 mL) gave N-(1-{3-[(3,4,5-trimethoxyphenyl)amino]-1,2,4-triazin-6-yl}ethyl)benzamide (0.30 g) as a white solid. MS m/z 410, (M+1).

EXAMPLE 1

5-Methyl-7-phenyl-N-(3,4,5-trimethoxyphenyl)imidazo[5,1-f][1,2,4]triazin-2-amine

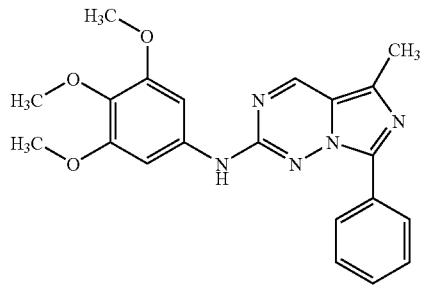

To a solution of N-(1-{3-[(3,4,5-trimethoxyphenyl)amino]-1,2,4-triazin-6-yl}ethyl)benzamide (150 mg, 0.38 mmol) in 1,2-dichloroethane (10 mL) was added phosphorus oxychloride (0.28 mL, 3.0 mmol). The mixture was heated to reflux for 24 hours. After cooling to room temperature, the excess phosphorus oxychloride was quenched with water and silica gel (0.5 g) was added to the reaction mixture, followed by evaporation of the volatiles under reduced pressure. The pre-adsorbed solids were loaded into a solid loading cartridge and subjected to a gradient elution using ethyl acetate:hexane (25:75) to ethyl acetate (100%) using a RediSep silica gel cartridge (4.2 g; ISCO). The appropriate fractions were combined and concentrated under reduced pressure to give 5-methyl-7-phenyl-N-(3,4,5-trimethoxyphenyl)imidazo[5,1-f][1,2,4]triazin-2-amine (0.014 g) as an off-white solid. $^1$H NMR (CDCl$_3$): δ8.78 (s, 1H), 8.43 (d, J=6.9 Hz, 2H), 7.49-7.35 (m, 3H), 6.94 (s, 1H), 6.68 (s, 2H), 3.83 (s, 3H), 3.81 (s, 6H), 2.59 (s, 3H). MS m/z 392 (M+1).

EXAMPLE 2

5-Methyl-7-(2-nitrophenyl)-N-(3,4,5-trimethoxyvhenyl)imidazo[5,1-f][1,2,4]triazin-2-amine

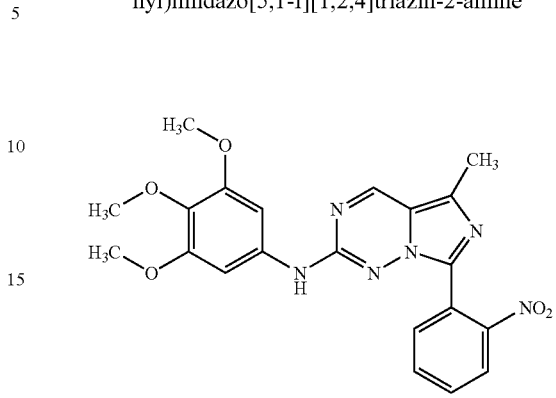

In a similar manner as described for Example 1, 2-nitro-N-(1-{3-[(3,4,5-trimethoxyphenyl)amino]-1,2,4-triazin-6-yl}ethyl)benzamide (Intermediate 10) (0.50 g, 1.5 mmol) in 1,2-dichloroethane (20 mL) and phosphorus oxychloride (1.1 mL, 12 mmol) gave 5-methyl-7-(2-nitrophenyl)-N-(3,4,5-trimethoxyphenyl)imidazo[5,1-f][1,2,4]triazin-2-amine (0.0046 g) as a yellow solid. $^1$H NMR (CDCl$_3$): δ8.82 (s, 1H), 8.09 (dd, J=8.0, 1.1 Hz, 1H), 7.90 (dd, J=7.7, 1.3 Hz, 1H), 7.76 (ddd, J=7.7, 7.5, 1.3 Hz, 1H), 7.64 (ddd, J=8.2, 7.5, 1.5 Hz, 1H), 6.89 (s, 1H), 6.67 (s, 2H), 3.79 (s, 3H), 3.66 (s, 6H), 2.63 (s, 3H). MS m/z 437 (M+1).

Intermediate 12: 2-Bromo-N-(1-{3-[(3,4,5-trimethoxyphenyl)amino]-1,2,4-triazin-6-yl}ethyl)benzamide

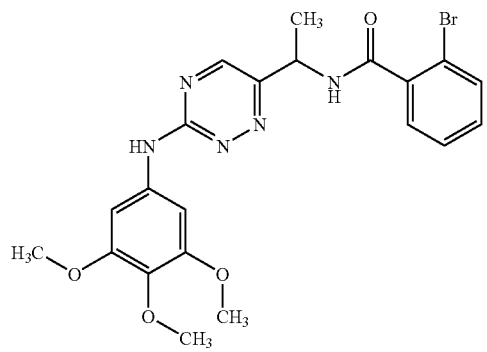

In a similar manner as described for Intermediate 10, 6-(1-aminoethyl)-N-(3,4,5-trimethoxyphenyl)-1,2,4-triazin-3-amine (Intermediate 9) (0.28 g, 0.92 mmol), triethylamine (0.28 mL, 2.0 mmol) and 2-bromobenzoyl chloride (0.22 g, 1.0 mmol) in dichloromethane (10 mL) gave 2-bromo-N-(1-{3-[(3,4,5-trimethoxyphenyl)amino]-1,2,4-triazin-6-yl}ethyl)benzamide (0.45 g) as a white solid. MS m/z 488, 490 (M+1, M+3).

EXAMPLE 3

7-(2-Bromophenyl)-5-methyl-N-(3,4,5-trimethoxyphenylyimidazo-[5,1-f][1,2,4]triazin-2-amine

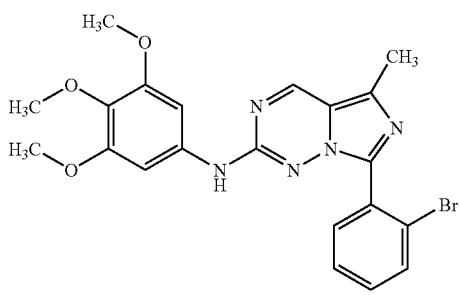

In a similar manner as described for Example 1, 2-bromo-N-(1-{3-[(3,4,5-trimethoxyphenyl)amino]-1,2,4-triazin-6-yl}ethyl)benzamide (Intermediate 12) (0.45 g, 0.92 mmol) in 1,2-dichloroethane (20 mL) and phosphorus oxychloride (0.69 mL, 7.4 mmol) gave 7-(2-bromophenyl)-5-methyl-N-(3,4,5-trimethoxyphenyl)imidazo[5,1-f][1,2,4]triazin-2-amine (0.0069 g) as a yellow solid. $^1$H NMR (CDCl$_3$): δ8.85 (s, 1H), 7.67 (d, J=7.9 Hz, 1H), 7.58 (dd, J=7.6, 1.4 Hz, 1H), 7.44 (dd, J=7.7, 7.3 Hz, 1H), 7.35 (ddd, J=7.9, 7.7, 1.4 Hz, 1H), 6.99 (s, 1H), 6.83 (s, 2H), 3.78 (s, 3H), 3.62 (s, 6H), 2.64 (s, 3H). MS m/z 470, 472 (M+1, M+3).

Intermediate 13: 4-Fluoro-N-(1-{3-[(3,4,5-trimethoxyphenyl)amino]-1,2,4-triazin-6-yl}ethyl)benzamide

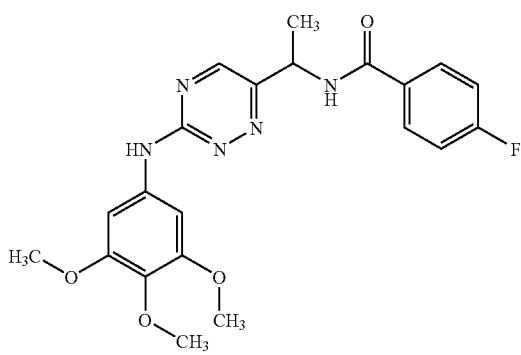

In a similar manner as described for Intermediate 10, 6-(1-aminoethyl)-N-(3,4,5-trimethoxyphenyl)-1,2,4-triazin-3-amine (Intermediate 9) (0.30 g, 1.0 mmol), triethylamine (0.28 mL, 2.0 mmol) and 4-fluorobenzoyl chloride (0.16 g, 1.0 mmol) in dichloromethane (10 mL) gave 4-fluoro-N-(1-{3-[(3,4,5-trimethoxyphenyl)amino]-1,2,4-triazin-6-yl}ethyl)benzamide (0.32 g) as a white solid. MS m/z 428 (M+1).

EXAMPLE 4

7-(4-Fluorophenyl)-5-methyl-N-(3,4,5-trimethoxyphenyl)imidazo-[5,1-f][1,2,4]triazin-2-amine

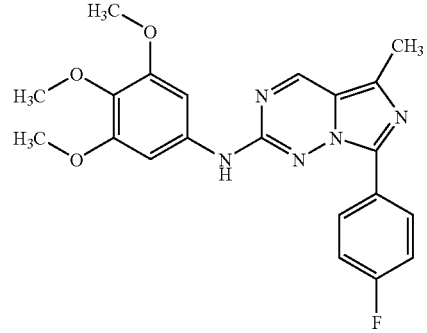

In a similar manner as described for Example 1, 4-fluoro-N-(1-{3-[(3,4,5-trimethoxyphenyl)amino]-1,2,4-triazin-6-yl}ethyl)benzamide (Intermediate 13) (0.16 g, 0.37 mmol) in 1,2-dichloroethane (20 mL) and phosphorus oxychloride (0.28 mL, 3.0 mmol) gave 7-(4-fluorophenyl)-5-methyl-N-(3,4,5-trimethoxyphenyl)imidazo[5,1-f][1,2,4]triazin-2-amine (0.024 g) as a yellow solid. $^1$H NMR (CDCl$_3$): δ8.78 (s, 1H), 8.50-8.42 (m, 2H), 7.17-7.10 (m, 2H), 7.01 (s, 1H), 6.86 (s, 2H), 3.85 (s, 3H), 3.82 (s, 6H), 2.58 (s, 3H). MS m/z 410 (M+1).

Intermediate 14: 3-(Trifluoromethyl)-N-(1-{3-[(3,4,5-trimethoxyphenyl)amino]-1,2,4-triazin-6-yl}ethyl)benzamide

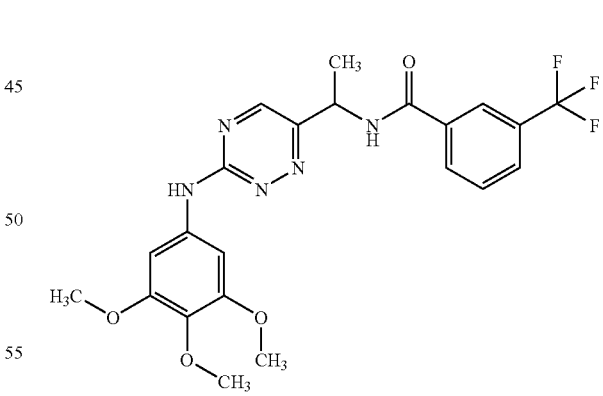

In a similar manner as described for Intermediate 10, 6-(1-aminoethyl)-N-(3,4,5-trimethoxyphenyl)-1,2,4-triazin-3-amine (Intermediate 9) (0.085 g, 0.28 mmol), triethylamine (0.10 mL, 0.72 mmol) and 3-(trifluoromethyl)-benzoyl chloride (0.065 g, 0.31 mmol) in dichloromethane (5 mL) gave 3-(trifluoromethyl)-N-(1-{3-[(3,4,5-trimethoxyphenyl)amino]-1,2,4-triazin-6-yl}ethyl)benzamide (0.12 g) as a yellow oil. MS m/z 478 (M+1).

EXAMPLE 5

5-Methyl-7-[3-(trifluoromethyl)phenyl]-N-(3,4,5-trimethoxyphenyl)-imidazo[5,1-f][1,2,4]triazin-2-amine

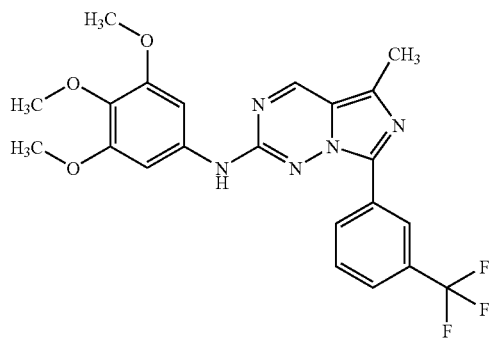

In a similar manner as described for Example 1, 3-(trifluoromethyl)-N-(1-{3-[(3,4,5-trimethoxyphenyl)amino]-1,2,4-triazin-6-yl}ethyl)benzamide (Intermediate 14) (0.12 g, 0.25 mmol) in 1,2-dichloroethane (20 mL) and phosphorus oxychloride (0.28 mL, 3.0 mmol) gave 5-methyl-7-[3-(trifluoromethyl)phenyl]-N-(3,4,5-trimethoxyphenyl)imidazo[5,1-f][1,2,4]triazin-2-amine (0.0038 g) as a yellow solid. $^1$H NMR (CD$_3$OD): δ9.08 (s, 1H), 8.72 (d, J=7.7 Hz, 1H), 8.59 (s, 1H), 7.76-7.65 (m, 2H), 7.00 (s, 2H), 6.99 (s, 1H), 3.76 (s, 3H), 3.74 (s, 6H), 2.60 (s, 3H). MS m/z 460 (M+1).

Intermediate 15: 2-[(2,2-Dimethylpropanoyl)amino]-N-(1-{3-[(3,4,5-trimethoxyphenyl)amino]-1,2,4-triazin-6-yl}ethyl)benzamide

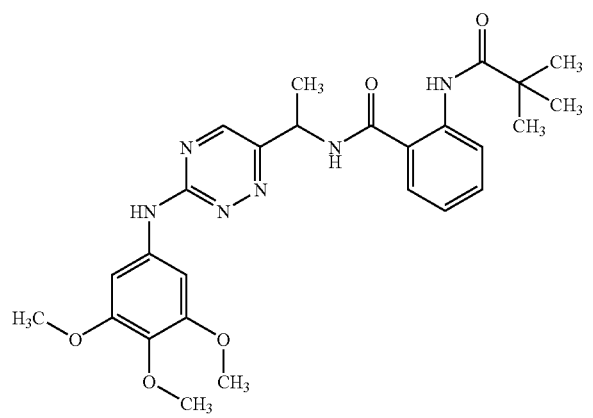

In a similar manner as described for Intermediate 18 (below), 6-(1-aminoethyl)-N-(3,4,5-trimethoxyphenyl)-1,2,4-triazin-3-amine (Intermediate 9) (0.050 g, 0.16 mmol) 2-[(2,2-dimethylpropanoyl)amino]benzoic acid (0.040 g, 0.18 mmol), O-(7-azabenzotriazol-1-yl-N,N,N'N'-tetramethyluronium hexafluorophospahte (0.068 g, 0.18 mmol) and triethylamine (0.048 mL, 0.34 mmol) in N,N-dimethylformamide (1.0 mL) gave 2-[(2,2-dimethylpropanoyl)amino]-N-(1-{3-[(3,4,5-trimethoxyphenyl)amino]-1,2,4-triazin-6-yl}ethyl)benzamide (0.040 g) as a white solid. MS m/z 509 (M+1).

EXAMPLE 6

2,2-Dimethyl-N-(2-{5-methyl-2-[(3,4,5-trimethoxyphenyl)amino]-imidazo[5,1-f][1,2,4]triazin-7-yl}phenyl)propanamide

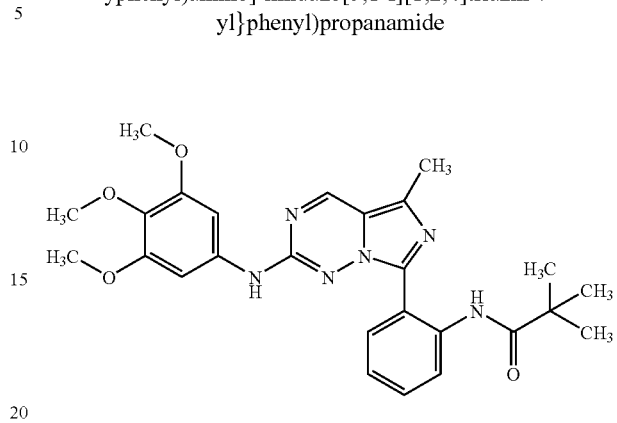

In a similar manner as described for Example 1, 2-[(2,2-dimethylpropanoyl)amino]-N-(1-{3-[(3,4,5-trimethoxyphenyl)amino]-1,2,4-triazin-6-yl}ethyl)benzamide (Intermediate 15) (0.040 g, 0.080 mmol) in 1,2-dichloroethane (10 mL) and phosphorus oxychloride (0.060 mL, 0.64 mmol) gave 2,2-dimethyl-N-(2-{5-methyl-2-[(3,4,5-trimethoxyphenyl)amino]-imidazo[5,1-f][1,2,4]triazin-7-yl}phenyl)propanamide (0.0039 g) as a yellow solid. $^1$H NMR (CDCl$_3$): δ8.87 (s, 1H), 8.66 (dd, J=8.6, 1.2 Hz, 1H), 8.62 (dd, J=8.1, 1.6 Hz, 1H), 7.43-7.37 (m, 1H), 7.16-7.11 (m, 1H), 6.98 (s, 1H), 6.90 (s, 1H), 6.87 (s, 2H), 3.84 (s, 3H), 3.77 (s, 6H), 2.62 (s, 3H), 1.34 (s, 9H). MS m/z 491 (M+1).

Intermediate 16: 2-[(Trifluoroacetyl)amino]-N-(1-{3-[(3,4,5-trimethoxyphenyl)-amino]-1,2,4-triazin-6-yl}ethyl)benzamide

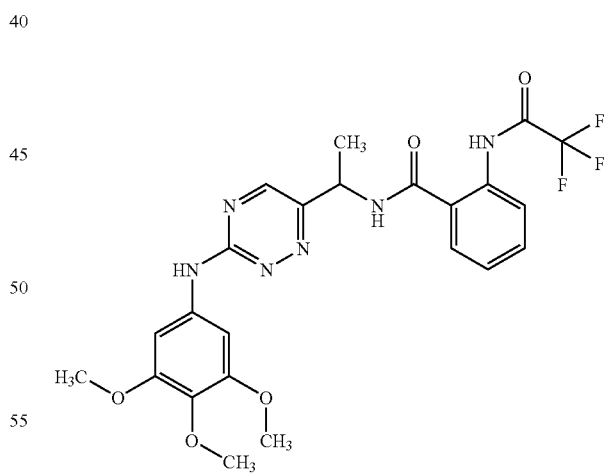

In a similar manner as described for Intermediate 18 (below), 6-(1-aminoethyl)-N-(3,4,5-trimethoxyphenyl)-1,2,4-triazin-3-amine (Intermediate 9) (0.10 g, 0.33 mmol), 2-[(trifluoroacetyl)amino]benzoic acid (0.084 g, 0.36 mmol), O-(7-azabenzotriazol-1-yl-N,N,N',N'-tetramethyluronium hexafluorophospahte (0.14 g, 0.36 mmol) and triethylamine (0.10 mL, 0.73 mmol) in N,N-dimethylformamide (2.0 mL) gave 2-[(trifluoroacetyl)amino]-N-(1-{3-[(3,4,5-trimethoxyphenyl)amino]-1,2,4-triazin-6-yl}ethyl)benzamide (0.12 g) as a white solid. MS m/z 521 (M+1).

azin-6-yl}ethyl)benzamide (0.12 g) as a white solid. MS m/z 435 (M+1).

EXAMPLE 7

2,2,2-Trifluoro-N-(2-{5-methyl-2-[(3,4,5-trimethoxyphenyl)amino]-imidazo[5,1-f][1,2,4]triazin-7-yl}phenyl)acetamide

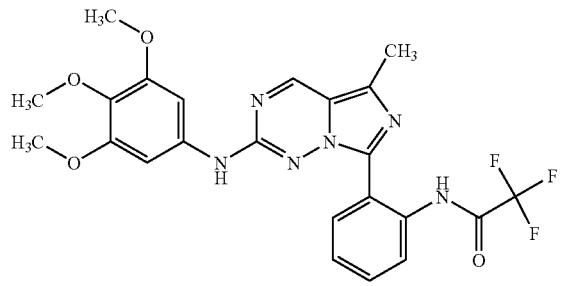

In a similar manner as described for Example 1, 2-[(trifluoroacetyl)amino]-N-(1-{3-[(3,4,5-trimethoxyphenyl)amino]-1,2,4-triazin-6-yl}ethyl)benzamide (Intermediate 16) (0.118 g, 0.23 mmol) in 1,2-dichloroethane (30 mL) and phosphorus oxychloride (1.0 mL, 11 mmol) gave 2,2,2-trifluoro-N-(2-{5-methyl-2-[(3,4,5-trimethoxyphenyl)amino]-imidazo[5,1-f][1,2,4]triazin-7-yl}phenyl)acetamide (0.012 g) as a yellow solid. $^1$H NMR (CDCl$_3$): δ13.87 (s, 1H), 8.91 (dd, J=8.0, 1.4 Hz, 1H), 8.88 (s, 1H), 8.63 (dd, J=8.4, 1.1 Hz, 1H), 7.47-7.41 (m, 1H), 7.28-7.22 (m, 1H), 7.08 (s, 1H), 6.86 (s, 2H), 3.85 (s, 3H), 3.80 (s, 6H), 2.60 (s, 3H). MS m/z 503 (M+1).

Intermediate 17: 3-Cyano-N-(1-{3-[(3,4,5-trimethoxyphenyl)amino]-1,2,4-triazin-6-yl}ethyl)benzamide

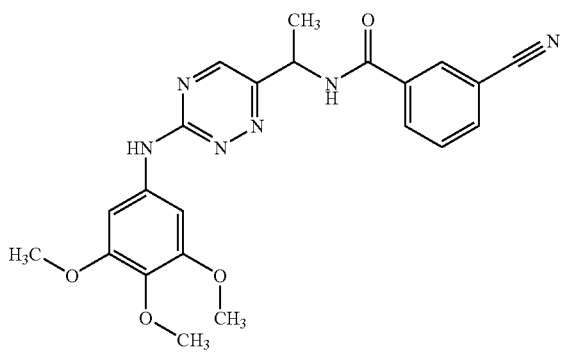

In a similar manner as described for Intermediate 18 (below), 6-(1-aminoethyl)-N-(3,4,5-trimethoxyphenyl)-1,2,4-triazin-3-amine (Intermediate 9) (0.10 g, 0.33 mmol), triethylamine (0.10 mL, 0.73 mmol) and 3-cyanobenzoyl chloride (0.059 g, 0.36 mmol) in dichloromethane (10 mL) gave 3-cyano-N-(1-{3-[(3,4,5-trimethoxyphenyl)amino]-1,2,4-tri-

EXAMPLE 8

3-{5-Methyl-2-[(3,4,5-trimethoxyphenyl)amino]imidazo[5,1-f][1,2,4]triazin-7-yl}benzonitrile

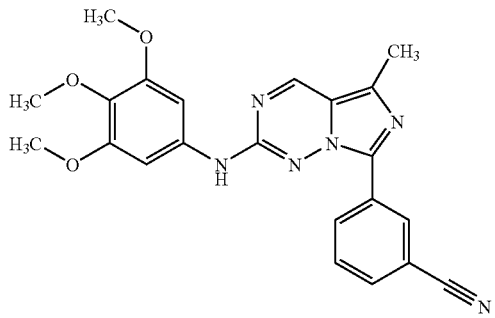

In a similar manner as described for Example 1,3-cyano-N-(1-{3-[(3,4,5-trimethoxyphenyl)amino]-1,2,4-triazin-6-yl}ethyl)benzamide (Intermediate 17) (0.12 g, 0.25 mmol) in 1,2-dichloroethane (20 mL) and phosphorus oxychloride (0.28 mL, 3.0 mmol) gave 3-{5-methyl-2-[(3,4,5-trimethoxyphenyl)amino]-imidazo[5,1-f][1,2,4]triazin-7-yl}benzonitrile (0.023 g) as a yellow solid. $^1$H NMR (CDCl$_3$): δ8.84 (s, 1H), 8.79 (d, J=8.1 Hz, 1H), 8.74 (s, 1H), 7.64 (d, J=7.9 Hz, 1H), 7.54 (dd, J=7.9, 7.8 Hz, 1H) 7.09 (s, 1H), 6.83 (s, 2H), 3.85 (s, 3H), 3.81 (s, 6H), 2.60 (s, 3H). MS m/z 417 (M+1).

Intermediate 18: 3-Bromo-N-(1-{3-[(3,4,5-trimethoxyphenyl)amino]-1,2,4-triazin-6-yl}ethyl)benzamide

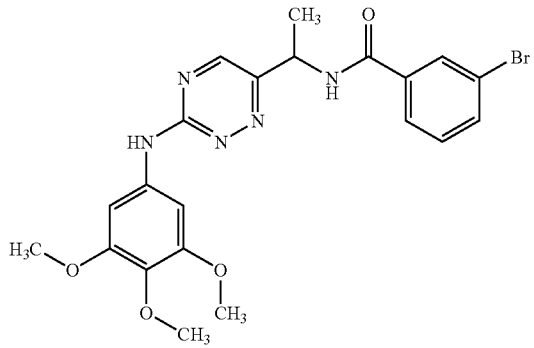

To a stirred solution of 6-(1-aminoethyl)-N-(3,4,5-trimethoxyphenyl)-1,2,4-triazin-3-amine (Intermediate 9) (1.0 g, 3.3 mmol) in N,N-dimethylformamide (10 mL) was added 3-bromobenzoic acid (0.72 g, 3.6 mmol), O-(7-azabenzotriazol-1-yl-N,N,N'N'-tetramethyluronium hexafluorophospahte (1.4 g, 3.6 mmol) and triethylamine (1.0 mL, 7.2 mmol). After stirring for 18 hours the solution was diluted with ethyl acetate (100 mL) and washed with 0.1 N HCl (2×100 mL) and saturated sodium bicarbonate solution (100 mL). The solution was dried with magnesium sulfate and filtered, and silica gel (5 g) was added to the solution, followed by evaporation of the volatiles under reduced pressure. The pre-adsorbed solids were loaded into a solid loading cartridge and subjected to a gradient elution using ethyl acetate:hexane (20:80) to ethyl acetate:hexanes (100:0) using a RediSep silica gel cartridge (40 g; ISCO). The appropriate fractions were combined and concentrated under reduced pressure to give 3-bromo-N-(1-{3-[(3,4,5-trimethoxyphenyl)amino]-1,2,4-triazin-6-yl}ethyl)benzamide (1.2 g) as a white solid. $^1$H NMR (CDCl$_3$): δ9.94(s, 1H), 9.05 (d, J=7.2 Hz, 1H), 8.53 (s, 1H), 8.10 (s, 1H), 7.89 (d, J=7.9 Hz, 1H), 7.73 (d, J=7.9 Hz, 1H), 7.43 (dd, J=8.0, 7.8 Hz, 1H), 7.19 (s, 2H), 5.29 (dd, J=7.2, 7.0 Hz, 1H), 3.75 (s, 6H), 3.61 (s, 3H), 1.59 (d, J=7.0 Hz, 3H). MS m/z 488, 500 (M+1, M+3).

EXAMPLE 9

7-(3-Bromophenyl)-5-methyl-N-(3,4,5-trimethoxyphenyl)imidazo-[5,1-f][1,2,4]triazin-2-amine

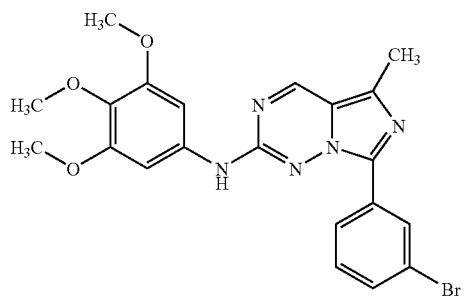

To a solution of 3-bromo-N-(1-{3-[(3,4,5-trimethoxyphenyl)amino]-1,2,4-triazin-6-yl}ethyl)benzamide (Intermediate 18) (490 mg, 1.0 mmol) and 1,2,4-triazole (210 mg, 3.0 mmol) in pyridine (10 mL) was added phosphorus oxychloride (0.14 mL, 1.5 mmol). The mixture was stirred at room temperature for 24 hours. The excess phosphorus oxychloride was quenched with methanol and ammonium hydroxide. The product was extracted into ethyl acetate (100 mL) and washed with 0.1N hydrochloric acid (3×50 mL). The solution was dried with magnesium sulfate and filtered. Silica gel (2.5 g) was added, followed by evaporation of the volatiles under reduced pressure. The pre-adsorbed solids were loaded into a solid loading cartridge and subjected to a gradient elution using ethyl acetate:hexanes (25:75) to ethyl acetate:hexanes (75:25) using a RediSep silica gel cartridge (12 g; ISCO). The appropriate fractions were combined and concentrated under reduced pressure to give 7-(3-bromophenyl)-5-methyl-N-(3, 4,5-trimethoxyphenyl)-imidazo[5,1-f][1,2,4]triazin-2-amine (0.23 g) as a yellow solid. $^1$H NMR (CD$_3$OD): δ9.01 (s, 1H) 8.51 (dd, J=1.9, 1.6 Hz, 1H), 8.33 (ddd, J=7.9, 1.4, 1.1 Hz, 1H), 7.57 (ddd, J=7.9, 1.9, 1.1 Hz, 1H), 7.38 (dd, J=8.1, 7.9 Hz, 1H), 6.99 (s, 2H), 3.76 (s, 6H), 3.75 (s, 3H), 2.56 (s, 3H). MS m/z 470, 472 (M+1, M+3).

Intermediate 19: 3-Bromo-N-(1-{3-[(3,4,5-trimethoxyphenyl)amino]-1,2,4-triazin-6-yl}ethyl)thiophene-2-carboxamide

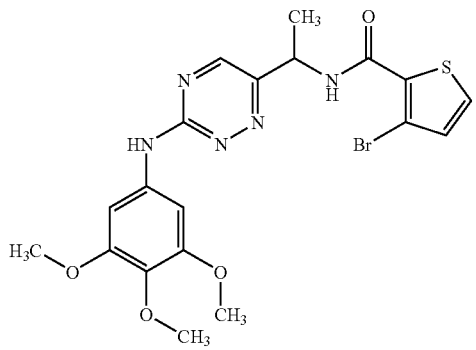

In a similar manner as described for Intermediate 18, 6-(1-aminoethyl)-N-(3,4,5-trimethoxyphenyl)-1,2,4-triazin-3-amine (Intermediate 9) (0.20 g, 0.67 mmol), 3-bromothiophene-2-carboxylic acid (0.27 g, 1.3 mmol), O-(7-azabenzotriazol-1-yl-N,N,N',N'-tetramethyluronium hexafluorophospahte (0.49 g, 1.3 mmol) and triethylamine (0.35 mL, 2.5 mmol) in N,N-dimethylformamide (10 mL) gave 3-bromo-N-(1-{3-[(3,4,5-trimethoxyphenyl)amino]-1, 2,4-triazin-6-yl}ethyl)thiophene-2-carboxamide (0.24 g) as a white solid. MS m/z 494, 496 (M+1, M+3).

EXAMPLE 10: 7-(3-Bromothien-2-yl)-5-methyl-N-(3,4,5-trimethoxyphenyl)-imidazo[1,5-f][1,2,4]triazin-2-amine

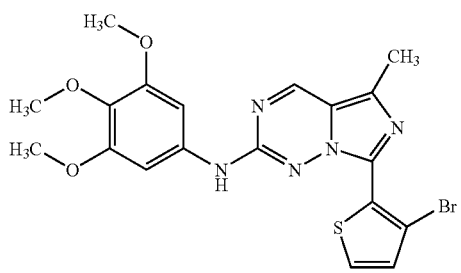

In a similar manner as described for Example 9, 3-bromo-N-(1-{3-[(3,4,5-trimethoxyphenyl)amino]-1,2,4-triazin-6-yl}ethyl)thiophene-2-carboxamide (Intermediate 19) (0.23 g, 0.47 mmol) and 1,2,4-triazole (100 mg, 1.5 mmol) in pyridine (4 mL) and phosphorus oxychloride (0.070 mL, 0.75 mmol) gave 7-(3-bromothien-2-yl)-5-methyl-N-(3,4,5-trimethoxyphenyl)imidazo[5,1-f][1,2,4]triazin-2-amine (0.033 g) as a yellow solid. $^1$H NMR (CDCl$_3$): δ8.82 (s, 1H), 7.47 (d, J=5.3 Hz, 1H), 7.13 (s, 1H), 7.10 (d, J=5.3 Hz, 1H), 6.89 (s, 2H), 3.80 (s, 3H), 3.75 (s, 6H), 2.63 (s, 3H). MS m/z 476, 478 (M+1, M+3).

Intermediate 20: 5-Bromo-N-(1-{3-[(3,4,5-trimethoxyphenyl)amino]-1,2,4-triazin-6-yl}ethyl) nicotinamide

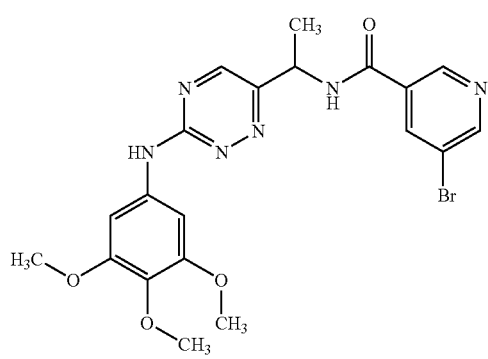

In a similar manner as described for Intermediate 18, 6-(1-aminoethyl)-N-(3,4,5-trimethoxyphenyl)-1,2,4-triazin-3-amine (Intermediate 9) (0.10 g, 033 mmol), 5-bromonicotinic acid (0.073 g, 0.36 mmol), O-(7-azabenzotriazol-1-yl-N,N,N'N'-tetramethyluronium hexafluorophospahte (0.14 g, 0.36 mmol) and triethylamine (0.10 mL, 0.72 mmol) in N,N-dimethylformamide (5 mL) gave 5-bromo-N-(1-{3-[(3,4,5-trimethoxyphenyl)amino]-1,2,4-triazin-6-yl}ethyl)nicotinamide (0.15 g) as a white solid. MS m/z 489, 491 (M+1, M+3).

Intermediate 21: Methyl 3-{[(1-{3-[(3,4,5-trimethoxyphenyl)amino]-1,2,4-triazin-6-yl}ethyl)amino]carbonyl}benzoate

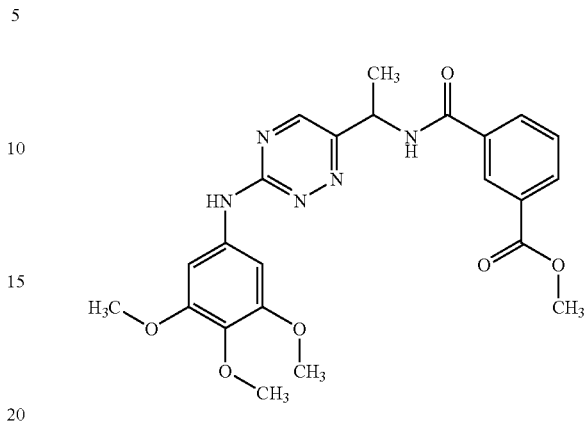

In a similar manner as described for Intermediate 18, 6-(1-aminoethyl)-N-(3,4,5-trimethoxyphenyl)-1,2,4-triazin-3-amine (Intermediate 9) (0.17 g, 0.56 mmol), 3-(methoxycarbonyl)benzoic acid (0.18 g, 0.62 mmol), O-(7-azabenzotriazol-1-yl-N,N,N'N'-tetramethyluronium hexafluorophospahte (0.24 g, 0.62 mmol) and triethylamine (0.17 mL, 1.2 mmol) in N,N-dimethylformamide (5 mL) gave methyl 3-{[(1-{3-[(3,4,5-trimethoxyphenyl)amino]-1,2,4-triazin-6-yl}ethyl)amino]carbonyl}benzoate (0.26 g) as a white solid. MS m/z 468 (M+1).

EXAMPLE 11

7-(5-Bromopyridin-3-yl)-5-methyl-N-(3,4,5-trimethoxyphenyl)-imidazo[5.1-f][1,2,4]triazin-2-amine

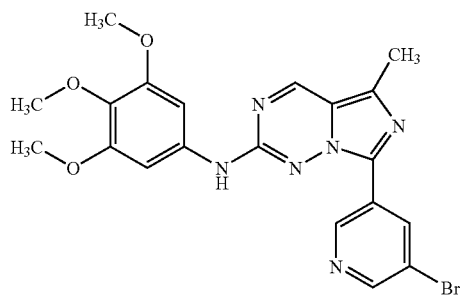

In a similar manner as described for Example 9, 5-bromo-N-(1-{3-[(3,4,5-trimethoxyphenyl)amino]-1,2,4-triazin-6-yl}ethyl)nicotinamide (Intermediate 20) (0.15 g, 0.31 mmol) and 1,2,4-triazole (128 mg, 1.9 mmol) in pyridine (4 mL) and phosphorus oxychloride (0.087 mL, 0.93 mmol) gave 7-(5-bromopyridin-3-yl)-5-methyl-N-(3,4,5-trimethoxyphenyl) imidazo[5,1-f][1,2,4]triazin-2-amine (0.011 g) as a yellow solid. $^1$H NMR (Acetone-$d_6$): δ9.81-9.78 (m, 1H), 9.18 (s, 1H), 8.93-8.90 (m, 1H), 8.73-8.70 (m, 1H), 8.57 (s, 1H) 7.12 (s, 2H), 3.73 (s, 3H), 3.73 (s, 3H), 3.70 (s, 3H), 2.59 (s, 3H). MS m/z 471, 473 (M+1, M+3).

EXAMPLE 12

Methyl 3-{5-methyl-2-[(3,4,5-trimethoxyphenyl)amino]imidazo[5,1-f][1,2,4]triazin-7-yl}benzoate

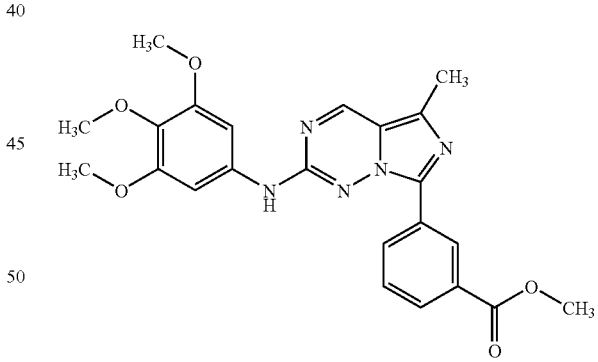

In a similar manner as described for Example 9, methyl 3-{[(1-{3-[(3,4,5-trimethoxyphenyl)amino]-1,2,4-triazin-6-yl}ethyl)amino]carbonyl}benzoate (Intermediate 21) (0.26 g, 0.56 mmol) and 1,2,4-triazole (240 mg, 3.4 mmol) in pyridine (4 mL) and phosphorus oxychloride (0.16 mL, 1.7 mmol) gave methyl 3-{5-methyl-2-[(3,4,5-trimethoxyphenyl)amino]imidazo[5,1-f][1,2,4]triazin-7-yl}benzoate (0.16 g) as a yellow solid. $^1$H NMR (DMSO-$d_6$): δ9.66 (s, 1H), 9.28 (s, 1H), 8.94 (dd, J=1.7, 1.3 Hz, 1H), 8.74 (ddd, J=8.5, 1.9, 1.2 Hz, 1H), 8.01 (ddd, J=7.7, 1.8, 1.2 Hz, 1H), 7.65 (dd, J=8.3, 7.9 Hz, 1H), 7.08 (s, 2H), 3.84 (s, 3H), 3.68 (s, 6H), 3.65 (s, 3H), 2.55 (s, 3H). MS m/z 450 (M+1).

Intermediate 22: 5-Bromo-N-(1-{3-[(3,4,5-trimethoxyphenyl)amino]-1,2,4-triazin-6-yl}ethyl)thiophene-2-carboxamide

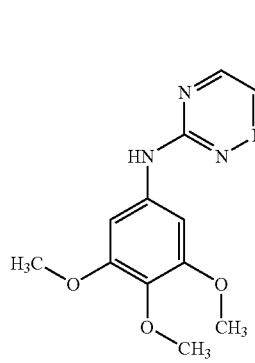

In a similar manner as described for Intermediate 18, 6-(1-aminoethyl)-N-(3,4,5-trimethoxyphenyl)-1,2,4-triazin-3-amine (Intermediate 9) (0.20 g, 0.67 mmol), 5-bromothiophene-2-carboxylic acid (0.15 g, 0.73 mmol), O-(7-azabenzotriazol-1-yl-N,N,N',N'tetramethyluronium hexafluorophospahte (0.28 g, 0.73 mmol) and triethylamine (0.20 mL, 1.4 mmol) in N,N-dimethylformamide (10 mL) gave 5-bromo-N-(1-{3-[(3,4,5-trimethoxyphenyl)amino]-1,2,4-triazin-6-yl}ethyl)thiophene-2-carboxamide (0.35 g) as a white solid. MS m/z 494, 496 (M+1, M+3).

EXAMPLE 13

7-(5-Bromothien-2-yl)-5-methyl-N-(3,4,5-trimethoxyphenyl)imidazo-[5,1-f][1,2,4]triazin-2-amine

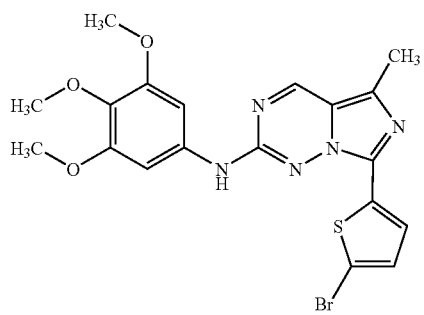

In a similar manner as described for Example 9, 5-bromo-N-(1-{3-[(3,4,5-trimethoxyphenyl)amino]-1,2,4-triazin-6-yl}ethyl)thiophene-2-carboxamide (Intermediate 22) (0.35 g, 0.70 mmol) and 1,2,4-triazole (290 mg, 4.2 mmol) in pyridine (5 mL) and phosphorus oxychloride (0.200 mL, 2.1 mmol) gave 7-(5-bromothien-2-yl)-5-methyl-N-(3,4,5-trimethoxyphenyl)imidazo[5,1-f][1,2,4]triazin-2-amine (0.026 g) as a yellow solid. $^1$H NMR (DMSO-d$_6$): δ9.70 (s, 1H), 9.24 (s, 1H), 7.83 (d, J=4.0 Hz, 1H), 7.38 (d, J=4.0 Hz, 1H), 7.10 (s, 2H), 3.81 (s, 6H), 3.66 (s, 3H), 2.51 (s, 3H). MS m/z 476, 478 (M+1, M+3).

Intermediate 23: 3-Bromo-N-[1-(3-{[5-(ethylsulfonyl)-2-methoxyphenyl]amino}-1,2,4-triazin-6-yl)ethyl]benzamide

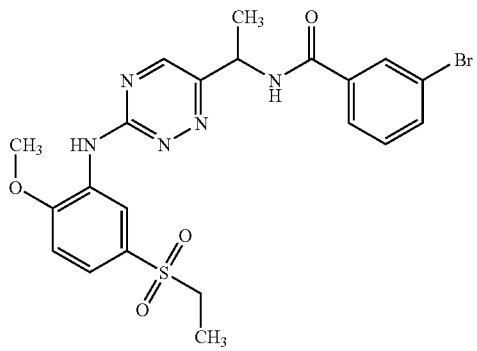

To a stirred solution of 3-bromo-N-{1-[3-(methylsulfonyl)-1,2,4-triazin-6-yl]ethyl}benzamide (Intermediate 6) (240 mg, 0.62 mmol) in tetrahydrofuran (10 mL) was added 5-(ethylsulfonyl)-2-methoxyaniline (270 mg, 1.2 mmol) and 4-toluenesulfonic acid monohydrate (20 mg). After stirring for 24 hours, silica gel (2.5 g) was added to the solution, followed by evaporation of the volatiles under reduced pressure. The pre-adsorbed solids were loaded into a solid loading cartridge and subjected to a gradient elution using ethyl acetate:hexane (20:80) to ethyl acetate:hexanes (80:20) using a RediSep silica gel cartridge (12 g; ISCO). The appropriate fractions were combined and concentrated under reduced pressure to give 3-bromo-N-[1-(3-{[5-(ethylsulfonyl)-2-methoxyphenyl]amino}-1,2,4-triazin-6-yl)ethyl]benzamide (110 mg) as a white solid. $^1$H NMR (CDCl$_3$): δ9.00 (d, J=2.2 Hz, 1H), 8.44 (s, 1H), 8.03 (s, 1H), 7.95 (dd, J=1.9, 1.4 Hz, 1H), 7.72 (d, J=8.5 Hz, 1H), 7.62 (d, J=7.4 Hz, 1H), 7.57-7.52 (m, 1H), 7.22 (dd, J=8.1, 7.7 Hz, 1H) 7.00 (d, J=8.8 Hz, 1H) 5.44 (dq, J=7.2, 7.0 Hz, 1H), 3.98 (s, 3H), 3.10 (q, J=7.3 Hz, 2H), 1.68 (d, J=7.0 Hz, 3H), 1.24 (t, J=7.3 Hz, 3H). MS m/z 520, 522 (M+1, M+3).

EXAMPLE 14

7-(3-Bromophenyl)-N-[5-(ethylsulfonyl)-2-methoxyphenyl]-5-methylimidazo[5,1-f][1,2,4]triazin-2-amine

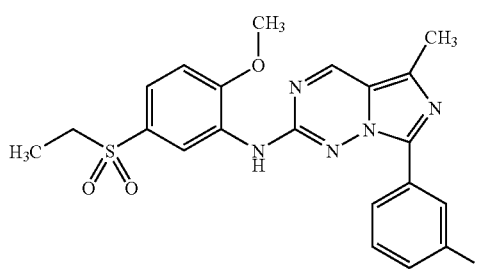

In a similar manner as described for Example 9, 3-bromo-N-[1-(3-{[5-(ethylsulfonyl)-2-methoxyphenyl]amino}-1,2,4-triazin-6-yl)ethyl]benzamide (Intermediate 23) (0.11 g, 0.20 mmol) and 1,2,4-triazole (83 mg, 1.2 mmol) in pyridine (2 mL) and phosphorus oxychloride (0.056 mL, 0.6 mmol)

gave 7-(3-bromophenyl)-N-[5-(ethylsulfonyl)-2-methoxyphenyl]-5-methylimidazo[5,1-f][1,2,4]triazin-2-amine (0.028 g) as a yellow solid. $^1$H NMR (CDCl$_3$): δ 8.89 (d, J=2.2 Hz, 1H), 8.85 (s, 1H), 8.69-8.60 (m, 1H), 8.43 (dd, J=1.8, 1.8 Hz, 1H), 7.81-7.75 (m, 2H), 7.63 (dd, J=8.5, 2.3 Hz, 1H), 7.58 (ddd, J=7.9, 2.0, 1.0 Hz, 1H), 7.04 (d, J=8.6 Hz, 1H), 4.04 (s, 3H), 3.06 (q, J=7.4 Hz, 2H), 2.63 (s, 3H), 1.23 (t, J=7.4 Hz, 3H). MS m/z 502, 504 (M+1, M+3).

Intermediate 24: 3-Bromo-N-(1-{3-[(3-chloro-4-morpholin-4-ylphenyl)amino]-1,2,4-triazin-6-yl}ethyl)benzamidene

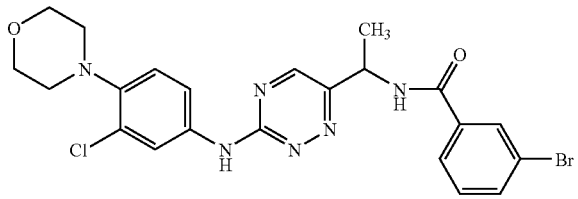

In a similar manner as described for Intermediate 23, 3-bromo-N{1-[3-(methylsulfonyl)-1,2,4-triazin-6-yl]ethyl}benzamide (Intermediate 6) (200 mg, 0.52 mmol), 3-chloro-4-morpholin-4-ylaniline (200 mg, 0.94 mmol) and 4-toluenesulfonic acid monohydrate (20 mg) in tetrahydrofuran (10 mL) gave 3-bromo-N-(1-{3-[(3-chloro-4-morpholin-4-ylphenyl)amino]-1,2,4-triazin-6-yl}ethyl)benzamide (0.045 g) as a white solid. MS m/z 517, 519 (M+1, M+3).

EXAMPLE 15

7-(3-Bromophenyl)-N-(3-chloro-4-morpholin-4-ylphenyl)-5-methylimidazo[5,1-f][1,2,4]triazin-2-amine

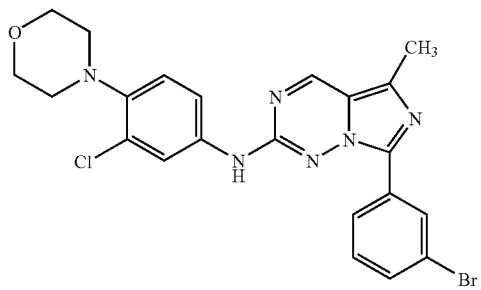

In a similar manner as described for Example 9, 3-bromo-N-(1-{3-[(3-chloro-4-morpholin-4-ylphenyl)amino]-1,2,4-triazin-6-yl}ethyl)benzamide (Intermediate 24) (0.040 g, 0.080 mmol) and 1,2,4-triazole (35 mg, 0.50 mmol) in pyridine (1 mL) and phosphorus oxychloride (0.023 mL, 0.24 mmol) gave 7-(3-bromophenyl)-N-(3-chloro-4-morpholin-4-ylphenyl)-5-methylimidazo[5,1-f][1,2,4]triazin-2-amine (0.0089 g) as a yellow solid. $^1$H NMR (DMSO-d$_6$): δ 9.92 (s, 1H), 9.29 (s, 1H), 8.61 (dd, J=1.9, 1.8 Hz, 1H), 8.45 (ddd, J=8.1, 1.5, 1.1 Hz, 1H), 7.88 (d, J=2.5 Hz, 1H), 7.72 (dd, J=8.7, 2.6 Hz, 1H) 7.67 (ddd, J=8.1, 2.0, 1.0 Hz, 1H) 7.54 (dd, J=8.1, 7.8 Hz, 1H), 7.23 (d, J=9.0 Hz, 1H), 3.78-3.73 (m, 4H), 2.98-2.94 (m, 4H), 2.55 (s, 3H). MS m/z 499, 501 (M+1, M+3).

EXAMPLE 16

3-{5-Methyl-2-[(3,4,5-trimethoxyphenyl)amino]imidazo[5,1-f][1,2,4]triazin-7-yl}benzamide

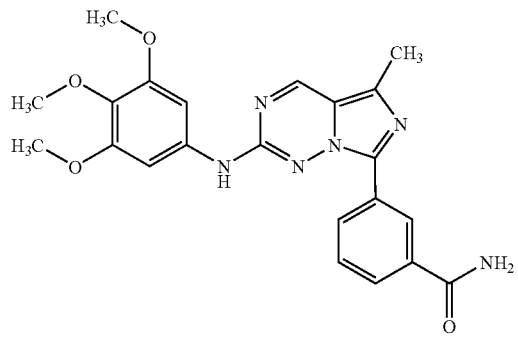

To methyl 3-{5-methyl-2-[(3,4,5-trimethoxyphenyl)amino]imidazo[5,1-f][1,2,4]triazin-7-yl}benzoate (Example 12) (0.020 g, 0.044 mmol) was added 7N ammonium in methanol (5 mL). The solution was heated in a sealed tube for 18 hours. After cooling to room temperature, the volatiles were removed under reduced pressure to give 3-{5-methyl-2-[(3,4,5-trimethoxyphenyl)amino]imidazo[5,1-f][1,2,4]triazin-7-yl}benzamide (0.015 g) as a yellow solid. $^1$H NMR (CDCl$_3$): δ 9.41 (s, 1H), 9.16 (s, 1H), 8.73 (d, J=7.3 Hz, 1H), 8.27 (d, J=7.6 Hz, 1H), 8.23-8.17 (m, 1H), 7.75-7.59 (m, 3H) 7.26 (s, 2H), 3.98 (s, 3H), 3.92 (s, 3H), 3.72 (s, 3H), 2.71 (s, 3H). MS m/z 435 (M+1).

EXAMPLE 17

(2E)-3-(3-{5-Methyl-2-[(3,4,5-trimethoxyphenyl)amino]imidazo[5,1-f][1 2,4]triazin-7-yl}phenyl)prop-2-enamide

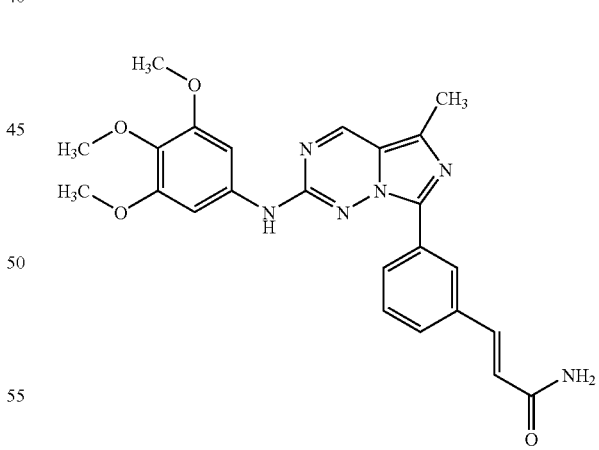

To a mixture of 7-(3-bromophenyl)-5-methyl-N-(3,4,5-trimethoxyphenyl)imidazo[5,1-f][1,2,4]triazin-2-amine (Example 9) (0.054 g, 0.12 mmol), acrylamide (0.025 g, 0.35 mmol), palladium (II) acetate (2.7 mg, 0.012 mmol) and tris(o-tolyl)phosphine (7.3 mg, 0.024 mmol) in acetonitrile (1 mL) was added triethylamine (0.050 mL, 0.35 mmol). The solution was heated to reflux for 30 minutes. After cooling to room temperature, the solution was filtered, and silica gel (1 g) was added, followed by evaporation of the volatiles under reduced pressure. The pre-adsorbed solids were loaded into a solid loading cartridge and subjected to a gradient elution using ethyl acetate:hexanes (50:50) to ethyl acetate:hexanes (100:0) to ethyl acetate:methanol (99:1) using a RediSep silica gel cartridge (4 g; ISCO). The appropriate fractions were combined and concentrated under reduced pressure to give (2E)-3-(3-{5-methyl-2-[(3,4,5-trimethoxyphenyl)amino]-imidazo[5,1-f][1,2,4]triazin-7-yl}phenyl)prop-2-enamide (0.0046 g) as a yellow solid. $^1$H NMR (CD$_3$OD): δ9.05 (s, 1H), 8.49 (s, 1H), 8.37 (d, J=7.3 Hz, 1H), 7.67-7.51 (m, 4H), 7.05 (s, 2H), 6.68 (d, J=15.9 Hz, 1H) 3.74 (s, 3H), 3.72 (s, 6H), 2.60 (s, 3H). MS m/z 461 (M+1).

EXAMPLE 18

5-Methyl-N-(4-nitrophenyl)-7-phenylimidazo[5,1-f][1,2,4]triazin-2-amine

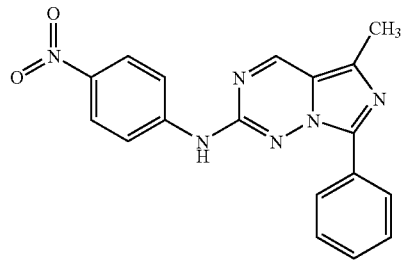

To a mixture of 5-methyl-7-phenylimidazo[5,1-f][1,2,4]triazin-2-amine hydrochloride (0.026 g, 0.10 mmol), 1-iodo-4-nitrobenzene (0.027 g, 0.11 mmol), tris(dibenzylideneacetone)dipalladium (2.7 mg, 0.0030 mmol), (S)-(−)-2,2'-bis(diphenylphosphino)-1,1'-binaphthyl (5.6 mg, 0.0090 mmol) and sodium t-butoxide (0.025 g, 0.23 mmol) was added toluene (1 mL). The solution was heated to 80° C. for two hours. After cooling to room temperature, the solution was filtered, and silica gel (1 g) was added, followed by evaporation of the volatiles under reduced pressure. The pre-adsorbed solids were loaded into a solid loading cartridge and subjected to a gradient elution using ethyl acetate:hexanes (50:50) to ethyl acetate:hexanes (100:0) using a RediSep silica gel cartridge (4 g; ISCO). The appropriate fractions were combined and concentrated under reduced pressure to give 5-methyl-N-(4-nitrophenyl)-7-phenylimidazo[5,1-f][1,2,4]triazin-2-amine (0.0080 g) as a yellow solid. $^1$H NMR (CDCl$_3$): δ8.86 (s, 1H), 8.78 (s, 1H), 8.48-8.40 (m, 2H), 8.26 (d, J=9.4 Hz, 2H), 7.81 (d, J=9.3 Hz, 2H), 7.61-7.36 (m, 3H), 2.65 (s, 3H). MS m/z 347 (M+1).

EXAMPLE 19

2-{3-[(5-Methyl-7-phenylimidazo[5,1-f][1,2,4]triazin-2-yl)amino]phenyl}ethanol

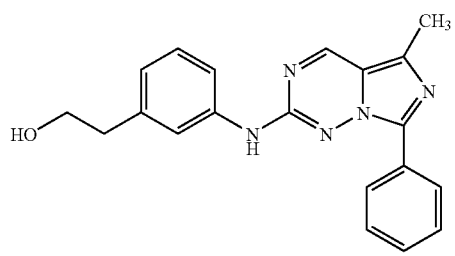

To a mixture of 5-methyl-7-phenylimidazo[5,1-f][1,2,4]triazin-2-amine hydrochloride (0.026 g, 0.10 mmol), 2-(3-bromophenyl)ethanol (0.022 g, 0.11 mmol), tris(dibenzylideneacetone)dipalladium (2.7 mg, 0.0030 mmol), (S)-(−)-2,2'-bis(diphenylphosphino)-1,1'-binaphthyl (5.6 mg, 0.0090 mmol) and sodium t-butoxide (0.025 g, 0.23 mmol) was added dioxane (1 mL). The solution was heated with microwave radiation to 160° C. for 15 minutes. After cooling to room temperature, the solution was filtered, and silica gel (1 g) was added, followed by evaporation of the volatiles under reduced pressure. The pre-adsorbed solids were loaded into a solid loading cartridge and subjected to a gradient elution using ethyl acetate:hexanes (50:50) to ethyl acetate:hexanes (100:0) using a RediSep silica gel cartridge (4 g; ISCO). The appropriate fractions were combined and concentrated under reduced pressure to give 2-{3-[(5-methyl-7-phenylimidazo[5,1-f][1,2,4]triazin-2-yl)amino]phenyl}ethanol (0.0097 g) as a yellow solid. $^1$H NMR (CDCl$_3$): δ8.75 (s, 1H), 8.51-8.45 (m, 2H), 7.74 (s, 1H), 7.56-7.26 (m, 5H), 7.04-6.95 (m, 2H), 3.91 (t, J=6.4 Hz, 2H), 2.92 (t, J=6.4 Hz, 2H), 2.59 (s, 3H). MS m/z 346 (M+1).

EXAMPLE 20:

4-[(5-Methyl-7-phenylimidazo[5,1-f][1,2,4]triazin-2-yl)amino]benzenesulfonamide

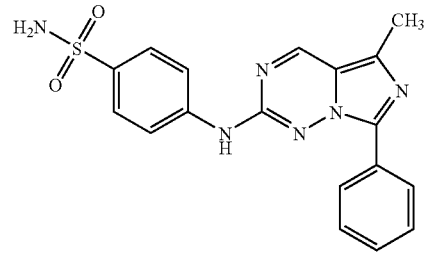

To a mixture of 5-methyl-7-phenylimidazo[5,1-f][1,2,4]triazin-2-amine hydrochloride (0.026 g, 0.10 mmol), 4-bromobenzenesulfonamide (0.026 g, 0.11 mmol), tris(dibenzylideneacetone)dipalladium (2.7 mg, 0.0030 mmol), (S)-(−)-2,2'-bis(diphenylphosphino)-1,1'-binaphthyl (5.6 mg, 0.0090 mmol) and sodium t-butoxide (0.025 g, 0.23 mmol) was added dioxane (1 mL). The solution was heated with microwave radiation to 160° C. for 15 minutes. After cooling to room temperature, the solution was filtered, and silica gel (1 g) was added, followed by evaporation of the volatiles under reduced pressure. The pre-adsorbed solids were loaded into a solid loading cartridge and subjected to a gradient elution using ethyl acetate:hexanes (50:50) to ethyl acetate:hexanes (100:0) using a RediSep silica gel cartridge (4 g; ISCO). The appropriate fractions were combined and concentrated under reduced pressure to give 4-[(5-methyl-7-phenylimidazo[5,1-f][1,2,4]triazin-2-yl)amino]benzenesulfonamide (0.0015 g) as a yellow solid. MS m/z 381 (M+1).

Intermediate 25: 2-Methoxy-N-(1-{3-[(3,4,5-trimethoxyphenyl)amino]-1,2,4-triazin-6-yl}ethyl)benzamide

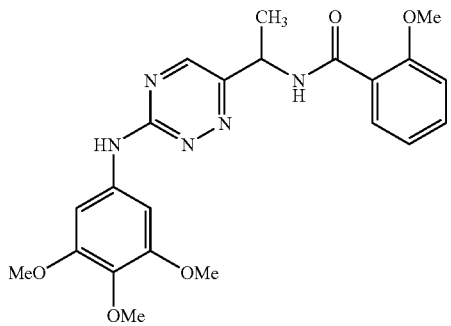

In a similar manner as described for Intermediate 10, 6-(1-aminoethyl)-N-(3,4,5-trimethoxyphenyl)-1,2,4-triazin-3-amine (Intermediate 9) (95 mg, 0.31 mmol), 2-methoxybenzoyl chloride (56 mg, 0.33 mmol), and triethylamine (0.050 mL, 0.36 mmol) in tetrahydrofuran (1 mL) gave 2-methoxy-N-(1-{3-[(3,4,5-trimethoxyphenyl)amino]-1,2,4-triazin-6-yl}ethyl)benzamide (37 mg) as an off yellow solid. MS m/z 439 (M+1).

EXAMPLE 21

7-(2-Methoxyphenyl)-5-methyl-N-(3,4,5-trimethoxyphenyl)-imidazo[5,1-f][1,2,4]triazin-2-amine

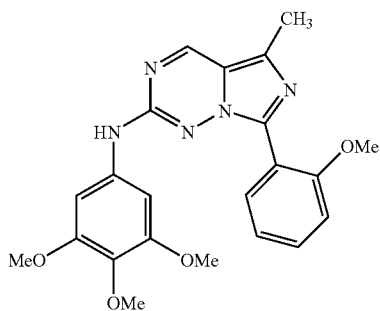

To a solution of 2-methoxy-N-(1-{3-[(3,4,5-trimethoxyphenyl)amino]-1,2,4-triazin-6-yl}ethyl)benzamide (Intermediate 25) (27 mg, 0.06 mmol) in 1,2-dichloroethane (4 mL) was added phosphorus oxychloride (45 microL, 0.5 mmol). The mixture was heated to reflux for 4 hours. After cooling to room temperature, the mixture was diluted with DCM (150 mL) and aqueous (saturated) $Na_2CO_3$ (25 mL). The aqueous layer was extracted with dichloromethane (DCM) and the combined organic layers were washed with brine, dried over $Na_2SO_4$, concentrated under vacuum, and purified by reverse-phase HPLC to give 7-(2-methoxyphenyl)-5-methyl-N-(3,4,5-trimethoxyphenyl)imidazo[5,1-f][1,2,4]triazin-2-amine (0.005 g) as a yellow solid. $^1$H NMR ($CDCl_3$): δ8.80 (s, 1H), 7.59 (dd J=7.51, 1.65 Hz, 1H), 7.44 (m, 1H), 7.00-7.07 (m, 3H), 6.84 (s, 1H), 3.78 (s, 6H), 3.59 (s, 6H), 2.63 (s, 3H). MS m/z 421 (M+1).

Intermediate 26: 2-{[(1-{3-[(3,4,5-Trimethoxyphenyl)amino]-1,2,4-triazin-6-yl}ethyl)amino]carbonyl}phenyl acetate

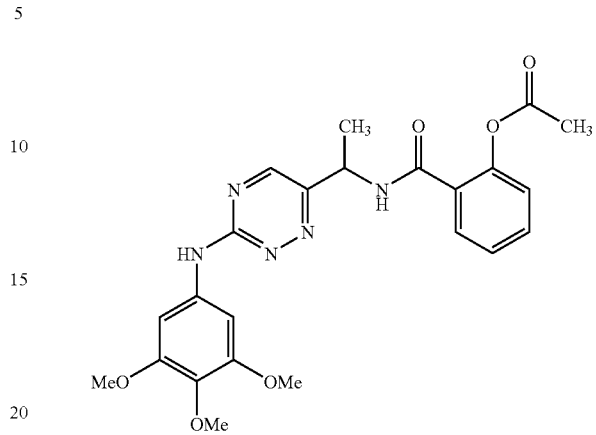

In a similar manner as described for Intermediate 10, 6-(1-aminoethyl)-N-(3,4,5-trimethoxyphenyl)-1,2,4-triazin-3-amine (Intermediate 9) (95 mg, 0.31 mmol), 2-(chlorocarbonyl)phenyl acetate (65 mg, 0.33 mmol), and triethylamine (0.050 mL, 0.36 mmol) in tetrahydrofuran (2 mL) gave 2-{[(1-{3-[(3,4,5-trimethoxyphenyl)amino]-1,2,4-triazin-6-yl}ethyl)amino]carbonyl}phenyl acetate (138 mg, 95%) as an off yellow solid. MS m/z 467 (M+1).

EXAMPLE 22

2-{5-Methyl-2-[(3,4,5-trimethoxyphenyl)amino]imidazo[5,1-f][1,2,4]triazin-7-yl}phenol

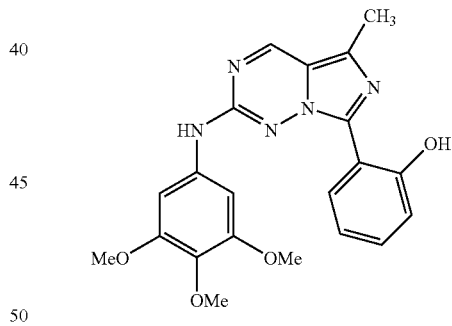

To a solution of 2-{5-methyl-2-[(3,4,5-trimethoxyphenyl)amino]imidazo[5,1-f][1,2,4]triazin-7-yl}phenyl acetate (Example 23 below) (26 mg, 0.058 mmol) in 5:1 THF/$H_2O$ (4 mL) was added LiOH (30 mg, 1.25 mmol). The reaction was stirred at room temperature for 3 hours then poured into EtOAc (100 mL) and water (20 mL) with aqueous 1 N HCl (2 mL). The aqueous layer was extracted with EtOAc and the combined organic layers then washed with brine, dried over $MgSO_4$, concentrated and purified by silica gel chromatography, eluting with 1% MeOH/DCM to give 2-{5-methyl-2-[(3,4,5-trimethoxyphenyl)amino]-imidazo[5,1-f][1,2,4]triazin-7-yl}phenol (13 mg, (56%)) as a yellow solid. $^1$H NMR ($CDCl_3$): δ12.73 (s, 1H), 8.94 (dd J=7.87, 1.46 Hz, 1H), 8.86 (s, 1H), 7.31 (m, 1H), 7.09 (d, J=8.06 Hz, 1H), 6.86-6.96 (m, 4H), 3.90 (s, 6H), 3.88 (s, 3H), 2.61 (s, 3H). MS m/z 407 (M+1).

EXAMPLE 23

2-{5-Methyl-2-[(3,4,5-trimethoxyphenyl)amino]imidazo[5,1-f][1,2,4]triazin-7-yl}phenyl acetate

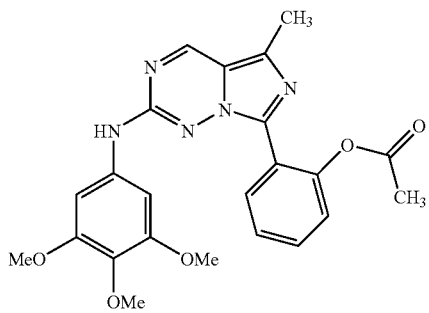

To a solution of 2-{[(1-{3-[(3,4,5-trimethoxyphenyl)amino]-1,2,4-triazin-6-yl}ethyl)amino]carbonyl}phenyl acetate (Intermediate 26) (60 mg, 0.13 mmol) in 1,2-dichloroethane (6 mL) was added phosphorous oxychloride (0.10 mL, 1.1 mmol). The mixture was heated to reflux for 5 hours. After cooling to room temperature the reaction was diluted with dichloromethane (125 mL), methanol (20 mL) and aqueous saturated $Na_2CO_3$ (40 mL). The aqueous layer was extracted with dichloromethane, then the combined organic layers were dried over $MgSO_4$, concentrated and chromatographed on silica gel, eluting with 2.5% MeOH/DCM to give 2-{5-methyl-2-[(3,4,5-trimethoxyphenyl)amino]imidazo[5,1-f][1,2,4]triazin-7-yl}phenyl acetate (26 mg) as a yellow oil. MS m/z 449 (M+1).

Intermediate 27: 4-(Trifluoromethyl)-N-(1-{3-[(3,4,5-trimethoxyphenyl)amino]-1,2,4-triazin-6-yl}ethyl)benzamide

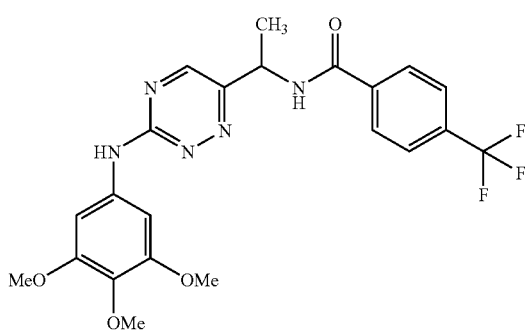

In a similar manner as described for Intermediate 10, 6-(1-aminoethyl)-N-(3,4,5-trimethoxyphenyl)-1,2,4-triazin-3-amine (Intermediate 9) (295 mg, 0.97 mmol), 4-(trifluoromethyl)benzoyl chloride (0.16 mL, 1.08 mmol), and triethylamine (0.168 mL, 1.20 mmol) in tetrahydrofuran (4 mL) gave 4-(trifluoromethyl)-N-(1-{3-[(3,4,5-trimethoxyphenyl)amino]-1,2,4-triazin-6-yl}ethyl)benzamide (284 mg, 59%) as a yellow solid. MS m/z 477 (M+1).

EXAMPLE 24

5-Methyl-7-[4-(trifluoromethyl)phenyl]-N-(3,4,5-trimethoxy-phenyl)imidazo[5,1-f][1,2,4]triazin-2-amine

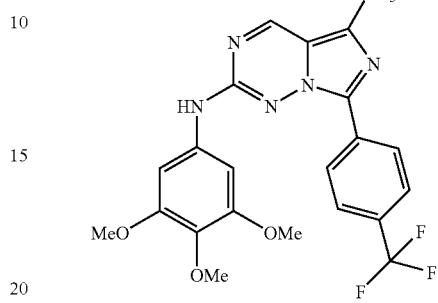

To a solution of 4-(trifluoromethyl)-N-(1-{3-[(3,4,5-trimethoxyphenyl)amino]-1,2,4-triazin-6-yl}ethyl)benzamide (Intermediate 27) (241 mg, 0.51 mmol) in 1,2-dichloroethane (20 mL) was added phosphorus oxychloride (0.37 mL, 4.0 mmol). The mixture was heated to reflux for 24 hours. After cooling to room temperature, the mixture was diluted with DCM and aqueous (saturated) $Na_2CO_3$. The aqueous was extracted with DCM and the combined organic layers were washed with brine, dried over $Na_2SO_4$, concentrated under vacuum and purified by silica gel chromatography to give 5-methyl-7-[4-(trifluoromethyl)phenyl]-N-(3,4,5-trimethoxyphenyl)imidazo[5,1-f][1,2,4]triazin-2-amine (0.007 g) as yellow solid. $^1$H NMR ($CDCl_3$): δ8.85 (s, 1H), 8.86 (d J=8.24 Hz, 2H), 7.72 (d, J=8.24 Hz, 2H), 6.88 (m, 3H), 3.87 (s, 3H), 3.83 (s, 6H), 2.63 (s, 3H). MS m/z 459 (M+1).

EXAMPLE 25

N-Methyl-N-{4-[(5-methyl-7-phenylimidazo[5,1-f][1,2,4]triazin-2-yl)amino]phenyl}urea

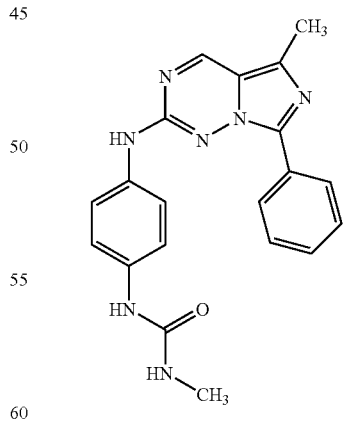

A solution of 5-methyl-7-phenylimidazo[5,1-f][1,2,4]triazin-2-amine hydrochloride (26 mg, 0.1 mmol), N-(4-bromophenyl)-N-methylurea (27 mg, 0.12 mmol), tris(dibenzylideneacetone)dipalladium (10 mg, 0.01 mmol), 2-(di-t-butylphosphino)biphenyl (10 mg, 0.03 mmol) and sodium t-butoxide (25 mg, 0.23 mmol) in dioxane (0.80 mL) was added to a Smithcreator microwave reaction vessal. The vessal was sealed, then heated in the Smithcreator microwave at 160° C. for 20 minutes. After cooling to room temperature, the mixture was purified by silica gel chromatography, eluting with 5% MeOH/DCM to give N-methyl-N-{4-[(5-methyl-7-phenylimidazo[5,1-f][1,2,4]triazin-2-yl)amino]phenyl}urea (14 mg, 38%) as a yellow solid. $^1$H NMR (DMSO-d$_6$): δ9.59 (s, 1H), 9.20 (s, 1H), 8.39-8.46 (m, 3H), 7.34-7.71 (m, 8H), 5.94 (d, J=4.67 Hz, 1H), 2.63 (d, J=4.53 Hz, 3H), 2.52 (s, 3H). MS m/z 373 (M+1).

EXAMPLE 26

5-Methyl-7-phenyl-N-[3-(trifluoromethyl)phenyl]imidazo[5,1-f][1,2,4]triazin-2-amine

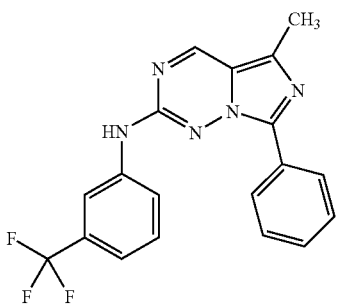

In a similar manner as described for Example 25, 5-methyl-7-phenylimidazo[5,1-f][1,2,4]triazin-2-amine hydrochloride (26 mg, 0.1 mmol), 1-iodo-3-(trifluoromethyl)benzene (33 mg, 0.12 mmol), tris(dibenzylideneacetone)dipalladium (10 mg, 0.01 mmol), 2-(di-t-butylphosphino)biphenyl (10 mg, 0.03 mmol) and sodium t-butoxide (25 mg, 0.23 mmol) in dioxane (0.80 mL) gave 5-methyl-7-phenyl-N-[3-(trifluoromethyl)phenyl]imidazo[5,1-f][1,2,4]triazin-2-amine (30 mg, 81%) as a yellow solid. $^1$H NMR (CDCl$_3$): δ8.83 (s, 1H), 8.46-8.49 (m, 2H), 8.33 (s, 1H), 7.43-7.57 (m, 5H), 7.35 (d, J=7.51 Hz, 1H), 7.08 (s, 1H), 2.63 (s, 3H). MS m/z 369 (M+1).

Intermediate 28: 3-Benzoyl-N-(1-{3-[(3,4,5-trimethoxyphenyl)amino]-1,2,4-triazin-6-yl}ethyl)benzamide

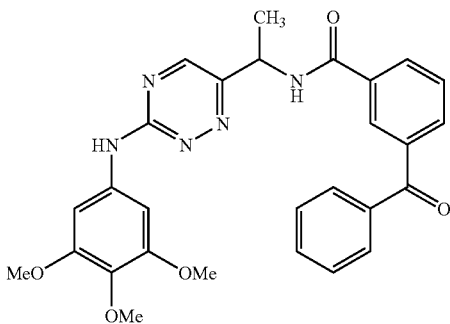

In a similar manner as described for Intermediate 18, 6-(1-aminoethyl)-N-(3,4,5-trimethoxyphenyl)-1,2,4-triazin-3-amine (Intermediate 9) (113 mg, 0.33 mmol), 3-benzoylbenzoic acid (100 mg, 0.43 mmol), diisopropylethylamine (0.28 mL, 1.60 mmol) and O-(7-azabenzotriazol-1-yl)-N,N,N',N'-tetramethyluronium hexafluorophosphate (182 mg, 0.48 mmol) in dimethylformamide (2 mL) gave 3-benzoyl-N-(1-{3-[(3,4,5-trimethoxyphenyl)amino]-1,2,4-triazin-6-yl}ethyl)benzamide (102 mg, 60%) as a yellow solid. MS m/z 513 (M+1).

EXAMPLE 27

(3-{5-Methyl-2-[(3,4,5-trimethoxyphenyl)amino]imidazo[5,1-f][1,2,4]triazin-7-yl}phenyl)(phenyl)methanone

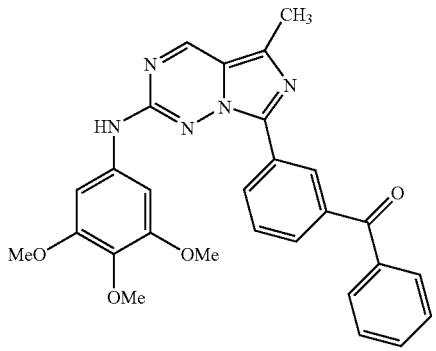

To a solution of 3-benzoyl-N-(1-{3-[(3,4,5-trimethoxyphenyl)amino]-1,2,4-triazin-6-yl}ethyl)benzamide (Intermediate 28) (95 mg, 0.18 mmol) in 1,2-dichloroethane was added catalytic dimethylformamide (3 drops) and thionyl chloride (0.36 mL, 5.0 mmol). The mixture was heated at 50° C. for 14 hours. After cooling to room temperature the mixture was concentrated under vacuum. The resulting solid was taken up in a mixture of dichloromethane and methanol, then concentrated ammonium hydroxide was added until the solution was basic. The solution was then concentrated under vacuum and purified by reverse-phase HPLC to give (3-{5-methyl-2-[(3,4,5-trimethoxyphenyl)-amino]imidazo[5,1-f][1,2,4]triazin-7-yl}phenyl)(phenyl)-methanone (8 mg) as a yellow solid. $^1$H NMR (DMSO-d$_6$): δ9.63 (s, 1H), 9.26 (s, 1H), 8.80 (d, J=7.87 Hz, 1H), 8.61 (s, 1H), 7.74-7.80 (m, 3H), 7.63 (t, J=7.69 Hz, 2H), 7.68 (t, J=7.69 Hz, 2H), 7.05 (s, 2H), 3.68 (s, 6H), 3.62 (s, 3H), 2.52 (s, 3H). MS m/z 495 (M+1).

Intermediate 29: N-(1-{3-[(3,4,5-Trimethoxyphenyl)amino]-1,2,4-triazin-6-yl}ethyl)-1,3-benzodioxole-5-carboxamide

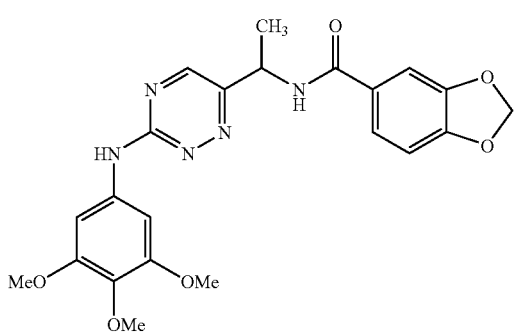

In a similar manner as described for Intermediate 18, 6-(1-aminoethyl)-N-(3,4,5-trimethoxyphenyl)-1,2,4-triazin-3-amine (Intermediate 9) (87 mg, 0.28 mmol), 1,3-benzodioxole-5-carboxylic acid (60 mg, 0.37 mmol), diisopropylethylamine (0.13 mL, 0.75 mmol) and O-(7-azabenzotriazol-1-yl)-N,N,N',N'-tetramethyluronium hexafluorophosphate (140 mg, 0.37 mmol) in dimethylformamide (2 mL) gave N-(1-{3-[(3,4,5-trimethoxyphenyl)amino]-1,2,4-triazin-6-yl}ethyl)-1,3-benzodioxole-5-carboxamide (127 mg, 100%) as a yellow oil. MS m/z 453 (M+1).

EXAMPLE 28:

7-(1,3-Benzodioxol-5-yl)-5-methyl-N-(3,4,5-trimethoxyphenyl)-imidazo[5,1-f][1,2,4]triazin-2-amine

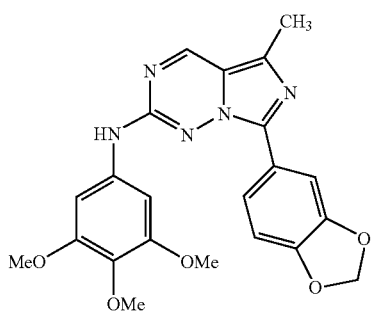

In a similar manner as described for Example 9, N-(1-{3-[(3,4,5-trimethoxyphenyl)amino]-1,2,4-triazin-6-yl}ethyl)-1,3-benzodioxole-5-carboxamide (Intermediate 29) (61 mg, 0.134 mmol), and 1,2,4-triazole (55 mg, 0.80 mmol) in pyridine (2 mL) and phosphorous oxychloride (0.037 mL, 0.40 mmol) gave 7-(1,3-benzodioxol-5-yl)-5-methyl-N-(3,4,5-trimethoxy-phenyl)imidazo[5,1-f][1,2,4]triazin-2-amine (25 mg, 43%) as a yellow solid. $^1$H NMR (CD$_3$OD): δ8.99 (s, 1H), 7.87 (s, 1H), 7.84 (d, J=1.65 Hz, 1H), 7.04 (s, 2H), 6.95 (d, J=7.87 Hz, 1H), 6.04 (s, 2H), 3.80 (s, 6H), 3.74 (s, 3H), 2.56 (s, 3H). MS m/z 435 (M+1).

Intermediate 30: Methyl 4-{[(1-{3-[(3,4,5-trimethoxyphenyl)amino]-1,2,4-triazin-6-yl}ethyl)amino]carbonyl}benzoate

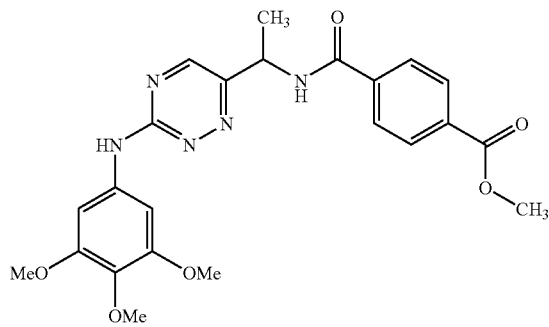

In a similar manner as described for Intermediate 18, 6-(1-aminoethyl)-N-(3,4,5-trimethoxyphenyl)-1,2,4-triazin-3-amine (Intermediate 9) (87 mg, 0.28 mmol), 4-(methoxycarbonyl)benzoic acid (67 mg, 0.37 mmol), diisopropylethylamine (0.13 mL, 0.75 mmol) and O-(7-azabenzotriazol-1-yl)-N,N,N',N'-tetramethyluronium hexafluorophosphate (140 mg, 0.37 mmol) in dimethylformamide (2 mL) gave methyl 4-{[(1-{3-[(3,4,5-trimethoxyphenyl)amino]-1,2,4-triazin-6-yl}ethyl)amino]carbonyl}benzoate (131 mg, 100%) as a yellow oil. MS m/z 467 (M+1).

EXAMPLE 29

Methyl 4-{5-methyl-2-[(3,4,5-trimethoxyphenyl)amino]imidazo-[5,1-f][1,2,4]triazin-7-yl}benzoate

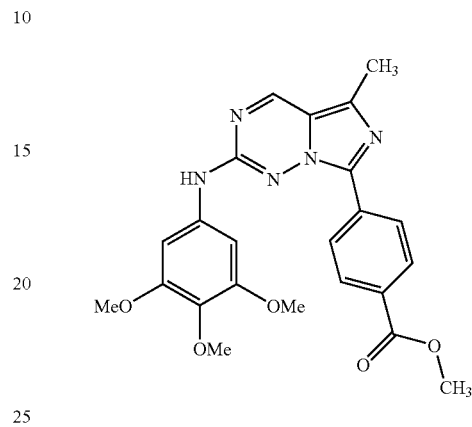

In a similar manner as described for Example 9, methyl 4-{[(1-{3-[(3,4,5-trimethoxyphenyl)amino]-1,2,4-triazin-6-yl}ethyl)amino]carbonyl}benzoate (Intermediate 30) (56 mg, 0.12 mmol), and 1,2,4-triazole (55 mg, 0.80 mmol) in pyridine (2 mL) and phosphorous oxychloride (0.037 mL, 0.40 mmol) gave methyl 4-{5-methyl-2-[(3,4,5-trimethoxyphenyl)amino]imidazo[5,1-f][1,2,4]triazin-7-yl}benzoate (11 mg, 20%) as a yellow solid. $^1$H NMR (CD$_3$OD): δ9.06 (s, 1H), 9.01 (s, 1H), 8.58 (d, J=7.87 Hz, 1H), 8.08 (d, J=7.87 Hz, 1H), 7.62 (t, J=7.87 Hz, 1H), 7.04 (s, 2H), 5.48 (s, 1H), 3.87 (s, 3H), 3.75 (s, 3H), 3.71 (s, 6H), 2.59 (s, 3H). MS m/z 449 (M+1).

Intermediate 31: 3-Phenoxy-N-(1-{3-[(3,4,5-trimethoxyphenyl)amino]-1,2,4-triazin-6-yl}ethyl)benzamide

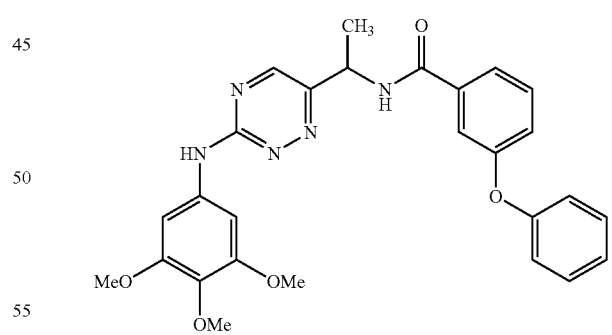

In a similar manner as described for Intermediate 18, 6-(1-aminoethyl)-N-(3,4,5-trimethoxyphenyl)-1,2,4-triazin-3-amine (Intermediate 9) (87 mg, 0.28 mmol), 3-phenoxybenzoic acid (80 mg, 0.37 mmol), diisopropylethylamine (0.13 mL, 0.75 mmol) and O-(7-azabenzotriazol-1-yl)-N,N,N',N'-tetramethyluronium hexafluorophosphate (140 mg, 0.37 mmol) in dimethylformamide (2 mL) gave 3-phenoxy-N-(1-{3-[(3,4,5-trimethoxyphenyl)amino]-1,2,4-triazin-6-yl}ethyl)benzamide (140 mg, 100%) as a yellow oil. MS m/z 501 (M+1).

EXAMPLE 30:

5-Methyl-7-(3-phenoxyphenyl)-N-(3,4,5-trimethoxyphenyl)-imidazo[5,1-f][1,2,4]triazin-2-amine

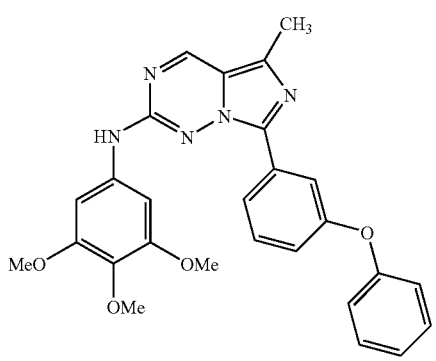

In a similar manner as described for Example 9, 3-phenoxy-N-(1-{3-[(3,4,5-trimethoxyphenyl)amino]-1,2,4-triazin-6-yl}ethyl)benzamide (Intermediate 31) (58 mg, 0.11 mmol), and 1,2,4-triazole (55 mg, 0.80 mmol) in pyridine (2 mL) and phosphorous oxychloride (0.037 mL, 0.40 mmol) gave 5-methyl-7-(3-phenoxyphenyl)-N-(3,4,5-trimethoxyphenyl)imidazo[5,1-f][1,2,4]triazin-2-amine (27 mg, 49%) as a tan-yellow solid. $^1$H NMR (CD$_3$OD): δ8.99 (s, 1H), 8.08 (d, J=7.87 Hz, 1H), 7.96 (t, J=1.92 Hz), 7.44 (t, J=8.06 Hz, 1H), 7.31 (t, J=7.87 Hz, 2H), 7.00-7.11 (m, 6H), 3.77 (s, 6H), 3.72 (s, 3H), 2.54 (s, 3H). MS m/z 448 (M+1).

Intermediate 32: 3-(Acetylamino)-N-(1-{3-[(3,4,5-trimethoxyphenyl)amino]-1,2,4-triazin-6-yl}ethyl)benzamide

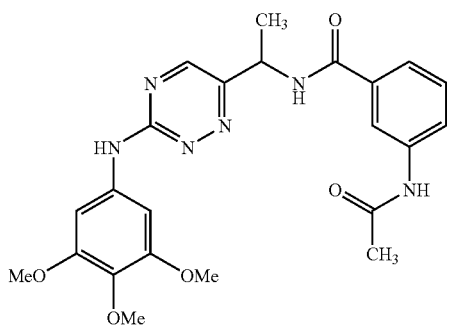

In a similar manner as described for Intermediate 18, 6-(1-aminoethyl)-N-(3,4,5-trimethoxyphenyl)-1,2,4-triazin-3-amine (Intermediate 9) (113 mg, 0.33 mmol), 3-(acetylamino)benzoic acid (110 mg, 0.61 mmol), diisopropylethylamine (0.40 mL, 2.3 mmol) and O-(7-azabenzotriazol-1-yl)-N,N,N',N'-tetramethyluronium hexafluorophosphate (252 mg, 0.66 mmol) in dimethylformamide (2 mL) gave 3-(acetylamino)-N-(1-{3-[(3,4,5-trimethoxyphenyl)amino]-1,2,4-triazin-6-yl}ethyl)benzamide (116 mg, 75%) as a yellow solid. MS m/z 466 (M+1).

EXAMPLE 31

7-(3-Aminophenyl)-5-methyl-N-(3,4,5-trimethoxyphenyl)imidazo-[5,1-f][1,2,4]triazin-2-amine

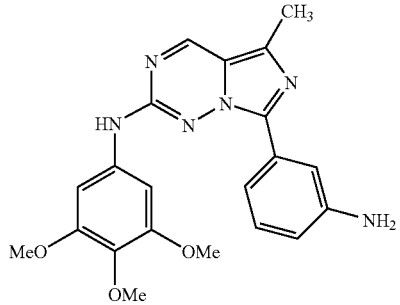

To a solution of 3-(acetylamino)-N-(1-{3-[(3,4,5-trimethoxyphenyl)amino]-1,2,4-triazin-6-yl}ethyl)benzamide (Intermediate 32) (110 mg, 0.24 mmol) in 1,2-dichloroethane (10 mL) was added phosphorous oxychloride (0.175 mL, 1.9 mmol). The mixture was refluxed for 6 hours, cooled to room temperature and more phosphorous oxychloride (0.10 mL, 1.0 mmol) was added. The reaction was then refluxed for 4 hours. After cooling to room temperature the reaction was diluted with methanol, then poured onto a mixture of ice and concentrated HCl. This mixture was brought to a pH of 8 by addition of concentrated aqueous NaOH. The mixture was then extracted with ethyl acetate, concentrated under vacuum and purified by reverse-phase HPLC to give 7-(3-aminophenyl)-5-methyl-N-(3,4,5-trimethoxyphenyl)imidazo[5,1-f][1,2,4]triazin-2-amine (2 mg) as a yellow solid. $^1$H NMR (CD$_3$OD): δ9.00 (s, 1H), 7.60 (d, J=7.87 Hz, 1H), 7.54 (s, 1H), 7.21 (t, J=7.78 Hz, 1H), 7.09 (s, 2H), 6.79 (dd, J=7.87 and 2.01 Hz, 1H), 3.77 (s, 6H), 3.73 (s, 3H), 2.56 (s, 3H). MS m/z 406 (M+1).

Intermediate 33: N-(1-{3-[(3,4,5-Trimethoxyphenyl)amino]-1,2,4-triazin-6-yl}ethyl)-1H-indole-2-carboxamide In a similar manner as described for Intermediate 18, 6-(1-aminoethyl)-N-(3,4,5-trimethoxyphenyl)-1,2,4-triazin-3-amine (Intermediate 9) (200 mg, 0.65 mmol), 1H-indole-2-carboxylic acid (136 mg, 0.85 mmol), diisopropylethylamine (0.33 mL, 1.9 mmol) and O-(7-azabenzotriazol-1-yl)-N,N,N',N'-tetramethyluronium hexafluorophosphate (360 mg, 0.94 mmol) in dimethylformamide (5 mL) gave N-(1-{3-

[(3,4,5-trimethoxyphenyl)amino]-1,2,4-triazin-6-yl}ethyl)-1H-indole-2-carboxamide (232 mg, 79%) as a yellow solid. MS m/z 448 (M+1).

EXAMPLE 32

7-(1H-Indol-2-yl)-5-methyl-N-(3,4,5-trimethoxyphenyl)imidazo-[5,1-f][1,2,4]triazin-2-amine

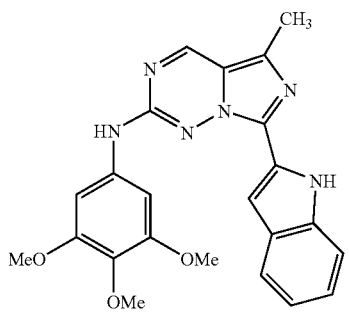

In a similar manner as described for Example 9, N-(1-{3-[(3,4,5-trimethoxyphenyl)amino]-1,2,4-triazin-6-yl}ethyl)-1H-indole-2-carboxamide (Intermediate 33) (219 mg, 0.491 mmol), and 1,2,4-triazole (210 mg, 3.0 mmol) in pyridine (10 mL) and phosphorous oxychloride (0.14 mL, 1.5 mmol) gave 7-(1H-indol-2-yl)-5-methyl-N-(3,4,5-trimethoxyphenyl)imidazo[5,1-f][1,2,4]triazin-2-amine (128 mg, 61%) as a yellow solid: $^1$H NMR (DMSO-d$_6$): δ11.85 (s, 1H), 9.67 (s, 1H), 9.26 (s, 1H) 7.55 (s, 1H), 7.52 (d, J=8.24 Hz, 1H), 7.46 (d, J=8.24 Hz, 1H), 7.21 (s, 2H), 7.15 (t, J=7.51, 1H), 7.04 (t, J=7.51 Hz, 1H), 3.82 (s, 6H), 3.68 (s, 3H), 2.58 (s, 3H). MS m/z 430 (M+1).

Intermediate 34: 5-Nitro-N-(1-{3-[(3,4,5-trimethoxyphenyl)amino]-1,2,4-triazin-6-yl}ethyl)-1H-pyrrole-2-carboxamide

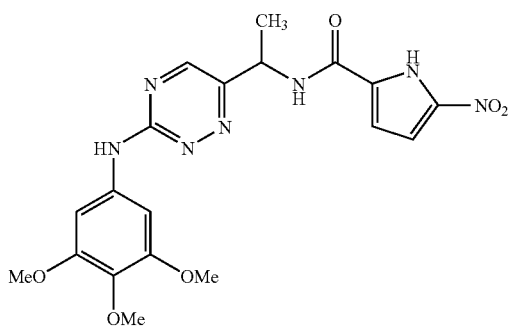

In a similar manner as described for Intermediate 18, 6-(1-aminoethyl)-N-(3,4,5-trimethoxyphenyl)-1,2,4-triazin-3-amine (Intermediate 9) (200 mg, 0.65 mmol), 5-nitro-1H-pyrrole-2-carboxylic acid (132 mg, 0.85 mmol), diisopropylethylamine (0.33 mL, 1.9 mmol) and O-(7-azabenzotriazol-1-yl)-N,N,N',N'-tetramethyluronium hexafluorophosphate (360 mg, 0.94 mmol) in dimethylformamide (5 mL) gave 5-nitro-N-(1-{3-[(3,4,5-trimethoxyphenyl)amino]-1,2,4-triazin-6-yl}ethyl)-1H-pyrrole-2-carboxamide (218 mg, 75%) as a yellow solid. MS m/z 443 (M+1).

EXAMPLE 33

5-Methyl-7-(5-nitro-1H-pyrrol-2-yl)-N-(3,4,5-trimethoxyphenyl)-imidazo[5,1-f][1,2,4]triazin-2-amine

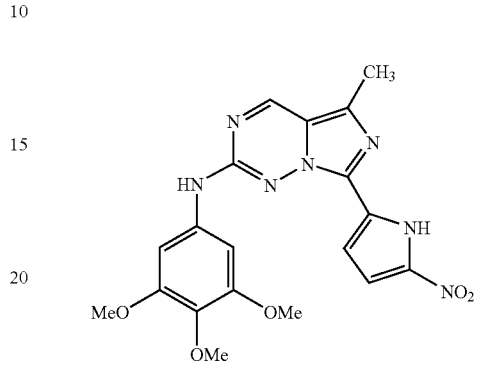

In a similar manner as described for Example 9, 5-nitro-N-(1-{3-[(3,4,5-trimethoxyphenyl)amino]-1,2,4-triazin-6-yl}ethyl)-1H-pyrrole-2-carboxamide (Intermediate 34) (201 mg, 0.45 mmol), and 1,2,4-triazole (190 mg, 2.72 mmol) in pyridine (10 mL) and phosphorous oxychloride (0.13 mL, 1.36 mmol) gave 5-methyl-7-(5-nitro-1H-pyrrol-2-yl)-N-(3,4,5-trimethoxyphenyl)-imidazo[5,1-f][1,2,4]triazin-2-amine (95 mg, 49%) as a yellow solid. $^1$H NMR (DMSO-d$_6$): δ13.04 (s, 1H), 9.63 (s, 1H), 9.25 (s, 1H), 7.98 (dd, J=3.30 and 1.65 Hz, 1H), 7.57 (t, J=2.01 Hz, 1H), 7.05 (s, 2H), 3.74 (s, 6H), 3.65 (s, 3H), 2.54 (s, 3H). MS m/z 425 (M+1).

Intermediate 35: 1-Methyl-N-(1-{3-[(3,4,5-trimethoxyphenyl)amino]-1,2,4-triazin-6-yl}ethyl)-1H-pyrrole-2-carboxamide

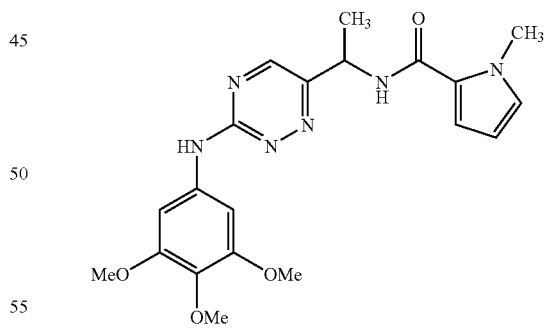

In a similar manner as described for Intermediate 18, 6-(1-aminoethyl)-N-(3,4,5-trimethoxyphenyl)-1,2,4-triazin-3-amine (Intermediate 9) (200 mg, 0.65 mmol), 1-methyl-1H-pyrrole-2-carboxylic acid (106 mg, 0.85 mmol), diisopropylethylamine (0.33 mL, 1.9 mmol) and O-(7-azabenzotriazol-1-yl)-N,N,N',N'-tetramethyluronium hexafluorophosphate (360 mg, 0.94 mmol) in dimethylformamide (5 mL) gave 1-methyl-N-(1-{3-[(3,4,5-trimethoxyphenyl)amino]-1,2,4-triazin-6-yl}ethyl)-1H-pyrrole-2-carboxamide (256 mg, 95%) as a yellow solid. MS m/z 412 (M+1).

EXAMPLE 34:

5-Methyl-7-(1-methyl-1H-pyrrol-2-yl)-N-(3,4,5-trimethoxyphenyl)-imidazo[5,1-f][1,2,4]triazin-2-amine

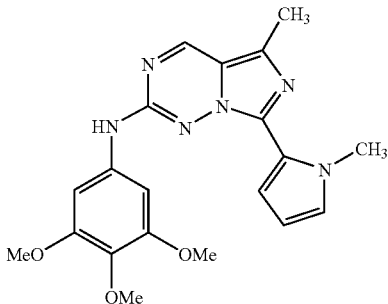

In a similar manner as described for Example 9, 1-methyl-N-(1-{3-[(3,4,5-trimethoxyphenyl)amino]-1,2,4-triazin-6-yl}ethyl)-1H-pyrrole-2-carboxamide (Intermediate 35) (222 mg, 0.54 mmol), and 1,2,4-triazole (220 mg, 3.2 mmol) in pyridine (10 mL) and phosphorous oxychloride (0.15 mL, 1.6 mmol) gave 5-methyl-7-(1-methyl-1H-pyrrol-2-yl)-N-(3,4,5-trimethoxyphenyl)imidazo[5,1-f][1,2,4]triazin-2-amine (52 mg, 25%) as a yellow solid. $^1$H NMR (DMSO-$d_6$): δ9.54 (s, 1H), 9.18 (s, 1H), 7.19 (d, J=2.01 Hz, 1H), 7.16 (s, 2H), 6.98 (s, 1H), 6.14 (t, J=3.02 Hz, 1H), 3.96 (s, 3H), 3.74 (s, 6H), 3.61 (s, 3H), 2.51 (s, 3H). MS m/z 394 (M+1).

Intermediate 36: 1-Methyl-N-(1-{3-[(3,4,5-trimethoxyphenyl)amino]-1,2,4-triazin-6-yl}ethyl)-1H-indole-3-carboxamide

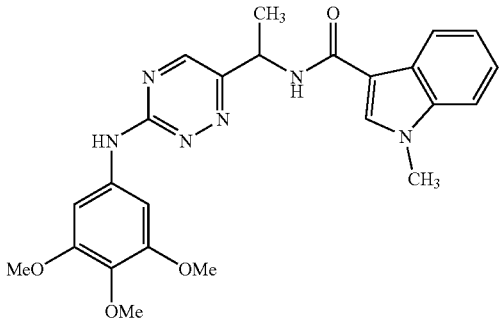

In a similar manner as described for Intermediate 18, 6-(1-aminoethyl)-N-(3,4,5-trimethoxyphenyl)-1,2,4-triazin-3-amine (Intermediate 9) (200 mg, 0.65 mmol), 1-methyl-1H-indole-3-carboxylic acid (150 mg, 0.85 mmol), diisopropylethylamine (0.34 mL, 1.95 mmol) and O-(7-azabenzotriazol-1-yl)-N,N,N',N'-tetramethyluronium hexafluorophosphate (350 mg, 0.92 mmol) in dimethylformamide (5 mL) gave 1-methyl-N-(1-{3-[(3,4,5-trimethoxyphenyl)amino]-1,2,4-triazin-6-yl}ethyl)-1H-indole-3-carboxamide (211 mg, 70%) as a yellow solid. MS m/z 462 (M+1).

EXAMPLE 35

5-Methyl-7-(1-methyl-1H-indol-3-yl)-N-(3,4,5-trimethoxyphenyl)-imidazo[5,1-f][1,2,4]triazin-2-amine

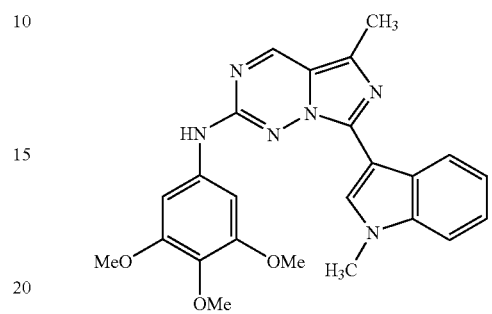

In a similar manner as described for Example 9, 1-methyl-N-(1-{3-[(3,4,5-trimethoxyphenyl)amino]-1,2,4-triazin-6-yl}ethyl)-1H-indole-3-carboxamide (Intermediate 36) (180 mg, 0.39 mmol), and 1,2,4-triazole (165 mg, 2.34 mmol) in pyridine (3 mL) and phosphorous oxychloride (0.11 mL, 1.2 mmol) gave 5-methyl-7-(1-methyl-1H-indol-3-yl)-N-(3,4,5-trimethoxyphenyl)-imidazo[5,1-f][1,2,4]triazin-2-amine (102 mg, 59%) as a yellow solid. $^1$H NMR (DMSO-$d_6$): δ9.47 (s, 1H), 9.16 (s, 1H), 8.52 (d, J=7.87 Hz, 1H), 8.40 (s, 1H), 7.54 (d, J=8.06 Hz, 1H), 7.28 (t, J=7.23 Hz, 1H), 7.20 (t, J=7.42 Hz, 1H), 7.11 (s, 2H), 3.86 (s, 3H), 3.74 (s, 6H), 3.67 (s, 3H), 2.57 (s, 3H). MS m/z 444 (M+1).

Intermediate 37: N-(1-{3-[(3,4,5-Trimethoxyphenyl)amino]-1,2,4-triazin-6-yl}ethyl)-3-furamide

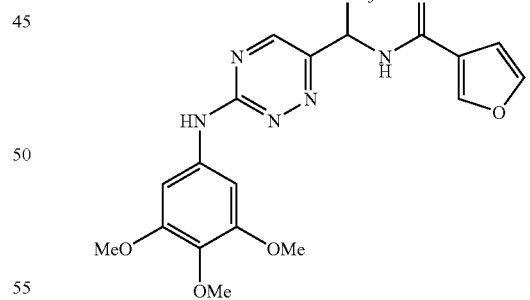

In a similar manner as described for Intermediate 18, 6-(1-aminoethyl)-N-(3,4,5-trimethoxyphenyl)-1,2,4-triazin-3-amine (Intermediate 9) (200 mg, 0.65 mmol), 3-furoic acid (95 mg, 0.85 mmol), diisopropylethylamine (0.34 mL, 1.95 mmol) and O-(7-azabenzotriazol-1-yl)-N,N,N',N'-tetramethyluronium hexafluorophosphate (350 mg, 0.92 mmol) in dimethylformamide (5 mL) gave N-(1-{3-[(3,4,5-trimethoxyphenyl)amino]-1,2,4-triazin-6-yl}ethyl)-3-furamide (226 mg, 86%) as a yellow solid. MS m/z 399 (M+1).

EXAMPLE 36

7-(3-Furyl)-5-methyl-N-(3,4,5-trimethoxyphenyl)imidazo[5,1-f][1,2,4]triazin-2-amine

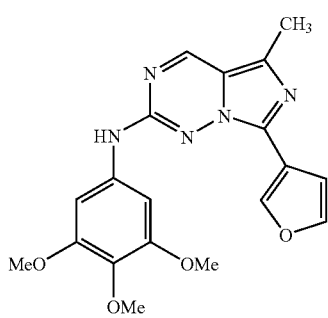

In a similar manner as described for Example 9, N-(1-{3-[(3,4,5-trimethoxyphenyl)amino]-1,2,4-triazin-6-yl}ethyl)-3-furamide (Intermediate 37) (211 mg, 0.53 mmol), and 1,2,4-triazole (220 mg, 3.18 mmol) in pyridine (4 mL) and phosphorous oxychloride (0.15 mL, 1.60 mmol) gave 7-(3-furyl)-5-methyl-N-(3,4,5-trimethoxyphenyl)imidazo[5,1-f][1,2,4]triazin-2-amine (102 mg, 51%) as a yellow solid. $^1$H NMR (CDCl$_3$): δ8.78 (s, 1H), 8.56 (s, 1H), 7.52 (t, J=1.65 Hz, 1H), 7.20 (d, J=1.65, 1H), 6.87 (s, 2H), 6.82 (s, 1H), 3.90 (s, 6H), 3.87 (s, 3H), 2.60 (s, 3H). MS m/z 381 (M+1).

Intermediate 38: N-(1-{3-[(3,4,5-Trimethoxyphenyl)amino]-1,2,4-triazin-6-yl}ethyl)-1H-indole-5-carboxamide

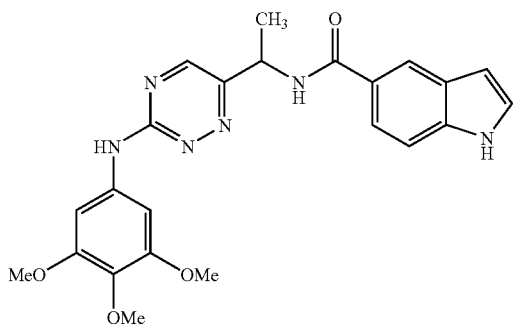

In a similar manner as described for Intermediate 18, 6-(1-aminoethyl)-N-(3,4,5-trimethoxyphenyl)-1,2,4-triazin-3-amine (Intermediate 9) (200 mg, 0.65 mmol), 1H-indole-5-carboxylic acid (140 mg, 0.85 mmol), diisopropylethylamine (0.34 mL, 1.95 mmol) and O-(7-azabenzotriazol-1-yl)-N,N,N',N'-tetramethyluronium hexafluorophosphate (350 mg, 0.92 mmol) in dimethylformamide (5 mL) gave N-(1-{3-[(3,4,5-trimethoxyphenyl)amino]-1,2,4-triazin-6-yl}ethyl)-1H-indole-5-carboxamide (187 mg, 64%) as a yellow solid. MS m/z 448 (M+1).

EXAMPLE 37

7-(1H-Indol-5-yl)-5-methyl-N-(3,4,5-trimethoxyphenyl)imidazo-[5,1-f][1,2,4]triazin-2-amine

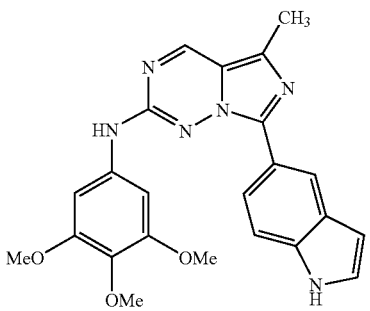

In a similar manner as described for Example 9, N-(1-{3-[(3,4,5-trimethoxyphenyl)amino]-1,2,4-triazin-6-yl}ethyl)-1H-indole-5-carboxamide (Intermediate 38) (176 mg, 0.39 mmol), and 1,2,4-triazole (161 mg, 2.34 mmol) in pyridine (4 mL) and phosphorous oxychloride (0.11 mL, 1.2 mmol) gave 7-(1H-indol-5-yl)-5-methyl-N-(3,4,5-trimethoxyphenyl)imidazo[5,1-f][1,2,4]triazin-2-amine (63 mg, 37%) as a yellow solid. $^1$H NMR (CDCl$_3$): δ8.87 (s, 1H), 8.79 (s, 1H), 8.35 (s, 1H), 8.29 (dd, J=8.61 and 1.46 Hz, 1H), 7.47 (d, J=8.61 Hz, 1H), 6.95 (s, 2H), 6.84 (s, 1H), 6.62 (s, 1H), 3.87 (s, 3H), 3.77 (s, 6H), 2.64 (s, 3H). MS m/z 430 (M+1).

Intermediate 39: 2-[(2-Cyanophenyl)thio]-N-(1-{3-[(3,4,5-trimethoxyphenyl)-amino]-1,2,4-triazin-6-yl}ethyl)benzamide

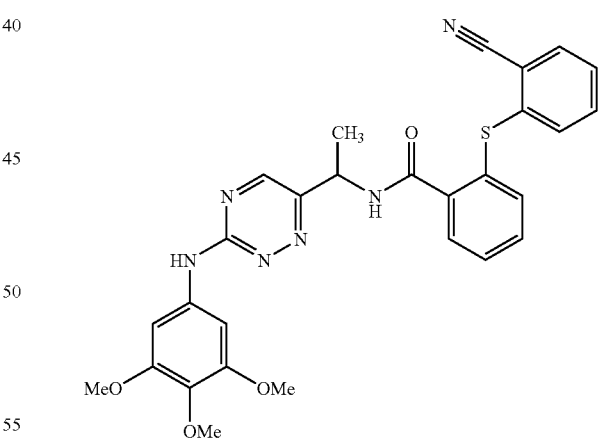

In a similar manner as described for Intermediate 18, 6-(1-aminoethyl)-N-(3,4,5-trimethoxyphenyl)-1,2,4-triazin-3-amine (Intermediate 9) (200 mg, 0.65 mmol), 2-[(2-cyanophenyl)thio]benzoic acid (217 mg, 0.85 mmol), diisopropylethylamine (0.34 mL, 1.95 mmol) and O-(7-azabenzotriazol-1-yl)-N,N,N',N'-tetramethyluronium hexafluorophosphate (350 mg, 0.92 mmol) in dimethylformamide (5 mL) gave 2-[(2-cyanophenyl)thio]-N-(1-{3-[(3,4,5-trimethoxyphenyl)amino]-1,2,4-triazin-6-yl}ethyl)benzamide (282 mg, 80%) as a yellow solid. MS m/z 542 (M+1).

EXAMPLE 38

2-[(2-{5-Methyl-2-[(3,4,5-trimethoxyphenyl)amino]imidazo[5,1-f][1,2,4]triazin-7-yl}phenyl)thio]benzonitrile

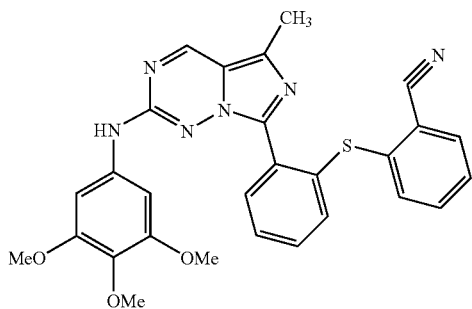

In a similar manner as described for Example 9, 2-[(2-cyanophenyl)thio]-N-(1-{3-[(3,4,5-trimethoxyphenyl)amino]-1,2,4-triazin-6-yl}ethyl)benzamide (Intermediate 39) (269 mg, 0.49 mmol), and 1,2,4-triazole (210 mg, 2.94 mmol) in pyridine (3 mL) and phosphorous oxychloride (0.14 mL, 1.5 mmol) gave 2-[(2-{5-methyl-2-[(3,4,5-trimethoxyphenyl)amino]imidazo[5,1-f][1,2,4]triazin-7-yl}phenyl)thio]benzonitrile (95 mg, 37%) as a yellow solid. $^1$H NMR (CDCl$_3$): δ8.77 (s, 1H), 7.70 (m, 1H), 7.57 (m, 1H), 7.42-7.47 (m, 3H), 7.10-7.23 (m, 3H), 6.85 (s, 1H), 6.79 (s, 2H), 3.80 (s, 3H), 3.63 (s, 6H), 2.57 (s, 3H). MS m/z 524 (M+1).

Intermediate 40: 2-{[3-(Trifluoromethyl)phenyl]amino}-N-(1-{3-[(3,4,5-trimethoxyphenyl)amino]-1,2,4-triazin-6-yl}ethyl)benzamide

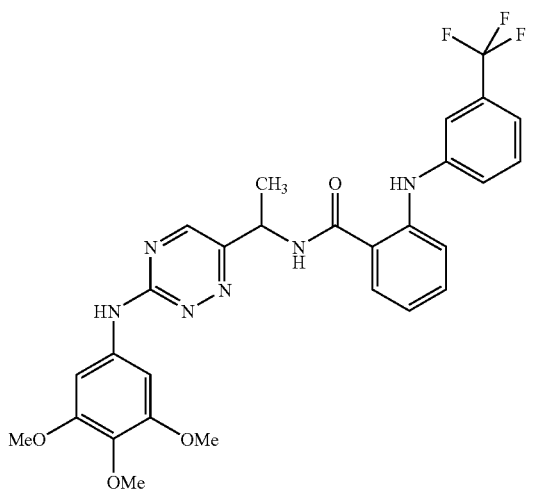

In a similar manner as described for Intermediate 18, 6-(1-aminoethyl)-N-(3,4,5-trimethoxyphenyl)-1,2,4-triazin-3-amine (Intermediate 9) (200 mg, 0.65 mmol), 2-{[3-(trifluoromethyl)phenyl]amino}benzoic acid (240 mg, 0.85 mmol), diisopropylethylamine (0.34 mL, 1.95 mmol) and O-(7-azabenzotriazol-1-yl)-N,N,N',N'-tetramethyluronium hexafluorophosphate (350 mg, 0.92 mmol) in dimethylformamide (5 mL) gave 2-{[3-(trifluoromethyl)phenyl]amino}-N-(1-{3-[(3,4,5-trimethoxyphenyl)amino]-1,2,4-triazin-6-yl}ethyl)benzamide (297 mg, 80%) as a yellow solid. MS m/z 568 (M+1).

EXAMPLE 39

5-Methyl-7-(2-{[3-(trifluoromethyl)phenyl]amino}phenyl)-N-(3,4,5-trimethoxyphenyl)imidazo[5,1-f][1,2,4]triazin-2-amine

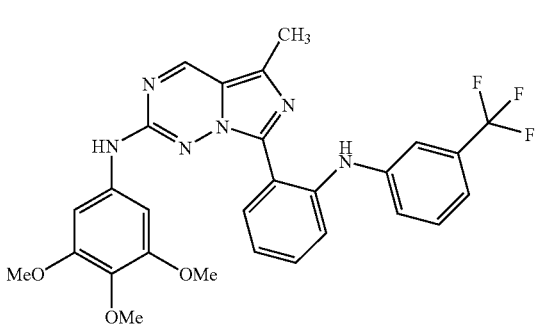

In a similar manner as described for Example 9, 2-{[3-(trifluoromethyl)phenyl]amino}-N-(1-{3-[(3,4,5-trimethoxyphenyl)amino]-1,2,4-triazin-6-yl}ethyl)benzamide (Intermediate 40) (276 mg, 0.48 mmol), and 1,2,4-triazole (200 mg, 2.91 mmol) in pyridine (3 mL) and phosphorous oxychloride (0.14 mL, 1.5 mmol) gave 5-methyl-7-(2-{[3-(trifluoromethyl)phenyl]amino}phenyl)-N-(3,4,5-trimethoxyphenyl)imidazo[5,1-f][1,2,4]triazin-2-amine (124 mg, 48%) as a yellow solid. $^1$H NMR (CDCl$_3$): δ9.53 (s, 1H), 8.83 (s, 1H), 8.39 (dd, J=7.87 and 1.28 Hz, 1H), 7.45 (d, J=8.06 Hz, 1H), 7.32 (t, J=7.78 Hz, 2H), 7.23 (m, 2H), 7.12 (d, J=7.51 Hz, 1H), 7.01 (t, J=7.32 Hz, 1H), 6.92 (s, 1H), 6.90 (s, 2H), 3.83 (s, 3H), 3.79 (s, 6H), 2.63 (s, 3H). MS m/z 550 (M+1).

Intermediate 41: N-(1-{3-[(3,4,5-Trimethoxyphenyl)amino]-1,2,4-triazin-6-yl}ethyl)quinoline-8-carboxamide

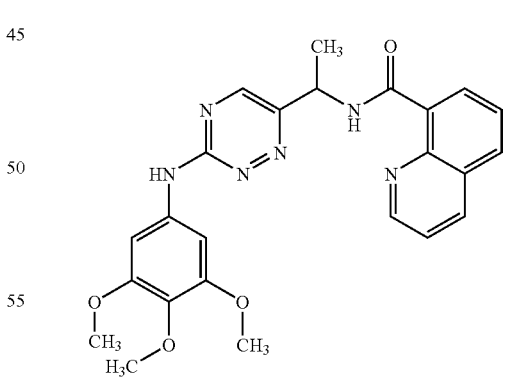

In a similar manner as described for Intermediate 18, 6-(1-aminoethyl)-N-(3,4,5-trimethoxyphenyl)-1,2,4-triazin-3-amine (Intermediate 9) (0.123 g, 0.40 mmol), O-(7-azabenzotriazol-1-yl)-N,N,N',N'-tetramethyluronium hexafluorophosphate (0.152 g, 0.40 mmol), quinoline-8-carboxylic acid (0.070 g, 0.40 mmol), diisopropylethylamine (0.14 mL, 0.80 mmol) in DMF (2 mL) gave N-(1-{3-[(3,4,5-trimethoxyphenyl)amino]-1,2,4-triazin-6-yl}ethyl)quinoline-8-carboxamide (0.180 g) as an orange solid. ¹H NMR (CDCl₃): δ8.95 (dd, J=4.4, 1.8 Hz, 1H), 8.83 (dd, J=7.4, 1.6 Hz, 1H), 8.50 (s, 1H), 8.30 (dd, J=8.2, 1.8 Hz, 1H), 7.99 (dd, J=8.3, 1.6 Hz, 1H), 7.71-7.65 (m, 1H), 7.53-7.48 (m, 1H), 7.42 (bs, 1H), 6.95 (s, 2H), 5.60 (p, J=7.1 Hz, 1H), 3.88 (s, 6H), 3.82 (s, 3H), 1.87 (d, J=7.1 Hz, 3H). MS m/z 461 (M+1).

EXAMPLE 40

5-Methyl-7-quinolin-8-yl-N-(3,4 5-trimethoxyphenyl)imidazo[5,1-f][1,2,4]triazin-2-amine

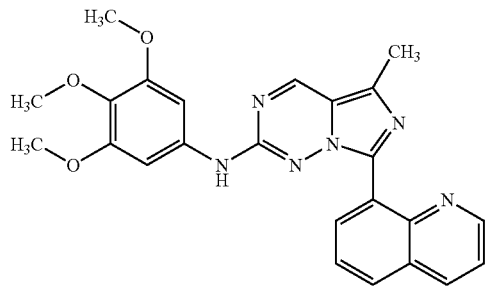

In a similar manner as described for Example 1, N-(1-{3-[(3,4,5-trimethoxyphenyl)amino]-1,2,4-triazin-6-yl}ethyl)quinoline-8-carboxamide (Intermediate 41) (0.080 g, 0.17 mmol) in 1,2-dichloroethane (5 mL) and phosphorus oxychloride (0.13 mL, 1.4 mmol) gave 5-methyl-7-quinolin-8-yl-N-(3,4,5-trimethoxyphenyl)imidazo[5,1-f][1,2,4]triazin-2-amine (0.022 g) as a yellow solid. ¹H NMR (CDCl₃): δ8.90 (dd, J=4.2, 1.8 Hz, 1H), 8.83 (s, 1H), 8.22 (dd, J=8.3, 1.8 Hz, 1H), 8.03 (dd, J=7.2, 1.5 Hz, 1H), 7.97 (dd, J=8.2, 1.5 Hz, 1H), 7.67 (dd, J=8.2, 7.1 Hz, 1H), 7.45-7.41 (m, 1H), 6.91 (bs, 1H), 6.58 (s, 2H), 3.69 (s, 3H), 3.25 (s, 6H), 2.67 (s, 3H). MS m/z 443 (M+1).

Intermediate 42: N-[1-(3-amino-5-oxo-4,5-dihydro-1,2,4-triazin-6-yl)ethyl]-3-(trifluoromethyl)benzamide

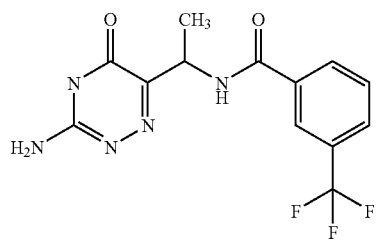

A solution of ethyl 2-oxo-3-{[3-(trifluoromethyl)benzoyl]amino}butanoate (8.75 g, 27.6 mmol) and aminoguanidine bicarbonate (3.75 g, 27.6 mmol) in EtOH₍aq₎ (80%, 200 mL) was heated at reflux for 3h. Concentration gave crude N-[1-(3-amino-5-oxo-4,5-dihydro-1,2,4-triazin-6-yl)ethyl]-3-(trifluoromethyl)benzamide (8.34 g) as a colourless solid which was used without further purification. ¹H NMR (DMSO-d₆): δ8.87 (d, J=7.5 Hz, 1H), 8.23 (s, 1H), 8.20-8.15 (m, 2H), 7.93-7.89 (m, 1H), 7.75-7.69 (m, 1H), 7.00 (bs, 1H), 5.16 (p, J=7.1 Hz, 1H), 1.40 (d, J=7.1 Hz, 3H). MS m/z 326 (M−1).

Intermediate 43: 2-Amino-5-methyl-7-[3-(trifluoromethyl)phenyl]imidazo[5,1-f][1,2,4]triazin-4(3H)-one

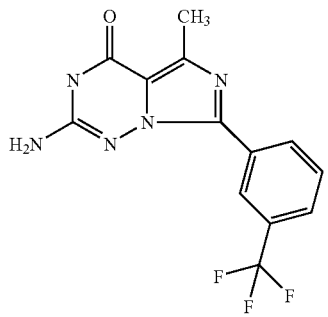

Crude N-[1-(3-amino-5-oxo-4,5-dihydro-1,2,4-triazin-6-yl)ethyl]-3-(trifluoromethyl)benzamide (Intermediate 42) (8.34 g, 25.5 mmol) was suspended in POCl₃ (30 mL) and heated in a sealed tube at 110° C. for 2h. After the reaction had cooled to rt, the solution was carefully poured onto ice, neutralized with NaOH₍aq₎ and extracted into EtOAc. The combined organic extracts were dried (MgSO₄), filtered, and concentrated. Purification of the residue by chromatography afforded 2-amino-5-methyl-7-[3-(trifluoromethyl)phenyl]imidazo[5,1-f][1,2,4]triazin-4(3H-one (1.63 g) as a pale yellow solid. ¹H NMR (DMSO-d₆): δ10.91 (s, 1H), 8.75-8.71 (m, 1H), 8.66 (s, 1H), 7.77-7.68 (m, 2H), 6.25 (bs, 2H), 2.48 (s, 3H). MS m/z 308 (M−1).

Intermediate 44: 5-Methyl-7-[3-(trifluoromethyl)phenyl]-3,4-dihydroimidazo[5,1-f][1,2,4]triazin-2-amine

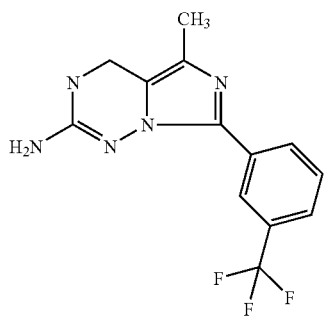

Lithium aluminum hydride was added in portions to a stirring solution of 2-amino-5-methyl-7-[3-(trifluoromethyl)phenyl]imidazo[5,1-f][1,2,4]triazin-4(3H)-one (Intermediate 43) (2.0 g, 6.47 mmol) in DME (50 mL) at rt. The resultant mixture was then heated to reflux for 2 h. The reaction mixture was then cooled to 0° C. and carefully quenched with H₂O. After extraction into EtOAc., the combined organic extracts were dried (MgSO₄), filtered, and concentrated. Purification of the residue by chromatography afforded 2-methyl-7-[3-(trifluoromethyl)phenyl]-3,4-dihydroimidazo[5,1-f][1,2,4]triazin-2-amine (0.60 g) as a pale yellow solid. ¹H NMR (DMSO-d₆): δ8.67-8.60 (m, 1H), 8.54 (s, 1H), 7.61-7.54 (m, 2H), 6.55 (s, 1H), 5.50 (s, 2H), 4.35 (s, 2H), 2.06 (s, 3H). MS m/z 294 (M−1).

Intermediate 45: 5-Methyl-7-[3-(trifluoromethyl)phenyl]imidazo[5,1-f][1,2,4]triazin-2-amine

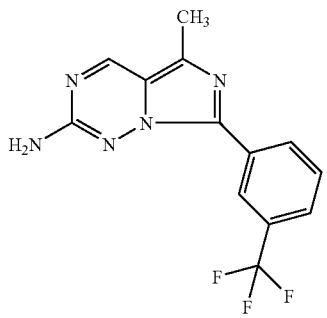

A mechanical mixture of 5-methyl-7-[3-(trifluoromethyl)phenyl]-3,4-dihydroimidazo[5,1-f][1,2,4]triazin-2-amine (Intermediate 44) (1.30 g, 4.41 mmol) and Pd/C (0.50 g) in EtOH (250 mL) was heated at reflux for 7 days. The reaction mixture was then cooled to rt and filtered through celite. Concentration of the filtrate followed by purification of the residue by chromatography afforded 5-methyl-7-[3-(trifluoromethyl)phenyl]-imidazo[5,1-f][1,2,4]triazin-2-amine (0.50 g) as a pale yellow solid. $^1$H NMR (Acetone-$d_6$): δ9.06 (s, 1H), 8.94 (s, 1H), 8.92-8.86 (m, 1H), 7.75-7.69 (m, 2H), 6.29 (bs, 2H), 2.55 (s, 3H). MS m/z 292 (M−1).

EXAMPLE 41

3-({5-Methyl-7-[3-(trifluoromethyl)phenyl]imidazo[5,1-f][1,2,4]triazin-2-yl}amino)benzenesulfonamide

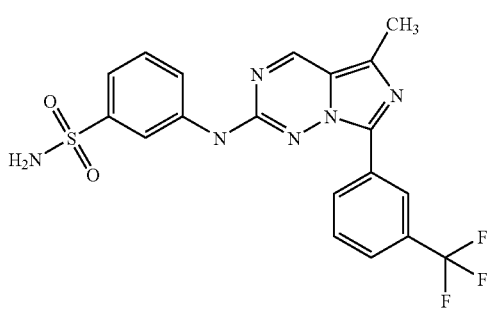

A mechanical mixture of 5-methyl-7-[3-(trifluoromethyl)phenyl]imidazo[5,1-f][1,2,4]triazin-2-amine (Intermediate 45) (0.025 g, 0.09 mmol), 3-bromobenzenesulfonamide (0.02 g, 0.09 mmol), Pd$_2$(dba)$_3$ (0.008 g, 0.01 mmol), 2-(Di-t-butylphosphino)biphenyl (0.008 g, 0.03 mmol), and NaOtBu (0.011 g, 0.11 mmol) in 1,4-dioxane (1 mL) was irradiated with microwave radiation for 1000 seconds at a temperature of 150° C. Filtration of the resultant through celite, followed by concentration and purification by preparative HPLC gave 3-({5-methyl-7-[3-(trifluoromethyl)phenyl]imidazo[5,1-f][1,2,4]triazin-2-yl}amino)benzenesulfonamide (0.008 g) as a yellow solid. $^1$H NMR (Acetone-d6): δ9.19 (s, 1H), 8.98-8.93 (m, 1H), 8.81 (bs, 1H), 8.42-8.37 (m, 1H), 8.10-8.05 (m, 1H), 7.95-7.90(m, 1H), 7.81-7.75 (m, 1H), 7.67-7.50 (m, 2H), 6.63 (bs, 1H), 2.60 (s, 3H). MS m/z 449 (M+1).

EXAMPLE 42

N-Methyl-N-[4-({5-methyl-7-[3-(trifluoromethyl)phenyl]imidazo[5,1-f][1,2,4]triazin-2-yl}amino)phenyl]urea

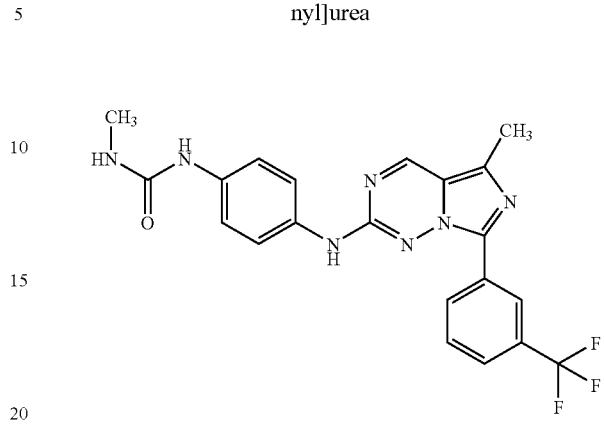

In a similar manner as described for Example 41, 5-methyl-7-[3-(trifluoromethyl)phenyl]imidazo[5,1-f][1,2,4]triazin-2-amine (Intermediate 45) (0.025 g, 0.09 mmol), N-(4-bromophenyl)-N-methylurea (0.02 g, 0.09 mmol), Pd$_2$(dba)$_3$ (0.008 g, 0.01 mmol), 2-(Di-t-butylphosphino)biphenyl (0.008 g, 0.03 mmol), and NaOtBu (0.011 g, 0.11 mmol) in 1,4-dioxane (1 mL) gave N-methyl-N-[4-({5-methyl-7-[3-(trifluoromethyl)phenyl]imidazo[5,1-f][1,2,4]triazin-2-yl}amino)phenyl]urea (0.016 g) as a yellow solid. $^1$H NMR (Acetone-d6): δ9.11 (s, 1H), 8.99-8.95 (m, 1H), 8.82-8.76 (m, 1H), 8.69-8.66 (m, 1H), 7.95-7.91 (m, 1H), 7.80-7.76 (m, 2H), 7.74-7.69 (m, 3H), 7.57-7.52 (m, 2H), 6.30 (bs, 1H), 5.61 (bs, 1H), 2.76 (d, J=4.8 Hz, 3H), 2.57 (s, 3H). MS m/z 442 (M+1).

EXAMPLE 43

N-[4-Methoxy-3-({5-methyl-7-[3-(trifluoromethyl)phenyl]imidazo-[5,1-f][1,2,4]triazin-2-yl}amino)phenyl]acetamide

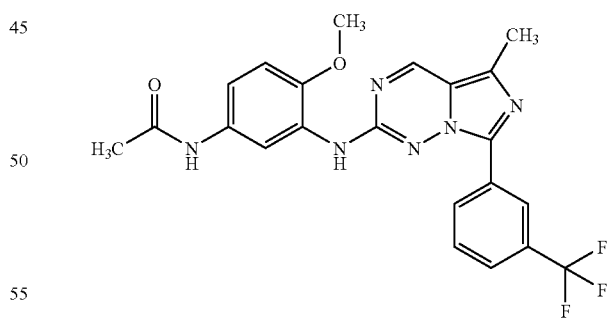

In a similar manner as described for Example 41, 5-methyl-7-[3-(trifluoromethyl)phenyl]imidazo[5,1-f][1,2,4]triazin-2-amine (intermediate 45) (0.025 g, 0.09 mmol), N-(3-bromo-4-methoxyphenyl)acetamide (0.044 g, 0.18 mmol), Pd$_2$(dba)$_3$ (0.008 g, 0.01 mmol), 2-(Di-t-butylphosphino)biphenyl (0.008 g, 0.03 mmol), and NaOtBu (0.011 g, 0.11 mmol) in 1,4-dioxane (1 mL) gave N-[4-methoxy-3-({5-methyl-7-[3-(trifluoromethyl)phenyl]imidazo[5,1-f][1,2,4]triazin-2-yl}amino)phenyl]acetamide (0.007 g) as a yellow solid. $^1$H NMR (Acetone-d6): δ9.15 (s, 1H), 9.06 (bs, 1H), 8.98 (d, J=7.6 Hz, 1H), 8.73 (s, 1H), 8.53 (d, J=2.4 Hz, 1H), 7.83-7.70 (m, 3H), 7.30 (dd, J=8.7, 2.3 Hz, 1H), 7.00 (d, J=8.8 Hz, 1H), 3.94 (s, 3H), 2.59 (s, 3H), 2.09 (s, 3H). MS m/z 457 (M+1).

EXAMPLE 44

2-[3-({5-Methyl-7-[3-(trifluoromethyl)phenyl]imidazo[5,1-f][1,2,4]triazin-2-yl}amino)phenyl]ethanol

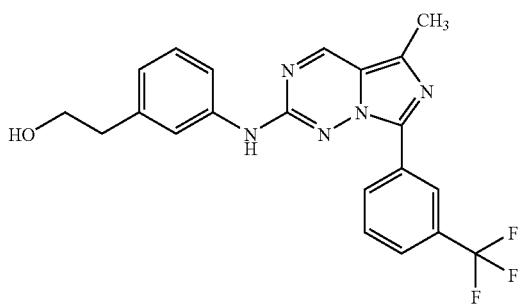

In a similar manner as described for Example 41, 5-methyl-7-[3-(trifluoromethyl)phenyl]imidazo[5,1-f][1,2,4]triazin-2-amine (Intermediate 45) (0.025 g, 0.09 mmol), 2-(3-bromophenyl)ethanol (0.012 mL, 0.09 mmol), $Pd_2(dba)_3$ (0.008 g, 0.01 mmol), 2-(Di-t-butylphosphino)biphenyl (0.008 g, 0.03 mmol), and NaOtBu (0.011 g, 0.11 mmol) in 1,4-dioxane (1 mL) gave 2-[3-({5-methyl-7-[3-(trifluoromethyl)phenyl]imidazo[5,1-f][1,2,4]triazin-2-yl}amino)phenyl]ethanol (0.020 g) as a yellow solid. $^1$H NMR (Acetone-d6): δ9.13 (s, 1H), 8.91 (d, J=7.9 Hz, 1H), 8.85 (s, 1H), 8.74 (bs, 1H), 7.89-7.75 (m, 3H), 7.76 (s, 1H), 7.33 (dd, J=7.8, 7.8 Hz, 1H), 7.22 (s, 1H), 7.00 (d, J=7.7 Hz, 1H), 3.81 (t, J=7.0 Hz, 2H), 2.87 (t, J=7.0 Hz, 2H), 2.57 (s, 3H). m/z 414 (M+1).

EXAMPLE 45

4-({5-Methyl-7-[3-(trifluoromethyl)phenyl]imidazo[5,1-f][1,2,4]triazin-2-yl}amino)benzenesulfonamide

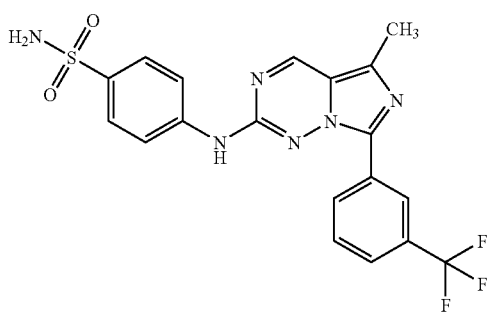

In a similar manner as described for Example 41, 5-methyl-7-[3-(trifluoromethyl)phenyl]imidazo[5,1-f][1,2,4]triazin-2-amine (Intermediate 45) (0.025 g, 0.09 mmol), 4-bromobenzenesulfonamide (0.020 g, 0.09 mmol), $Pd_2(dba)_3$ (0.008 g, 0.01 mmol), 2-(Di-t-butylphosphino)biphenyl (0.008 g, 0.03 mmol), and NaOtBu (0.011 g, 0.11 mmol) in 1,4-dioxane (1 mL) gave 4-({5-methyl-7-[3-(trifluoromethyl)phenyl]imidazo[5,1-f][1,2,4]triazin-2-yl}amino)benzenesulfonamide (0.008 g) as a yellow solid. $^1$H NMR (Acetone-d6): δ9.24 (bs, 1H), 9.21 (s, 1H), 8.93 (s, 1H), 8.80-8.75 (m, 1H), 8.05-8.00 (m, 2H), 7.95-7.90 (m, 2H), 7.88-7.82 (m, 2H), 6.53 (bs, 2H), 2.61 (s, 3H). MS m/z 449 (M+1).

EXAMPLE 46

N-[4-({5-Methyl-7-[3-(trifluoromethyl)phenyl]imidazo[5,1-f][1,2,4]triazin-2-yl}amino)phenyl]acetamide

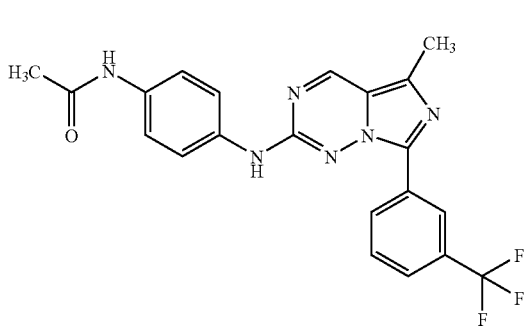

In a similar manner as described for Example 41, 5-methyl-7-[3-(trifluoromethyl)phenyl]imidazo[5,1-f][1,2,4]triazin-2-amine (Intermediate 45) (0.025 g, 0.09 mmol), N-(4-bromophenyl)acetamide (0.018 g, 0.09 mmol), $Pd_2(dba)_3$ (0.008 g, 0.01 mmol), 2-(Di-t-butylphosphino)biphenyl (0.008 g, 0.03 mmol), and NaOtBu (0.011 g, 0.11 mmol) in 1,4-dioxane (1 mL) gave N-[4-({5-methyl-7-[3-(trifluoromethyl)phenyl]imidazo[5,1-f][1,2,4]triazin-2-yl}amino)phenyl]acetamide (0.015 g) as a yellow solid. $^1$H NMR (DMSO-d6): δ9.92 (s, 1H), 9.82 (s, 1H), 9.26 (s, 1H), 8.87 (s, 1H), 8.59 (d, J=7.4 Hz, 1H), 7.86-7.70 (m, 2H), 7.68-7.63 (m, 2H), 7.60-7.53 (m,2H), 2.53 (s, 3H), 2.02 (s, 3H). MS m/z 427 (M+1).

EXAMPLE 47

N-[3-({5-Methyl-7-[3-(trifluoromethyl)phenyl]imidazo[5,1-f][1,2,4]triazin-2-yl}amino)phenyl]acetamide

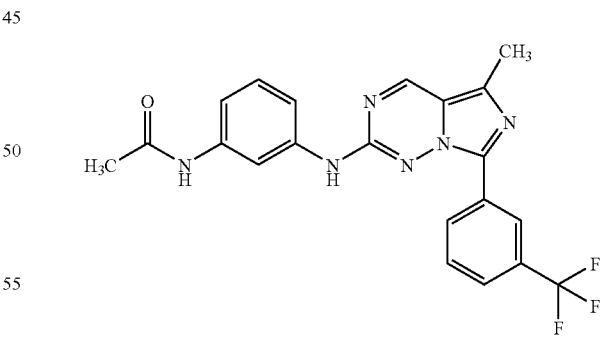

In a similar manner as described for Example 41, 5-methyl-7-[3-(trifluoromethyl)phenyl]imidazo[5,1-f][1,2,4]triazin-2-amine (Intermediate 45) (0.025 g, 0.09 mmol), N-(3-bromophenyl)acetamide (0.018 g, 0.09 mmol), $Pd_2(dba)_3$ (0.008 g, 0.01 mmol), 2-(Di-t-butylphosphino)biphenyl (0.008 g, 0.03 mmol), and NaOtBu (0.011 g, 0.11 mmol) in 1,4-dioxane (1 mL) gave N-[3-({5-methyl-7-[3-(trifluoromethyl)phenyl]imidazo[5,1-f][1,2,4]triazin-2-yl}amino)phenyl]acetamide (0.011 g) as a yellow solid. $^1$H NMR (DMSO-d6): δ9.94

(s, 1H), 9.87 (s, 1H), 9.31 (s, 1H), 8.81 (s, 1H), 8.71 (d, J=8.8 Hz, 1H), 7.87 (s, 1H), 7.83-7.72 (m, 2H), 7.59-7.54 (m, 1H), 7.28-7.20 (m, 2H), 2.56 (s, 3H), 2.04 (s, 3H). MS m/z 427 (M+1).

EXAMPLE 48 tert-Butyl 3-({5-methyl-7-[3-(trifluoromethyl)phenyl]imidazo[5,1-f][1,2,4]triazin-2-yl}amino)benzylcarbamate

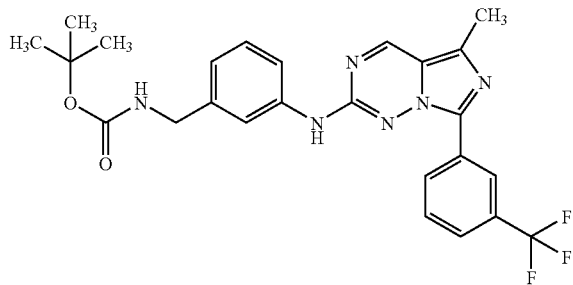

In a similar manner as described for Example 41, 5-methyl-7-[3-(trifluoromethyl)phenyl]imidazo[5,1-f][1,2,4]triazin-2-amine (Intermediate 45) (0.025 g, 0.09 mmol), tert-butyl 3-iodobenzylcarbamate (0.028 g, 0.09 mmol), $Pd_2(dba)_3$ (0.008 g, 0.01 mmol), 2-(Di-t-butylphosphino)biphenyl (0.008 g, 0.03 mmol), and NaOtBu (0.011 g, 0.11 mmol) in 1,4-dioxane (1 mL) gave tert-butyl 3-({5-methyl-7-[3-(trifluoromethyl)phenyl]imidazo[5,1-f][1,2,4]triazin-2-yl}amino)benzylcarbamate (0.014 g) as a yellow solid. $^1$H NMR (CDCl$_3$): δ8.82 (s, 1H), 8.80 (s, 1H), 8.66 (d, J=7.3 Hz, 1H), 7.79-7.73 (m, 1H), 7.70-7.60 (m, 2H), 7.42-7.28 (m, 4H), 7.18 (bs, 1H), 7.04 (d, J=7.7 Hz, 1H), 4.32 (bs, 2H), 2.61 (s, 3H), 1.46 (s, 9H). MS m/z 499 (M+1).

EXAMPLE 49:

4-({5-Methyl-7-[3-(trifluoromethyl)phenyl]imidazo[5,1-f][1,2,4]triazin-2-yl}amino)phenol

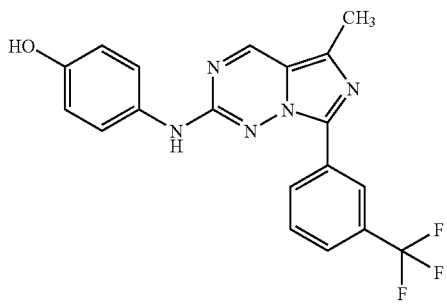

In a similar manner as described for Example 41, 5-methyl-7-[3-(trifluoromethyl)phenyl]imidazo[5,1-f][1,2,4]triazin-2-amine (Intermediate 45) (0.025 g, 0.09 mmol), 4-bromophenol (0.015 g, 0.09 mmol), $Pd_2(dba)_3$ (0.008 g, 0.01 mmol), 2-(Di-t-butylphosphino)biphenyl (0.008 g, 0.03 mmol), and NaOtBu (0.011 g, 0.11 mmol) in 1,4-dioxane (1 mL) gave 4-({5-methyl-7-[3-(trifluoromethyl)phenyl]imidazo[5,1-f][1,2,4]triazin-2-yl}amino)phenol (0.020 g) as a yellow solid. $^1$H NMR (Acetone-d6): δ9.06 (s, 1H), 8.91 (s, 1H), 8.68 (d, J=4.8 Hz, 1H), 7.77-7.70 (m, 3H), 7.59 (d, J=8.4 Hz, 2H), 6.84 (d, J=8.4 Hz, 2H), 2.55 (s, 3H). MS m/z 386 (M+1).

EXAMPLE 50

5-Methyl-N-[4-(2-pyrrolidin-1-ylethoxy)phenyl]-7-[3-(trifluoromethyl)phenyl]imidazo[5,1-f][1,2,4]triazin-2-amine

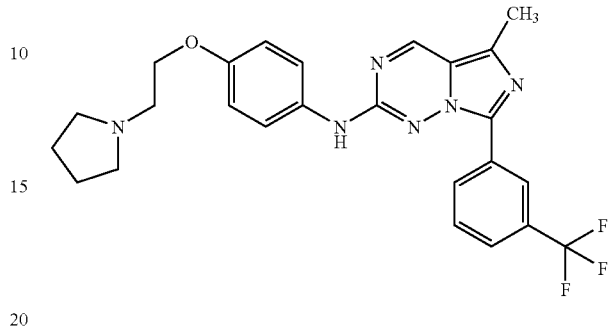

In a similar manner as described for Example 41, 5-methyl-7-[3-(trifluoromethyl)phenyl]imidazo[5,1-f][1,2,4]triazin-2-amine (Intermediate 45) (0.025 g, 0.09 mmol), 1-[2-(4-bromophenoxy)ethyl]pyrrolidine (0.016 mL, 0.09 mmol), $Pd_2(dba)_3$ (0.008 g, 0.01 mmol), 2-(Di-t-butylphosphino)biphenyl (0.008 g, 0.03 mmol), and NaOtBu (0.011 g, 0.11 mmol) in 1,4-dioxane (1 mL) gave 5-methyl-N-[4-(2-pyrrolidin-1-ylethoxy)phenyl]-7-[3-(trifluoromethyl)phenyl]imidazo[5,1-f][1,2,4]triazin-2-amine (0.031 g) as a yellow solid. $^1$H NMR (CD$_3$OD): δ9.04 (s, 1H), 8.84 (s, 1H), 8.53 (d, J=7.3 Hz, 1H), 8.34 (bs, 2H), 7.75-7.64 (m, 4H), 7.02 (d, J=8.8 Hz, 2H), 4.33 (t, J=4.8 Hz, 2H), 3.66 (t, J=4.8 Hz, 2H), 3.48 (bs, 4H), 2.58 (s, 3H), 2.13 (bs, 4H). MS m/z 483 (M+1).

EXAMPLE 51

N-(5-Fluoro-2-methoxyphenyl)-5-methyl-7-[3-(trifluoromethyl)phenyl]-imidazo[5,1-f][1,2,4]triazin-2-amine

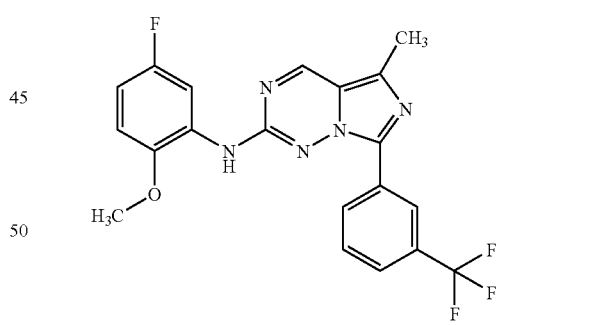

In a similar manner as described for Example 41, 5-methyl-7-[3-(trifluoromethyl)phenyl]imidazo[5,1-f][1,2,4]triazin-2-amine (Intermediate 45) (0.025 g, 0.09 mmol), 2-bromo-4-fluoro-1-methoxybenzene (0.017 g, 0.09 mmol), $Pd_2(dba)_3$ (0.008 g, 0.01 mmol), 2-(Di-t-butylphosphino)biphenyl (0.008 g, 0.03 mmol), and NaOtBu (0.011 g, 0.11 mmol) in 1,4-dioxane (1 mL) gave N-(5-fluoro-2-methoxyphenyl)-5-methyl-7-[3-(trifluoromethyl)phenyl]imidazo[5,1-f][1,2,4]triazin-2-amine (0.011 g) as a yellow solid. $^1$H NMR (Acetone-d6): δ9.17 (s, 1H), 8.83-8.79 (m, 1H), 8.76 (s, 1H), 8.16 (dd, J=10.9, 3.0 Hz, 1H), 7.87-7.74 (m, 3H), 7.09-7.04 (m, 1H), 6.83-6.76 (m, 1H), 3.98 (s, 3H), 2.59 (s, 3H). MS m/z 418 (M+1).

EXAMPLE 52

N-{2-[4-Methoxy-3-({5-methyl-7-[3-(trifluoromethyl)phenyl]-imidazo[5,1-f][1,2,4]triazin-2-yl}amino)phenyl]ethyl}acetamide

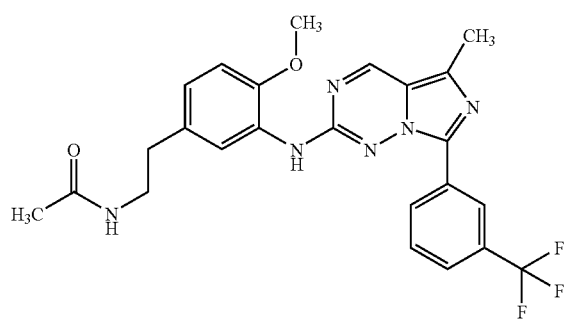

In a similar manner as described for Example 41, 5-methyl-7-[3-(trifluoromethyl)-phenyl]imidazo[5,1-f][1,2,4]triazin-2-amine (Intermediate 45) (0.050 g, 0.17 mmol), N-[2-(3-bromo-4-methoxyphenyl)ethyl]acetamide (0.046 g, 0.17 mmol), Pd$_2$(dba)$_3$ (0.016 g, 0.02 mmol), 2-(Di-t-butylphosphino)biphenyl (0.015 g, 0.05 mmol), and NaOtBu (0.033 g, 0.34 mmol) in 1,4-dioxane (2 mL) gave N-{2-[4-methoxy-3-({5-methyl-7-[3-(trifluoromethyl)phenyl]imidazo[5,1-f][1,2,4]triazin-2-yl}amino)phenyl]-ethyl}acetamide (0.057 g) as a yellow solid. $^1$H NMR (CDCl$_3$): δ 8.85 (s, 1H), 8.80 (d, J=7.7 Hz, 1H), 8.62 (s, 1H), 8.23 (s, 1H), 7.73-7.63 (m, 3H), 6.88 (s, 2H), 5.83 (s, 1H), 5.39 (bs, 1H), 3.93 (s, 3H), 3.50 (q, J=6.6 Hz, 2H), 2.81 (t, J=6.6 Hz, 2H), 2.24 (s, 3H), 1.86 (s, 3H). MS m/z 485 (M+1).

EXAMPLE 53

N-[5-(2-Aminoethyl)-2-methoxyphenyl]-5-methyl-7-[3-(trifluoromethyl)phenyl]imidazo[5,1-f][1,2,4]triazin-2-amine

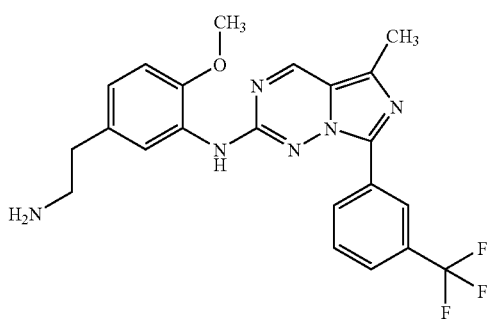

A solution of N-{2-[4-methoxy-3-({5-methyl-7-[3-(trifluoromethyl)phenyl]-imidazo[5,1-f][1,2,4]triazin-2-yl}amino)phenyl]ethyl}acetamide (Example 52) (0.050 g, 0.17 mmol) in dilute HCl$_{(aq)}$ (1N, 15 mL) was heated to reflux for 5 h. Neutralization with NaOH$_{(aq)}$ (1N) and extraction into EtOAc followed by concentration and preparative HPLC gave N-[5-(2-aminoethyl)-2-methoxyphenyl]-5-methyl-7-[3-(trifluoromethyl)-phenyl]imidazo[5,1-f][1,2,4]triazin-2-amine (0.013 g) as a yellow solid. $^1$H NMR (Acetone-d6): δ 9.17 (s, 1H), 9.08 (d, J=8.1 Hz, 1H), 8.64 (s, 1H), 8.33-8.30 (m, 1H), 8.13 (s, 1H), 7.97-7.90 (m, 1H), 7.80-7.77 (m, 1H), 7.02-6.95 (m, 2H), 3.96 (s, 3H), 3.48 (t, J=7.4 Hz, 2H), 2.95 (t, J=7.4 Hz, 2H), 2.60 (s, 3H). MS m/z 443 (M+1).

EXAMPLE 54

N-(2,4-Dimethoxyphenyl)-5-methyl-7-[3-(trifluoromethyl)phenyl]-imidazo[5,1-f][1,2,4]triazin-2-amine

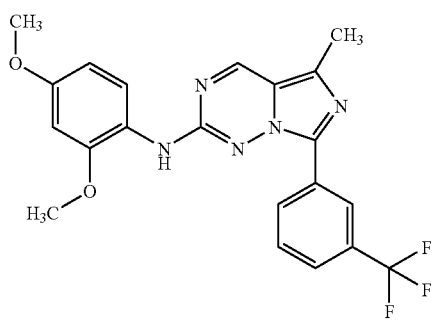

In a similar manner as described for Example 41, 5-methyl-7-[3-(trifluoromethyl)phenyl]imidazo[5,1-f][1,2,4]triazin-2-amine (Intermediate 45) (0.025 g, 0.09 mmol), 1-bromo-2,4-dimethoxybenzene (0.019 g, 0.09 mmol), Pd$_2$(dba)$_3$ (0.008 g, 0.01 mmol), 2-(Di-t-butylphosphino)biphenyl (0.008 g, 0.03 mmol), and NaOtBu (0.011 g, 0.11 mmol) in 1,4-dioxane (1 mL) gave N-(2,4-dimethoxyphenyl)-5-methyl-7-[3-(trifluoromethyl)phenyl]imidazo[5,1-f][1,2,4]triazin-2-amine (0.018 g) as a yellow solid. $^1$H NMR (CDCl$_3$): δ 8.95 (s, 1H), 8.82 (s, 1H), 8.61 (d, J=7.3 Hz, 1H), 8.25 (d, J=8.8 Hz, 1H), 7.72-7.59 (m, 2H), 7.45 (s, 1H), 6.61-6.53 (m, 2H), 3.91 (s, 3H), 3.85 (s, 3H), 2.62 (s, 3H). MS m/z 430 (M+1).

EXAMPLE 55:

N-(2,5-Dimethoxyphenyl)-5-methyl-7-[3-(trifluoromethyl)phenyl]-imidazo[5,1-f][1,2,4]triazin-2-amine

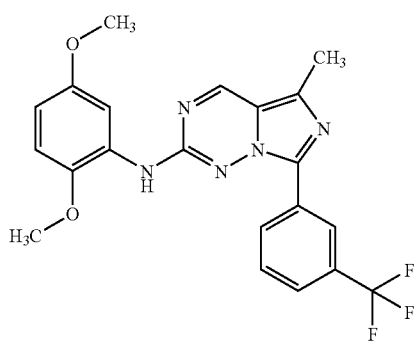

In a similar manner as described for Example 41, 5-methyl-7-[3-(trifluoromethyl)phenyl]imidazo[5,1-f][1,2,4]triazin-2-amine (Intermediate 45) (0.025 g, 0.09 mmol), 2-bromo-1,4-dimethoxybenzene (0.019 g, 0.09 mmol), Pd$_2$(dba)$_3$ (0.008 g, 0.01 mmol), 2-(Di-t-butylphosphino)biphenyl (0.008 g, 0.03 mmol), and NaOtBu (0.011 g, 0.11 mmol) in 1,4-dioxane (1 mL) gave N-(2,5-dimethoxyphenyl)-5-methyl-7-[3-(trifluoromethyl)phenyl]imidazo[5,1-f][1,2,4]triazin-2-amine (0.020 g) as a yellow solid. $^1$H NMR (CDCl$_3$): δ8.85 (s, 1H), 8.84-8.80 (m, 1H), 8.66 (s, 1H), 8.05 (d, J=3.0 Hz, 1H), 7.71-7.60 (m, 3H), 6.84 (d, J=8.8 Hz, 1H), 6.55 (dd, J=8.8, 3.0 Hz, 1H), 3.90 (s, 3H), 3.76 (s, 3H), 2.63 (s, 3H). MS m/z 430 (M+1).

EXAMPLE 56

Ethyl 5-({5-methyl-7-[3-(trifluoromethyl)phenyl]imidazo[5,1-f][1,2,4]triazin-2-yl}amino)nicotinate

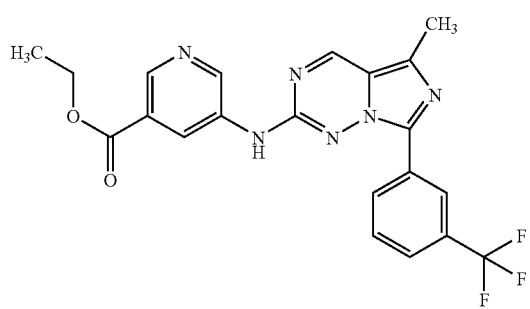

In a similar manner as described for Example 41, 5-methyl-7-[3-(trifluoromethyl)-phenyl]imidazo[5,1-f][1,2,4]triazin-2-amine (Intermediate 45) (0.025 g, 0.09 mmol), ethyl 5-bromonicotinate (0.020 g, 0.09 mmol), Pd$_2$(dba)$_3$ (0.008 g, 0.01 mmol), 2-(Di-t-butylphosphino)biphenyl (0.008 g, 0.03 mmol), and NaOtBu (0.011 g, 0.11 mmol) in 1,4-dioxane (1 mL) gave ethyl 5-({5-methyl-7-[3-(trifluoromethyl)phenyl]-imidazo[5,1-f][1,2,4]triazin-2-yl}amino)nicotinate (0.020 g) as a yellow solid. $^1$H NMR (Acetone-d$_6$): δ9.24 (bs, 1H), 9.22 (s, 1H), 9.08 (d, J=2.4 Hz, 1H), 8.96-8.92 (m, 2H), 8.85 (d, J=1.4 Hz, 1H), 8.75 (s, 1H), 7.91-7.86 (m, 1H), 7.83-7.74 (m, 1H), 4.41 (q, J=7.1 Hz, 2H), 2.61 (s, 3H), 1.33 (t, J=7.1 Hz, 3H). MS m/z 443 (M+1).

EXAMPLE 57

2-{3-[(5-Methyl-7-phenylimidazo[5,1-f][1,2,4]triazin-2-yl)amino]phenyl}ethanesulfonic acid

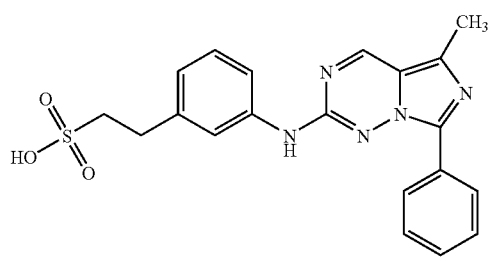

To a solution of 5-methyl-7-phenylimidazo[5,1-f][1,2,4]triazin-2-amine hydrochloride (28 mg, 0.107 mmol) in 1,4-dioxane (0.8 mL) was added 2-(3-bromophenyl)ethanesulfonic acid (28.25 mg, 0.107 mmol), 2-(ditbutylphosphino)biphenyl (9.6 mg, 0.032 mmol), Tris(dibenzylidineacetone)-dipalladium (0) (9.8 mg, 0.011 mmol) and sodium t-butoxide (23.65 mg, 0.246 mmol). In a sealed reaction vessel, the mixture was heated with microwave radiation at 160° C. for 13 minutes. After cooling to room temperature, methanol (5 mL) and silica gel (1.0 g) were added to the reaction mixture, followed by evaporation of the volatiles under reduced pressure. The pre-adsorbed solids were loaded into a solid loading cartridge and subjected to isocratic elution using ethyl acetate:hexanes (50:50) followed by ethyl acetate:methanol (80:20) using a Biotage silica gel cartridge (8.0 g). The appropriate fractions were combined and concentrated under reduced pressure to give 2-{3-[(5-methyl-7-phenylimidazo[5,1-f][1,2,4]triazin-2-yl)amino]phenyl}-ethanesulfonic acid (0.029 g) as a yellow solid. $^1$H NMR (DMSO-d$_6$): δ9.73 (s, 1H), 9.23 (s, 1H), 8.42 (d, J=7.5 Hz, 2H), 7.74 (s, 1H), 7.63 (dd, J=7.70 Hz, 2H), 7.49-7.07 (m, 3H), 6.86 (d, J=7.3 Hz, 1H), 2.94-2.82 (m, 2H), 2.71-2.62 (m, 2H), 2.52 (s, 3H). MS m/z 410 (M+1).

EXAMPLE 58

5-Methyl-7-[3-(1H-pyrazol-4-ylethynyl)phenyl]-N-(3,4,5-trimethoxyphenyl)imidazo[5,1-f][1,2,4]triazin-2-amine

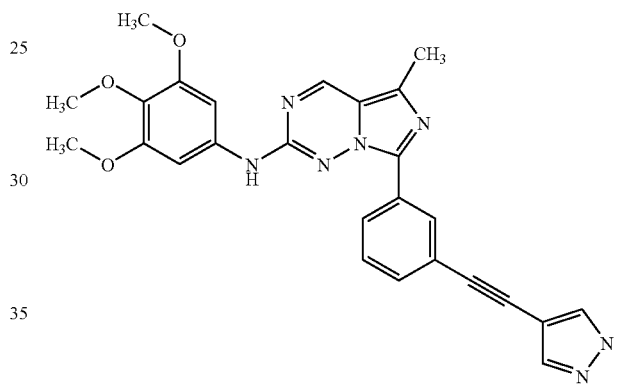

To a solution of 7-(3-bromophenyl)-5-methyl-N-(3,4,5-trimethoxyphenyl)imidazo[5,1-f][1,2,4]triazin-2-amine (Example 9) (27 mg, 0.05 mmol) in DMF (1.0 mL) was added 4-ethynyl-1H-pyrazole (6.9 mg, 0.07 mmol), bis(triphenylphosphine)-palladium (II) chloride (4.0 mg, 0.006 mmol), copper (I) iodide (2.0 mg, 0.01 mmol) and triethyl amine (0.06 mL, 0.43 mmol). In a sealed reaction vessel, the mixture was heated with microwave radiation at 150° C. for 20 minutes. After cooling to room temperature, removed solvent under reduced pressure to give an oily residue which was treated with methanol (5 mL) forming a suspension. Filtered solids and washed with ethyl acetate (10 mL) and DMF (1 mL). The combined filtrate was concentrated under reduced pressure and resulting brown oil was dissolved in ethyl acetate (50 mL), washed with 0.1N HCl (3×50 mL), saturated NaHCO$_3$ aqueous solution (2×50 mL) and brine (1×50 mL). Dried over MgSO$_4$, filtered and solvent removed under reduced pressure to give a light brown oil. Dissolved oil in hot ethyl acetate and silica gel (2.0 g) was added followed by evaporation of the volatiles under reduced pressure. The pre-adsorbed solids were loaded into a solid loading cartridge and subjected to isocratic elution using ethyl acetate:hexanes (50:50) followed by ethyl acetate:methanol (85:15) using a Biotage silica gel cartridge (8.0 g). The appropriate fractions were combined and concentrated under reduced pressure to give 5-methyl-7-[3-(1H-pyrazol-4-ylethynyl)phenyl]-N-(3,4,5-trimethoxyphenyl)imidazo[5,1-f][1,2,4]triazin-2-amine (0.0053 g) as a tan solid. MS m/z 482 (M+1).

EXAMPLE 59

3'-{5-Methyl-2-[(3,4,5-trimethoxyphenyl)amino]imidazo[5,1-f][1,2,4]triazin-7-yl}-1,1'-biphenyl-3-carboxylic acid

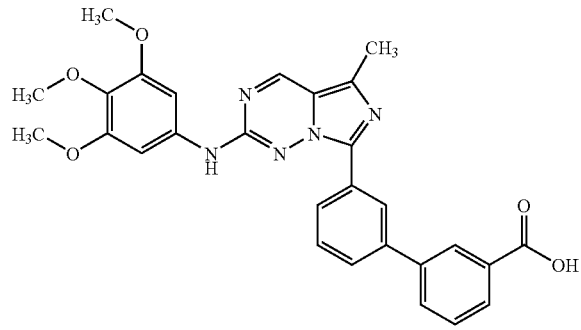

To a mixture of 7-(3-bromophenyl)-5-methyl-N-(3,4,5-trimethoxyphenyl)imidazo[5,1-f][1,2,4]triazin-2-amine (Example 9) (25 mg, 0.05 mmol), 3-(dihydroxyboryl)benzoic acid (10.6 mg, 0.06 mmol), tetrakis(triphenylphosphine) palladium (0) (3.1 mg, 0.003 mmol) and potassium carbonate (11.0 mg, 0.08 mmol) was added DME (0.9 mL) and distilled water (0.3 mL). In a sealed reaction vessel, the mixture was heated with microwave radiation at 110° C. for 20 minutes. After cooling to room temperature, removed solvent under reduced pressure, dissolved residue in dichloromethane and methanol, and added silica gel (200 mg). Following evaporation of the volatiles under reduced pressure, the pre-adsorbed solids were loaded into a solid loading cartridge and subjected to a gradient elution using dichloromethane:methanol (100:0) to (80:20) using a RediSep silica gel cartridge (4.2 g; ISCO). The appropriate fractions were combined and concentrated under reduced pressure to give a solid that was suspended in dichloromethane and vacuum filtered to give 3'-{5-methyl-2-[(3,4,5-trimethoxyphenyl)amino]imidazo[5,1-f][1,2,4]triazin-7-yl}-1,1'-biphenyl-3-carboxylic acid (0.0164 g) as a yellow solid. $^1$H NMR (DMSO-d$_6$): δ9.63 (s, 1H), 9.26 (s, 1H), 8.57-8.53 (m, 2H), 8.21 (s, 1H), 7.95-7.92 (m, 2H), 7.78 (d, J=6.2 Hz, 1H), 7.62-7.55 (m, 2H), 7.07 (s, 2H), 3.63 (s, 6H), 3.58 (s, 3H), 2.55 (s, 3H). MS m/z 512 (M+1).

EXAMPLE 60

2-Amino-3-(3'-{5-methyl-2-[(3,4,5-trimethoxyphenyl)amino]imidazo-[5,1-f][1,2,4]triazin-7-yl}-1,1'-biphenyl-4-yl)propanoic acid

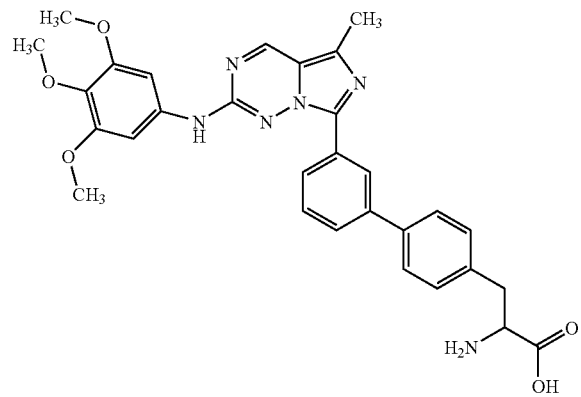

To a mixture of 7-(3-bromophenyl)-5-methyl-N-(3,4,5-trimethoxyphenyl)imidazo[5,1-f][1,2,4]triazin-2-amine (Example 9) (40 mg, 0.085 mmol), 4-(dihydroxyboryl)phenylalanine (57.6 mg, 0.275 mmol), tetrakis(triphenylphosphine) palladium (0) (15.0 mg, 0.013 mmol) and potassium carbonate (52.8 mg, 0.382 mmol) was added DME (1.8 mL) and distilled water (0.6 mL). In a sealed reaction vessel, the mixture was heated with microwave radiation at 130° C. for a total time of 1.5 hours. After cooling to room temperature, removed solvent under reduced pressure, dissolved residue in methanol (25 mL), and added silica gel (1 g). Following evaporation of the volatiles under reduced pressure, the pre-adsorbed solids were loaded into a solid loading cartridge and subjected to a gradient elution using dichloromethane:methanol (100:0 to 65:35) followed by ethyl acetate:methanol (80:20) using a RediSep silica gel cartridge (12 g; ISCO). The appropriate fractions were combined and concentrated under reduced pressure to give 2-amino-3-(3'-{5-methyl-2-[(3,4,5-trimethoxyphenyl)amino]-imidazo[5,1-f][1,2,4]triazin-7-yl}-1,1'-biphenyl-4-yl)propanoic acid (0.0199 g) as a yellow solid. $^1$H NMR (DMSO-d$_6$): δ9.63 (s, 1H), 9.26 (s, 1H), 8.55 (s, 1H), 8.45 (d, J=7.9 Hz, 1H), 7.73 (d, J=8.1 Hz, 1H), 7.61-7.21 (m, 5H), 7.09 (s, 2H), 3.65 (s, 6H), 3.63 (s, 3H), 3.43-3.12 (m, 1H), 2.92-2.80 (m, 2H). MS m/z 555 (M+1).

EXAMPLE 61

5-Methyl-7-[2'-(trifluoromethyl)-1,1'-biphenyl-3-yl]-N-(3,4,5-trimethoxyphenyl)imidazo[5,1-f][1,2,4]triazin-2-amine

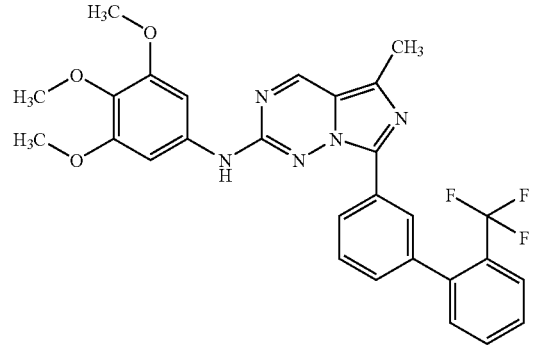

To a mixture of 7-(3-bromophenyl)-5-methyl-N-(3,4,5-trimethoxyphenyl)-imidazo[5,1-f][1,2,4]triazin-2-amine (Example 9) (50 mg, 0.106 mmol), 2-trifluoromethylphenyl boronic acid (30.3 mg, 0.159 mmol), potassium carbonate (44.1 mg, 0.318 mmol), and Combiphos catalyst POPd1 ((dihydrogen di-κ-chlorotetrakis(di-tert-butylphosphinito-κP) dipalladate(2-)) (5.0 mg, 0.005 mmol) was added 1,4-dioxane (1.8 mL) and distilled water (0.2 mL). In a sealed reaction vessel, the mixture was heated with microwave radiation at 150° C. for a total time of 1 hour. After cooling to room temperature, poured reaction mixture into dichloromethane (50 mL) and washed with distilled water (3×25 mL) and brine (1×25 mL). Dried over MgSO$_4$, filtered and removed solvent under reduced pressure to give a gold oil. Dissolved oil in dichloromethane and added silica gel (200 mg). Following evaporation of the volatiles under reduced pressure, the pre-adsorbed solids were loaded into a solid loading cartridge and subjected to a gradient elution using ethyl acetate:hexanes (20:80 to 70:30) using a RediSep silica gel cartridge (4.2 g; ISCO). The appropriate fractions were combined and concentrated under reduced pressure to give 5-methyl-7-[2'-(trifluoromethyl)-1,1'-biphenyl-3-yl]-N-(3,4,5-trimethoxyphenyl) imidazo[5,1-f][1,2,4]triazin-2-amine (0.0154 g) as a yellow solid. $^1$H NMR (DMSO-d$_6$): δ9.63 (s, 1H), 9.26 (s, 1H), 8.59 (d, J=7.90 Hz, 1H), 8.14 (s, 1H), 7.83 (d, J=8.4 Hz, 1H), 7.71 (dd, J=7.9, 7.1 Hz, 1H), 7.62 (dd, J=7.3, 7.5 Hz, 1H), 7.54 (dd, J=7.7, 7.9 Hz, 1H), 7.45 (d, J=6.6 Hz, 1H), 7.39 (d, J=7.1 Hz, 1H), 7.05 (s, 2H), 3.67 (s, 6H), 3.61 (s, 3H), 2.51 (s, 3H). MS m/z 536 (M+1).

EXAMPLE 62

(2Z)-3-(3-{5-Methyl-2-[(3,4,5-trimethoxyphenyl) amino]-imidazo[5,1-f][1,2,4]triazin-7-yl}phenyl)-3-phenylprop-2-enamide

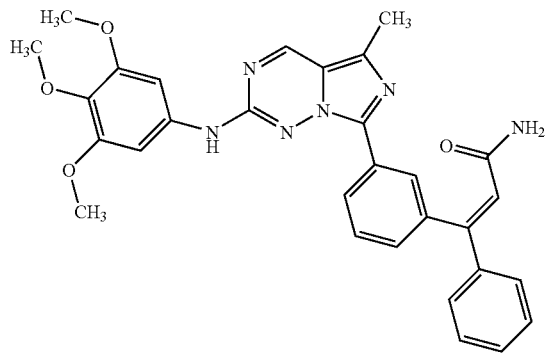

To a mixture of 7-(3-bromophenyl)-5-methyl-N-(3,4,5-trimethoxyphenyl)imidazo[5,1-f][1,2,4]triazin-2-amine (Example 9) (40 mg, 0.085 mmol), (2E)-3-phenylprop-2-enamide (15.0 mg, 0.10 mmol), tetrakis(triphenylphosphine) palladium (0) (5.0 mg, 0.004 mmol) and potassium carbonate (17.6 mg, 0.127 mmol) was added 1,4-dioxane (1.0 mL). In a sealed reaction vessel, the mixture was heated with microwave radiation at 110° C. for 20 minutes. Analysis by LCMS indicated that no reaction occurred. To the mixture was added diisopropylethylamine (0.044 mL, 0.255 mmol), Combiphos catalyst POPd (Dihydrogen dichlorobis(di-tert-butylphosphinito-κP)palladate(2-)) (5.0 mg, 0.01 mmol) and tetrabutylammonium bromide (5.0 mg, 0.015 mmol) and heated with microwave radiation at 130° C. for 70 minutes. After cooling to room temperature, removed solvent under reduced pressure, dissolved residue in methanol (25 mL), and added silica gel (200 mg). Following evaporation of the volatiles under reduced pressure, the pre-adsorbed solids were loaded into a solid loading cartridge and subjected to a gradient elution using ethylacetate:methanol (100:0 to 80:20) using a RediSep silica gel cartridge (4.2 g; ISCO). The appropriate fractions were combined and concentrated under reduced pressure to give a gold oil. Added diethyl ether (15 mL) to precipitate, and vacuum filtered to give (2Z)-3-(3-{5-methyl-2-[(3,4,5-trimethoxyphenyl)amino]imidazo[5,1-f][1,2,4]triazin-7-yl}phenyl)-3-phenylprop-2-enamide (0.009 g) as a yellow solid. $^1$H NMR (CDCl$_3$): δ8.80 (s, 1H), 8.48-8.46 (m, 1H), 7.40-7.28 (m, 7H), 7.17-7.15 (m, 1H), 7.02 (s, 1H), 6.89-6.86 (m, 2H), 6.44 (m, 1H), 5.34 (s, 2H), 3.83-3.79 (m, 9H), 2.60-2.57 (m, 3H). MS m/z 537 (M+1).

EXAMPLE 63

7-(3-{[5-(Ethylsulfonyl)-2-methoxyphenyl] amino}phenyl)-5-methyl-N-(3,4,5-trimethoxyphenyl)imidazo[5,1-f][1,2,4]triazin-2-amine

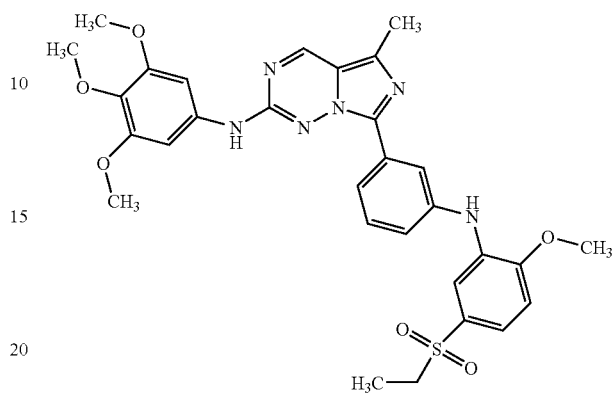

To a mixture of 7-(3-bromophenyl)-5-methyl-N-(3,4,5-trimethoxyphenyl)imidazo[5,1-f][1,2,4]triazin-2-amine (Example 9) (49.1 mg, 0.104 mmol), 5-(ethylsulfonyl)-2-methoxyaniline (22.5 mg, 0.104 mmol), 2-(dit-butylphosphino) biphenyl (16.3 mg, 0.054 mmol), Tris(dibenzylidineacetone) dipalladium (0) (16.6 mg, 0.018 mmol) and sodium t-butoxide (26.0 mg, 0.28 mmol) was added 1,4-dioxane (1.0 mL). In a sealed reaction vessel, the mixture was heated with microwave radiation at 130° C. for 50 minutes. After cooling to room temperature, removed solvent under reduced pressure and diluted residue in dichloromethane. Filtered and added silica gel (500 mg) to filtrate followed by evaporation of the volatiles under reduced pressure. The pre-adsorbed solids were loaded into a solid loading cartridge and subjected to a gradient elution using ethyl acetate:hexanes (25:75) to ethyl acetate:hexanes (95:5) using a RediSep silica gel cartridge (4.2 g; ISCO). The appropriate fractions were combined and concentrated under reduced pressure to give 7-(3-{[5-ethylsulfonyl)-2-methoxyphenyl]amino}phenyl)-5-methyl-N-(3,4,5-trimethoxyphenyl)imidazo-[5,1-f][1,2,4] triazin-2-amine (0.0195 g) as a yellow solid. $^1$H NMR (CDCl$_3$): δ8.82 (s, 1H), 8.39 (s, 1H), 8.17 (d, J=7.7 Hz, 1H), 7.82 (s, 1H), 7.42-7.19 (m, 4H), 6.97 (d, J=7.3 Hz, 1H), 6.88 (s, 2H), 6.45 (s, 1H) 4.00 (s, 3H) 3.84 (s, 9H), 3.06 (d, J=6.6 Hz, 2H), 2.60 (s, 3H), 1.25 (m, 3H). MS m/z 605 (M+1).

EXAMPLE 64

5-Methyl-7-(3-{[4-(1H-1,2,4-triazol-1-ylmethyl) phenyl]amino}-phenyl)-N-(3,4,5-trimethoxyphenyl) imidazo[5,1-f][1,2,4]triazin-2-amine

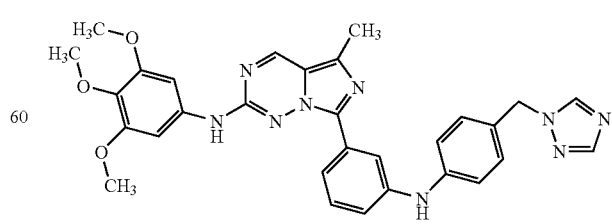

In a similar manner as described in Example 63, a mixture of 7-(3-bromophenyl)-5-methyl-N-(3,4,5-trimethoxyphenyl)imidazo[5,1-f][1,2,4]triazin-2-amine (Example 9) (40 mg, 0.085 mmol), 4-(1H, 1,2,4-triazol-1-ylmethyl)aniline (14.8 mg, 0.085 mmol), 2-(dit-butylphosphino)biphenyl (15.2 mg, 0.051 mmol), Tris(dibenzylidineacetone)-dipalladium (0) (15.6 mg, 0.017 mmol) and sodium t-butoxide (13.1 mg, 0.136 mmol) in 1,4-dioxane (1.5 mL) gave 5-methyl-7-(3-{[4-(1H-1,2,4-triazol-1-ylmethyl)phenyl]amino}phenyl)-N-(3,4,5-trimethoxyphenyl) imidazo[5,1-f][1,2,4]triazin-2-amine (0.0147 g) as a yellow solid. $^1$H NMR (CDCl$_3$): δ8.79 (s, 1H), 8.16 (s, 1H), 8.05-8.03 (m, 2H), 7.97 (s, 1H), 7.36-7.33 (m, 1H), 7.23-7.09 (m, 5H), 6.99 (s, 1H), 6.93 (s, 2H), 6.15 (s, 1H), 5.25 (s, 2H), 3.82 (s, 9H), 2.59 (s, 3H). MS m/z 564 (M+1).

EXAMPLE 65: 7-(3-{[4-(1H-Imidazol-1-yl)phenyl]amino}phenyl-5-nv-5-methyl-N-(3,4,5-trimethoxyphenyl)imidazo[5,1-f][1,2,4]triazin-2-amine

In a similar manner as described in Example 63, a mixture of 7-(3-bromophenyl)-5-methyl-N-(3,4,5-trimethoxyphenyl)imidazo[5,1-f][1,2,4]triazin-2-amine (Example 9) (40 mg, 0.085 mmol), 4-(1H-imidazol-1-yl)aniline (13.5 mg, 0.085 mmol), 2-(dit-butylphosphino)biphenyl (15.2 mg, 0.051 mmol), Tris(dibenzylidineacetone)-dipalladium (0) (15.6 mg, 0.017 mmol) and sodium t-butoxide (13.1 mg, 0.136 mmol) in 1,4-dioxane (1.5 mL) gave 7-(3-{[4-(1H-imidazol-1-yl)phenyl]amino}phenyl)-5-methyl-N-(3,4,5-trimethoxyphenyl)-imidazo[5,1-f][1,2,4]triazin-2-amine (0.0126 g) as a yellow solid. $^1$H NMR (CDCl$_3$): δ8.80 (s, 1H), 8.24 (s, 1H), 8.05 (d, J=7.3 Hz, 1H), 7.78 (s, 1H), 7.40-7.35 (m, 1H), 7.26-7.19 (m, 7H), 6.97-6.93 (s, 3H), 6.21 (s, 1H), 3.82 (s, 9H), 2.60 (s, 3H) MS m/z 549 (M+1).

EXAMPLE 66

7-{3-[(3-Chloro-4-morpholin-4-ylphenyl)amino]phenyl}-5-methyl-N-(3,4,5-trimethoxyphenyl)imidazo[5,1-f][1,2,4]triazin-2-amine

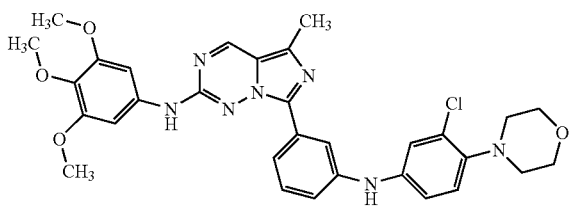

To a mixture of 7-(3-bromophenyl)-5-methyl-N-(3,4,5-trimethoxyphenyl)imidazo[5,1-f][1,2,4]triazin-2-amine (Example 9) (40 mg, 0.085 mmol), 3-chloro-4-morpholin-4-ylaniline (21.7 mg, 0.102 mmol), (S)-(-)-2,2'-Bis(diphenylphosphino)-1,1'-binaphthyl ((S)-BINAP) (15.9 mg, 0.026 mmol), Tris(dibenzylidineacetone)dipalladium (0) (7.8 mg, 0.008 mmol) and sodium t-butoxide (11.4 mg, 0.12 mmol) was added 1,4-dioxane (1.5 mL). In a sealed reaction vessel, the mixture was heated with microwave radiation at 130° C. for 30 minutes. After cooling to room temperature, removed solvent under reduced pressure and diluted residue in DMSO (1.0 mL). Filtered and injected (2×0.5 mL) on an Agilent reverse phase prep LC subjected to a gradient elution using acetonitrile (0.1% Formic acid):water (0.1% Formic acid) (10:90 to 90:10). Combined appropriate fractions and removed solvent under reduced pressure. Added methanol, dichloromethane and silica gel (100 mg) followed by evaporation of the volatiles under reduced pressure. The pre-adsorbed solids were loaded into a solid loading cartridge and subjected to a gradient elution using ethyl acetate:hexanes (30:70) to ethyl acetate:hexanes (90:10) using a RediSep silica gel cartridge (4.2 g; ISCO). The appropriate fractions were combined and concentrated under reduced pressure to give 7-{3-[(3-chloro-4-morpholin-4-ylphenyl)amino]phenyl}-5-methyl-N-(3,4,5-trimethoxyphenyl)imidazo[5,1-f][1,2,4]triazin-2-amine (0.020 g) as a yellow solid. $^1$H NMR (CDCl$_3$): δ8.79 (s, 1H), 8.09 (dd, J=2.0, 1.9 Hz, 1H), 8.01-7.98 (m, 1H), 7.33 (dd, J=8.0, 7.9 Hz, 1H), 7.18 (d, J=2.6 Hz, 1H), 7.15 (ddd, J=8.2, 2.3, 0.9 Hz, 1H), 7.02 (dd, J=8.6, 2.5 Hz, 1H), 6.95-6.93 (m, 3H), 6.90 (s, 1H), 5.95 (s, 1H), 3.88-3.86 (m, 4H), 3.84 (s, 9H), 3.01-2.98 (m, 4H) 2.60 (s, 3H). MS m/z 602 (M+1).

EXAMPLE 67

N,N-Dimethyl-1-{3-[(3-{5-methyl-2-[(3,4,5-trimethoxyphenyl)amino]imidazo[5,1-f][1,2,4]triazin-7-yl}phenyl)amino]phenyl}methanesulfonamide

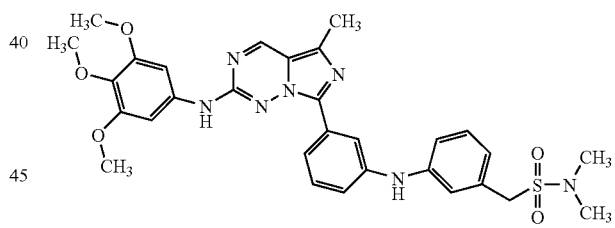

In a similar manner as described in Example 66, 7-(3-bromophenyl)-5-methyl-N-(3,4,5-trimethoxyphenyl)imidazo[5,1-f][1,2,4]triazin-2-amine (Example 9) (40 mg, 0.085 mmol), 1-(3-aminophenyl)-N,N-dimethylmethanesulfonamide (21.9 mg, 0.102 mmol), (S)-(-)-2,2'-Bis(diphenylphosphino)-1,1'-binaphthyl ((S)-BINAP) (15.9 mg, 0.026 mmol), Tris(dibenzylidineacetone)dipalladium (0) (7.8 mg, 0.008 mmol) and sodium t-butoxide (11.4 mg, 0.12 mmol) in 1,4-dioxane (1.5 mL) were heated with microwave radiation at 140° C. for 60 minutes in a sealed reaction vessel to give N,N-dimethyl-1-{3-[(3-{5-methyl-2-[(3,4,5-trimethoxyphenyl)amino]imidazo[5,1-f][1,2,4]triazin-7-yl}phenyl)amino]phenyl}methanesulfonamide (0.0125 g) as a yellow solid. $^1$H NMR (CDCl$_3$) δ8.80 (s, 1H), 8.15 (dd, J=1.8, 1.8 Hz, 1H), 8.06-8.04 (m, 1H), 7.36 (dd, J=8.0, 7.9 Hz, 1H), 7.25-7.22 (m, 2H), 7.16 (dd, J=1.9, 1.8 Hz, 1H), 7.10 (ddd, J=8.1, 2.4, 0.9 Hz, 1H), 6.93-6.91 (m, 4H), 6.10 (s, 1H), 4.17 (s, 2H), 3.84-3.83 (m, 9H) 2.76 (s, 6H), 2.60 (s, 3H). MS m/z 605 (M+1).

EXAMPLE 68: 5-Methyl-7-[3-({4-[(4-methylpiperazin-1-yl)methyl]phenyl}-amino)phenyl]-N-/(3,4,5-trimethoxyphenyl)imidazo[5,1-f][1,2,4]triazin-2-amine

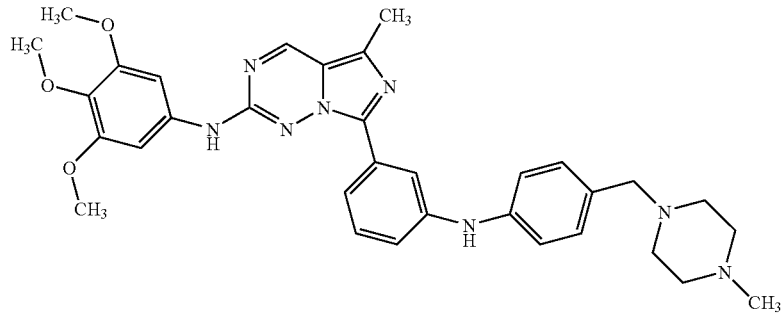

To a mixture of 7-(3-bromophenyl)-5-methyl-N-(3,4,5-trimethoxyphenyl)imidazo[5,1-f][1,2,4]triazin-2-amine (Example 9) (40 mg, 0.085 mmol), 4-[(4-methylpiperazin-1-yl)methyl]aniline (20.9 mg, 0.102 mmol), (S)-(−)-2,2'-Bis(diphenylphosphino)-1,1'-binaphthyl ((S)-BINAP) (15.9 mg, 0.026 mmol), Tris(dibenzylidineacetone)dipalladium (0) (7.8 mg, 0.008 mmol) and sodium t-butoxide (11.4 mg, 0.12 mmol) was added 1,4-dioxane (1.5 mL). In a sealed reaction vessel, the mixture was heated with microwave radiation at 140° C. for 60 minutes. After cooling to room temperature, diluted mixture with methanol (5 mL) and ethyl acetate (5 mL) followed by filtration over celite. Removed solvent under reduced pressure and diluted brown residue in DMSO (1.0 mL). Injected (2×0.5 mL) on an Agilent reverse phase prep LC subjected to a gradient elution using acetonitrile (0.1% Formic acid):water(0.1% Formic acid) (10:90 to 90:10). The appropriate fractions were combined and concentrated under reduced pressure to give 5-methyl-7-[3-({4-[(4-methylpiperazin-1-yl)methyl]phenyl}amino)phenyl]-N-(3,4,5-trimethoxyphenyl)imidazo[5,1-f][1,2,4]triazin-2-amine (0.021 g) as a yellow solid. $^1$H NMR (CDCl$_3$): δ8.78 (s, 1H), 8.47 (s, 1H), 8.09 (dd, J=1.9, 1.8 Hz, 1H), 8.0-7.98 (m, 1H), 7.33 (dd, J=7.9, 7.8 Hz, 1H), 7.19 (ddd, J=7.9, 2.2, 0.8 Hz, 1H), 7.16-7.14 (m, 2H), 7.11 (s, 1H), 7.07-7.05 (m, 2H), 6.94 (m, 2H), 3.82 (s, 9H), 3.53 (s, 2H), 2.90-2.54 (m, 14H). MS m/z 595 (M+1).

EXAMPLE 69

N-Cyclopropyl-3-[(3-{5-methyl-2-[(3,4,5-trimethoxyphenyl)amino] imidazo[5,1-f][1,2,4]triazin-7-yl}phenyl)amino]benzenesulfonamide

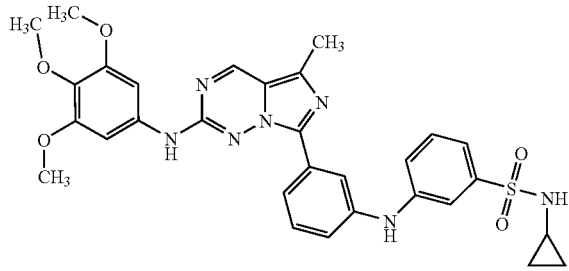

To a mixture of 7-(3-bromophenyl)-5-methyl-N-(3,4,5-trimethoxyphenyl)-imidazo[5,1-f][1,2,4]triazin-2-amine (Example 9) (20 mg, 0.042 mmol), 3-amino-N-cyclopropyl-benzenesulfonamide (10.8 mg, 0.051 mmol), (S)-(−)-2,2'-Bis(diphenylphosphino)-1,1'-binaphthyl ((S)-BINAP) (15.9 mg, 0.026 mmol), Tris(dibenzylidineacetone)dipalladium (0) (7.8 mg, 0.008 mmol) and sodium t-butoxide (13.8mg, 0.144 mmol) was added 1,4-dioxane (1.5 mL). In a sealed reaction vessel, the mixture was heated with microwave radiation at 140° C. for 60 minutes. After cooling to room temperature, diluted mixture with methanol (5 mL) and ethyl acetate (5 mL) followed by filtration over celite. Removed solvent under reduced pressure and diluted brown residue in DMSO (1.0 mL). Injected (2×0.5mL) on an Agilent reverse phase prep LC subjected to a gradient elution using acetonitrile (0.1% Formic acid):water(0.1% Formic acid) (10:90 to 90:10). Combined appropriate fractions and removed solvent under reduced pressure. The solid material was dissolved in methanol and dichloromethane and added silica gel (100 mg). Followed by evaporation of the volatiles under reduced pressure, the pre-adsorbed solids were loaded into a solid loading cartridge and subjected to a gradient elution using ethyl acetate:hexanes (30:70 to 90:10) using a RediSep silica gel cartridge (4.2 g; ISCO). The appropriate fractions were combined and concentrated under reduced pressure to give solid material that was again dissolved in dichlormethane and adsorbed onto a silica gel prep plate (20 cm×20 cm, 1000 μm). Eluted with ethyl acetate:hexanes (70:30), removed silica from plate and washed with ethyl acetate/methanol/dichloromethane (25 mL). Removed solvent under reduced pressure to give N-cyclopropyl-3-[(3-{5-methyl-2-[(3,4,5-trimethoxyphenyl)-amino]imidazo[5,1-f][1,2,4]triazin-7-yl}phenyl)amino]benzenesulfonamide (0.0076 g) as a yellow solid. $^1$H NMR (CD$_3$OD) δ9.01 (s, 1H), 8.09 (dd, J=2.0, 1.6 Hz, 1H), 7.85-7.82 (m, 1H), 7.60-7.59 (m, 1H), 7.4 (dd, J=7.9, 8.0 Hz, 1H), 7.33-7.29 (m, 2H), 7.28-7.25 (m, 1H), 7.21 (ddd, J=8.2, 2.4, 1.1 Hz, 1H), 7.03 (s, 2H), 3.74 (s, 6H), 3.69 (s, 3H), 2.57 (s, 3H), 2.15-2.10 (m, 1H), 0.49-0.45 (m, 4H). MS m/z 602 (M+1).

Intermediate 46: 1,1-Dimethylethyl [1-(3-{[4-(methyloxy)phenyl]amino}-1,2,4-triazin-6-yl)ethyl]carbamate

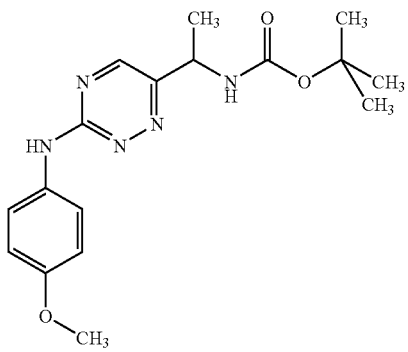

To a stirred solution of tert-Butyl 1-[3-(methylsulfonyl)-1,2,4-triazin-6-yl]ethylcarbamate (Intermediate 7) (4.11 g, 13.59 mmol) in tetrahydrofuran (50 mL) was added panisidine (2.00 g, 16.24 mmol) and 4-toluenesulfonic acid monohydrate (100 mg, 0.53 mmol). The mixture was then heated at reflux overnight and then concentrated under vacuum. The residue was partitioned between ethyl acetate and saturated sodium bicarbonate solution and the layers separated. The organic layer was dried with magnesium sulfate, filtered and reduced and then purified by chromatography on silica gel eluting with 30 to 50% ethyl acetate in petrol to afford 1,1-dimethylethyl [1-(3-{[4-(methyloxy)phenyl]amino}-1,2,4-triazin-6-yl)ethyl]carbamate (3.00 g) as a yellow solid. $^1$H NMR (CDCl$_3$): δ8.25 (s, 1H), 7.51 (d, J=9.0 Hz, 2H), 7.20 (s, 1H), 6.92 (d, J=9.0 Hz, 2H), 5.36 (m, 1H), 4.94 (m, 1H), 3.81 (s, 3H), 1.55 (d, J=2.5 Hz, 3H), 1.43 (s, 9H).

Intermediate 47: 6-(1-Aminoethyl)-N-[4-(methyloxy)phenyl]-1,2,4-triazin-3-amine

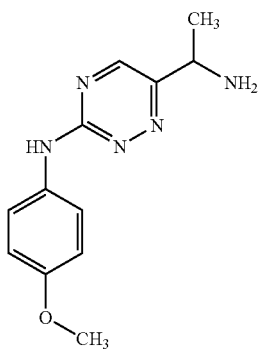

To a stirred solution of 1,1-dimethylethyl [1-(3-{[4-(methyloxy)phenyl]amino}-1,2,4-triazin-6-yl)ethyl]carbamate (Intermediate 46) (3.00 g, 8.69 mmol) in ethanol saturated with hydrogen chloride (30 mL) was stirred overnight at room temperature. The resulting mixture was reduced under vacuum, partitioned between ethyl acetate and saturated sodium bicarbonate solution and the mixture filtered to give a solid residue. The aqueous layer was re-extracted with ethyl acetate (5×) and the combined organic layers dried with magnesium sulfate, filtered and reduced under vacuum. The residue was purified by chromatography on silica gel eluting with 50% ethyl acetate in petrol to afford a solid which was combined with the initial solid to give 6-(1-aminoethyl)-N-[4-(methyloxy)phenyl]-1,2,4-triazin-3-amine (1.70 g) as a yellow solid. $^1$H NMR (CDCl$_3$): δ8.35 (s, 1H), 7.53 (d, J=9.0 Hz, 2H), 7.34 (s, 1H), 6.92 (d, J=9.0 Hz, 2H), 4.33 (q, J=6.7 Hz, 1H), 3.82 (s, 3H), 1.51 (d, J=6.7 Hz, 3H).

Intermediate 48: 5-Bromo-N-[1-(3-{[4-(methyloxy)phenyl]amino}-1,2,4-triazin-6-yl)ethyl]-2-thiophenecarboxamide

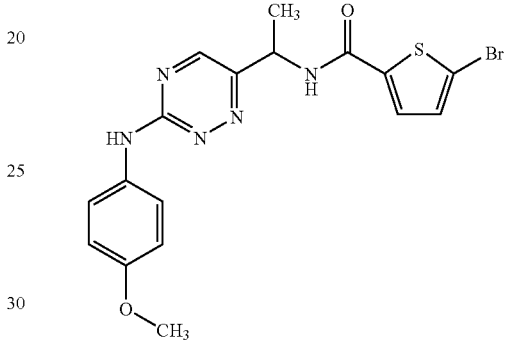

To a stirred solution of 6-(1-aminoethyl)-N-[4-(methyloxy)phenyl]-1,2,4-triazin-3-amine (Intermediate 47) (100 mg, 0.41 mmol), 5-bromothiophene-2-carboxylic acid (93 mg, 0.45 mmol) and O-(7-azabenzotriazol-1-yl-N,N,N'N'-tetramethyluronium hexafluorophospahte (186 mg, 0.49 mmol) in N,N-dimethylformamide (5 mL) was added triethylamine (0.170 mL, 1.22 mmol) and the resulting mixture stirred at room temperature, under nitrogen, for 2 h 50 min. The mixture was then reduced under vacuum and the residue purified by SPE (Si, 10 g cartridge) eluting with hexane/ethyl acetate (10:1 to 0:1) and then methanol. The appropriate fractions containing product were combined and then purified further by SPE (SCX, 5 g cartridge) eluting with methanol then ammonia in methanol (0.5 N to 2.0 N) to afford 5-bromo-N-[1-(3-{[4-(methyloxy)phenyl]amino}-1,2,4-triazin-6-yl)ethyl]-2-thiophenecarboxamide (109 mg) as a yellow solid. MS m/z 434/436 (M+1).

Cyclization Procedure 1:

Similar to the procedure described in Example 1, to a solution of amide (1 eq) in 1,2-dichloroethane (0.03-0.07M) was added phosphorus oxychloride (8 eq) and the mixture heated at reflux (oil bath temperature 95 to 100° C.) under an inert atmosphere until complete (2-28 h). If appropriate, more phosphorus oxychloride (5 eq) was added to drive the reaction towards completion. The mixture was then left to cool to room temperature and was then added carefully to a rapidly stirred mixture of ice and ammonia (0.88) and stirring continued for 0.5 to 1 h. The resulting mixture was diluted with water and extracted three times with dichloromethane or ethyl acetate and the combined organic layers washed with brine, dried with magnesium sulfate, filtered and reduced. The crude

EXAMPLE 70

7-(5-Bromo-2-thienyl)-5-methyl-N-[4-(methyloxy)phenyl]imidazo[5,1-f][1,2,4]triazin-2-amine

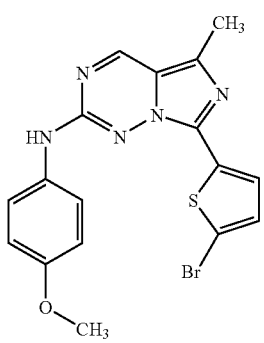

Applying the Cyclization Procedure 1, using 5-bromo-N-[1-(3-{[4-(methyloxy)phenyl]amino}-1,2,4-triazin-6-yl)ethyl]-2-thiophenecarboxamide (Intermediate 48) (106 mg, 0.24 mmol), 1,2-dichloroethane (5 mL) and phosphorus oxychloride (0.182 mL, 1.95 mmol), to afford 7-(5-bromo-2-thienyl)-5-methyl-N-[4-(methyloxy)phenyl]imidazo[5,1-f][1,2,4]triazin-2-amine (24 mg) as a yellow solid. MS m/z 416/418 (M+1).

Intermediate 49: 3-Bromo-N-[1-(3-{[4-(methyloxy)phenyl]amino}-1,2,4-triazin-6-yl)ethyl]-2-thiophenecarboxamide

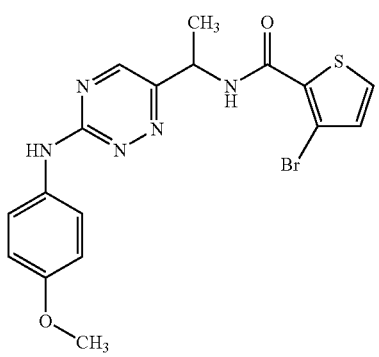

In a similar manner as described for Intermediate 48, using 6-(1-aminoethyl)-N-[4-(methyloxy)phenyl]-1,2,4-triazin-3-amine (Intermediate 47) (100 mg, 0.41 mmol), and 3-bromothiophene-2-carboxylic acid (93 mg, 0.45 mmol), except the reaction was stirred for 6.5 h and purification using silica SPE was omitted, to give 3-bromo-N-[1-(3-{[4-(methyloxy)phenyl]amino}1,2,4-triazin-6-yl)ethyl]-2-thiophenecarboxamide (162 mg) as a yellow solid. MS m/z 434/436 (M+1).

EXAMPLE 71

7-(3-Bromo-2-thienyl)-5-methyl-N-[4-(methyloxy)phenyl]imidazo[5,1-f][1,2,4]triazin-2-amine

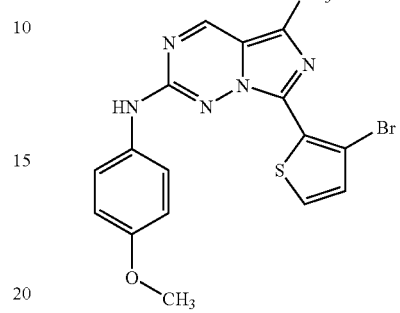

Applying the Cyclization Procedure 1, using 3-bromo-N-[1-(3-{[4-(methyloxy)phenyl]amino}-1,2,4-triazin-6-yl)ethyl]-2-thiophenecarboxamide (Intermediate 49) (159 mg, 0.37 mmol), 1,2-dichloroethane (7.3 mL) and phosphorus oxychloride (0.273 mL, 2.93 mmol), to afford 7-(3-bromo-2-thienyl)-5-methyl-N-[4-(methyloxy)phenyl]imidazo[5,1-f][1,2,4]triazin-2-amine (35 mg) as a yellow solid. MS m/z 416/418 (M+1).

Intermediate 50: N-[1-(3-{[4-(Methyloxy)phenyl]amino}-1,2,4-triazin-6-yl)ethyl]tetrahydro-2H-pyran-4-carboxamide

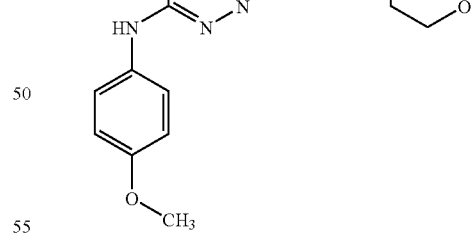

In a similar manner as described for Intermediate 49, using 6-(1-aminoethyl)-N-[4-(methyloxy)phenyl]-1,2,4-triazin-3-amine (Intermediate 47) (100 mg, 0.41 mmol), and tetrahydropyran-4-yl-carboxylic acid (58 mg, 0.45 mmol), except the reaction was stirred for 16.5 h and a 10 g SCX cartridge was used, to give N-[1-(3-{[4-(methyloxy)phenyl]amino}-1,2,4-triazin-6-yl)ethyl]tetrahydro-2H-pyran-4-carboxamide (81 mg) as a yellow solid. MS m/z 358 (M+1).

EXAMPLE 72

5-Methyl-N-[4-(methyloxy)phenyl]-7-(tetrahydro-2H-pyran-4-yl)imidazo[5,1-f][1,2,4]triazin-2-amine

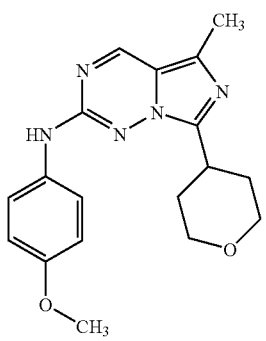

Applying the Cyclization Procedure 1, using N-[1-(3-{[4-(methyloxy)phenyl]amino}-1,2,4-triazin-6-yl)ethyl]tetrahydro-2H-pyran-4-carboxamide (Intermediate 50) (81 mg, 0.23 mmol), 1,2-dichloroethane (4.5 mL) and phosphorus oxychloride (0.169 mL, 1.81 mmol), to afford 5-methyl-N-[4-(methyloxy)phenyl]-7-(tetrahydro-2H-pyran-4-yl)imidazo[5,1-f][1,2,4]triazin-2-amine (35 mg) as a yellow solid. MS m/z 340 (M+1).

Intermediate 51: 2-(Methyloxy)-N-[1-(3-{[4-(methyloxy)phenyl]amino}-1,2,4-triazin-6-yl)ethyl]benzamide

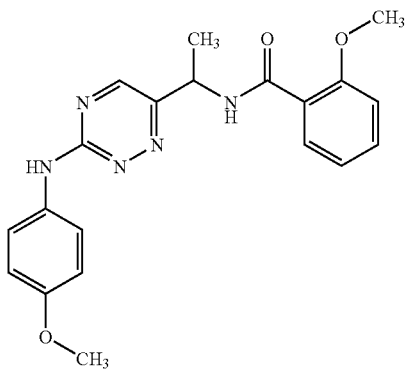

In a similar manner as described for Intermediate 50, using 6-(1-aminoethyl)-N-[4-(methyloxy)phenyl]-1,2,4-triazin-3-amine (Intermediate 47) (100 mg, 0.41 mmol), and 2-methoxybenzoic acid (68 mg, 0.45 mmol) to give 2-(methyloxy)-N-[1-(3-{[4-(methyloxy)phenyl]amino-}-1,2,4-triazin-6-yl)ethyl]benzamide (145 mg) as a yellow solid. MS m/z 380 (M+1).

EXAMPLE 73

5-Methyl-7-[2-(methyloxy)phenyl]-N-[4-(methyloxy)phenyl]-imidazo[5,1-f][1,2,4]triazin-2-amine

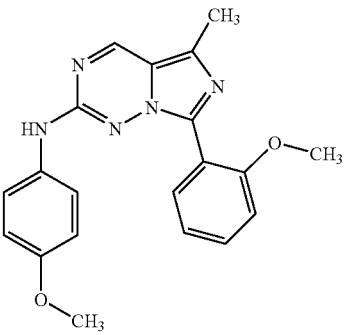

Applying the Cyclization Procedure 1, 2-(methyloxy)-N-[1-(3-{[4-(methyloxy)phenyl]amino}-1,2,4-triazin-6-yl)ethyl]benzamide (Intermediate 51) (145 mg, 0.38 mmol), 1,2-dichloroethane (4.5 mL) and phosphorus oxychloride (0.285+0.178 mL, 4.97 mmol), to afford 5-methyl-7-[2-(methyloxy)phenyl]-N-[4-(methyloxy)phenyl]imidazo[5,1-f][1,2,4]triazin-2-amine (21 mg) as a yellow solid. MS m/z 362 (M+1).

Intermediate 52: 3-(Methyloxy)-N-[1-(3-{[4-(methyloxy)phenyl]amino}-1,2,4-triazin-6-yl)ethyl]benzamide

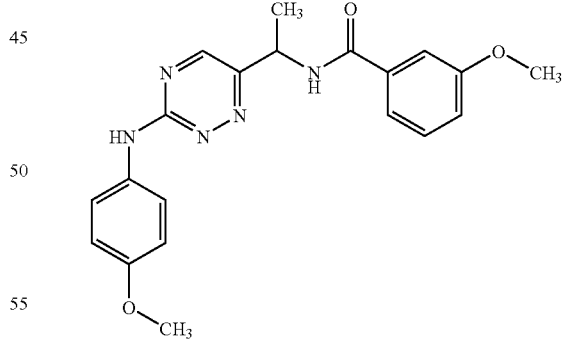

In a similar manner as described for Intermediate 50, using 6-(1-aminoethyl)-N-[4-(methyloxy)phenyl]-1,2,4-triazin-3-amine (Intermediate 47) (100 mg, 0.41 mmol), and 3-methoxybenzoic acid (68 mg, 0.45 mmol) to give 3-(methyloxy)-N-[1-(3-{[4-(methyloxy)phenyl]amino}-1,2,4-triazin-6-yl)ethyl]benzamide (41 mg) as a yellow solid. MS m/z 380 (M+1).

EXAMPLE 74

5-Methyl-7-[3-(methyloxy)phenyl]-N-[4-(methyloxy)phenyl]-imidazo[5,1-f][1,2,4]triazin-2-amine

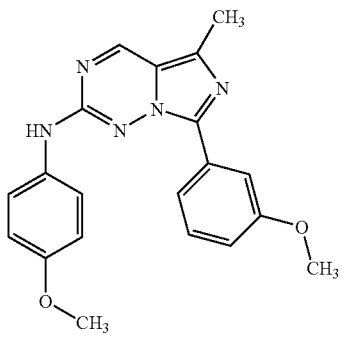

Applying the Cyclization Procedure 1, 3-(methyloxy)-N-[1-(3-{[4-(methyloxy)phenyl]amino}-1,2,4-triazin-6-yl)ethyl]benzamide (Intermediate 52) (41 mg, 0.11 mmol), 1,2-dichloroethane (2.2 mL) and phosphorus oxychloride (0.081 mL, 0.87 mmol), to afford 5-methyl-7-[3-(methyloxy)phenyl]-N-[4-(methyloxy)phenyl]imidazo[5,1-f][1,2,4]triazin-2-amine (12 mg) as a yellow solid. MS m/z 362 (M+1).

Intermediate 53: 2-Chloro-N-[1-(3-{[4-(methyloxy)phenyl]amino}-1,2,4-triazin-6-yl)ethyl]benzamide

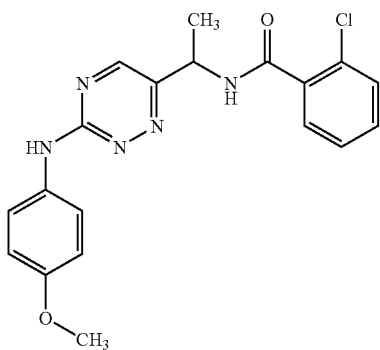

In a similar manner as described for Intermediate 50, using 6-(1-aminoethyl)-N-[4-(methyloxy)phenyl]-1,2,4-triazin-3-amine (Intermediate 47) (100 mg, 0.41 mmol), and 2-chlorobenzoic acid (70 mg, 0.45 mmol) to give 2-chloro-N-[1-(3-{[4-(methyloxy)phenyl]amino}-1,2,4-triazin-6-yl)ethyl]benzamide (127 mg) as a yellow solid. MS m/z 384 (M+1).

EXAMPLE 75

7-(2-Chlorophenyl)-5-methyl-N-[4-(methyloxy)phenyl]imidazo[5,1-f][1,2,4]triazin-2-amine

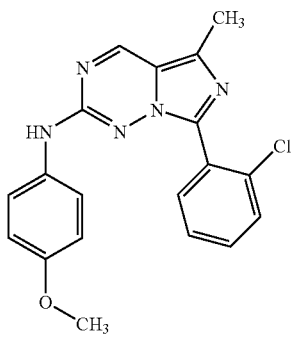

Applying the Cyclization Procedure 1, 2-chloro-N-[1-(3-{[4-(methyloxy)phenyl]amino}-1,2,4-triazin-6-yl)ethyl]benzamide (Intermediate 53) (127 mg, 0.33 mmol), 1,2-dichloroethane (6.6 mL) and phosphorus oxychloride (0.250+0.154 mL, 4.33 mmol), to afford 7-(2-chlorophenyl)-5-methyl-N-[4-(methyloxy)phenyl]imidazo[5,1-f][1,2,4]triazin-2-amine (39 mg) as a yellow solid. MS m/z 366 (M+1).

Intermediate 54: 1-Methyl-N-[1-(3-{[4-(methyloxy)phenyl]amino}-1,2,4-triazin-6-yl)ethyl]-1H-indole-3-carboxamide

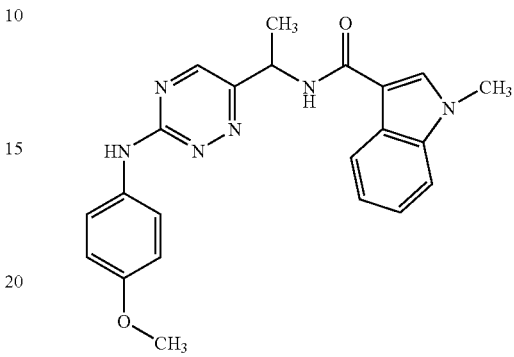

In a similar manner as described for Intermediate 50, using 6-(1-aminoethyl)-N-[4-(methyloxy)phenyl]-1,2,4-triazin-3-amine (Intermediate 47) (100 mg, 0.41 mmol), and 1-methyl-1h-indole-3-carboxylic acid (79 mg, 0.45 mmol) to give 1-methyl-N-[1-(3-{[4-(methyloxy)phenyl]amino}-1,2,4-triazin-6-yl)ethyl]-1H-indole-3-carboxamide (107 mg) as a yellow solid. MS m/z 403 (M+1).

Cyclization Procedure 2

Similar to the procedure described in Example 9, to a solution of amide (1 eq) in pyridine (0.01-0.1M) was added 1,2,4 triazole (3 eq) followed by phosphorus oxychloride (1.5 eq) and the mixture stirred under an inert atmosphere at room temperature until complete (19-25 h). If appropriate, more phosphorus oxychloride (0.5-1.5 eq) was added to drive the reaction towards completion. The mixture was then added carefully to a rapidly stirred mixture of ice and ammonia (0.88) and stirring continued for 0.5-2 h. The resulting mixture was diluted with water and extracted with dichloromethane (3×) or ethyl acetate (3×) and the combined organic layers washed with brine, dried with magnesium sulfate filtered and reduced. The crude product was then purified, if appropriate by trituration with methanol, by mass directed autoprep or by chromatography on silica gel eluting with an appropriate mixture of ethyl acetate/hexane.

EXAMPLE 76

5-Methyl-7-(1-methyl-1H-indol-3-yl)-N-[4-(methyloxy)phenyl]imidazo[5,1-f][1,2,4]triazin-2-amine

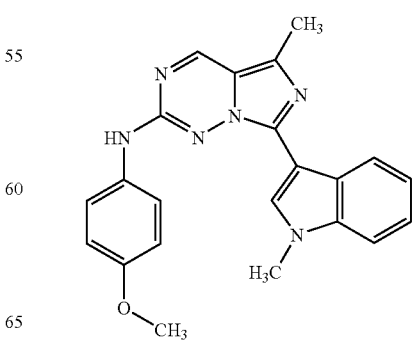

Applying the Cyclization Procedure 2, using 1-methyl-N-[1-(3-{[4-(methyloxy)phenyl]amino}-1,2,4-triazin-6-yl)ethyl]-1H-indole-3-carboxamide (Intermediate 54) (107 mg, 0.26 mmol), pyridine (2.65 mL), 1,2,4 triazole (55 mg, 0.80 mmol) and phosphorus oxychloride (0.037+0.010 mL, 0.50 mmol), to afford 5-methyl-7-(1-methyl-1H-indol-3-yl)-N-[4-(methyloxy)phenyl]imidazo[5,1-f][1,2,4]triazin-2-amine (54 mg) as a yellow solid. MS m/z 385 (M+1).

Intermediate 55: N-[1-(3-{[4-(Methyloxy)phenyl]amino}-1,2,4-triazin-6-yl)ethyl]-2-phenylpropanamide

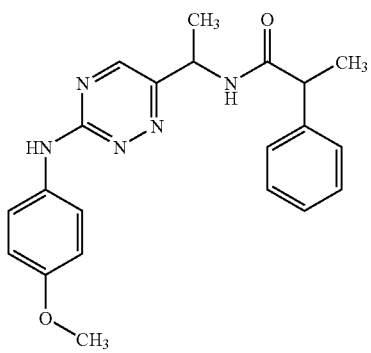

In a similar manner as described for Intermediate 50, using 6-(1-aminoethyl)-N-[4-(methyloxy)phenyl]-1,2,4-triazin-3-amine (Intermediate 47) (100 mg, 0.41 mmol), and 2-phenylpropionic acid (0.061 mL, 0.45 mmol), except the reaction was stirred for 15 h, to give N-[1-(3-{[4-(methyloxy)phenyl]amino}-1,2,4-triazin-6-yl)ethyl]-2-phenylpropanamide (134 mg) as: a yellow solid. MS m/z 376 (M−1).

EXAMPLE 77

5-Methyl-N-[4-(methyloxy)phenyl]-7-(1-phenylethyl)imidazo[5,1-f][1,2,4]triazin-2-amine

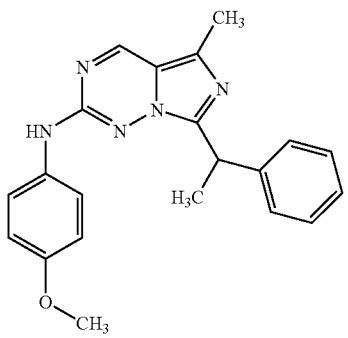

Applying the Cyclization Procedure 2, using N-[1-(3-{[4-(methyloxy)phenyl]amino}-1,2,4-triazin-6-yl)ethyl]-2-phenylpropanamide (Intermediate 55) (129 mg, 0.34 mmol), pyridine (3.4 mL), 1,2,4 triazole (71 mg, 1.03 mmol) and phosphorus oxychloride (0.048+0.048 mL, 1.03 mmol), to afford 5-methyl-N-[4-(methyloxy)phenyl]-7-(1-phenylethyl)imidazo[5,1-f][1,2,4]triazin-2-amine (15 mg) as a yellow solid. MS m/z 360 (M+1).

Intermediate 56: 1-Methyl-N-[1-(3-{[4-(methyloxy)phenyl]-amino}-1,2,4-triazin-6-yl)ethyl]-1H-indole-2-carboxamide

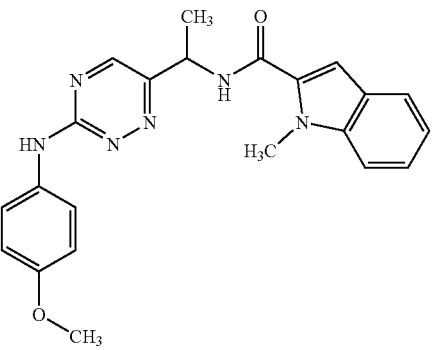

In a similar manner as described for Intermediate 55, using 6-(1-aminoethyl)-N-[4-(methyloxy)phenyl]-1,2,4-triazin-3-amine (Intermediate 47) (100 mg, 0.41 mmol), and 1-methylindole-2-carboxylic acid (79 mg, 0.45 mmol), to give 1-methyl-N-[1-(3-{[4-(methyloxy)phenyl]amino}-1,2,4-triazin-6-yl)ethyl]-1H-indole-2-carboxamide (158 mg) as a yellow solid. MS m/z 403 (M+1).

EXAMPLE 78

5-Methyl-7-(1-methyl-1H-indol-2-yl)-N-[4-(methyloxy)phenyl]imidazo[5,1-f][1,2,4]triazin-2-amine

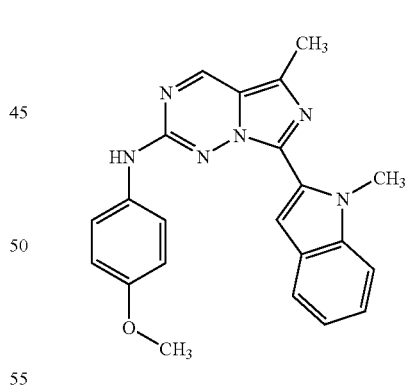

Applying the Cyclization Procedure 2, using 1-methyl-N-[1-(3-{[4-(methyloxy)phenyl]amino}-1,2,4-triazin-6-yl)ethyl]-1H-indole-2-carboxamide (Intermediate 56) (151 mg, 0.38 mmol), pyridine (3.7 mL), 1,2,4 triazole (78 mg, 1.13 mmol) and phosphorus oxychloride (0.052+0.052 mL, 1.12 mmol), to afford 5-methyl-7-(1-methyl-1H-indol-2-yl)-N-[4-(methyloxy)phenyl]imidazo[5,1-f][1,2,4]triazin-2-amine (11 mg) as a yellow solid. MS m/z 385 (M+1).

Intermediate 57: N-[1-(3-{[4-(Methyloxy)phenyl]amino}-1,2,4-triazin-6-yl)ethyl]-3-thiophenecarboxamide

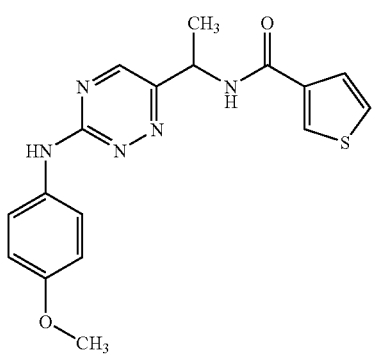

In a similar manner as described for Intermediate 48, using 6-(1-aminoethyl)-N-[4-(methyloxy)phenyl]-1,2,4-triazin-3-amine (Intermediate 47) (100 mg, 0.41 mmol), and 3-thiophenecarboxylic acid (57 mg, 0.45 mmol). Except, that after 3 hours, the crude reaction mixture was diluted with ethyl acetate and washed twice with dilute aqueous hydrochloric acid (0.2 N) followed by saturated sodium bicarbonate solution. The organic layer was separated, dried with magnesium sulfate, filtered, reduced and then purified by chromatography on silica gel eluting with 40% ethyl acetate, in petrol to afford N-[1-(3-{[4-(methyloxy)phenyl]amino}-1,2,4-triazin-6-yl)ethyl]-3-thiophenecarboxamide (95 mg) as a yellow solid. MS m/z 356 (M+1).

EXAMPLE 79

5-Methyl-N-[4-(methyloxy)phenyl]-7-(3-thienyl)imidazo[5,1-f][1,2,4]triazin-2-amine

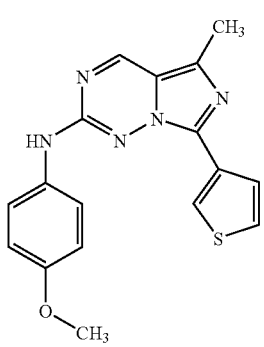

Applying the Cyclization Procedure 1, using N-[1-(3-{[4-(methyloxy)phenyl]amino}-1,2,4-triazin-6-yl)ethyl]-3-thiophenecarboxamide (Intermediate 57) (95 mg, 0.27 mmol), 1,2-dichloroethane (5 mL) and phosphorus oxychloride (0.20 mL, 2.14 mmol), to afford 5-methyl-N-[4-(methyloxy)phenyl]-7-(3-thienyl)imidazo[5,1-f][1,2,4]triazin-2-amine (45 mg) as a yellow solid. MS m/z 338 (M+1).

Intermediate 58: N-[1-(3-{[4-(Methyloxy)phenyl]amino}-1,2,4-triazin-6-yl)ethyl]-3-furancarboxamide

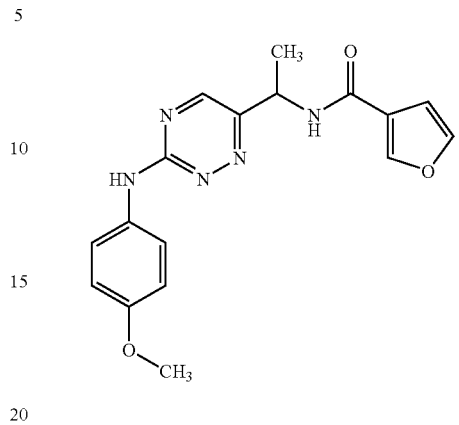

In a similar manner as described for Intermediate 57, using 6-(1-aminoethyl)-N-[4-(methyloxy)phenyl]-1,2,4-triazin-3-amine (Intermediate 47) (100 mg, 0.41 mmol), and 3-furoic acid (50 mg, 0.45 mmol). Except, that during the saturated sodium bicarbonate solution wash, a solid was formed which was collected by filtration and dried to give N-[1-(3-{[4-(methyloxy)phenyl]amino}-1,2,4-triazin-6-yl)ethyl]-3-furancarboxamide (110 mg) as a yellow solid. MS m/z 340 (M+1).

EXAMPLE 80

7-(3-Furanyl)-5-methyl-N-[4-(methyloxy)phenyl]imidazo-[5,1-f][1,2,4]triazin-2-amine

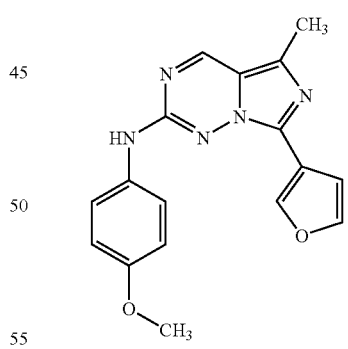

Applying the Cyclization Procedure 1, using N-[1-(3-{[4-(methyloxy)phenyl]amino}-1,2,4-triazin-6-yl)ethyl]-3-furancarboxamide (Intermediate 58) (110 mg, 0.32 mmol), 1,2-dichloroethane (5 mL) and phosphorus oxychloride (0.20 mL, 2.14 mmol), to afford 7-(3-furanyl)-5-methyl-N-[4-(methyloxy)phenyl]imidazo[5,1-f][1,2,4]triazin-2-amine (55 mg) as a yellow solid. MS m/z 322 (M+1).

Intermediate 59: N-[1-(3-{[4-(Methyloxy)phenyl]amino}-1,2,4-triazin-6-yl)ethyl]-2-furancarboxamide

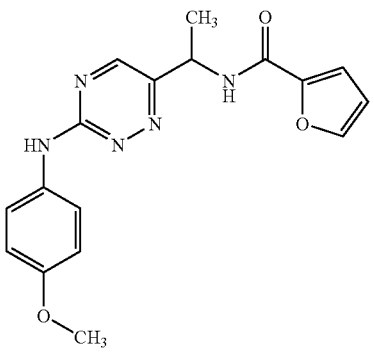

A mixture of 6-(1-aminoethyl)-N-[4-(methyloxy)phenyl]-1,2,4-triazin-3-amine (Intermediate 47) (100 mg, 0.41 mmol) and triethylamine (0.170 mL, 1.22 mmol) in dichloromethane (5 mL) at −78° C., was treated with 3-2-furoyl chloride (0.044 mL, 0.45 mmol) and the resulting mixture stirred at this temperature for 0.5 h. The reaction was then quenched with water and allowed to warm to room temperature overnight. The mixture was then washed twice with aqueous hydrochloric acid (0.1 N) followed by brine. The organic layer was separated, dried with magnesium sulfate, filtered, reduced and then purified by chromatography on silica gel eluting with 50 to 60% ethyl acetate in petrol to afford N-[1-(3-{[4-(methyloxy)phenyl]amino}-1,2,4-triazin-6-yl)ethyl]-2-furancarboxamide (85 mg) as a yellow solid. MS m/z 340 (M+1).

EXAMPLE 81

7-(2-Furanyl)-5-methyl-N-[4-(methyloxy)phenyl]imidazo-[5,1-f][1,2,4]triazin-2-amine

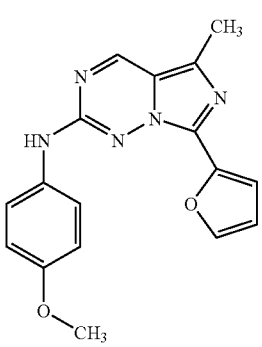

Applying the Cyclization Procedure 1, using N[1-(3-{[4-(methyloxy)phenyl]amino}-1,2,4-triazin-6-yl)ethyl]-2-furancarboxamide (Intermediate 59) (85 mg, 0.25 mmol), 1,2-dichloroethane (5 mL) and phosphorus oxychloride (0.19 mL, 2.04 mmol), to afford 7-(2-furanyl)-5-methyl-N-[4-(methyloxy)phenyl]imidazo[5,1-f][1,2,4]triazin-2-amine (20 mg) as a yellow solid. MS m/z 322 (M+1).

Intermediate 60: 4-Fluoro-N-[1-(3-{[4-(methyloxy)phenyl]amino}-1,2,4-triazin-6-yl)ethyl]benzamide

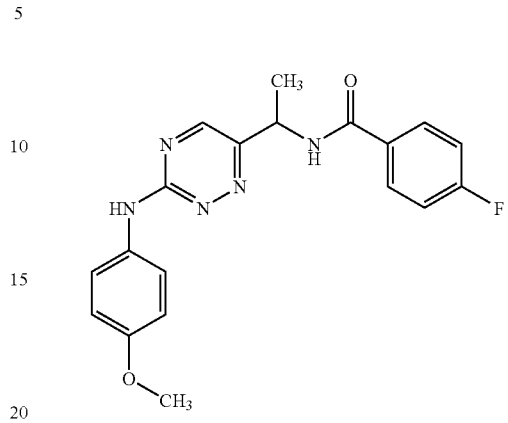

In a similar manner as described for Intermediate 59, using 6-(1-aminoethyl)-N-[4-(methyloxy)phenyl]-1,2,4-triazin-3-amine (Intermediate 47) (100 mg, 0.41 mmol), and 4-fluorobenzoyl chloride (0.053 mL, 0.45 mmol). Except, that the crude reaction mixture was triturated with methanol to afford N-[1-(3-{[4-(methyloxy)phenyl]amino}1,2,4-triazin-6-yl)ethyl]-2-furancarboxamide (85 mg) as a yellow solid. MS m/z 368 (M+1).

EXAMPLE 82

7-(4-Fluorophenyl)-5-methyl-N-[4-(methyloxy)phenyl]-imidazo[5,1-f][1,2,4]triazin-2-amine

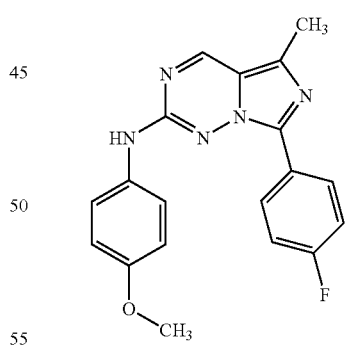

Applying the Cyclization Procedure 1, using N-[1-(3-{[4-(methyloxy)phenyl]amino}-1,2,4-triazin-6-yl)ethyl]-2-furancarboxamide (Intermediate 60) (85 mg, 0.23 mmol), 1,2-dichloroethane (5 mL) and phosphorus oxychloride (0.20 mL, 2.14 mmol), to afford 7-(4-fluorophenyl)-5-methyl-N-[4-(methyloxy)phenyl]imidazo[5,1-f][1,2,4]triazin-2-amine (30 mg) as a yellow solid. MS m/z 350 (M+1).

Intermediate 61: N-[1-(3-{[4-(Methyloxy)phenyl]amino}-1,2,4-triazin-6-yl)ethyl]-2-thiophenecarboxamide

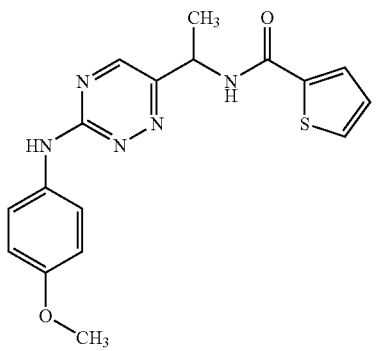

In a similar manner as described for Intermediate 59, using 6-(1-aminoethyl)-N-[4-(methyloxy)phenyl]-1,2,4-triazin-3-amine (Intermediate 47) (100 mg, 0.41 mmol), and thiophene-2-carbonyl chloride (0.048 mL, 0.45 mmol) to afford N-[1-(3-{[4-(methyloxy)phenyl]amino}-1,2,4-triazin-6-yl)ethyl]-2-thiophenecarboxamide (115 mg) as a yellow solid. MS m/z 356 (M+1).

Intermediate 62: N-[1-(3-{[4-(Methyloxy)phenyl]amino}-1,2,4-triazin-6-yl)ethyl]cyclopropanecarboxamide

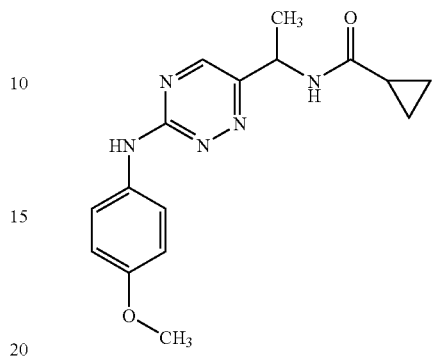

In a similar manner as described for Intermediate 59, using 6-(1-aminoethyl)-N-[4-(methyloxy)phenyl]-1,2,4-triazin-3-amine (Intermediate 47) (100 mg, 0.41 mmol), and cyclopropanecarbonyl chloride (0.043 mL, 0.45 mmol), except the reaction was stirred for 1 h at −78° C., to afford N-[1-(3-{[4-(methyloxy)phenyl]amino}-1,2,4-triazin-6-yl)ethyl]cyclopropanecarboxamide (110 mg) as a yellow solid. $^1$H NMR (DMSO): δ9.87 (s, 1H), 8.64 (d, J=8.0 HZ, 1H), 8.35 (s, 1H), 7.62 (d, J=8.6 Hz, 2H), 6.91 (d, J=8.6 Hz, 2H), 5.05 (m, 1H), 3.74 (s, 3H), 1.63 (m, 1H), 1.47 (d, J=7.0 Hz, 3H), 0.65 (m, 4H).

EXAMPLE 83

5-Methyl-N-[4-(methyloxy)phenyl]-7-(2-thienyl)imidazo[5,1-f][1,2,4]triazin-2-amine

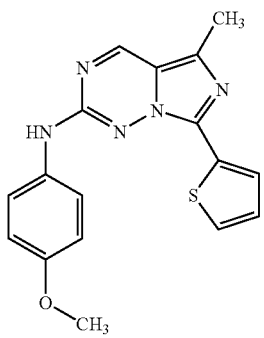

Applying the Cyclization Procedure 1, using N-[1-(3-{[4-(methyloxy)phenyl]amino}-1,2,4-triazin-6-yl)ethyl]-2-thiophenecarboxamide (Intermediate 61) (115 mg, 0.32 mmol), 1,2-dichloroethane (5 mL) and phosphorus oxychloride (0.24 mL, 2.57 mmol), to afford 5-methyl-N-[4-(methyloxy)phenyl]-7-(2-thienyl)imidazo[5,1-f][1,2,4]triazin-2-amine (45 mg) as a yellow solid. MS m/z 338 (M+1).

EXAMPLE 84

7-Cyclopropyl-5-methyl-N-[4-(methyloxy)phenyl]-imidazo[5,1-f][1,2,4]triazin-2-amine

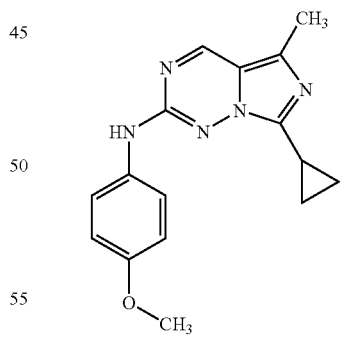

Applying the Cyclization Procedure 1, using N-[1-(3-{[4-(methyloxy)phenyl]amino}-1,2,4-triazin-6-yl)ethyl]cyclopropanecarboxamide (Intermediate 62) (103 mg, 0.33 mmol), 1,2-dichloroethane (5 mL) and phosphorus oxychloride (0.25 mL, 2.68 mmol), to afford 7-cyclopropyl-5-methyl-N-[4-(methyloxy)phenyl]imidazo[5,1-f][1,2,4]triazin-2-amine (53 mg) as a yellow solid. MS m/z 296 (M+1).

Intermediate 63: N-[1-(3-{[4-(Methyloxy)phenyl]amino}-1,2,4-triazin-6-yl)ethyl]cyclohexanecarboxamide

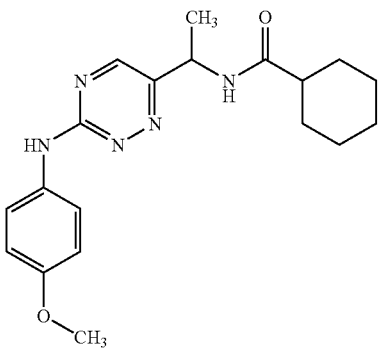

In a similar manner as described for Intermediate 62, using 6-(1-aminoethyl)-N-[4-(methyloxy)phenyl]-1,2,4-triazin-3-amine (Intermediate 47) (100 mg, 0.41 mmol), and cyclohexanecarbonyl chloride (0.065 mL, 0.45 mmol) to afford N-[1-(3-{[4-(methyloxy)phenyl]amino}-1,2,4-triazin-6-yl)ethyl]cyclohexane-carboxamide (90 mg) as a yellow solid. MS m/z 356 (M+1).

Intermediate 64: 2-Fluoro-N-[1-(3-{[4-(methyloxy)phenyl]amino}-1,2,4-triazin-6-yl)ethyl]benzamide

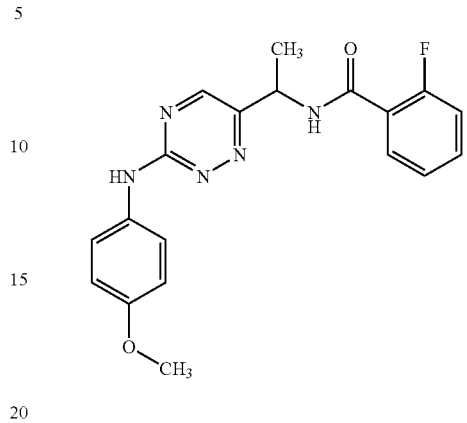

In a similar manner as described for Intermediate 59, using 6-(1-aminoethyl)-N-[4-(methyloxy)phenyl]-1,2,4-triazin-3-amine (Intermediate 47) (100 mg, 0.41 mmol), and 2-fluorobenzoyl chloride (0.059 mL, 0.45 mmol) to afford 2-fluoro-N-[1-(3-{[4-(methyloxy)phenyl]amino}-1,2,4-triazin-6-yl)ethyl]benzamide (100 mg) as a yellow solid. MS m/z 368 (M+1).

EXAMPLE 85

7-Cyclohexyl-5-methyl-N-[4-(methyloxy)phenyl]imidazo[5,1-f][1,2,4]triazin-2-amine

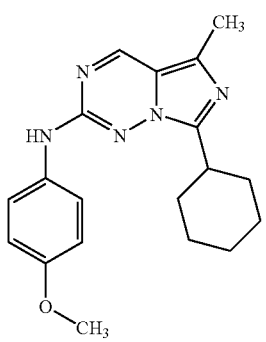

Applying the Cyclization Procedure 1, using N-[1-(3-{[4-(methyloxy)phenyl]amino}-1,2,4-triazin-6-yl)ethyl]cyclohexane-carboxamide (Intermediate 63) (90 mg, 0.25 mmol), 1,2-dichloroethane (5 mL) and phosphorus oxychloride (0.25 mL, 2.68 mmol), to afford 7-cyclohexyl-5-methyl-N-[4-(methyloxy)phenyl]imidazo[5,1-f][1,2,4]triazin-2-amine (28 mg) as a yellow solid. $^1$H NMR (DMSO): δ9.46 (s, 1H), 9.06 (s, 1H), 7.71 (d, J=8.7 Hz, 2H), 6.91 (d, J=8.7 Hz, 2H), 3.75 (s, 3H), 3.14 (m, 1H), 2.43 (s; 3H), 1.95 (m, 2H), 1.84 (m, 2H), 1.80-1.60 (m, 3H), 1.51-1.36 (m, 2H), 1.36-1.25 (m,1H).

EXAMPLE 86

7-(2-FluorophenylFluorophenyl)-5-methyl-N-[4-(methyloxy)phenyl]imidazo[5,1-f][1,2,4]triazin-2-amine

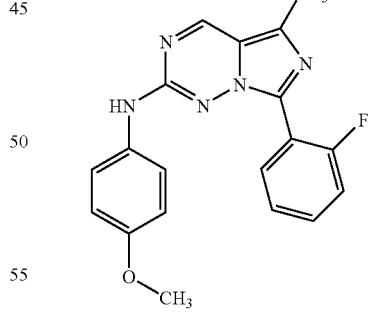

Applying the Cyclization Procedure 1, using 2-fluoro-N-[1-(3-{[4-(methyloxy)phenyl]amino}-1,2,4-triazin-6-yl)ethyl]benzamide (Intermediate 64) (100 mg, 0.27 mmol), 1,2-dichloroethane (5 mL) and phosphorus oxychloride (0.20 mL, 2.14 mmol), to afford 7-(2-fluorophenyl)-5-methyl-N-[4-(methyloxy)phenyl]imidazo[5,1-f][1,2,4]triazin-2-amine (35 mg) as a yellow solid. MS m/z 350 (M+1).

137

Intermediate 65: 4-(Methyloxy)-N-[1-(3-{[4-(methyloxy)phenyl]amino}-1,2,4-triazin-6-yl)ethyl]benzamide

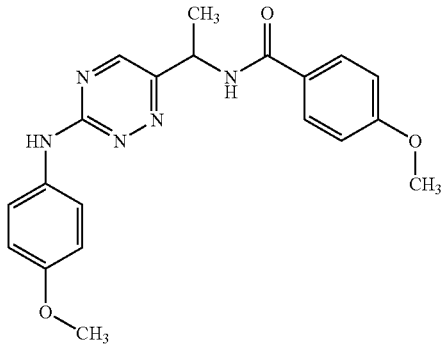

In a similar manner as described for Intermediate 59, using 6-(1-aminoethyl)-N-[4-(methyloxy)phenyl]-1,2,4-triazin-3-amine (Intermediate 47) (100 mg, 0.41 mmol), and p-anisoyl chloride (0.070 mL, 0.45 mmol), except that after quenching the mixture was allowed to warm over 1 h, and was further purified by SPE (SCX, 5 g cartridge) eluting with methanol then ammonia in methanol (0.5 N to 2.0 N), to afford 2-fluoro-N-[1-(3-{[4-(methyloxy)phenyl]amino}-1,2,4-triazin-6-yl)ethyl]benzamide (34 mg) as a yellow solid. MS m/z 380 (M+1).

138

Intermediate 66: N-[1-(3-{[4-(Methyloxy)phenyl]amino}-1,2,4-triazin-6-yl)ethyl]-2-phenylacetamide

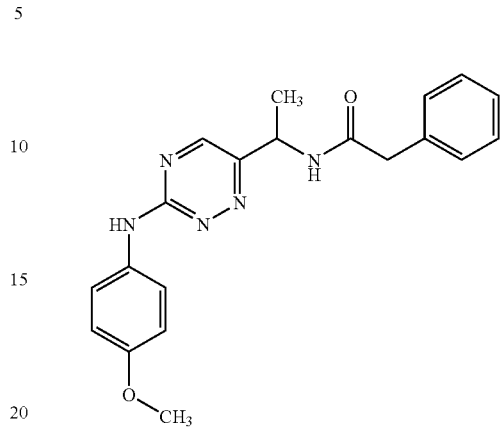

In a similar manner as described for Intermediate 59, using 6-(1-aminoethyl)-N-[4-(methyloxy)phenyl]-1,2,4-triazin-3-amine (Intermediate 47) (100 mg, 0.41 mmol), and phenylacetyl chloride (0.059 mL, 0.45 mmol) to afford N-[1-(3-{[4-(methyloxy)phenyl]amino}-1,2,4-triazin-6-yl)ethyl]-2-phenylacetamide (50 mg) as a yellow solid. MS m/z 364 (M+1).

EXAMPLE 87

5-Methyl-N,7-bis[4-(methyloxy)phenyl]imidazo[5,1-f][1,2,4]triazin-2-amine

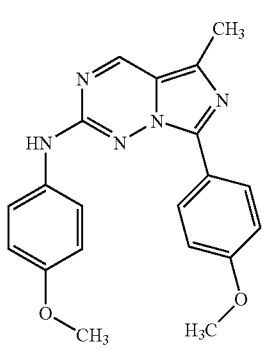

Applying the Cyclization Procedure 1, using 4-(methyloxy)-N-[1-(3-{[4-(methyloxy)phenyl]amino}-1,2,4-triazin-6-yl)ethyl]benzamide (Intermediate 65) (35 mg, 0.09 mmol), 1,2-dichloroethane (1.8 mL) and phosphorus oxychloride (0.068 mL, 0.73 mmol), to afford 5-methyl-N,7-bis[4-(methyloxy)phenyl]imidazo[5,1-f][1,2,4]triazin-2-amine (24 mg) as a yellow solid. MS m/z 362 (M+1).

EXAMPLE 88

5-Methyl-N-[4-(methyloxy)phenyl]-7-(phenylmethyl)imidazo[5,1-f][1,2,4]triazin-2-amine

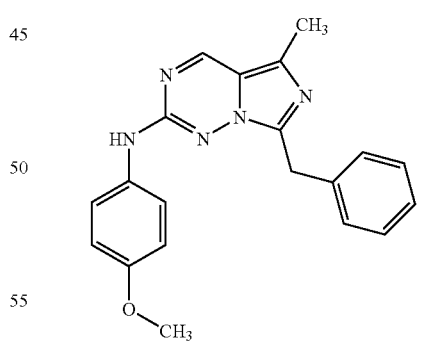

Applying the Cyclization Procedure 1, using N-[1-(3-{[4-(methyloxy)phenyl]amino}-1,2,4-triazin-6-yl)ethyl]-2-phenylacetamide (Intermediate 66) (90 mg, 0.25 mmol), 1,2-dichloroethane (5 mL) and phosphorus oxychloride (0.20 mL, 2.14 mmol), to afford 5-methyl-N-[4-(methyloxy)phenyl]-7-(phenylmethyl)imidazo[5,1-f][1,2,4]triazin-2-amine (45 mg) as a yellow solid. MS m/z 346 (M+1).

Intermediate 67: 3-Fluoro-N-[1-(3-{[4-(methyloxy)phenyl]amino}-1,2,4-triazin-6-yl)ethyl]benzamide

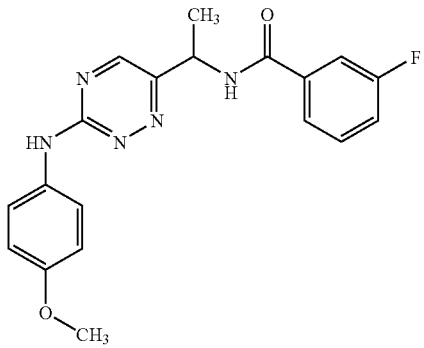

In a similar manner as described for Intermediate 59, using 6-(1-aminoethyl)-N-[4-(methyloxy)phenyl]-1,2,4-triazin-3-amine (Intermediate 47) (100 mg, 0.41 mmol), and 3-fluorobenzoyl chloride (0.059 mL, 0.45 mmol) to afford 3-fluoro-N-[1-(3-{[4-(methyloxy)phenyl]amino}-1,2,4-triazin-6-yl)ethyl]benzamide (130 mg) as a yellow solid. MS m/z 368 (M+1).

Intermediate 68: N-[1-(3-{[3,4,5-Tris(methyloxv)phenyl]amino}1,2,4-triazin-6-yl)ethyl]cyclohexanecarboxamide

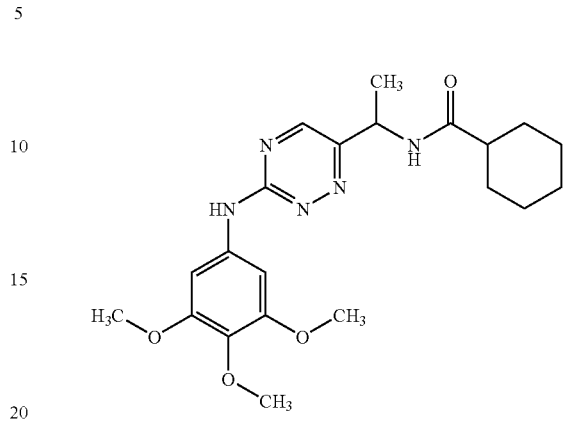

In a similar manner as described for Intermediate 59, using 6-(1-aminoethyl)-N-(3,4,5-trimethoxyphenyl)-1,2,4-triazin-3-amine (Intermediate 9) (170 mg, 0.56 mmol), triethylamine (0.120 mL, 0.84 mmol) and cyclohexanecarbonyl chloride (0.082 mL, 0.61 mmol) to afford N-[1-(3-{[3,4,5-tris(methyloxy)phenyl]amino}-1,2,4-triazin-6-yl)ethyl]cyclohexanecarboxamide (140 mg) as a yellow solid. MS m/z 416 (M+1).

EXAMPLE 89

7-(3-Fluorophenyl)-5-methyl-N-[4-(methyloxy)phenyl]imidazo[5,1-f][1,2,4]triazin-2-amine

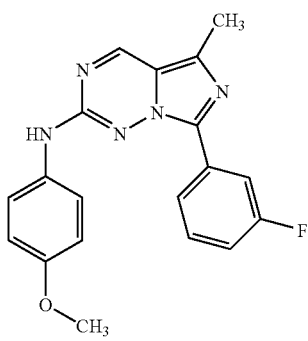

Applying the Cyclization Procedure 1, using 3-fluoro-N-[1-(3-{[4-(methyloxy)phenyl]amino}-1,2,4-triazin-6-yl)ethyl]benzamide (Intermediate 67) (130 mg, 0.35 mmol), 1,2-dichloroethane (5 mL) and phosphorus oxychloride (0.25 mL, 2.68 mmol), to afford 7-(3-fluorophenyl)-5-methyl-N-[4-(methyloxy)phenyl]imidazo[5,1-f][1,2,4]triazin-2-amine (25 mg) as a yellow solid. MS m/z 350 (M+1).

EXAMPLE 90

7-Cyclohexyl-5-methyl-N-[3,4,5-tris(methyloxy)phenyl]imidazo[5,1-f][1,2,4]triazin-2-amine

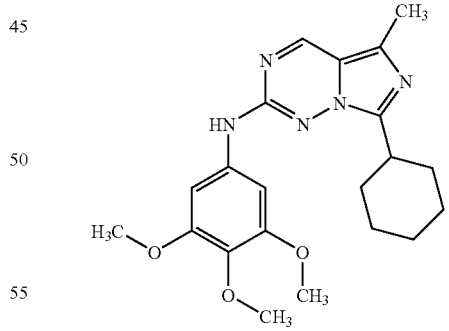

Applying the Cyclization Procedure 1, using N-[1-(3-{[3,4,5-tris(methyloxy)phenyl]amino}-1,2,4-triazin-6-yl)ethyl]cyclohexane-carboxamide (Intermediate 68) (140 mg, 0.34 mmol), 1,2-dichloroethane (5 mL) and phosphorus oxychloride (0.25 mL, 2.68 mmol), to afford 7-cyclohexyl-5-methyl-N-[3,4,5-tris(methyloxy)phenyl]-imidazo[5,1-f][1,2,4]triazin-2-amine (35 mg) as a yellow solid. MS m/z 398 (M+1).

Intermediate 69: 2-Cyclohexyl-N-[1-(3-{[4-(methyloxy)phenyl]amino}-1,2,4-triazin-6-yl)ethyl]acetamide

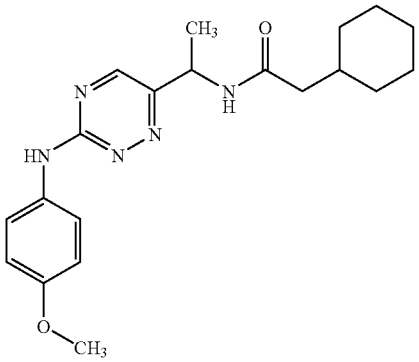

In a similar manner as described for Intermediate 48, using 6-(1-aminoethyl)-N-[4-(methyloxy)phenyl]-1,2,4-triazin-3-amine (Intermediate 47) (100 mg, 0.41 mmol), and cyclohexylacetic acid (64 mg, 0.45 mmol), except that the reaction was stirred for 4 h and the crude reaction mixture reduced under vacuum, partitioned between dichloromethane and saturated sodium bicarbonate solution and the layers separated. The aqueous was re-extracted with dichloromethane and the combined organic layers washed with brine, dried with magnesium sulfate, filtered and reduced to give 2-cyclohexyl-N-[1-(3-{[4-(methyloxy)phenyl]amino}-1,2,4-triazin-6-yl)ethyl]acetamide (100 mg) as a yellow solid. MS m/z 370 (M+1).

EXAMPLE 91

7-(Cyclohexylmethyl)-5-methyl-N-[4-(methyloxy)phenyl]-imidazo[5,1-f][1,2,4]triazin-2-amine

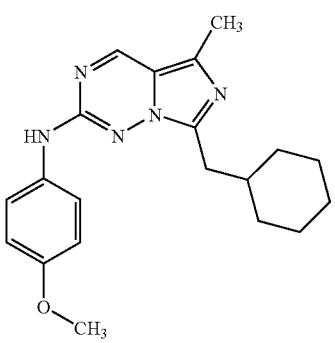

Applying the Cyclization Procedure 2, using 2-cyclohexyl-N-[1-(3-{[4-(methyloxy)phenyl]amino}-1,2,4-triazin-6-yl)ethyl]acetamide (Intermediate 69) (100 mg, 0.27 mmol), pyridine (25 mL), 1,2,4 triazole (56 mg, 0.81 mmol) and phosphorus oxychloride (0.040 mL, 0.43 mmol), to afford 7-(cyclohexylmethyl)-5-methyl-N-[4-(methyloxy)phenyl]-imidazo[5,1-f][1,2,4]triazin-2-amine (68 mg) as a yellow solid. MS m/z 352 (M+1).

Intermediate 70: N-{1-[3-(Methylthio)-1,2,4-triazin-6-yl]ethyl}benzamide

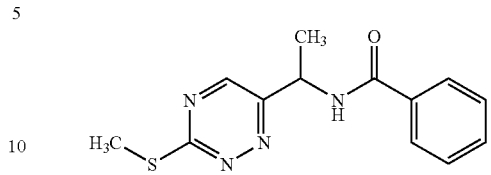

In a similar manner as described for Intermediate 59, using 1-[3-(Methylthio)-1,2,4-triazin-6-yl]ethanamine (Intermediate 4) (1.00 g, 5.90 mmol), benzoyl chloride (0.75 mL, 6.50 mmol), to give N-{1-[3-(methylthio)-1,2,4-triazin-6-yl]ethyl}benzamide (1.35 g) as a yellow solid. MS m/z 275 (M+1).

Intermediate 71: 5-Methyl-2-(methylthio)-7-phenylimidazo[5,1-f][1,2,4]triazine

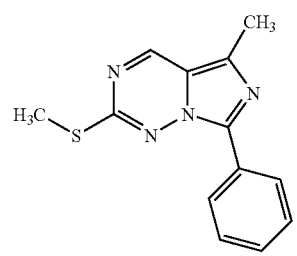

Applying the Cyclization Procedure 1, using N-{1-[3-(methylthio)-1,2,4-triazin-6-yl]ethyl}benzamide (Intermediate 70) (590 mg, 2.15 mmol), 1,2-dichloroethane (10 mL) and phosphorus oxychloride (1.60 mL, 17.17 mmol), to afford 5-methyl-2-(methylthio)-7-phenylimidazo[5,1-f][1,2,4]triazine (350 mg) as a yellow solid. MS m/z 257 (M+1).

Intermediate 72: 5-Methyl-2-(methylsulfonyl)-7-phenylimidazo[5,1-f][1,2,4]triazine

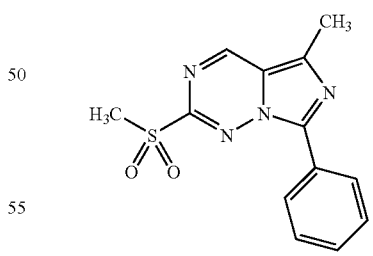

A mixture of 5-methyl-2-(methylthio)-7-phenylimidazo[5,1-f][1,2,4]triazine (Intermediate 71) (175 mg, 0.68 mmol) in dichloromethane (5 mL) was treated with 3-chloroperoxybenzoic acid (50-55%, 470 mg, 1.37 mmol) and the resulting mixture stirred at room temperature overnight. The mixture was then washed with saturated sodium bicarbonate solution, dried with magnesium sulfate, filtered and reduced under vacuum. The crude product was then purified by chromatography on silica gel eluting with 0 to 2% methanol in ethyl acetate to give 5-methyl-2-(methylthio)-7-phenylimidazo[5,1-f][1,2,4]triazine (140 mg) as a yellow solid. ¹H NMR (CDCl₃): δ9.06 (s, 1H), 8.53 (m, 2H), 7.60-7.50 (m, 3H), 3.05 (s, 3H), 2.73 (s, 3H).

Displacement Procedure

A stirred solution of the aniline (1 eq) and 5-methyl-2-(methylthio)-7-phenylimidazo[5,1-f][1,2,4]triazine (Intermediate 72) (1 eq) in ethanol (0.07 M) was heated at 180° C. in the microwave until complete (ca. 0.7-2.5 h). The mixture was then reduced under vacuum and the residue purified using SPE (Si) eluting with an appropriate mixture of ethyl acetate/hexane or methanol/dichloromethane) and/or by trituration with diethyl ether. Alternatively, purification was performed by SPE (SCX) eluting with methanol then ammonia in methanol (0.5 N to 2.0 N) or by mass director autoprep.

EXAMPLE 92

N-[3,4-Bis(methyloxy)phenyl]-5-methyl-7-phenylimidazo[5,1-f][1,2,4]triazin-2-amine

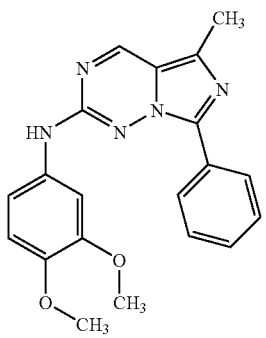

Applying the displacement procedure, using 5-methyl-2-(methylthio)-7-phenylimidazo[5,1-f][1,2,4]triazine (Intermediate 72) (50 mg, 0.17 mmol), 3,4-dimethoxyaniline (26.5 mg, 0.17 mmol) and ethanol (2.5 mL) to afford N-[3,4-bis (methyloxy)phenyl]-5-methyl-7-phenylimidazo[5,1-f][1,2,4]triazin-2-amine (22.5 mg) as a yellow solid. MS m/z 362 (M+1).

EXAMPLE 93

N-[3,5-Bis(methyloxy)phenyl]-5-methyl-7-phenylimidazo[5,1-f][1,2,4]triazin-2-amine

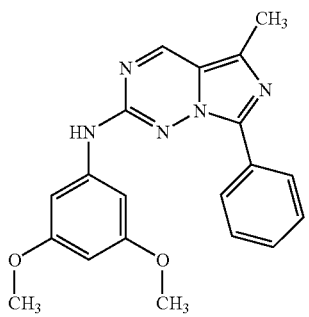

Applying the displacement procedure, using 5-methyl-2-(methylthio)-7-phenylimidazo[5,1-f][1,2,4]triazine (Intermediate 72) (50 mg, 0.17 mmol), 3,5-dimethoxyaniline (26.5 mg, 0.17 mmol) and ethanol (2.5 mL) to afford N-[3,5-bis (methyloxy)phenyl]-5-methyl-7-phenylimidazo[5,1-f][1,2,4]triazin-2-amine (23 mg) as a yellow solid. MS m/z 362 (M+1).

EXAMPLE 94

N-{4-[(5-Methyl-7-phenylimidazo[5,1-f][1,2,4]triazin-2-yl)amino]phenyl}acetamide

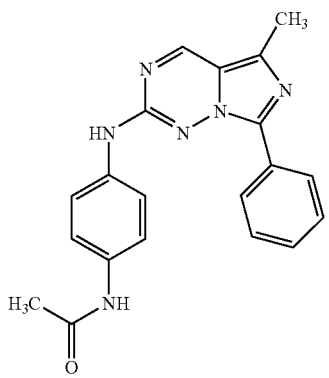

Applying the displacement procedure, using 5-methyl-2-(methylthio)-7-phenylimidazo[5,1-f][1,2,4]triazine (Intermediate 72) (50 mg, 0.17 mmol), 4-aminoacetanilide (26 mg, 0.17 mmol) and ethanol (2.5 mL) to afford N-{4-[(5-methyl-7-phenylimidazo[5,1-f][1,2,4]triazin-2-yl)amino] phenyl}acetamide (19 mg) as a yellow solid. MS m/z 359 (M+1).

EXAMPLE 95:

5-Methyl-N-[4-(methylthio)phenyl]-7-phenylimidazo[5,1-f][1,2,4]triazin-2-amine

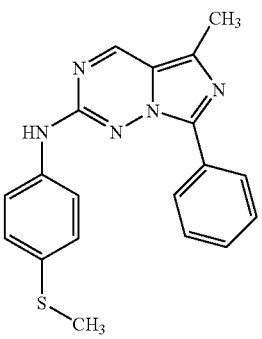

Applying the displacement procedure, using 5-methyl-2-(methylthio)-7-phenylimidazo[5,1-f][1,2,4]triazine (Intermediate 72) (50 mg, 0.17 mmol), 4-(methylthio)aniline (0.022 mL, 0.17 mmol) and ethanol (2.5 mL) to afford 5-methyl-N-[4-(methylthio)phenyl]-7-phenylimidazo[5,1-f][1,2,4]triazin-2-amine (30 mg) as a yellow solid. MS m/z 348 (M+1).

EXAMPLE 96

N-(4-{[2-(Dimethylamino)ethyl]oxy}phenyl)-5-methyl-7-phenylimidazo[5.1-f][1,2,4]triazin-2-amine

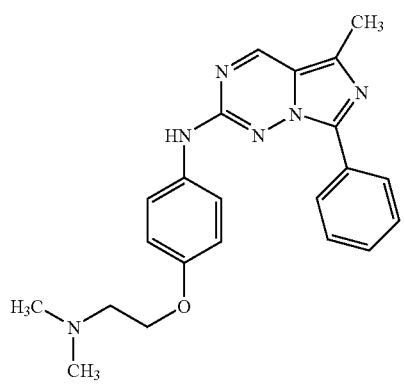

Applying the displacement procedure, using 5-methyl-2-(methylthio)-7-phenylimidazo[5,1-f][1,2,4]triazine (Intermediate 72) (50 mg, 0.17 mmol), {2-[(4-aminophenyl)oxy]ethyl}dimethylamine (32 mg, 0.17 mmol) and ethanol (2.5 mL) to afford N-(4-{[2-(dimethylamino)ethyl]oxy}-phenyl)-5-methyl-7-phenylimidazo[5,1-f][1,2,4]triazin-2-amine (16 mg) as a yellow solid. MS m/z 389 (M+1).

EXAMPLE 97:

5-Methyl-7-phenyl-N-(4-{[2-(1-piperidinyl)ethyl]-oxy}phenyl)-imidazo[5,1-f][1,2,4]triazin-2-amine

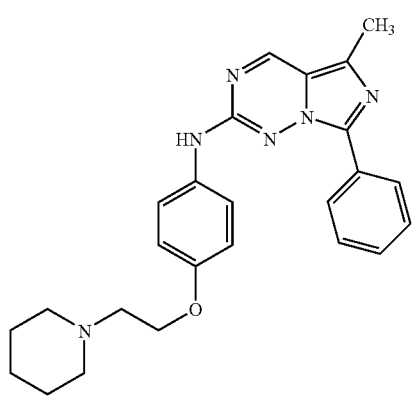

Applying the displacement procedure, using 5-methyl-2-(methylthio)-7-phenylimidazo[5,1-f][1,2,4]triazine (Intermediate 72) (50 mg, 0.17 mmol), (4-{[2-(1-piperidinyl)ethyl]oxy}phenyl)amine hydrochloride (45 mg, 0.17 mmol), triethylamine (0.024 mL, 0.17 mmol) and ethanol (2.5 mL) to afford 5-methyl-7-phenyl-N-(4-{[2-(1-piperidinyl)ethyl]oxy}phenyl)imidazo[5,1-f][1,2,4]triazin-2-amine (6 mg) as a yellow solid. MS m/z 429 (M+1).

EXAMPLE 98

N-(3-{[2-(Dimethylamino)ethyl]oxy}phenyl)-5-methyl-7-phenylimidazo[5,1-f][1,2,4]triazin-2-amine

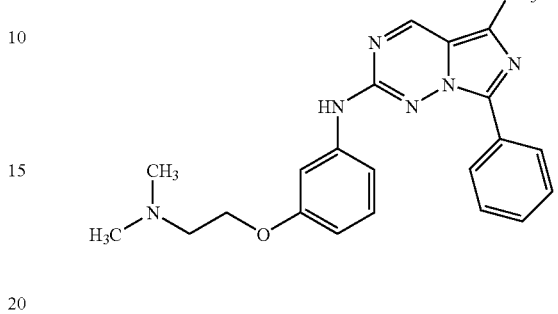

Applying the displacement procedure, using 5-methyl-2-(methylthio)-7-phenylimidazo[5,1-f][1,2,4]triazine (Intermediate 72) (50 mg, 0.17 mmol), {2-[(3-aminophenyl)oxy]ethyl}dimethylamine hydrochloride (37.5 mg, 0.17 mmol) and ethanol (2.5 mL) to afford M(3-{[2-(dimethylamino)ethyl]oxy}phenyl)-5-methyl-7-phenylimidazo[5,1-f][1,2,4]triazin-2-amine (2 mg) as a yellow solid. MS m/z 389 (M+1).

EXAMPLE 99

N-(1-Acetyl-2,3-dihydro-1H-indol-5-yl)-5-methyl-7-phenylimidazo[5,1-f][1,2,4]triazin-2-amine

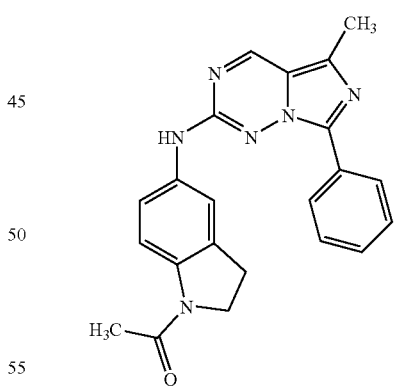

Applying the displacement procedure, using 5-methyl-2-(methylthio)-7-phenylimidazo[5,1-f][1,2,4]triazine (Intermediate 72) (50 mg, 0.17 mmol), 1-acetyl-5-amino-2,3-dihydro-(1h)-indole (30.5 mg, 0.17 mmol) and ethanol (2.5 mL) to afford N-(1-acetyl-2,3-dihydro-1H-indol-5-yl)-5-methyl-7-phenylimidazo[5,1-f][1,2,4]triazin-2-amine (20 mg) as a yellow solid. MS m/z 385 (M+1).

EXAMPLE 100

N-Cyclohexyl-5-methyl-7-phenylimidazo[5,1-f][1,2,4]triazin-2-amine

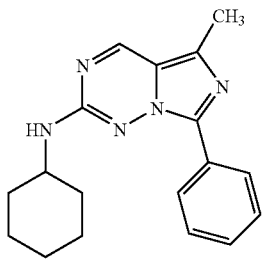

Applying the displacement procedure, using 5-methyl-2-(methylthio)-7-phenylimidazo[5,1-f][1,2,4]triazine (Intermediate 72) (50 mg, 0.17 mmol), cyclohexylamine (0.02 mL, 0.17 mmol) and ethanol (2.5 mL) to afford N-cyclohexyl-5-methyl-7-phenylimidazo[5,1-f][1,2,4]triazin-2-amine (8 mg) as a yellow solid. MS m/z 308 (M+1).

Example 101:

5-Methyl-7-phenyl-N-(tetrahydro-2H-pyran-4-yl)imidazo[5,1-f][1,2,4]triazin-2-amine

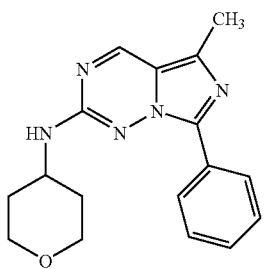

Applying the displacement procedure, using 5-methyl-2-(methylthio)-7-phenylimidazo[5,1-f][1,2,4]triazine (Intermediate 72) (45 mg, 0.16 mmol), cyclohexylamine hydrochloride (21.5 mg, 0.16 mmol) and ethanol (2.5 mL) except that after 1 h, the mixture was treated with triethylamine (0.022 mL, 0.16 mmol), and heating continued for 0.5 h, to afford 5-methyl-7-phenyl-N-(tetrahydro-2H-pyran-4-yl)imidazo[5,1-f][1,2,4]triazin-2-amine (15 mg) as a yellow solid. MS m/z 310 (M+1).

EXAMPLE 102

5-Methyl-N-(4-{[2-(4-morpholinyl)ethyl]oxy}phenyl)-7-phenylimidazo[5,1-f][1,2,4]triazin-2-amine

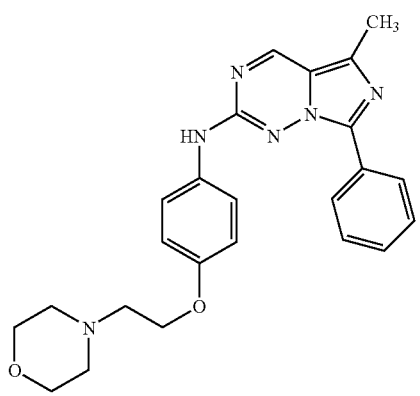

Applying the displacement procedure, using 5-methyl-2-(methylthio)-7-phenylimidazo[5,1-f][1,2,4]triazine (Intermediate 72) (50 mg, 0.17 mmol), (4-{[2-(4-morpholinyl)ethyl]oxy}phenyl)amine (38.5 mg, 0.17 mmol) and ethanol (2.5 mL) to afford 5-methyl-N-(4-{[2-(4-morpholinyl)ethyl]oxy}phenyl)-7-phenylimidazo[5,1-f][1,2,4]triazin-2-amine (29 mg) as a yellow solid. MS m/z 431 (M+1).

EXAMPLE 103

5-Methyl-N-(3-{[2-(4-morpholinyl)ethyl]oxy}phenyl)-7-phenylimidazo[5,1-f][1,2,4]triazin-2-amine

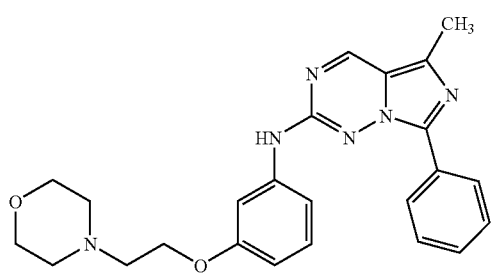

Applying the displacement procedure, using 5-methyl-2-(methylthio)-7-phenylimidazo[5,1-f][1,2,4]triazine (Intermediate 72) (50 mg, 0.17 mmol), (3-{[2-(4-morpholinyl)ethyl]oxy}phenyl)amine (38 mg, 0.17 mmol) and ethanol (2.5 mL) to afford 5-methyl-N-(3-{[2-(4-morpholinyl)ethyl]oxy}phenyl)-7-phenylimidazo[5,1-f][1,2,4]triazin-2-amine (18 mg) as a yellow solid. MS m/z 431 (M+1).

EXAMPLE 104

5-Methyl-N-[4-(methyloxy)phenyl]-7-phenylimidazo[5,1-f][1,2,4]triazin-2-amine

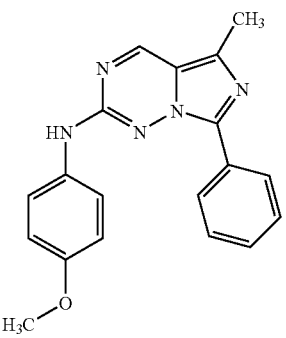

A mixture of 5-methyl-2-(methylthio)-7-phenylimidazo[5,1-f][1,2,4]triazine (Intermediate 72) (75 mg, 0.26 mmol), p-anisidine (32 mg, 0.26 mmol) and p-toluenesulfonic acid (5 mg, 0.03 mmol) in tetrahydrofuran (5 mL) was stirred at reflux overnight. The mixture was then reduced under vacuum, and purified by chromatography on silica gel eluting with 40% ethyl acetate in petrol to give a solid which was purified further by trituration with diethyl ether to afford 5-methyl-N-[4-(methyloxy)phenyl]-7-phenylimidazo[5,1-f][1,2,4]triazin-2-amine (20 mg) as a yellow solid. MS m/z 332 (M+1).

EXAMPLE 105

5-Methyl-N,7-diphenylimidazo[5,1-f][1,2,4]triazin-2-amine

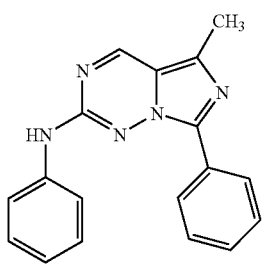

A solution of aniline (18 mg, 0.19 mmol) in tetrahydrofuran (5 mL) at −78° C. was treated with n-butyllithium (0.13 mL of a 1.6M solution in hexanes, 0.21 mmol) and the resulting mixture stirred at this temperature for 0.5 h. The mixture was then treated with a solution of of 5-methyl-2-(methylthio)-7-phenylimidazo[5,1-f][1,2,4]triazine (Intermediate 72) (50 mg, 0.17 mmol) in tetrahydrofuran (5 mL) and the mixture allowed to warm slowly to room temperature overnight. The mixture was then reduced under vacuum and partitioned between ethyl acetate and saturated aqueous sodium bicarbonate and the layers separated. The organic layer was then dried with magnesium sulfate, filtered and reduced. The crude product was purified by chromatography on silica gel eluting with 50% ethyl acetate in petrol to afford 5-methyl-N,7-diphenylimidazo[5,1-f][1,2,4]triazin-2-amine (10 mg) as a yellow solid. MS m/z 302 (M+1).

Intermediate 73: N-{1-[3-(Methylsulfonyl)-1,2,4-triazin-6-yl]ethyl}benzamide

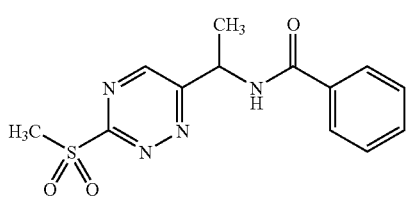

A mixture of N-{1-[3-(methylthio)-1,2,4-triazin-6-yl]ethyl}benzamide (Intermediate 73) (1.35 g, 4.92 mmol) in dichloromethane (20 mL) at 0° C. was treated with 3-chloroperoxybenzoic acid (50-55%, 5.70 g, 16.4 mmol) portionwise. The resulting mixture stirred at room temperature until complete by tlc. The resulting solution was then washed twice with saturated sodium bicarbonate solution, dried with magnesium sulfate and reduced under vacuum. The crude product was then purified by chromatography on silica gel eluting with 80 to 100% ethyl acetate in petrol to give N-{1-[3-(methylsulfonyl)-1,2,4-triazin-6-yl]ethyl}benzamide as a white solid (550 mg). MS m/z 307 (M+1).

Intermediate 74: N-[1-(3-{[3-(Methyloxy)phenyl]amino}-1,2,4-triazin-6-yl)ethyl]benzamide

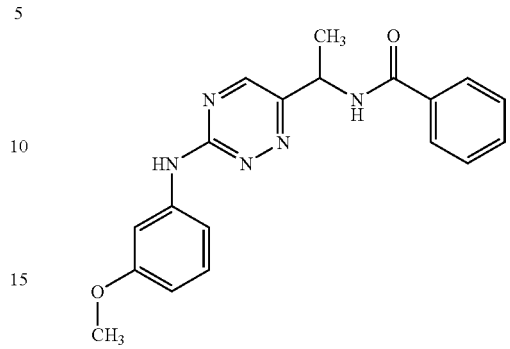

A mixture of N-{1-[3-(methylsulfonyl)-1,2,4-triazin-6-yl]ethyl}benzamide (Intermediate 73) (100 mg) and m-anisidine (1 mL) was heated at 50° C. overnight. The crude reaction mixture was then purified by chromatography on silica gel eluting with 30% ethyl acetate in petrol to give N-[1-(3-{[3-(methyloxy)phenyl]amino}-1,2,4-triazin-6-yl)ethyl]benzamide as a yellow solid (35 mg). $^1$H NMR (CDCl$_3$): δ8.39 (s, 1H), 7.82 (m, 2H), 7.51-7.32 (m, 5H), 7.28-7.13 (m, 3H), 6.68 (m, 1H) 5.47 (m, 1H), 3.84 (s, 3H), 1.70 (d, J=6.9 Hz, 3H).

EXAMPLE 106

5-Methyl-N-[3-(methyloxy)phenyl]-7-phenylimidazo[5,1-f][1,2,4]triazin-2-amine

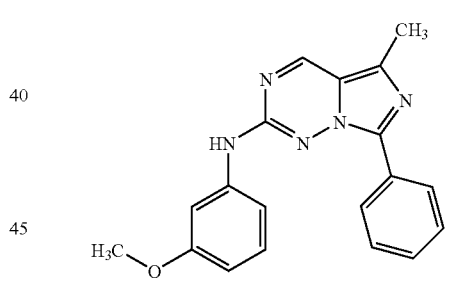

Applying the Cyclization Procedure 1, using N-[1-(3-{[3-(methyloxy)phenyl]amino}-1,2,4-triazin-6-yl)ethyl]benzamide (Intermediate 74) (55 mg, 0.16 mmol), 1,2-dichloroethane (5 mL) and phosphorus oxychloride (0.20 mL, 2.14 mmol), to afford 5-methyl-N-[3-(methyloxy)phenyl]-7-phenylimidazo[5,1-f][1,2,4]triazin-2-amine (3 mg) as a yellow solid. MS m/z 332 (M+1).

Biological Examples

I. Assay for Inhibition of PLK1

A. Preparation of 6× N-Terminal His-Tagged PLK Kinase Domain

6× N-terminal His-tagged PLK kinase domain (amino acids 21-346 preceded by MKKGHHHHHHD (SEQ ID No. 1)) is prepared from baculovirus infected T. ni cells under polyhedrin promoter control. All procedures are performed at 4° C. Cells are lysed in 25 mM HEPES, 200 mM NaCl, 25 mM imidazole; pH 8.0. The homogenate is centrifuged at 14K rpm in a SLA-1500 rotor for 40 min and the supernatant filtered through a 1.2 micron filter. The supernatant is loaded onto a Nickel chelating Sepharose (Amersham Pharmacia) column and washed with 25 mM HEPES, 500 mM NaCl, 25 mM imidazole; pH 8.0. The column is then washed with a 16.6% B step where buffer B is 25 mM HEPES, 500 mM NaCl, 300 mM imidazole; pH 8.0. Protein is eluted using a 10-column volume linear gradient from 16.6% B to 100% B. Fractions containing PLK are determined by SDS-PAGE. PLK is concentrated using a 10 kDa molecular weight cutoff membrane and then loaded onto a Superdex 75 gel filtration (Amersham BioSciences) column equilibrated in 25 mM HEPES, 1 mM DTT, 500 mM NaCl; pH 8.0. Fractions containing PLK are determined by SDS-PAGE. PLK is pooled, aliquoted and stored at 480° C. Samples are quality controlled using mass spectrometry.

B. Enzyme Activity±Inhibitors is Determined As Follows:

Compounds are added to the plate (1 μL in 100% DMSO). DMSO (5% final) and EDTA (62.5 mM final in reaction) are used as controls. The Reaction Mix is prepared as follows at 22° C.:

Reaction Mix:
  25 mM HEPES, pH 7.2
  15 mM MgCl2
  1 μM ATP
  0.05 μCi/well $^{33}$P-γ ATP (3000 Ci/mmol)
  1 μM substrate peptide (Biotin-Ahx-SFNDTLDFD (SEQ ID No. 2))
  0.15 mg/ml BSA
  1 mM DTT
  2 nM truncated human PLK1 (kinase domain) (added last)

Immediately upon addition of enzyme and thorough mixing, add 20 uL per well into 384-well white plates containing compounds and controls. Incubate 1-1.5 hrs. at RT to achieve 10-25% substrate phosphorylation. The enzymatic reaction is stopped with 50 μl of bead mix (50 mM EDTA, 2 mg/ml Streptavidin-coated SPA beads in Standard Dulbecco's PBS (without Mg$^{2+}$ and Ca$^{2+}$), and 60 μM ATP). Plates are sealed, spun at 500×g for 1 min or settled overnight, then counted in Packard TopCount for 30 seconds/well.

C. Results

The data obtained is reported in Table 1 below. In Table 1, +=pIC50<5; ++=pIC50 5-7; +++=pIC50>7.

II. Methylene Blue Growth Inhibition Assay

Normal Human foreskin fibroblasts (HFF) and human colon (HCT116, RKO), lung (H460), prostate (PC3), and breast tumor (MCF7) cell lines were cultured in high glucose DMEM (Life Technologies) containing 10% fetal bovine serum (FBS) at 37° C. in a humidified 10% CO$_2$, 90% air incubator. Cells were harvested using trypsin/EDTA, counted using a haemocytometer, and plated in 100 μl of the appropriate media, at the following densities, in a 96-well tissue culture plate (Falcon 3075): HFF 5,000 cells/well, HCT116 3,000 cells/well, RKO 2,500 cells/well, H460 2,000 cells/well, PC3 8,000 cells/well, MCF7 4,000 cells/well. The next day, compounds were diluted in DMEM containing 100 μg/ml gentamicin, at twice the final required concentration, from 10 mM stock solutions in DMSO. 100 μl/well of these dilutions were added to the 100 μl of media currently on the cell plates. Medium containing 0.6% DMSO was added to control wells. Compounds diluted in DMEM were added to all cell lines. The final concentration of DMSO in all wells was 0.3%. Cells were incubated at 37° C., 10% CO$_2$ for 3 days. Medium was removed by aspiration. Cell biomass was estimated by staining cells with 90 μl per well methylene blue (Sigma M9140, 0.5% in 50:50 ethanol:water), and incubation at room temperature for at least 30 minutes. Stain was removed, and the plates rinsed under a gentle stream of water, and air-dried. To release stain from the cells 100 μl of solubilization solution was added (1% N-lauroyl sarcosine, Sodium salt, Sigma L5125, in PBS), and plates were shaken gently for about 30 minutes. Optical density at 620 nM was measured on a microplate reader. Percent inhibition of cell growth was calculated relative to vehicle treated control wells. Concentration of compound that inhibits 50% of cell growth (IC$_{50}$) was interpolated using nonlinear regression (Levenberg-Marquardt) and the equation, $y=V_{max}*(1-(x/(K+x)))+Y2$, where "K" was equal to the IC$_{50}$. The data obtained reported in Table 1 below. In Table 1, +=10→30 uM; ++=1-10 uM: +++=<1 uM.

TABLE 1

| Example | Ave pIC50 PLK Enzyme Inhibition | MeB Cell Line | IC50 (μM) |
|---|---|---|---|
| 1 | +++ | COLO205 | ++ |
|   |     | H460    | ++ |
|   |     | HCT116  | ++ |
|   |     | HFF     | +  |
|   |     | IMR90   | +  |
|   |     | MCF7    | ++ |
|   |     | MDA435  | ++ |
|   |     | PC3     | +  |
|   |     | RKO     | ++ |
|   |     | SAOS2   | ++ |
| 2 | ++  |         |    |
| 3 | ++  |         |    |
| 4 | +++ |         |    |
| 5 | +++ | H460    | ++ |
|   |     | HCT116  | ++ |
|   |     | HFF     | ++ |
|   |     | MCF7    | ++ |
|   |     | PC3     | ++ |
|   |     | RKO     | ++ |
| 6 | +   | —       |    |
| 7 | ++  | —       |    |
| 8 | +++ | H460    | +  |
|   |     | HCT116  | +  |
|   |     | HFF     | +  |
|   |     | MCF7    | +  |
|   |     | PC3     | +  |
|   |     | RKO     | +  |
|   |     | HCT116  | +  |
| 9 | +++ | H460    | ++ |
|   |     | HCT116  | ++ |
|   |     | HFF     | +  |
|   |     | MCF7    | ++ |
|   |     | PC3     | +  |
|   |     | RKO     | ++ |
| 10 | ++ |         |    |
| 11 | ++ |         |    |
| 12 | ++ |         |    |
| 13 | ++ |         |    |
| 14 | ++ |         |    |
| 15 | ++ |         |    |
| 16 | ++ | H460    | +  |
|    |    | HCT116  | +  |
|    |    | HFF     | +  |
|    |    | MCF7    | +  |
|    |    | PC3     | +  |
|    |    | RKO     | +  |
| 17 | +++ |        |    |
| 18 | ++  |        |    |
| 19 | +++ | H460   | ++ |
|    |     | HCT116 | ++ |
|    |     | HFF    | +  |
|    |     | MCF7   | ++ |
|    |     | PC3    | +  |
|    |     | RKO    | ++ |
| 20 | ++  |        |    |
| 21 | ++  |        |    |

TABLE 1-continued

| Example | Ave pIC50 PLK Enzyme Inhibition | MeB Cell Line | IC50 (μM) |
|---|---|---|---|
| 22 | ++ | H460 | + |
|  |  | HCT116 | + |
|  |  | HFF | + |
|  |  | MCF7 | + |
|  |  | PC3 | + |
|  |  | RKO | + |
| 24 | ++ | H460 | + |
|  |  | HCT116 | + |
|  |  | HFF | + |
|  |  | MCF7 | + |
|  |  | PC3 | + |
|  |  | RKO | + |
| 25 | +++ | H460 | ++ |
|  |  | HCT116 | ++ |
|  |  | HFF | + |
|  |  | MCF7 | ++ |
|  |  | PC3 | ++ |
|  |  | RKO | ++ |
| 26 | ++ |  |  |
| 27 | ++ |  |  |
| 28 | ++ |  |  |
| 29 | ++ |  |  |
| 30 | ++ |  |  |
| 31 | +++ |  |  |
| 32 | ++ |  |  |
| 33 | ++ |  |  |
| 34 | ++ |  |  |
| 35 | ++ |  |  |
| 36 | ++ |  |  |
| 37 | ++ |  |  |
| 38 | ++ |  |  |
| 39 | + |  |  |
| 40 | + |  |  |
| 41 | ++ | H460 | ++ |
|  |  | HCT116 | ++ |
|  |  | HFF | + |
|  |  | MCF7 | ++ |
|  |  | PC3 | + |
|  |  | RKO | ++ |
| 42 | +++ | H460 | + |
|  |  | HCT116 | ++ |
|  |  | HFF | + |
|  |  | MCF7 | ++ |
|  |  | PC3 | + |
|  |  | RKO | ++ |
| 43 | +++ | H460 | ++ |
|  |  | HCT116 | ++ |
|  |  | HFF | + |
|  |  | MCF7 | ++ |
|  |  | PC3 | + |
|  |  | RKO | ++ |
| 44 | +++ | H460 | ++ |
|  |  | HCT116 | ++ |
|  |  | HFF | + |
|  |  | MCF7 | + |
|  |  | PC3 | + |
|  |  | RKO | ++ |
| 45 | ++ |  |  |
| 46 | +++ | H460 | + |
|  |  | HCT116 | ++ |
|  |  | HFF | + |
|  |  | MCF7 | ++ |
|  |  | PC3 | + |
|  |  | RKO | ++ |
| 47 | +++ | H460 | + |
|  |  | HCT116 | ++ |
|  |  | HFF | + |
|  |  | MCF7 | + |
|  |  | PC3 | + |
|  |  | RKO | + |
| 48 | ++ | H460 | + |
|  |  | HCT116 | + |
|  |  | HFF | + |
|  |  | MCF7 | + |
|  |  | PC3 | + |
|  |  | RKO | ++ |
| 49 | +++ |  |  |
| 50 | ++ |  |  |
| 51 | ++ |  |  |
| 52 | +++ |  |  |
| 53 | +++ |  |  |
| 54 | ++ |  |  |
| 55 | ++ |  |  |
| 56 | ++ |  |  |
| 57 | +++ | H460 | + |
|  |  | HCT116 | + |
|  |  | HFF | + |
|  |  | MCF7 | + |
|  |  | PC3 | + |
|  |  | RKO | + |
| 58 | ++ |  |  |
| 59 | ++ |  |  |
| 60 | ++ |  |  |
| 61 | ++ |  |  |
| 62 | ++ |  |  |
| 63 | + |  |  |
| 64 | ++ |  |  |
| 65 | + |  |  |
| 66 | ++ |  |  |
| 67 | ++ |  |  |
| 68 | + |  |  |
| 69 | ++ |  |  |
| 70 | ++ |  |  |
| 71 | ++ |  |  |
| 72 | ++ |  |  |
| 73 | ++ |  |  |
| 74 | ++ |  |  |
| 75 | ++ |  |  |
| 76 | ++ |  |  |
| 77 | + |  |  |
| 78 | + |  |  |
| 79 | ++ |  |  |
| 80 | ++ |  |  |
| 81 | ++ |  |  |
| 82 | ++ |  |  |
| 83 | ++ |  |  |
| 84 | ++ |  |  |
| 85 | ++ |  |  |
| 86 | ++ |  |  |
| 87 | ++ |  |  |
| 88 | ++ |  |  |
| 89 | ++ |  |  |
| 90 | ++ |  |  |
| 91 | ++ |  |  |
| 92 | ++ |  |  |
| 93 | ++ |  |  |
| 94 | ++ |  |  |
| 95 | ++ |  |  |
| 96 | ++ |  |  |
| 99 | ++ |  |  |
| 100 | + |  |  |
| 101 | + |  |  |
| 102 | ++ |  |  |
| 104 | ++ |  |  |
| 105 | ++ |  |  |
| 106 | ++ |  |  |

That which is claimed is:

1. A compound of formula (I):

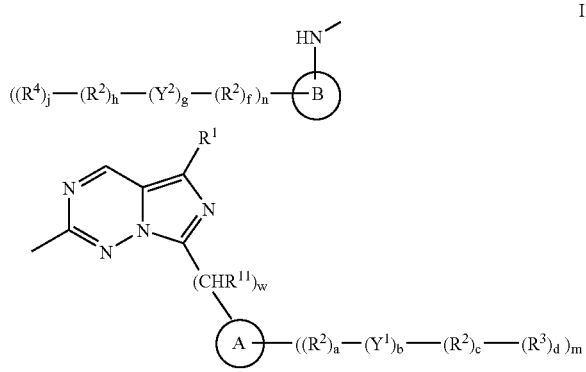

wherein:
$R^1$ is alkyl;
w is 0 or 1;
$R^{11}$ is H or $C_{1-3}$ alkyl;
Ring A is selected from the group consisting of cycloalkyl, cycloalkenyl, aryl, 5-13 membered heterocycle and 5-13 membered heteroaryl;
Ring B is selected from the group consisting of cycloalkyl, cycloalkenyl, aryl, 5-13 membered heterocycle and 5-13 membered heteroaryl;
a, b, c, f, g, and h are the same or different and are each independently 0 or 1;
d and j are the same or different and are independently 1 or 2;
each $R^2$ is the same or different and is independently selected from the group consisting of alkylene, alkenylene and alkynylene;
$Y^1$ and $Y^2$ are the same or different and are each independently selected from the group consisting of —O—, —S(O)$_q$— and —N($R^5$)—;
q is 0, 1 or 2;

each $R^3$ and $R^4$ are the same or different and are each independently selected from the group consisting of H, halo, alkyl, alkenyl, alkynyl, cycloalkyl, cycloalkenyl, Ph, Het, —COR$^5$, —CSR$^5$, —CO$_2$R$^5$, —COPh, —CO$_2$Ph, —C(O)Het, —C(O)NR$^5$R$^6$, —C(S)NR$^5$R$^6$, —C(=NR$^5$)R$^6$, —C(=NR$^5$)NR$^5$R$^6$, —CR$^5$=N—OR$^6$, —OR$^5$, —OCOR$^5$, —S(O)$_p$R$^5$, —S(O)$_2$OH, —S(O)$_p$NR$^5$R$^6$, —NR$^5$R$^6$, —NR$^5$COR$^6$, —NR$^5$CO$_2$R$^6$, —NR$^5$SO$_2$R$^6$, —NO$_2$, —CN, —SCN and —N$_3$;
each p is the same or different and is 0, 1 or 2;
m and n are the same or different and are each independently 0, 1, 2, 3, 4 or 5;
each $R^5$ and each $R^6$ are the same or different and are each independently selected from the group consisting of H, alkyl, alkenyl, alkynyl, cycloalkyl and cycloalkenyl;
Ph is phenyl optionally substituted by one or more substituents selected from the group consisting of halo, alkyl, —CO$_2$R$^5$, —OR$^5$, —SO$_2$R$^5$, —SO$_2$NR$^5$R$^6$, —NR$^5$R$^6$, —R$^2$—(NR$^5$R$^6$)CO$_2$R$^5$, Het, —R$^2$-Het, —CN and —N$_3$; and
Het is a monocyclic 5-6 membered heterocycle or heteroaryl group containing 1, 2 or 3 heteroatoms selected from the group consisting of N, O and S optionally substituted by one or more substituents selected from the group consisting of halo, alkyl, —CO$_2$R$^5$, —C(O)NR$^5$R$^6$, —OR$^5$, —SO$_2$R$^5$, —SO$_2$NR$^5$R$^6$, —NR$^5$R$^6$, oxo, —CN and —N$_3$;
or a pharmaceutically acceptable salt thereof.

2. The compound according to claim 1, wherein $R^1$ is methyl.

3. The compound according to claim 1, wherein Ring A is selected from the group consisting of aryl and 5-13 membered heteroaryl.

4. The compound according to claim 1, wherein Ring A is phenyl.

5. The compound according to claim 1, wherein Ring B is selected from the group consisting of phenyl, pyridine and pyrimidine.

6. The compound according to claim 1, wherein Ring B is phenyl.

7. The compound according to claim 1, wherein each $R^2$ is the same or different and is independently selected from the group consisting of alkylene and alkenylene.

8. The compound according to claim 1, wherein b is 0.

9. The compound according to claim 1, wherein b is 1 and $Y^1$ is selected from the group consisting of —O— and —N($R^5$)—.

10. The compound according to claim 1, wherein g is 0.

11. The compound according to claim 1, wherein g is 1 and $Y^2$ is —O—.

12. The compound according to claim 1, wherein d is 1.

13. The compound according to claim 1, wherein j is 1.

14. The compound according to claim 1, wherein each $R^3$ is the same or different and is independently selected from the group consisting of H, halo, alkyl, alkenyl, cycloalkyl, Ph, Het, —COR$^5$, —CO$_2$R$^5$, —COPh, —C(O)NR$^5$R$^6$, —OR$^5$, —S(O)$_p$R$^5$, —S(O)$_p$NR$^5$R$^6$, —NR$^5$R$^6$, —NO$_2$, —CN and N$_3$.

15. The compound according to claim 1, wherein d is 1 and $R^3$ is selected from the group consisting of H, halo, alkyl, Ph, —COR$^5$, —CO$_2$R$^5$, —COPh, —C(O)NR$^5$R$^6$, —OR$^5$, —NR$^5$R$^6$, —NO$_2$ and —CN.

16. The compound according to claim 1, wherein each $R^4$ is the same or different and is independently selected from the group consisting of H, halo, alkyl, alkenyl, cycloalkyl, Ph, Het, —COR$^5$, —CO$_2$R$^5$, —C(O)NR$^5$R$^6$, —OR$^5$, —S(O)$_p$R$^5$, —S(O)$_2$OH, —S(O)$_p$NR$^5$R$^6$, —NR$^5$R$^6$, —NR$^5$COR$^5$, —NO$_2$ and —CN.

17. The compound according to claim 1, wherein j is 1 and $R^4$ is selected from the group consisting of H, halo, alkyl, —COR$^5$, —CO$_2$R$^5$, —C(O)NR$^5$R$^6$, —OR$^5$, —S(O)$_p$R$^5$, —S(O)$_2$OH, —S(O)$_p$NR$^5$R$^6$ and —NO$_2$.

18. The compound according to claim 1, wherein m is 0, 1, 2 or 3.

19. The compound according to claim 1, wherein n is 1, 2, or 3.

20. The compound according to claim 1, wherein each $R^5$ and each $R^6$ are the same or different and are each independently selected from the group consisting of H, alkyl, alkenyl and cycloalkyl.

21. The compound according to claim 1, wherein each $R^5$ and each $R^6$ are the same or different and are each independently selected from the group consisting of H and alkyl.

22. A compound selected from the group consisting of:
5-Methyl-7-phenyl-N-(3,4,5-trimethoxyphenyl)imidazo[5,1-f][1,2,4]triazin-2-amine
5-Methyl-7-(2—Nitrophenyl)-N-(3,4,5-trimethoxyphenyl)imidazo[5,1-f][1,2,4]triazin-2-amine;
7-(2-Bromophenyl)-5-methyl-N-(3,4,5-trimethoxyphenyl)imidazo[5,1-f][1,2,4]triazin-2-amine;
7-(4-Fluorophenyl)-5-methyl-N-(3,4,5-trimethoxyphenyl)imidazo[5,1-f][1,2,4]triazin-2-amine;
5-Methyl-7-[3-(trifluoromethyl)phenyl]-N-(3,4,5-trimethoxyphenyl)imidazo[5,1-f][1,2,4]triazin-2-amine;
2,2-Dimethyl-N-(2-{5-methyl-2-[(3,4,5-trimethoxyphenyl)amino]imidazo[5,1-f][1,2,4]triazin-7-yl}phenyl)propanamide;
2,2,2-Trifluoro-N-(2-{5-methyl-2-[(3,4,5-trimethoxyphenyl)amino]imidazo[5,1-f][1,2,4]triazin-7-yl}phenyl)acetamide;
3-{5-Methyl-2-[(3,4,5-trimethoxyphenyl)am i no]imidazo[5,1-f][1,2,4]triazin-7-yl}benzonitrile;
7-(3-Bromophenyl)-5-methyl-N-(3,4,5-trimethoxyphenyl)imidazo[5,-f][1,2,4]triazin-2-amine;
7-(3-Bromothien-2-yl)-5-methyl-N-(3,4,5-trimethoxyphenyl)imidazo[5,1-f][1,2,4]triazin-2-amine;
7-(5-Bromopyridin-3-yl)-5-methyl-N-(3,4,5-trimethoxyphenyl)imidazo-[5,1-f][1,2,4]triazin-2-amine;
Methyl 3-{5-methyl-2-[(3,4,5-trimethoxyphenyl)amino]imidazo[5,1-f][1,2,4]triazin-7-yl}benzoate;
7-(5-Bromothien-2-yl)-5-methyl-N-(3,4,5-trimethoxyphenyl)imidazo[5,1-f][1,2,4]triazin-2-amine;
7-(3-Bromophenyl)-N-[5-(ethylsulfonyl)-2-methoxyphenyl]-5-methylimidazo[5,1-f][1,2,4]triazin-2-amine;
7-(3-Bromophenyl)-N-(3—Chloro-4-morpholin-4-ylpheny)-5methylimidazo[5,1-f][1,2,4]triazin-2-amine;
3-{5-Methyl-2-[(3,4,5-trimethoxyphenyl)amino]imidazo[5,1-f][1,2,4]triazin-7-yl}benzamide;
(2E)-3-(3-{5-Methyl-2-[(3,4,5-trimethoxyphenyl)amino]imidazo[5,1-f][1,2,4]triazin-7-yi}phenyl)prop-2-enamide;
5-Methyl-N-(4-Nitrophenyl)-7-phenylimidazo[5,1-f][1,2,4]triazin-2-amine;
2-{3-[(5-Methyl-7-phenylimidazo[5,1-f][1,2,4]triazin-2-yl)amino]phenyl}ethanol;
4-[(5-Methyl-7-phenylimidazo[5,1-f][2,4]triazin-2-yl)amino]benzene-sulfonamide;
7-(2-Methoxyphenyl)-5-methyl-N-(3,4,5-trimethoxyphenyl)imidazo[5,1f][1,2,4]triazin-2-amine;
2-{5-Methyl-2-[(3,4,5-trimethoxyphenyl)amino]imidazo[5,1f][1,2,4]triazin-7-yl}phenol;
2-{5-Methyl-2-[(3,4,5-trimethoxyphenyl)amino]imidazo[5,1-f][1,2,4]triazin-7-yl}phenyl acetate;
5-Methyl-7-[4-(trifluoromethyl)phenyl]-N-(3,4,5-trimethoxyphenyl)-imidazo[5,1-f][1,2,4]triazin-2-amine;
N-Methyl-N'-{4-[(5-methyl-7-phenylimidazo[5,1-f][1,2,4]triazin-2-yl)amino]phenyl}urea;
5-Methyl-7-phenyl-N-[3-(trifluoromethyl)phenyl]imidazol[5,1-f][1,2,4]triazin-2-amine;
(3-{5-Methyl-2-[(3,4,5-trimethoxyphenyl)amino]imidazo[5,1-f][1,2,4]triazin-7-yl}phenyl)(phenyl)methanone;
7-(1,3-Benzodioxol-5-yl)-5-methyl-N-(3,4,5-trimethoxyphenyl)imidazo-[5,1-f][1,2,4]triazin-2-amine;
Methyl 4-{5-methyl-2-[(3,4,5-trimethoxyphenyl)amino]imidazo[5,1-f][1,2,4]triazin-7-yl}benzoate;
5-Methyl-7-(3-phenoxyphenyl)-N-(3,4,5-trimethoxyphenyl)imidazo[5,1-f][1,2,4]triazin-2-amine;
7-(3-Aminophenyl)-5-methyl-N-(3,4,5-trimethoxyphenyl)imidazo[5,1-f][1,2,4]triazin-2-amine;
7-(1H-Indol-2-yl)-5-methyl-N-(3,4,5-trimethoxyphenyl)imidazo[5,1-f][1,2,4]triazin-2-amine;
5-Methyl-7-(5-nitro-1H-pyrrol-2-yl)-N-(3,4,5-trimethoxyphenyl)imidazo[5,1-f][1,2,4]triazin-2-amine;
5-Methyl-7-(1-methyl-1H-pyrrol-2-yl)-N-(3,4,5-trimethoxyphenyl)-imidazo[5,1-f][1,2,4]triazin-2-amine;
5-Methyl-7-(1-methyl-1H-indol-3-yl)-N-(3,4,5-trimethoxyphenyl)i midazo[5,1-f][1,2,4]triazin-2-amine;
7-(3-Furyl)-5-methyl-N-(3,4,5-trimethoxyphenyl)imidazo[5,1-f][1,2,4]triazin-2-amine;
7-(1H-Indol-5-yl)-5-methyl-N-(3,4,5-trimethoxyphenyl)imidazo[5,1-f][1,2,4]triazin-2-amine;
2-[(2-{5-Methyl-2-[(3,4,5-trimethoxyphenyl)amino]imidazo[5,1-f][1,2,4]triazin-7-yl}phenyl)thio]benzonitrile;
5-Methyl-7-(2-{[3-(trifluoromethyl)phenyl]amino}phenyl)-N-(3,4,5-trimethoxyphenyl)imidazo[5,1-f][1,2,4]triazin-2-amine;
5-Methyl-7-quinolin-8-yl-N-(3,4,5-trimethoxyphenyl)imidazo[5,1-f][1,2,4]triazin-2-amine;
3-({5-Methyl-7-[3-(trifluoromethyl)phenyl]imidazo[5,1-f][1,2,4]triazin-2-yl}amino)benzenesulfonamide;

N-Methyl-N-[4-({5-methyl-7-[3-(trifluoromethyl)phenyl]imidazo[5,1-f][1,2,4]triazin-2-yl}amino)phenyl]urea;
N-[4-Methoxy-3-({5-methyl-7-[3-(trifluoromethyl)phenyl]imidazo[5,1-f][1,2,4]triazin-2-yl}amino)phenyl]acetamide;
2-[3-({5-Methyl-7-[3-(trifluoromethyl)phenyl]imidazo[5,1-f][1,2,4]triazin-2-yl}amino)phenyl]ethanol;
4-({5-Methyl-7-[3-(trifluoromethyl)phenyl]imidazo[5,1-f][1,2,4]triazin-2-yl}amino)benzenesulfonamide;
N-[4-({5-Methyl-7-[3-(trifluoromethyl)phenyl]imidazo[5,1-f][1,2,4]triazin-2-yl}amino)phenyl]acetamide;
N-[3-({5-Methyl-7-[3-(trifluoromethyl)phenyl]imidazo[5,1-f][1,2,4]triazin-2-yl}amino)phenyl]acetamide;
tert-Butyl 3-({5-methyl-7-[3-(trifluoromethyl)phenyl]imidazo[5,1-f][1,2,4]triazin-2-yl}amino)benzylcarbamate;
4-({5-Methyl-7-[3-(trifluoromethyl)phenyl]imidazo[5,1-f][1,2,4]triazin-2-yl}amino)phenol;
5-Methyl-N-[4-(2-pyrrolidin-1-ylethoxy)phenyl]-7-[3-(trifluoromethyl)phenyl]-imidazo[5,1-f][1,2,4]triazin-2-amine;
N-(5-Fluoro-2-methoxyphenyl)-5-methyl-7-[3-(trifluoromethyl)phenyl]-imidazo[5,1-f][1,2,4]triazin-2-amine;
N-{2-[4-Methoxy-3-({5-methyl-7-[3-(trifluoromethyl)phenyl]imidazo[5,1-f][1,2,4]triazin-2-yl}amino)phenyl]ethyl}acetamide;
N-[5-(2-Aminoethyl)-2-methoxyphenyl]-5-methyl-7-[3-(trifluoromethyl)-phenyl]imidazo[5,1-f][1,2,4]triazin-2-amine;
N-(2,4-Dimethoxyphenyl)-5-methyl-7-[3-(trifluoromethyl)phenyl]imidazo[5,1-f][1,2,4]triazin-2-amine;
N-(2,5-Dimethoxyphenyl)-5-methyl-7-[3-(trifluoromethyl)phenyl]imidazo[5,1-f][1,2,4]triazin-2-amine;
Ethyl 5-({5-methyl-7-[3-(trifluoromethyl)phenyl]imidazo[5,1-f][1,2,4]triazin-2-yl}amino)nicotinate;
2-{3-[(5-Methyl-7-phenylimidazo[5,1-f][1,2,4]triazin-2-yl)amino]phenyl}-ethanesutfonic acid;
5-Methyl-7-[3-(1H-pyrazol-4-ylethynyl)phenyl]-N-(3,4,5-trimethoxyphenyl)-imidazo[5,1-f][2,4]triazin-2-amine;
3'-{5-Methyl-2-[(3,4,5-trimethoxyphenyl)amino]imidazo[5,1-f][1,2,4]triazin-7-yl}-1,1'-biphenyl-3-carboxylic acid;
2-Amino-3-(3+-{5-methyl-2-[(3,4,5-trimethoxyphenyl)amino]imidazo-[5,1-f][1,2,4]triazin-7-yl}-1,1'-biphenyl-4-yl)propanoic acid;
5-Methyl-7-[2-(trifluoromethyl)-1,1 '-biphenyl-3-yl]-N-(3,4,5-trimethoxyphenyl)-imidazo[5,1-t][1,2,4]triazin-2-amine;
(2Z)-3-(3-{5-Methyl-2-[(3,4,5-trimethoxyphenyl)amino]imidazo[5,1-t][1,2,4]triazin-7-yl}phenyl)-3-phenylprop-2-enamide;
7-(3-{[5-(Ethylsultonyl)-2-methoxyphenyl]amino}phenyl)-5-methyl-N-(3,4,5-trimethoxyphenyl)imidazo[5,1-f][1,2,4]triazin-2-amine;
5-Methyl-7-(3-{[4-(1 H-1,2,4-triazol-1-ylmethyl)phenyl]amino}phenyl)-N-(3,4,5-trimethoxyphenyl)imidazo[5,1-f][1,2,4]triazin-2-amine;
7-(3-{[4-(1H-imidazol-1-yl)phenyl]amino}phenyl)-5-methyl-N-(3,4,5-trimethoxyphenyl)imidazo[5,1-f][1,2,4]triazin-2-amine;
7-{3-[(3-Chloro-4-morpholin-4-ylphenyl)amino]phenyl}-5-methyl-N-(3,4,5-trimethoxyphenyl)imidazo[5,1-f][1,2,4]triazin-2-amine;
N,N-Dimethyl-1-{3-[(3-{5-methyl-2-[(3,4,5-trimethoxyphenyl)amino]imidazo[5,1-f][1,2,4]triazin-7-yl}phenyl)amino]phenyl}-methanesulfonamide;
5-Methyl-7-[3-({4-[(4-methylpiperazin-1-yl)methyl]phenyl}-amino)phenyl]-N-(3,4,5-trimethoxyphenyl)imidazo[5,1-f][1,2,4]triazin-2-amine;
N—Cyclopropyil-3-[(3-{5-methyl-2-[(3,4,5-trimethoxyphenyl)amino]imidazo[5,1-f][1,2,4]triazin-7-yl}phenyl)amino]benzenesulfonamide;
7-(5-Bromo-2-thienyl)-5-methyl-N-[4-(methyloxy)phenyl]imidazo[5,1-f][1,2,4]triazin-2-amine;
7-(3-Bromo-2-thienyl)-5-methyl-N-[4-(methyloxy)phenyl]imidazo[5,1-f][1,2,4]triazin-2-amine;
5-Methyl-N-[4-(methyloxy)phenyl]-7-(tetrahydro-2H-pyran-4-yl)imidazo[5,1-f][1,2,4]triazin-2-amine;
5-Methyl-7-[2-(methyloxy)phenyl]-N-[4-(methyloxy)phenyl]imidazo[5,1-f][1,2,4]triazin-2-amine;
5-Methyl-7-[3-(methyloxy)phenyl]-N-[4-(methyloxy)phenyl]imidazo[5,1-f][1,2,4]triazin-2-amine;
7-(2-Chlorophenyl)-5-methyl-N-[4-(methyloxy)phenyl]imidazo[5,1-f][1,2,4]triazin-2-amine;
5-Methyl-7-(1-methyl-1H-indol-3-yl)-N-[4-(methyloxy)phenyl]imidazo[5,1-f][1,2,4]triazin-2-amine;
5-Methyl-N-[4-(methyloxy)phenyl]-7-(1-phenylethyl)imidazo[5,1-f][1,2,4]triazin-2-amine;
5-Methyl-7-(1-methyl-1H-indol-2-yl)-N-[4-(methyloxy)phenyl]imidazo[5,1-f][1,2,4]triazin-2-amine;
5-Methyl-N-[4-(methyloxy)phenyl]-7-(3-thienyl)imidazo[5,1-f][1,2,4]triazin-2-amine;
7-(3-Furanyl)-5-methyl-N-[4-(methyloxy)phenyl]imidazo-[5,1-f][1,2,4]triazin-2-amine;
7-(2-Furanyl)-5-methyl-N-[4-(methyloxy)phenyl]imidazo-[5,1-f][1,2,4]triazin-2-amine;
7-(4-Fluorophenyl)-5-methyl-N-[4-(methyloxy)phenyl]-imidazo[5,1-f][1,2,4]triazin-2-amine;
5-Methyl-N-[4-(methyloxy)phenyl]-7-(2-thienyl)imidazo[5,1-f][1,2,4]triazin-2-amine;
7-Cyclopropyl-5-methyl-N-[4-(methyloxy)phenyl]-imidazo[5,1-f][1,2,4]triazin-2-amine;
7-Cyclohexyl-5-methyl-N-[4-(methyloxy)phenyl]imidazo[5,1-f][1,2,4]triazin-2-amine;
7-(2-FluorophenylFluorophenyl)-5-methyl-N-[4-(methyloxy)phenyl]imidazo[5,1-f][1,2,4]triazin-2-amine;
5-Methyl-N,7-bis[4-(methyloxy)phenyl]imidazo[5,1-f][1,2,4]triazin-2-amine;
5-Methyl-N-[4-(methyloxy)phenyl]-7-(phenylmethyl)imidazo[5,1-f][1,2,4]triazin-2-amine;
7-(3-Fluorophenyl)-5-methyl-N-[4-(methyloxy)phenyl]imidazo[5,1-f][1,2,4]triazin-2-amine;
7-Cyclohexyl-5-methyl-N-[3,4,5-tris(methyloxy)phenyl]imidazo[5,1-f][1,2,4]triazin-2-amine;
7-(Cyclohexylmethyl)-5-methyl-N-[4-(methyloxy)phenyl]-imidazo[5,1-f][1,2,4]triazin-2-amine;
N-[3,4-Bis(methyloxy)phenyl]-5-methyl-7-phenylimidazo[5,1-f][1,2,4]triazin-2-amine;
N-[3,5-Bis(methyloxy)phenyl]-5-methyl-7-phenylimidazo[5,1-f][1,2,4]triazin-2-amine;
N-{4-[(5-Methyl-7-phenylimidazo[5,1-f][1,2,4]triazin-2-yl)amino]phenyl}acetamide;
5-Methyl-N-[4-(methylthio)phenyl]-7-phenylimidazo[5,1-f][1,2,4]triazin-2-amine;
N-(4-{[2-(Dimethylamino)ethyl]oxy}phenyl)-5-methyl-7-phenylimidazo[5,1-f][1,2,4]triazin-2-amine;
5-Methyl-7-phenyl-N-(4-{[2-(1-piperidinyl)ethyl]oxy}phenyl)-imidazo[5,1-f][1,2,4]triazin-2-amine;
N-(3-{[2-(Dimethylamino)ethyl]oxy}phenyl)-5-methyl-7phenylimidazo[5,1-f][1,2,4]triazin-2-amine;

N-(1-Acetyl-2,3-dihydro-1H-indol-5-yl)-5-methyl-7-phenylimidazo[5,1-f][1,2,4]triazin-2-amine;
N—Cyclohexyl-5-methyl-7-phenylimidazo[5,1-f][1,2,4]triazin-2-amine;
5-Methyl-7-phenyl-N-(tetrahydro-2H-pyran-4-yl)imidazo[5,1-][1,2,4]triazin-2-amine;
5-Methyl-N-(4-{[2-(4-morpholinyl)ethyl]oxy}phenyl)-7-phenylimidazo[5,1-f][1,2,4]triazin-2-amine;
5-Methyl-N-(3-{[2-(4-morpholinyl)ethyl]oxy}phenyl)-7-phenylimidazo[5,1-f][1,2,4]triazin-2-amine;
5-Methyl-N-[4-(methyloxy)phenyl]-7-phenylimidazo[5,1-f][1,2,4]triazin-2-amine;
5-Methyl-N,7-diphenylimidazo[5,1-f][1,2,4]triazin-2-amine;
5-Methyl-N-[3-(methyloxy)phenyl]-7-phenyl imidazo[5,1-f][1,2,4]triazin-2-amine; and pharmaceutically acceptable salts thereof.

23. A pharmaceutical composition comprising a compound according to claim 1 and a pharmaceutically acceptable carrier, diluent or excipient.

24. The pharmaceutical composition according to claim 23 further comprising a chemotherapeutic agent.

25. A process for preparing a compound according to claim 1, said process comprising reacting a compound of formula (X):

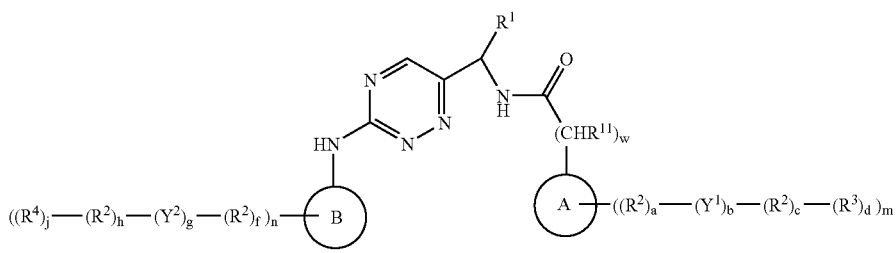

X with a cyclization reagent.

26. A process for preparing a compound according to claim 1, said process comprising reacting the compound of formula (XIII):

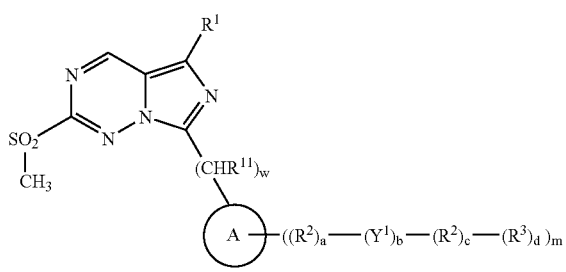

XIII with a compound of formula (VI):

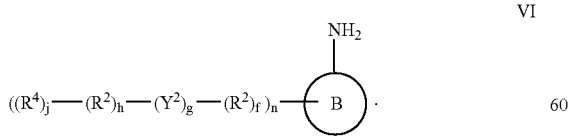

VI

27. A process for preparing a compound according to claim 1 wherein:

Ring A is selected from the group consisting of cycloalkyl, aryl, 5-13 membered heterocycle and 5-13 membered heteroaryl;

each $R^2$ is the same or different and is alkylene;

each $R^3$ and $R^4$ are the same or different and are each independently selected from the group consisting of H, halo, alkyl, alkenyl, alkynyl, cycloalkyl, Ph, Het, —$OR^5$, —$S(O)_pR^5$, —$S(O)_2OH$, —$S(O)_pNR^5R^6$, —$NR^5R^5$ and —$NR^5SO_2R^6$;

each $R^5$ and each $R^5$ are the same or different and are each independently selected from the group consisting of H, alkyl and cycloalkyl;

Ph is phenyl optionally substituted by one or more substituents selected from the group consisting of halo, alkyl, —$OR^5$, —$SO_2R^5$, —$SO_2NR^5R^6$, —$NR^5R^6$, Het, and —$R^2$-Het; and Het is a monocyclic 5-6 membered heterocycle or heteroaryl group containing 1, 2 or 3 heteroatoms selected from the group consisting of N, o and S optionally substituted by one or more substituents selected from the group consisting of halo, alkyl, —$OR^5$, —$SO_2R^5$, —$SO_2NR^5R^6$, —$NR^5R^6$ and oxo; and said process comprising coupling a compound of formula (XVIII):

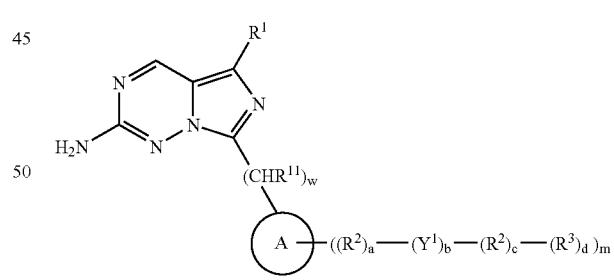

XVIII with a compound of formula (XIX):

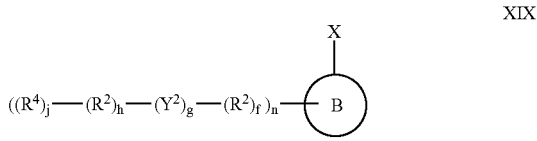

XIX wherein X is Cl, Br, I or triflate.

* * * * *